US012115248B2

(12) United States Patent
Lay et al.

(10) Patent No.: US 12,115,248 B2
(45) Date of Patent: *Oct. 15, 2024

(54) DEVICES AND METHODS FOR DELIVERING METHANE INHIBITING COMPOUNDS TO ANIMALS

(71) Applicant: Ruminant Biotech Corp Limited, Hamilton (NZ)

(72) Inventors: Mark Christopher Lay, Hamilton (NZ); Geoffrey Earle Corbett, Hamilton (NZ); Neil Richard Gladden, Hamilton (NZ); Prabhat Bhusal, Hamilton (NZ); Junfeng Yan, Hamilton (NZ); Seyedehsara Masoomi Dezfooli, Hamilton (NZ)

(73) Assignee: Ruminant Biotech Corp Limited, Hamilton (NZ)

( * ) Notice: Subject to any disclaimer, the term of this patent is extended or adjusted under 35 U.S.C. 154(b) by 0 days.

This patent is subject to a terminal disclaimer.

(21) Appl. No.: 18/498,661

(22) Filed: Oct. 31, 2023

(65) Prior Publication Data

US 2024/0139103 A1 May 2, 2024

(30) Foreign Application Priority Data

Nov. 2, 2022 (EP) .................. 22205176

(51) Int. Cl.
| *A61K 9/00* | (2006.01) |
| *A61D 7/00* | (2006.01) |
| *A61K 31/02* | (2006.01) |
| *A61K 47/02* | (2006.01) |
| *A61K 47/34* | (2017.01) |
| *A61K 47/44* | (2017.01) |

(52) U.S. Cl.
CPC .............. *A61K 9/0068* (2013.01); *A61D 7/00* (2013.01); *A61K 31/02* (2013.01); *A61K 47/02* (2013.01); *A61K 47/34* (2013.01); *A61K 47/44* (2013.01)

(58) Field of Classification Search
CPC ...... A61K 9/0068; A61K 31/02; A61K 47/02; A61K 47/34; A61K 47/44; A61D 7/00
See application file for complete search history.

(56) References Cited

U.S. PATENT DOCUMENTS

| 3,660,562 A | * | 5/1972 | Grass et al. | ........... A23K 40/35 514/743 |
| 4,251,506 A | * | 2/1981 | Laby | ................ A61K 9/0068 424/484 |
| 4,955,881 A | | 9/1990 | Eckenhoff | |
| 5,074,857 A | | 12/1991 | Shepherd et al. | |
| 5,807,594 A | | 9/1998 | King et al. | |
| 5,985,314 A | | 11/1999 | Porter | |
| 7,354,870 B2 | | 4/2008 | Luan | |
| 11,116,813 B2 | | 9/2021 | Peng et al. | |
| 11,529,310 B2 | | 12/2022 | Lay et al. | |
| 2016/0339067 A1 | | 11/2016 | Machado et al. | |
| 2020/0138056 A1 | | 5/2020 | Graz et al. | |
| 2021/0128479 A1 | | 5/2021 | Cheng et al. | |
| 2022/0175670 A1 | | 6/2022 | Lay et al. | |
| 2023/0083835 A1 | | 3/2023 | Lay et al. | |
| 2023/0085030 A1 | | 3/2023 | Lay et al. | |
| 2023/0165274 A1 | | 6/2023 | Hay et al. | |

FOREIGN PATENT DOCUMENTS

| AU | 520409 | 1/1982 |
| AU | 555998 | 10/1986 |
| AU | 558009 | 1/1987 |
| AU | 2013242835 | 10/2013 |
| AU | 2022100024 | 5/2022 |
| EP | 0164241 | 12/1985 |
| EP | 2767289 | 8/2014 |
| GB | 2353707 | 3/2001 |
| WO | WO 198906943 | 8/1989 |
| WO | WO 199519763 | 7/1995 |
| WO | WO 1996014062 | 5/1996 |
| WO | WO 2011014078 | 2/2011 |
| WO | WO 2016102931 | 6/2016 |
| WO | WO 2015109362 | 7/2016 |
| WO | WO 2017120495 | 7/2017 |
| WO | WO 2019145345 | 8/2019 |
| WO | WO 2020113279 | 6/2020 |
| WO | WO 2020245303 | 12/2020 |
| WO | WO 2021005202 | 1/2021 |
| WO | WO 2021116395 | 6/2021 |
| WO | WO 2021163148 | 8/2021 |

(Continued)

OTHER PUBLICATIONS

Abbott et al., "Seaweed and Seaweed Bioactives for Mitigation of Enteric Methane: Challenges and Opportunities," Animals (Basel)., Dec. 2020, 10(12):2432, 28 pages.
Alvarez-Hess et al., "Twice daily feeding of canola oil steeped with *Asparagopsis armata* reduced methane emissions of lactating dairy cows," Animal Feed Science and Technology, Mar. 2023, 297(3):115579.
Cardinal, "Intraruminal controlled release boluses," Controlled Release Veterinary Drug Delivery, 2000, 51-82.
Grainger et al., "Can enteric methane emissions from ruminants be lowered without lowering their production?" Anim. Feed Sci. Technol., Jun. 2011, 166-167:308-320.
Henderson et al., "Enzyme- and gene-based approaches for developing methanogen-specific compounds to control ruminant methane emissions: a review," Animal Production Science, Apr. 2016, 58(6):1017-1026.

(Continued)

*Primary Examiner* — Robert A Wax
*Assistant Examiner* — Quanglong N Truong
(74) *Attorney, Agent, or Firm* — Fish & Richardson P.C.

(57) ABSTRACT

The invention provides a dosage form and a bolus configured for administration to an animal, wherein said dosage form and said bolus is configured to release a methane inhibitor to the animal over a period of time. Preferably the methane inhibitor is a haloform. Also provided is the use of the bolus of the invention to reduce methane production in a ruminant animal. Also provided is the method of manufacturing a bolus of the invention.

30 Claims, 51 Drawing Sheets

(56) References Cited

FOREIGN PATENT DOCUMENTS

| WO | WO 2021205420 | 10/2021 |
| --- | --- | --- |
| WO | WO 2022124914 | 6/2022 |
| WO | WO 2022136857 | 6/2022 |
| WO | WO 2022218967 | 10/2022 |
| WO | WO 2022221925 | 10/2022 |
| WO | WO 2023163600 | 8/2023 |
| WO | WO 2023247942 | 12/2023 |
| WO | WO 2024011207 | 1/2024 |

OTHER PUBLICATIONS

Invitation to Pay Additional Fees in International Appln. No. PCT/NZ2023/050118, mailed on Mar. 4, 2024, 15 pages.
Kinley et al., "Mitigating the carbon footprint and improving productivity of ruminant livestock agriculture using a red seaweed," Journal of Cleaner Production, Jun. 2020, 259:120836, 10 pages.
Kinley et al., "The red macroalgae *Asparagopsis taxiformis* is a potent natural antimethanogenic that reduces methane production during in vitro fermentation with rumen fluid," Animal Production Science, Feb. 2016, 56(3):282-289.
Kurt, "Enteric Fermentation / Enteric Methane," Foundation for Food and Agriculture Research (FFAR), ARPA-E Remedy Workshop, virtual, Oct. 20, 2020, 13 pages.
Magnusson et al., "Using oil immersion to deliver a naturally-derived, stable bromoform product from the red seaweed *Asparagopsis taxiformis*," Algal Research, Oct. 2020, 51:102065, 7 pages.
McGinn et al., "Assessment of the SF6 tracer technique for measuring enteric methane emissions from cattle," J. Environ. Qual., Aug. 2006, 35(5):1686-1691.
Morais et al., "Seaweed Potential in the Animal Feed: a Review," J. Marine Sci. & Eng., Jul. 2020, 8(8):559, 24 pages.
Odongo et al., "Long-Term Effects of Feeding Monensin on Methane Production in Lactating Dairy Cows," J. Dairy Sci., Apr. 2007, 90(4):1781-1788.
Roque et al., "Inclusion of Asparagopsis armata in lactating dairy cows' diet reduces enteric methane emission by over 50 percent," Journal of Cleaner Production, Oct. 2019, 234:132-138.
Tan et al., "Shelf-Life stability of Asparagopsis bromoform in oil and freeze-dried powder," Journal of Applied Physiology, Nov. 2022, 35:291-299.
Thompson and Rowntree, "Invited Review: Methane sources, quantification, and mitigation in grazing beef systems", Applied Animal Science, Aug. 2020, 36(4):556-573.
Patent Examination Report in New Zealand Appln. No. 796269, dated May 24, 2024, 3 pages.
Aliotta et al., "A Brief Review of Poly (Butylene Succinate) (PBS) and Its Main Copolymers: Synthesis, Blends, Composites, Biodegradability, and Applications," Polymers (Basel), Feb. 2022, 14(4):844, 23 pages.
Byford et al., "A Sustained-release Oxytetracycline Bolus for Ruminants," Bovine Practitioner, Nov. 1980, 15:91-94.
Byford, "Prophylaxis and control of vector borne anaplasmosis with sustained-release boluses," Thesis for the degree of Master of Science, Oklahoma State University, May 1980, 84 pages.
Coiai et al., "Binary Green Blends of Poly(lactic acid) with Poly(butylene adipate-co-butylene terephthalate) and Poly(butylene succinate-co-butylene adipate) and Their Nanocomposites," Polymers (Basel), Jul. 2021, 13(15):2489, 32 pages.
Conrad et al., "Controlled sustained delivery of monensin in cattle: the Monensin R.D.D," Journal of Controlled Release, Jul. 1989, 9(2):133-147.
Controlled Release Veterinary Delivery, 1st ed., Rathbone M.J. & Gurny R. (Eds.), Jul. 2000, Chapters 2 and 3, 66 pages.
"Declaration of Stephen Page," Exhibit 1 in Opposition to Australian Appln. No. 2022100024, dated May 8, 2024, 107 pages.
Formulation of Veterinary Dosage Forms, 1st ed., Blodinger (ed.), 1983, Chapters 2-4, 134 pages.
Hajnal et al., "Dairy Cattle Rumen Bolus Developments with Special Regard to the Applicable Artificial Intelligence (AI) Methods," Sensors, Sep. 2022, 22(6812), 16 pages.
Honan et al., "Feed additives as a strategic approach to reduce enteric methane production in cattle: modes of action, effectiveness and safety," Animal Production Science, Feb. 2021, 62:1303-1317.
International Search Report and Written Opinion in International Appln. No. PCT/NZ2023/050118, mailed on Jun. 5, 2024, 27 pages.
Kinley et al., "Asparagopsis feedlot feeding trial," Meat & Livestock Australia, May 2018, 42 pages.
McGurrin et al., "Anti-methanogenic potential of seaweeds and seaweed-derived compounds in ruminant feed: current perspectives, risks and future prospects," Journal of Animal Science and Biotechnology, Dec. 2023, 14:145, 27 pages.
Office Action in U.S. Appl. No. 17/987,983, dated May 28, 2024, 21 pages.
Riner, "Sustained-release ruminal boluses and factors determining their release rates," Thesis for the degree of Doctor of Philosophy, Oklahoma State University, Dec. 1981, 97 pages.
Statement of Grounds and Particulars dated May 21, 2024, in corresponding AU patent application No. 2022100024, 36 pages.
Teel, "A sustained-release systemic acaracide bolus for tick control in bovine," Thesis for the degree of Doctor of Philosophy, Oklahoma State University, May 1978, 127 pages.
Thombre et al., "A delivery device containing a poorly water-soluble drug in a hydrophobic medium: ruminal delivery application," Journal of Controlled Release, 1992, 18(3):221-233.
Tomkins et al., "A bromochloromethane formulation reduces enteric methanogenesis in cattle fed grain-based diets," Animal Production Science, Nov. 2009, 49(12):1053-1058.
Vandamme et al., "Controlled release of levamisole from poly-($\epsilon$-caprolactone) matrices: III. Effects of molecular weight and polymer coating on drug release," International Journal of Pharmaceutics, Dec. 1996, 145(1-2):77-86.
Zhao et al., "Super tough poly(lactic acid) blends: a comprehensive review," RSC Advances, Jan. 2020, 10(22):13316-13368.
Machado et al. "In Vitro Reponse of Rumen Microbiota to the Antimethanogenic Red Macroalga Asparagopsis taxiformis," Microb. Ecol., Apr. 2018, 75(3):811-818.
Office Action in U.S. Appl. No. 17/987,983, dated Aug. 15, 2024, 22 pages.
Beauchemin et al., "Review: Fifty years of research on rumen methanogenesis: lessons learned and future challenges for mitigation," Animal, Mar. 2020, 14(S1):s2-s16.
Biomaterials Science: An Introduction to Materials in Medicine, 3rd ed., Ratner (ed.), Oct. 2012, Chapter 1, 30 pages.
Introduction to Polymers, 3rd ed., Young (ed.), Mar. 2013, Chapter 18, 20 pages.
Polymer Blends and Composites, 1st ed., Manson (ed.), 1976, Chapter 2, 68 pages.
Statement of Grounds and Particulars dated Aug. 22, 2024 in AU patent application No. 2023200195, 36 pages.
Su et al., "Uncompatibilized PBAT/PLA Blends: Manufacturability, Miscibility and Properties,"Materials, Oct. 2020, 13:4897, 17 pages.

* cited by examiner

Figure 22A
Figure 22B
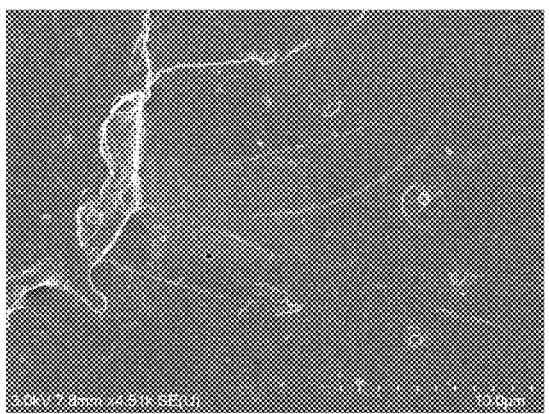
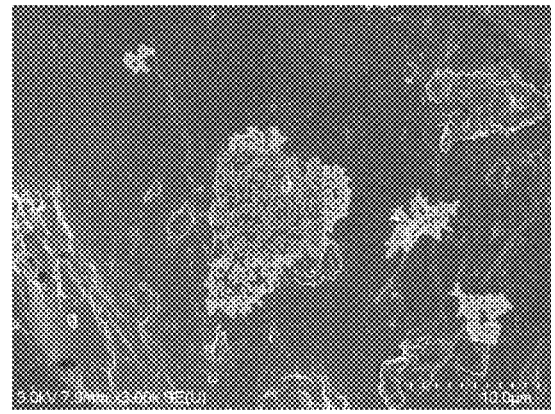

Panel a                                          Panel b

Panel c                                          Panel d

DEVICES AND METHODS FOR DELIVERING METHANE INHIBITING COMPOUNDS TO ANIMALS

CROSS-REFERENCE TO RELATED APPLICATION

This application claims priority to and the benefit of EP application Ser. No. 22/205,176.5, filed Nov. 2, 2022, which is incorporated herein by reference in its entirety.

FIELD OF INVENTION

The present invention relates to improvements in devices and methods for delivery of substances to animals, and in particular to devices and methods for administering at least one methane inhibiting substance to an animal, and methods of manufacturing of the devices.

BACKGROUND OF THE INVENTION

In farming it is often necessary to deliver substances to animals. This can be for any of various purposes, including but not limited to treatment or prevention of disease and to increase animal production.

There are various devices and methods to deliver substances such as medicament to animals. However, one class of compounds that are difficult to deliver to animals are hydrophobic compounds. The properties of these compounds present challenges to developing technology for the controlled release of these hydrophobic substances, particularly via an animal's stomach.

One specific purpose to administer substances to animals is to reduce the adverse effects of agriculture. For instance, various methane and nitrification inhibitors are known to be administered to animals to reduce or mitigate the adverse effects of the methane and nitrate containing compounds produced by the animals.

However, despite current efforts, climate change is creating a wide range of environmental and social impacts globally. It is widely understood that these impacts will only continue to increase over time. As a result, there has been a global push to reduce harmful greenhouse gas (GHG) emissions in an effort to avoid the worst effects of climate change.

The agricultural sector is considered to be a major source of GHG emissions. Total emissions of methane from global livestock accounts for an estimated 7.1 gigatons of $CO_2$-equivalent per year, representing 14.5% of all anthropogenic GHG emissions. Therefore, this sector will play a key role in reducing overall GHG emissions.

The main GHGs released by agriculture are methane ($CH_4$) and nitrous oxide ($N_2O$), with the main source of methane emission attributed to livestock. Most methane is emitted when cattle burp. The amount of methane produced for each farm is directly related to the total animal feed intake.

Countries which have a strong agricultural sector such as New Zealand and other countries, face challenging goals of reducing agricultural emissions. For instance, the New Zealand government has introduced policies aimed to reduce methane emission by 24-50% before 2050. In New Zealand livestock methane production is estimated to comprise as much as half of the country's total GHG emissions. The reduction of methane is a critical component of meeting targets for emissions of GHGs and reducing the effects of global warming.

Release of GHGs by animals also has adverse effects on animal productivity. Any feed that is converted to a compound which is subsequently expired or released by the animal is an energy source that has not been converted to a productive use. Accordingly, for efficiency, it is important to optimise conversion of feeds into animal productivity in the form of weight gain or milk production.

SUMMARY OF THE INVENTION

It is an object of the present invention to provide improved devices and methods to deliver substances to an animal, e.g. methane inhibitors.

It is an object of the invention to provide devices and methods to reduce emission of GHGs.

It is an object of the invention to provide devices and methods to improve or optimise animal productivity.

Additionally, it is an object of the invention to provide devices and methods to improve animal production gains e.g. through reduction of methane production.

It is an object of the invention to provide a formulation to reduce emission of GHGs by one or more animals e.g. a ruminant animal.

The object of the invention includes the provision of devices and methods that can release substances at different rates over a period of time, for example sustained release dosage forms comprising a methane inhibiting substance.

The object of the invention includes the provision of methods of manufacturing devices to deliver substances to an animal e.g. substances to reduce emission of GHGs.

Additionally, it is an object of the invention to overcome some of the disadvantages of the prior art.

Additionally, it is an object of the present invention to provide the public with a useful choice of treating methane production in ruminant animals.

The present invention is exemplified with reference to preferred embodiments, which however, are not to be seen as limiting on the scope of the invention. One skilled in the art understands how to apply the teachings herein to devices for delivery of other substances to animals. All documents cited herein are incorporated by reference. Embodiments disclosed herein can be combined unless stated otherwise.

Prior art devices for administering a methane inhibiting agent to an animal known from the literature can still be further improved in terms of durability, controlled release rate of the inhibiting agent and reduced size and manufacturing costs.

Due to the volatility of some methane inhibiting agents such as bromoform and its reactivity with many compounds including organic compounds, it can be difficult to contain such methane inhibiting compound in a stable way and at a high concentration (to be able to reduce the size of the formulation) in a delivery device such as a bolus. Using fumed silica as carrier in a bolus will stabilize the formulation, improve the stability and increase the loading capacity of the drug formulation for the methane inhibiting compound.

Accordingly, in a first aspect the present invention provides a bolus for administration to a ruminant animal, wherein said bolus is configured to release a methane inhibiting agent in the animal, wherein said bolus comprises:
    a core, wherein the core comprises the inhibiting agent (such as a haloform or bromoform) and a carrier; and
    a housing which covers at least a portion of the core;
    wherein said carrier comprises or consists of hydrophobic fumed silica and/or comprises a combination of ethyl cellulose and HPMC.

The core may comprise further components, for instance, but not limited to metal (preferably steel) particles. If the bolus of the invention comprises a housing, the "core" may also refer to the entire volume inside the housing. In the absence of a housing, the core may be compacted such that it forms a bolus on its own.

In a preferred embodiment the core comprises tribromomethane, hydrophobic fumed silica and a filling agent, for example selected from castor wax, ethyl cellulose, and/or polycaprolactone (PCL). Preferably the filling agent (e.g. castor wax, ethyl cellulose, and/or polycaprolactone (PCL)) is comprised in the core in an amount of 15 and 40% (w/w) and more preferably between 20% and 35% (w/w). It is clear, that the indicated weight percentages relate to the weight of filling agent in relation to the total weight of the core.

In a preferred embodiment of the bolus the core comprises less than 75% (w/w) bromoform, and further comprises both castor wax and fumed silica.

In a preferred embodiment of the bolus the core comprises less than 75% (w/w) bromoform, and further comprises both ethyl cellulose and fumed silica.

In a preferred embodiment of the bolus the core comprises less than 75% (w/w) bromoform, and further comprises both castor wax of less than 40% (w/w) and fumed silica of less than 15% (w/w).

In a preferred embodiment of the bolus the core comprises bromoform but in an amount of less than 75% (w/w) bromoform, and further comprises both castor wax and fumed silica.

In a preferred embodiment of the bolus the core comprises bromoform but in an amount of less than 75% (w/w) bromoform, and further comprises both ethyl cellulose and fumed silica.

In a preferred embodiment of the bolus the core comprises bromoform but in an amount of less than 75% (w/w) bromoform, and further comprises both castor wax of less than 40% (w/w) and fumed silica of less than 15% (w/w).

In a preferred embodiment of the bolus the core comprises less than 75% (w/w) bromoform, and further comprises both ethyl cellulose of less than 40% (w/w) and fumed silica of less than 15% (w/w). It is clear from the above mentioned embodiments, that the respectively indicated weight percentages relate to the weight of the sum of the named core components in relation to the total weight of the core.

Suitable carrier materials used in the bolus of the invention may advantageously have a high capacity to hold the active ingredient, i.e. the methane inhibiting agent. One example of especially suitable carrier material is fumed silica, preferably hydrophobic fumed silica, which can consist of particles of amorphous silica that can be fused into branched particles. Fumed silica, available for instance as a powder, provides a low bulk density and high surface area.

In one embodiment, a bolus of the invention as described comprises hydrophilic silica.

Furthermore, the invention provides in a further aspect a bolus for administering to a ruminant animal, wherein said bolus is configured to release a methane inhibiting agent in the animal, wherein said bolus comprises:
 a core, wherein the core comprises the inhibiting agent and preferably a carrier; and
 a housing which covers at least a portion of the core;
 wherein the material of the housing comprises poly lactic acid (PLA) and a polybutylene polymer in a PLA: polybutylene polymer weight ratio of between 95:5 to 70:30.

Preferably, said polybutylene polymer is selected from the group consisting of polybutylene adipate terephthalate (PBAT), polybutylene succinate (PBS) and polybutylene succinate adipate (PBSA).

In a preferred embodiment the invention provides a bolus for administration to a ruminant animal, wherein said bolus is configured to release a methane inhibiting agent in the animal, wherein said bolus comprises:
 a core, wherein the core comprises the inhibiting agent and preferably a carrier; and
 a housing which covers at least a portion of the core;
 wherein the material of the housing comprises poly lactic acid (PLA) and polybutylene adipate terephthalate (PBAT); or
 wherein the material of the housing comprises poly lactic acid (PLA) and polybutylene adipate terephthalate (PBAT) in a PLA:PBAT weight ratio of between 95:5 to 80:20; or
 wherein the material of the housing comprises poly lactic acid (PLA) and polybutylene succinate (PBS) in a PLA:PBS weight ratio of between 95:5 to 70:30; or
 wherein the material of the housing comprises poly lactic acid (PLA) and polybutylene succinate adipate (PBSA) in a PLA:PBSA weight ratio of between 95:5 to 70:30.

More preferred weight ratios of the poly lactic acid (PLA) to polybutylene polymer in the blend used as housing material include between 75:25 and 95:5, and more preferably between 80:20 and 95:5, even more preferably between 85:15 and 95:5, most preferably 90:10. It was surprisingly found that by using a mixture or blend of biodegradable plastic materials for the housing of the bolus of the invention the housing features can be improved, such as its resilience against mechanical stress. For instance, mixing/blending a polybutylene polymer such as PBAT with PLA increased the plasticity of the housing compared to a housing made of PLA alone, while preserving the biodegradability of the housing material. This stability improving effect is particularly beneficial when using haloforms, such as bromoform, as methane inhibiting agents since such haloforms can otherwise promote brittleness of the housing material. Furthermore, the use of a polybutylene polymer/PLA blend compared to PLA alone improved the durability of the housing and reduced the risk of fracturing under mechanical stress such as when placed into the rumen of an animal. Additionally, the polybutylene polymer such as PBAT is biodegradable just like PLA, and thus, the housing will remain biodegradable despite mixing of different polymer components.

In some embodiments a material is considered biodegradable, if the material is considered to be biodegradable under the standard set out in ISO 14855-1:2012 (biodegradability of plastic materials under controlled composting conditions). According to this method the percentage of biodegradation is given by the ratio of the $CO_2$ produced from the test material to the maximum theoretical amount of $CO_2$ that can be produced from the test material (not including the amount of carbon converted to new cell biomass, i.e. not metabolized to $CO_2$). The maximum theoretical amount of $CO_2$ produced is calculated from the total organic carbon content of the test material. The threshold for industrial composting biodegradability is a biodegradation for least 90% by mass of the total mass of the test material in less than 6 months. Thus, for instance, 90% of the carbon of the test material may be converted to $CO_2$ within less than 6 months for the testing material to be considered biodegradable. Surprisingly, when investigating suitable ratios of polybutylene polymers, it was found that when mixing polybutylene in a mixture with PLA in rather high amounts, this can result in a mixture which is less ideal for manufacturing a bolus housing. For instance, using more than 30 wt % of a polybutylene polymer such as PBAT mixed with PLA to make the housing material (e.g. a PLA/PBAT ratio of about 60:40) results in less beneficial material properties: upon heating for shaping the bolus housing the composition can become viscous hampering 3D printing or injection molding and, moreover, PLA/polybutylene polymer blends comprising high amounts of polybutylene polymer tend to be inhomogeneous. In particular, such mixtures can also have a tendency to form bubbles when subjecting the mixture to injection molding, which complicates the process of manufacturing a suitable bolus housing. Therefore, it is preferred that a housing material that comprises both PLA and PBAT does not comprise PBAT in an amount of more than 30 wt %.

As is already clear from the above, the indicated weight percentages for the indicated housing materials refer to the indicated weight percentage in relation to the total weight of the housing.

The housing of the bolus may for instance comprise biodegradable and/or non-biodegradable materials, but preferably comprises biodegradable polymers. Such materials may be synthetic or naturally or essentially naturally derived. It is preferred that materials are selected from biodegradable polymers. Examples of such polymers comprise, without limitation, poly lactic acid (PLA), polybutylene terephthalate (PBT), polybutylene adipate-terephthalate (PBAT), polybutylene succinate (PBS) and/or polybutylene succinate adipate (PBSA).

In one embodiment the material of the housing comprises poly lactic acid (PLA) and polybutylene adipate-terephthalate (PBAT) in a PLA:PBAT weight ratio of between 95:5 to 70:30.

In yet another embodiment the material of the housing comprises poly lactic acid (PLA) and polybutylene adipate-terephthalate (PBAT) in a PLA:PBAT weight ratio of between 95:5 to 70:30.

In yet another embodiment the material of the housing comprises poly lactic acid (PLA) and polybutylene adipate-terephthalate (PBAT) in a PLA:PBAT weight ratio of between 95:5 to 70:30.

More preferred ratios include between 85:15 to 95:5 PLA:polybutylene polymer (such as PBAT, PBS and/or PBSA). In a more preferred embodiment the housing comprises PLA and PBAT, wherein the ratio is between 85:15 to 95:5 PLA:PBAT. In an even more preferred embodiment the housing comprises PLA and PBAT, wherein the ratio is between 85:15 to 95:5 PLA:PBAT and wherein the methane inhibiting agent is bromoform.

In one embodiment the methane inhibiting agent comprised in the core comprised in the bolus is a haloform, preferably selected from the list of bromoform, chloroform, iodoform, and combinations thereof.

In a preferred embodiment the methane inhibiting agent is bromoform.

The methane inhibiting agent may be synthetic or derived from a naturally occurring source such as from a plant such as from algae. In one embodiment the methane inhibiting agent is Asparagopsis or a derivative thereof. The methane inhibiting agent, may for instance be obtained from Asparagopsis by extraction. For example, lysing of the algae can be achieved by breaking the algal cell wall or membrane to separate the methane inhibiting substances from the rest of the algae biomass. The algae such as Asparagopsis or parts and derivatives thereof may also be directly included in the bolus, as a source that releases the methane inhibiting agent, such as bromoform. In a preferred embodiment the methane inhibiting agent is a bromoform containing algae extract. In an even more preferred embodiment, the algae extract is a concentrated extract, more preferably wherein one of the concentrated components of the extract is concentrated bromoform, wherein the concentrated extract comprises at least 80 vol % of bromoform in relation to the total volume of the extract.

In one embodiment, the hydrophobic fumed silica comprised in the carrier comprised in the bolus is amorphous or consists of or comprises hydrophobic fumed silica nanoparticles (HFSNPs).

In a preferred embodiment the carrier comprises at most 20 wt %, at most 15 wt %, or at most 10 wt % of said hydrophobic fumed silica. Preferably, the carrier comprises at most 10 wt % of said hydrophobic fumed silica, wherein the methane inhibiting agent is bromoform.

In another embodiment the carrier comprises from 1 wt % to 25 wt % of hydrophobic fumed silica in relation to the total combined weight of the carrier and the methane inhibiting agent, preferably from 3 wt % to 15 wt % of said hydrophobic fumed silica. More preferably, in another embodiment the carrier comprises from 3 wt % to 10 wt % of hydrophobic fumed silica, more preferably from 3 wt % to 7 wt % of said hydrophobic fumed silica and most preferably from 5 wt % to 7 wt % of said hydrophobic fumed silica in relation to the total combined weight of the carrier and the methane inhibiting agent.

It is understood that the carrier of a bolus of the invention can comprise additional compounds such as ethyl cellulose, HPMC and mixtures of the aforementioned. In another preferred embodiment the average particle diameter of said hydrophobic fumed silica is between 5 nm and 15 nm.

In a preferred embodiment the hydrophobic fumed silica consists of or comprises treated fumed silica which is fumed silica that has been contacted with a hydrophobic silane and preferably contacted with a compound or compounds chosen from the group of DDS, methyl acrylic silane, octyl silane, octamethylcyclotetrasiloxane, hexadecyl silane, octylsilane, methylacrylsilane, polydimethylsiloxane, hexamethyldisilazane (HMDS), silicone oil, silicone oil plus aminosilane, HMDS plus aminosilane, and organic phosphates and most preferably contacted with dimethyldichlorosilane (DDS) and/or HMDS (hexamethyldisilazane).

In one embodiment, the core of the bolus of the invention further comprises a wax and/or a polyol and/or a polyester; wherein the wax is preferably a compound selected from the group consisting of myristic acid, lauric acid, stearic acid, steryl alcohol, cetyl alcohol, cetosteryl alcohol, castor wax, bee's wax, paraffin wax, PEG4000, Carnauba, Candellila, Jojoba, Lanolin, and a combination thereof, preferably castor wax; and wherein the polyol is preferably a compound selected from the group consisting of polyols, preferably cellulose derivates, more preferably ethyl cellulose; and wherein the polyester is preferably Poly(ε-caprolactone) (PCL). In one embodiment the core comprises hydroxypropyl methylcellulose (HPMC). In any of the aforementioned embodiments, the core may comprise the inhibiting agent and a carrier, wherein the carrier may be selected from any one of the aforementioned compounds.

In one embodiment, the core comprises ethyl cellulose and/or HPMC. In a more preferred embodiment, the core comprises ethyl cellulose and HPMC. In a preferred embodiment the HPMC has a methoxy content of from 19 to 24% and a hydroxypropyl content of from 4 to 12% and/or is preferably HPMC K-100. In a preferred embodiment the ratio of ethyl cellulose:HPMC is from 35:65 to 70:30.

In one embodiment, the core comprises ethyl cellulose and fumed silica. In a preferred embodiment the core comprises ethyl cellulose and fumed silica in a ratio of ethyl cellulose to fumed silica of from 70:30 to 90:10.

In one embodiment, the core comprises ethyl cellulose in an amount of from 10 to 40 wt %. In a preferred embodiment, the core comprises ethyl cellulose in an amount of from 15 to 30 wt %.

In one embodiment, the core comprises HPMC in an amount of from 10 to 30 wt %. In a preferred embodiment, the core comprises HPMC in an amount of from 12 to 25 wt %.

Only for the sake of completeness, in the context of the aforementioned embodiments "wt %" is the weight percent in relation to the total weight of the core. It is understood that the core of a bolus of the invention can comprise additional compounds such as ethyl cellulose, HPMC, fumed silica and mixtures of the aforementioned. In one embodiment at least 50% of the core of the bolus of the invention comprises the methane inhibiting agent. In another embodiment at least 60%, at least 70%, at least 80%, or at least 90% of the core of the bolus of the invention comprises the methane inhibiting agent.

In another embodiment the haloform, preferably bromoform, is comprised in the core of the bolus of the invention in an amount of between 30 wt % to 80 wt % and preferably in an amount of between 30 wt % and 70 wt %, preferably in an amount of at most 55 wt %.

In this context "wt %" refers to the weight percent of the haloform, in relation to the total weight of the bolus.

In another embodiment the haloform, preferably bromoform, is comprised in the core in an amount of at least 50 wt %, of at least 58 wt %, of at least 60 wt %, of at least 61 wt %, or of at least 64 wt %, wherein the wt % is the weight percent in relation to the total weight of the core. Carriers useful in the context of a bolus of the invention include for instance a carrier selected from the group consisting of ethyl cellulose, HPMC, hydrophobic fumed silica, and mixtures of the aforementioned.

In a preferred embodiment of the bolus of the invention the PLA:PBAT weight ratio is about 90:10; the PLA:PBS weight ratio is about 90:10; or the PLA:PBSA weight ratio is about 90:10.

In an even more preferred embodiment of the bolus of the invention the PLA:PBS weight ratio is about 80:20. The PLA:PBS weight ratio of about 80:20 is even more preferred than the 90:10 ratio, since the housing at this ratio surprisingly exhibited improved ductility and stability features. Despite the overall good performance of the PLA:PBS blend, this blend has a window in which an improved performance can be seen (see Table 8A).

In a preferred embodiment of the bolus of the invention the material of the housing comprises PLA:PBAT in a ratio of about 90:10 and in a preferable embodiment the housing remains stable in the environment of an animal's rumen for at least 5 months. It is even more preferred that the housing remains stable in the environment of an animal's rumen for at least 6 months.

The term "about" used herein in the context of a numerical value refers to a numerical range extending from −10% of that numerical value to +10% of that numerical value.

The housing of the bolus of the invention may be designed in a way to allow the active ingredient, i.e. the methane inhibitor, to pass through the housing and provide a sustainable controlled release. In one embodiment, the methane inhibiting agent can perfuse through the housing material of the bolus of the invention.

Methods to determine, whether a bolus housing is permeable or impervious to an active agent and the degree to which said housing is permeable or impervious to an active agent are known in the art and are also described herein, see for instance the examples section.

The housing of the bolus of the invention may be given further functional features, for example, but not limited to, by adding further components to the housing material or by modifying housing's dimensions and nature. In one embodiment the housing material of the bolus of the invention comprises one or more excipients. In a preferred embodiment the one or more excipients includes plasticizers, hardeners and/or colorants.

In one embodiment the housing has a material thickness (material thickness is the housing wall thickness) of below 2 mm and preferably a material thickness in the range of 0.3-1.5 mm. In a preferred embodiment the housing has a wall thickness of about 1.2 mm.

In one embodiment the housing is configured to degrade over a predetermined period of time. The predetermined period time may for instance be adjusted via the material thickness, i.e. the wall thickness, of the housing, the selection of housing materials or the manufacturing process of the housing. The predetermined period of time may for instance also be adjusted by the carrier components used in the bolus of the invention.

In one embodiment the housing includes a cavity in which at least a portion of the core is located. In one embodiment the housing includes an opening. In a preferred embodiment the housing includes a cap configured to close the opening. In another embodiment the housing comprises no openings and completely surrounds the core. In another embodiment the housing completely covers and surrounds the core.

In one embodiment the housing is formed from a substance having a Shore D hardness of at least 40. In another embodiment the housing is formed from a substance having a Shore D hardness of less than 70. In another embodiment the housing is formed from a substance having a Shore D hardness of less than 90. Shore D hardness may for instance be adjusted via the selection of housing materials or the manufacturing process of the housing. In one embodiment the core of the bolus of the invention comprises one or more metal particles (preferably steel particles), wherein the particles are preferably rounded and wherein the total of all particles per bolus has a mass of at least 100 g. In one embodiment the core of the bolus comprises a portion, which comprises metal particles and a filling agent. In a preferred embodiment the ratio of metal particles:filling agent is from 90:10 to 95:5. In a preferred embodiment the filling agent is a wax. In a preferred embodiment the wax is paraffin wax. In a preferred embodiment the metal particles are stainless steel particles. In a preferred embodiment the metal particles are evenly distributed throughout the filling agent. In a preferred embodiment the metal particles are stainless steel particles and the metal particles are evenly distributed throughout the filling agent. In one embodiment the core and/or carrier of the bolus of the invention has a melting point greater than 37° C. In a preferred embodiment the core and/or carrier of the bolus of the invention has a melting point greater than 42° C. In a more preferred embodiment the core and/or carrier of the bolus of the invention has a melting point greater than 45° C. These features may enable the bolus to sustain and stay intact in an animal's rumen.

In one embodiment the core of the bolus of the invention further comprises a barrier layer between at least a portion of the housing and the core to isolate the portion of the housing and the core from contact with each other. Thus, potentially undesirable interactions between housing and core materials and components can be avoided.

In one embodiment the bolus of the invention is adapted to reach a maximum release rate of approximately 0.05 g to 2 g of bromoform per day into the rumen. In a preferred embodiment release rates for bromoform include from approximately 0.1-approximately 0.5 g per day, and more preferably approximately 0.2 g per day. Such release rates may provide a sustained release of bromoform or another methane inhibitor. A bolus with such release rate is for instance suitable for use in cattle and sheep. To reach a preferred release rate, also in smaller farm animals, the concentration of the haloform or the housing material thickness, i.e. the wall thickness, may for instance be adjusted. Furthermore, to achieve a desired release rate for the inhibiting agent, the overall polarity of the carrier material may be adjusted to achieve the desired affinity for the inhibiting agent.

The release rate of a methane inhibiting agent such as a haloform and preferably bromoform from a bolus described herein can be determined as described in the examples section of the application, e.g. via in vitro testing by placing the inhibiting agent loaded bolus in a solution with conditions that simulate the rumen environment and measuring the concentration of the released methane inhibiting agent in the solution over time.

In one embodiment the bolus is adapted to release the substance over a period of at least two months. In a preferred embodiment, the bolus is adapted to release the substance over a period of at least three months. In a preferred embodiment, the bolus is adapted to release the substance over a period of at least six months, such as at least seven, eight, nine or at least ten months and more.

In a further embodiment of the invention the core of the bolus comprises the following ingredients (A) through (F) below in the indicated amounts, wherein the weight is indicated as weight percent in relation to the total weight of the core:

| Embodiment | Filler (w/w %) | Tribromomethane (w/w %) | Silicon dioxide (fumed silica) (w/w %) |
| --- | --- | --- | --- |
| A | 20 (Ethyl cellulose) | 70 | 10 |
| B | 26 (Ethyl cellulose) | 64 | 10 |
| C | 33 (Castor wax) | 65 | 2 |
| D | 20 (PCL) | 65 | 15 |
| E | 25 (ethyl cellulose) | 70 | 5 |
| F | 33 (castor wax) | 65 | 2 |

Also preferred is a bolus of the invention where the core comprises the ingredients shown in the table above selected from (A) through (F) wherein the relative amounts (shown in the table as % w/w) are comprised in the core of the bolus in a range between -20% of the indicated amount to +20% of the indicated amount.

Also preferred is a bolus of the invention where the core comprises the ingredients shown in the table above selected from (A) through (F) wherein the relative amounts (shown in the table as % w/w) are comprised in the core of the bolus in a range between -10% of the indicated amount to +10% of the indicated amount.

In a further aspect the invention provides a bolus for administration of a first and a second active agent in the rumen of a ruminant animal, wherein said bolus comprises a first segment and a second segment, wherein said first segment comprises a first core comprising said first active agent, and wherein said second segment comprises a second core comprising said second active agent, wherein said first and said second active agent may be the same or different.

Preferably, said first and second active agent is each individually selected from the group consisting of therapeutic agents, growth promotants, vaccine formulations, nutrients, agents affecting fertility and other substances promoting the physical wellbeing of the ruminant, anti-infectives, e.g., an antiviral agent such as acyclovir, idoxuridine or vidarabine; anti-bacterial agents such as penicillins, tetracyclines, erythromycin, neomycin, polymyxin 8, gentamycin, nystatin, benzylpyrimidines such as trimethoprim or baquiloprim optionally in combination with a sulphonamide such as sulphadiazine, sulphadimidine, sulphadoxine or sulphadimethoxine, or bacitracin; and anti-protozoals such as anti-coccidials, anti-parasitic agents such as anthelmintics, for example oxfendazole (i.e. 2-methoxycarbonylamino-5-phenylsulphinylbenzimidazole), oxibendazole, parbendazole, niridazole, mebendazole, fenbendazole, cambendazole, albendazole, metronidazole, thiabendazole, levamisole, tetramisole, closantel, bromoxanide, rafoxanide, clioxanide, oxyclozanide, salantel, morantel, resorantel, pyrantel, praziquantel, febantel, oxantel, carbantel, piperazine, nicolosamide, brotianide, thiophanate, bephenium, pyrvinium, diethylcarbamazine, suramin, dichlorophen, paromomycin, stibophen, antimony sodium dimercaptosuccinate, hycanthone, metrifonate, antimony barium tartrate, antimony potassium tartrate, chloroquine, emethine, bithionol, hexylresorcinol, tetrachloroethylene, mirasan, miracil, lucanthone, furapromidium, oxamniquine, tubercidin, amphotalide, nicarbazin, Hetol (Trade Name), Hetolin (Trade Name), nitroxynil, disophenol, Bitin-S(Trade Name), bromofenophos, menichlopolan, thiosalicylanilide, diamphenethide, bunamidine, bitoscanate, nitroscanate, amoscanate, diuredosan, arsenamide, thiazothienol, thiazothielite, haloxon, dithiazanide iodide, bidimazium iodide, methyridine dymanthine trichlabendazole, chlorsulan and avermectins such as ivermectin, a vitamin, sodium chloride, a sugar, for example glucose, magnesium, zinc, copper, cobalt and selenium.

In one embodiment, the first and second segment are respectively defined by a first and second housing, wherein the first and the second segment are detachable from each other.

In a further aspect the invention provides a bolus for administration to a ruminant animal comprising at least a first and a second segment, wherein said first and said second segment are each configured to release an active agent in the rumen of the ruminant animal; wherein said first segment comprises (a) a first core comprising a first active agent, and (b) a first housing which covers at least a portion of said first core; and wherein said second segment comprises (c) a second core comprising a second active agent, and (d) a second housing which covers at least a portion of said second core; wherein said first and said second active agent may be the same or different.

In one embodiment, the first and the second segment are detachable from each other. The segments are thereby preferably connected via a releasable connector. The releasable connector is preferably made from or comprises a water soluble material preferably selected from the group consisting of gelatin, collagenous materials, hydroxy propyl cellulose, cellulose derivatives, paper, agar and guar gum and mixtures of the aforementioned.

When the first and the second segment are detached from each other, e.g. due to the dissolution of a releasable connector connecting the segments, one segment will no longer be weighed down by the additional weight of the respective other segment in the rumen. Thus, it is understood that the first and the second segment may be configured to have a sufficient weight of their own to be separately retained in the rumen and not regurgitated. Alternatively, one of the segments may be configured to be separately retained in the rumen due to its own sufficient weight, while the other segment may be configured to have a lighter weight, so that the lighter segment may be regurgitated upon detachment from the heavier segment. This may allow the combination of different release rate systems provided by the different segments. For example, a lighter immediate-release bolus segment may be regurgitated after separation from a heavier delayed-release bolus segment, which is retained in the rumen due to its greater weight. The weight of the respective segment may for instance be adapted by varying the amount of metal particles comprised in the respective bolus segment.

In one embodiment, the first and the second active agent are the same active agent. In a preferred embodiment, the first and the second active agent is each a methane inhibiting agent. In a more preferred embodiment, the active agent is a haloform. In an even more preferred embodiment, the active agent is bromoform.

In one embodiment, the active agent is a haloform, preferably bromoform, and each of the first and the second core comprises the respective active agent in an amount of between 30 wt % to 80 wt % related to the total weight of the respective core. In a preferred embodiment, the active agent is a haloform, preferably bromoform, and each of the first and the second core comprises the respective active agent in an amount of between 30 wt % and 70 wt %. In a preferred embodiment, the active agent is a haloform, preferably bromoform, and each of the first and the second core comprises the respective active agent in an amount of between 50 and 70 wt %. In a preferred embodiment, each of the first and the second core comprises the haloform in a different amount.

In one embodiment, the first core and/or second core comprises one or more compounds of hydrophobic fumed silica and/or a wax and/or a polyol and/or a polyester; wherein the wax is preferably a compound selected from the group consisting of myristic acid, stearic acid, steryl alcohol, cetyl alcohol, cetosteryl alcohol, castor wax, bee's wax, paraffin wax, PEG4000, Carnauba, Candellila, Jojoba, Lanolin, and a combination thereof, preferably castor wax; and wherein the polyol is preferably a compound selected from the group consisting of polyols, preferably cellulose derivates, more preferably ethyl cellulose and/or hydroxypropyl methylcellulose (HPMC); and wherein the polyester is preferably Poly(&-caprolactone) (PCL). In one embodiment, the first core and/or second core comprises ethyl cellulose and/or HPMC. In a preferred embodiment the first core and/or second core comprises ethyl cellulose and HPMC. In a preferred embodiment HPMC is HPMC K-100. In one embodiment the first core and/or second core comprises ethyl cellulose, HPMC and/or fumed silica. In one embodiment, the first core comprises at least one compound selected from the group consisting of PCL, ethyl cellulose and HPMC and the second core comprises at least one compound selected from the group consisting of hydrophobic fumed silica and waxes, such as myristic acid, stearic acid, steryl alcohol, cetyl alcohol, cetosteryl alcohol, castor wax, bee's wax, paraffin wax, PEG4000, Carnauba, Candellila, Jojoba, Lanolin, castor wax and a combination thereof. In a preferred embodiment, the second core comprises castor wax.

In a preferred embodiment of the bolus of the invention which comprises at least two cores, the first core comprises a carrier composition as defined herein.

In one embodiment, the first housing comprises at least one compound selected from the group consisting of PLA, PCL, talc and PDLA, and the second housing comprises at least one compound of PLA, PBAT or PBS, preferably in a ratio as for instance defined in table 8.A, or at least one compound selected from the group consisting of PBAT, PBSA, PBS and PVA.

In one embodiment, each of the first and the second segments has a length of between 50 and 100 mm. In a preferred embodiment each of the first and the second segments has a length of about 72 mm. It is preferred that one segment, i.e. a half size cylindrical bolus, has dimensions of about 72 mm (length)×35 mm (diameter). In one embodiment, each of the first and the second segments has a cylindrical shape.

In one embodiment, each of the first and the second segments is encapsulated by its own housing. In one embodiment, the housing of each of the first and the second segment has a wall thickness of below 2 mm. In a preferred embodiment, the housing of each of the first and the second segment has a wall thickness in the range of 0.3-1.5 mm. In an even more preferred embodiment the wall thickness is about 1.2 mm.

In one embodiment, the first and second segment are attached to each other. In a preferred embodiment, the first and second segment are attached to each other via an attachment. In a more preferred embodiment, the attachment is selected from the group consisting of an adhesive, a string, a tape and a pluggable connector. In a preferred embodiment, the attachment is dissolvable in the animal's rumen and/or comprises a compound that is dissolvable in water. As described herein further above, the attachment may also be a releasable connector.

Testing whether an attachment between a first and a second bolus segment is dissolvable in the animal's rumen can be performed for instance via in vitro testing by placing two attached bolus segments in an aqueous solution having a temperature of 40° C., a pH of 7 and optionally comprising a rumen enzyme such as a protease, lipase and/or a cellulose and then determining whether the two segments become detached from each other in the solution within 24 hours of exposure to the solution. Optionally, the solution containing the attached bolus segments can be agitated to simulate agitation in the rumen.

In one embodiment, the first and/or second segment comprise one or more metal particles. In a preferred embodiment the metal particles are steel particles.

In a further aspect the invention provides a bolus for administration to a ruminant animal, wherein said bolus is configured to release an active agent in the rumen of the animal, wherein said bolus comprises a first and a second core, wherein the first core is enclosed within the second core.

In one embodiment, the first core comprises a first active agent and the second core comprises a second active agent. In one embodiment, the bolus comprises a third core which is located in the second core and wherein the third core comprises a third active agent.

In one embodiment the first, the second and the third active agent are the same active agent, preferably wherein said active agent is a haloform, more preferably bromoform. In on embodiment the active agent is comprised within the first and second core in different concentrations.

In one embodiment, each core comprises a carrier compound selected from the group consisting of hydrophobic fumed silica, a wax, a polyol, a polyester or a mixture comprising one or more of the aforementioned compounds; wherein the wax is preferably a compound selected from the group consisting of myristic acid, stearic acid, steryl alcohol, cetyl alcohol, cetosteryl alcohol, castor wax, bee's wax, paraffin wax, PEG4000, Carnauba, Candellila, Jojoba, Lanolin, and a combination thereof, preferably castor wax; and wherein the polyol is preferably a compound selected from the group consisting of polyols, preferably cellulose derivates, more preferably ethyl cellulose and/or hydroxypropyl methylcellulose (HPMC); and wherein the polyester is preferably Poly(ε-caprolactone) (PCL). In one embodiment, the first core and/or second core comprises ethyl cellulose and/or HPMC. In a preferred embodiment the first core and/or second core comprises ethyl cellulose and HPMC. In a preferred embodiment HPMC is HPMC K-100. In one embodiment the first core and/or second core comprises ethyl cellulose, HPMC and/or fumed silica. In one embodiment, the first core comprises at least one compound selected from the group consisting of PCL, ethyl cellulose and HPMC and the second core comprises at least one compound selected from the group consisting of hydrophobic fumed silica and waxes, such as myristic acid, stearic acid, steryl alcohol, cetyl alcohol, cetosteryl alcohol, castor wax, bee's wax, paraffin wax, PEG4000, Carnauba, Candellila, Jojoba, Lanolin, castor wax and a combination thereof. In a preferred embodiment, the second core comprises castor wax. In a preferred embodiment, the first core comprises PCL and/or the second core comprises ethyl cellulose.

In a further embodiment the bolus of the invention is coated with a material that is impervious to a haloform and preferably to bromoform, and the coating has a thickness that allows the coating to become permeable for said haloform when exposed to the abrasive forces within the rumen of a living animal.

Whether a bolus housing is permeable or impervious to an active agent or how permeable or impervious said housing is to an active agent, i.e. whether and how much of an active agent is able to perfuse out of a bolus, and in some instances through the housing of a bolus, can be determined by methods well known in the art and by methods as disclosed herein (see for instance examples section). For instance, the degree of permeability or imperviousness of a bolus housing can be determined by measuring the rate of release of a methane inhibiting agent from a bolus through its housing and by measuring the resulting concentration of said methane inhibiting agent in the surrounding media. This measurement method is particularly applicable for boluses, which are completely surrounded by a housing and/or a coating, i.e. allow the methane inhibiting agent to be released only through said housing and after at least partial removal of said coating.

In one embodiment, the coating comprises at least one compound selected from the group consisting of hydrophobic polymers, methyl cellulose, PLA, silicates, metal coatings, wax or gelatin, starch, collagen and chitosan. In one embodiment, the coating has a thickness of from 50 to 250 μm. In one embodiment, the coating is partially or completely removable in the rumen within a time period of less than 12 hours after administration to the animal. In a preferred embodiment the coating is partially or completely removable in the rumen within a time period of less than 6 hours after administration to the animal. In an even more preferred embodiment the coating is partially or completely removable in the rumen within a time period of less than 1 hour after administration to the animal.

In a further aspect the invention provides a method for administering a methane inhibitor to an animal, the method comprising the step of administering to said animal the bolus of the invention. In a further aspect the invention provides a method for reducing methane production in the rumen of a ruminant animal, the method comprising the step of administering to said ruminant animal the bolus of the invention. In a preferred embodiment the bolus is administered orally. In another preferred embodiment the bolus is configured to remain in the rumen after administration.

In a further aspect the invention provides a bolus of the invention for use in the treatment of an animal and preferably of a ruminant animal and most preferably of cattle or sheep. In a further aspect the invention provides a bolus of the invention for use in reducing methane emission in a ruminant animal and most preferably in cattle or sheep. In one embodiment the ruminant animal may also be a goat or deer. In one embodiment methane emission in a ruminant animal may for be reduced by at least 30%, preferably by as at least 50%, more preferably by at least 70%, 80% most preferably by at least 90%. In another embodiment methane emission in a ruminant animal may be reduced at least 99%.

In yet another aspect the invention provides a method of manufacturing a bolus, comprising the steps:
(1) providing a housing made of a polymer material, preferably a biodegradable polymer and most preferably a housing of the invention as disclosed herein; and
(2) filling a core, preferably as disclosed herein into said housing;
wherein the bolus comprises: a core, wherein the core comprises a methane inhibiting agent that inhibits the production of methane in the rumen of a ruminant animal and a carrier and a housing which houses the core.

Providing the housing in step (1) may for instance and without limitation be performed by 3D printing or injection molding. Filling a core into said housing in step (2) may for instance and without limitation be performed by melting and/or mixing the core materials and filling the core material components or mixtures into the housing while the components are flowable or at least flexible or malleable.

In a preferred embodiment the method of manufacturing a bolus further comprises the step (3) closing the housing that contains the core with a cap, wherein the housing is closed with the cap by friction-welding the cap to the housing. Unexpectedly, other means of closing the housing, such as screwing the cap onto the housing or gluing the cap to the housing provided a less durable bolus forms. A screw-cap could become lose or be pushed out of the housing when the bolus is exposed to the mechanical stress and turbulent motion in the rumen of an animal. Also, field tests showed that a glued cap became detached from the housing because the haloform released from the core may tend to dissolve the glue upon contact over time. In a preferred embodiment, the housing is provided in step (1) by injection molding. In one embodiment the method of manufacturing a bolus further comprises a step (4) which is carried out prior to step (3), wherein in step (4) said housing and/or said core is exposed to a reduced pressure in order to reduce the amount of gas remaining inside of the bolus after closing the housing in step (3). In one embodiment, the closed bolus comprises less than about 1 cm³ of gases at 20° C. at atmospheric pressure. Advantageously, the bolus assembly method may provide the benefit of reducing overall buoyancy of the bolus, which may improve the bolus' retention in the rumen of the animal.

In a further aspect the invention provides a bolus obtainable or obtained by carrying out a method of the invention of manufacturing a bolus.

In a further aspect the invention provides a methane inhibitor for use in the reduction of methane production in a ruminant animal, wherein the methane inhibitor is administered to the animal in an amount of from 30 to 300 mg per day. In a preferred embodiment, the methane inhibitor is administered to the animal in an amount of from 104 to 260 mg per day. In an even more preferred embodiment, the methane inhibitor is administered to the animal in an amount of from 150 to 220 mg per day. In a further preferred embodiment, the methane inhibitor is administered to the animal in an amount of from an amount of about 208 mg per day.

In a further aspect the invention provides a methane inhibitor for use in the reduction of methane production in a ruminant animal, wherein the methane inhibitor is administered to the animal in an amount of at least 0.20 mg per kg animal weight per day. In a preferred embodiment, the methane inhibitor is administered to the animal in an amount of at least 0.30 mg per kg animal weight per day. In a preferred embodiment, the methane inhibitor is administered to the animal in an amount of between 0.30 and 0.70 mg per kg animal weight per day. In an even more preferred embodiment, the methane inhibitor is administered to the animal in an amount of at least 0.55 mg per kg animal weight per day. In view of the doses and dose ranges disclosed herein, it is understood that the lowest doses, such as starting from about 30 mg per day or from at least 0.2 mg per kg animal weight per day, are suitable for administration to small and/or immature animals, since these animals have a lower body weight, a lower feed conversion rate and lower methane production and emission rates.

In particular, experimental results presented herein (see for instance Table 19) confirmed that a minimum amount to be administered to a ruminant to completely mitigate methane emissions is achievable by administering to an average sized large ruminant (i.e. having a weight of about 350-400 kg) an amount of at least about 200 mg/d on average over at least about 10 to 22 days. However, an effective dose is already achieved at about 104-156 mg per—for example— 378 kg cow per day, which corresponds to a dose of 0.28-0.4 mg/kg/d.

In one embodiment, the rumen of the ruminant animal is exposed to the methane inhibitor over a time period of at least 10 days. In a preferred embodiment, the rumen of the ruminant animal is exposed to the methane inhibitor over a time period of at least 20 days. In an even more preferred embodiment, the rumen of the ruminant animal is exposed to the methane inhibitor over a time period of at least 1 month. In an even more preferred embodiment, the rumen of the ruminant animal is exposed to the methane inhibitor over a time period of at least 3 months. In another preferred embodiment, the rumen of the ruminant animal is exposed to the methane inhibitor over a time period of at least 6 months.

In one embodiment, the methane inhibitor is a haloform, preferably wherein the haloform is bromoform. In one embodiment, the animal is cattle.

In one aspect the invention provides a method of treating an animal comprising administering to said animal a bolus as defined herein to said animal. In a preferred embodiment said animal is a ruminant animal. In an even more preferred embodiment said animal is cattle.

In a particularly preferred embodiment, the invention provides a bolus for administration to a ruminant animal, wherein said bolus is configured to release a methane inhibiting agent in the animal, wherein said bolus comprises:
 (i) a core, wherein the core comprises the methane inhibiting agent, wherein the methane inhibiting agent is bromoform, preferably wherein bromoform is comprised in the core in an amount of about 60 wt %, and wherein the core comprises ethyl cellulose and HPMC, preferably wherein the weight ratio of ethyl cellulose: HPMC is about 50:50, optionally wherein the core comprises hydrophobic fumed silica; and
 (ii) a housing which fully covers the core, wherein the material of the housing comprises poly lactic acid (PLA) and polybutylene adipate terephthalate (PBAT), preferably wherein the PLA:PBAT weight ratio is about 90:10, preferably wherein the housing has a wall thickness of about 1.2 mm; and
 (iii) a portion comprising paraffin wax and stainless steel particles, for instance grade 304 or 316 stainless steel particles, preferably wherein the weight ratio of paraffin wax:steel particles is from 15:85 to 5:95, more preferably wherein the weight ratio is about 8:92, and preferably wherein the stainless steel particles are evenly dispersed in the paraffin wax,
 wherein the bolus preferably has a length of about 72 mm and a diameter of about 35 mm, and preferably wherein the bolus is configured to release the methane inhibiting agent at a rate of between 50 and 250 mg per day, more preferably at a rate of between 100 and 200 mg per day, optionally wherein the bolus comprises means for identification, preferably a chip for Radio Frequency Identification (RFID).

In a further embodiment of the bolus of the invention the methane inhibiting agent may also be a bromoform containing algae extract.

The following embodiments can also be used for the aspects of the invention:

According to one embodiment, there is provided a bolus configured for administration to an animal, wherein said bolus is configured to release a hydrophobic substance to the animal over a period of time.

According to one embodiment, there is provided a bolus for administration to a ruminant animal, wherein said bolus is configured to release an effective amount of the substance, wherein the substance is preferably at least one inhibiting agent.

According to a further embodiment, there is provided a method for reducing emission of gas (preferably methane) from a ruminant animal, the method comprising the step of administering to said ruminant animal a bolus comprising at least one inhibiting agent.

According to another embodiment, there is provided a use of a methane inhibitor and a carrier in a bolus for reducing methane production in a ruminant animal.

According to another embodiment, there is provided a use of a methane inhibitor and a carrier in a bolus for reducing methane emission from a ruminant animal.

According to another embodiment, there is provided a use of a haloform in the manufacture of a bolus for reducing the emission of one or more greenhouse gases ("GHGs") from a ruminant animal.

In a preferred embodiment, the bolus may be configured to be administered to a ruminant, the ruminant may include beef or dairy cows, sheep, goats, buffalo, deer, elk, giraffes or camels.

In one embodiment, the bolus may be adapted to reduce the release of one or more greenhouse gases ("GHGs") from the ruminant.

In another embodiment, the bolus may be a slow-release bolus, configured to release the at least one inhibiting agent in the ruminant animal over a period of time e.g. in the animal's rumen.

According to a further aspect, there is provided a bolus for administration to a ruminant animal, wherein the bolus comprises:
- a core, wherein the core includes at least one substance to be administered to the ruminant animal mixed with a carrier; and
- a housing which covers at least a portion of the core;
- wherein, the bolus is configured to release the substance through the housing over a period of time.

In another embodiment, there is provided a bolus comprising
- a core which contains a substance to be administered to an animal, and
- a housing which at least partially covers a portion of the core;
- wherein the housing is formed from at least one polylactic acid (PLA).

In a further embodiment, there is provided a bolus comprising
- a core,
- wherein the core comprises a mixture of at least one wax and a haloform.

The inventors have surprisingly found that the technology described herein may provide a number of benefits. These benefits may be the result of the unique synergistic interactions between different aspects of the technology. The technology of the present invention is therefore described based on the inventor's current understanding of these interactions. It should be appreciated any aspect described herein, or the interaction of two or more aspects, may form a distinct invention.

Throughout the present specification reference will be made to the term "substance" or "substance to be administered to an animal". This should be understood as meaning any substance which provides benefits to the animal e.g. a drug for treatment or prevention of disease, which improves animal productivity, or mitigates at least one adverse effect of agriculture.

In preferred embodiments, the substance may be hydrophobic substance.

In particularly preferred embodiments the hydrophobic substance may be an inhibiting agent. Reference will be made herein to the substance as an inhibiting agent. However, this should not be seen as limiting on the scope of the present invention and alternatives are envisaged for the e.g. it may be a hydrophilic substance.

In an embodiment, the at least one inhibiting agent may be a methane inhibitor. The use of a methane inhibitor may provide a number of advantages. For instance, a methane inhibitor will reduce, or eliminate, production of methane by the ruminant e.g. in the rumen. As a result, there is less methane in the rumen which could be emitted by the ruminant and therefore emission of GHGs are effectively reduced.

In addition, reducing production of methane may provide animal production benefits. For instance, reduction of methane ensures that relatively more of the feed ingested is available for digestion and conversion into protein (either milk or meat). As a result, farmers may be able to improve efficiency by either securing greater productivity for a given feed volume or reduce feed accordingly.

In an embodiment, the methane inhibitor may be a haloform.

In a preferred embodiment, the methane inhibitor may be selected from the list of chloroform, bromoform, iodoform, or combinations thereof.

In a particularly preferred form, the haloform may be bromoform ($CHBr_3$). The use of bromoform may provide a number of advantages. For instance, it has a high efficacy for a relatively small dose, which enables one device to deliver sufficient amounts of the inhibiting agent over an extended period of time. In addition, bromoform also has a relatively high density which adds to the overall weight of the bolus and allows for the bolus to be retained in the rumen i.e. it sinks to the ventral part of the rumen rather than floats reducing regurgitation.

However, despite these advantages the inventors have faced a number of challenges and problems to developing a bolus for the controlled release of a haloform, particularly bromoform, to a ruminant.

In a further embodiment, the bolus may comprise a core. The core may be formed by the inhibiting agent mixed with a carrier.

However, in alternative embodiments, the inhibiting agent may be provided in a substantially pure form e.g. is not mixed with a carrier.

In embodiments, the carrier may have a structure which promotes or facilitates affinity for the carrier by the inhibiting agent. For instance, the carrier may have polar functional groups.

In embodiments, the carrier may be a relatively polar substance e.g. it has a relatively high % w/w of polar functional groups. The inventors have surprisingly found that the carrier and the inhibiting agent can interact with each other, and the interaction can affect the release rate of the inhibiting agent from the bolus. This embodiment should become clearer from the following description.

Examples of suitable functional groups for the carrier to include are ester, fatty acids, fatty alcohols, carbonyls and fatty amines. Without being limited to a specific mechanism, the inventors believe that the inhibiting agents may interact with polar functional groups in waxes, potentially via creation of hydrogen bonds. The amount of polar functional groups present in the carrier will affect the affinity of the carrier and the inhibiting agent for each other.

The inventors have found that a range of substances may be suitable for use as a carrier in the present invention. For instance, the carrier may be selected from the list of waxes, myristic acid, stearic acid, steryl alcohol, cetyl alcohol, cetosteryl alcohol or a combination thereof.

In a particularly preferred embodiment, the carrier may be a waxy substance. For example, the carrier may be selected from the list of bee's wax, paraffin wax, PEG4000, Carnauba, castor wax, Candellila, Jojoba, or Lanolin or a combination thereof.

In a particularly preferred embodiment, the carrier may comprise paraffin wax and castor wax.

In a particularly preferred embodiment, the carrier may comprise paraffin wax and castor wax in a ratio of about 50:50 (parts by weight).

In another embodiment, the carrier may comprise a mixture of two or more components. For example, the carrier may comprise a mixture of at least one relatively polar substance with a relatively non-polar substance. For instance, in some forms the carrier may include a mixture of paraffin wax (a mixture of alkanes with no polar functional groups) and castor wax and/or carnauba wax (which have a relatively high amount of polar functional groups). As a result, the overall polarity of the carrier may be adjusted to achieve the desired affinity for the inhibiting agent. This can be used to achieve a desired release rate for the inhibiting agent.

Additionally, to the above, solid carriers such as powdered activated carbon, zeolite or bentonite may also be used as a carrier. Accordingly, the discussion herein should not be seen as limiting on the scope of the present invention.

In a further embodiment, the carrier may also include one or more additional components. For example, additional components such as elemental zinc or zinc oxide may be incorporated. Preferably, a high-density material, such as a piece of metal (preferably steel) may be comprised in the carrier. The additional components may be used to achieve a desired density for the core and/or bolus.

It should also be understood that additional components may be added to a cavity of the bolus separate to, and not mixed with, the carrier. This may be particularly beneficial to form a core having a desired release profile, where the density of the bolus can be adjusted to a desired amount by including the additional components.

Other suitable additives for incorporation into the carrier may also include colloidal silicon dioxide, charcoal, bentonite and zeolite(s).

Further aspects of the carrier and its effect on the release of the inhibiting agent from the bolus, together with the interaction of the carrier and housing, should become clearer from the following description.

In a preferred embodiment, the carrier may have a melting point between substantially 50-90° C.

In a particularly preferred embodiment, the carrier has a melting point which is less than the boiling point of the inhibiting agent. This may be useful as the carrier can be melted and mixed with the inhibiting agent without substantial loss of the inhibiting agent due to evaporation.

In a preferred embodiment, the core may have a melting point greater than 37° C.

In a particularly preferred embodiment, the core may have a melting point greater than 40° C.

The melting point of the core may be beneficial to the function of the present technology in several ways. For instance, having a melting point above 37° C., and more preferably 40° C., can assist the carrier in stabilising the inhibiting agent when the bolus is in the rumen. This could be beneficial to control release of the inhibiting agent e.g. movement of the inhibiting agent through the material forming the housing.

In an embodiment, the bolus may be adapted to reach a maximum release rate of approximately 0.05 g to 2 g of bromoform per day into the rumen.

In an embodiment, the bolus may be adapted to release bromoform in an amount of between 0.02 g and 0.5 g per day into the rumen.

In a particularly preferred embodiment, the bolus may be adapted to reach a maximum release rate of approximately 0.1 to 0.5 g of bromoform per day into the rumen.

In a preferred embodiment, the bolus is configured to release bromoform in the amount of between 0.02 g and 0.3 g per day into the rumen.

In an embodiment, the core of the bolus may comprise the haloform, preferably bromoform, in an amount of 30% (by weight) to 80% (by weight), preferably in an amount of 55% (by weight) to 75% (by weight), more preferably in an amount of 50% (by weight).

In a particularly preferred embodiment, the core comprises the haloform, preferably bromoform, in a concentration of no more than 55% (by weight).

The inventors have found that the rate of release of the inhibiting agent into the rumen increases overtime. This may be the result of several factors. Therefore, the rate of release starts from zero on administration of the animal and increases to a maximum. However, the foregoing should not be seen as limiting, and other release rates are envisaged as within the scope of the present invention.

In a further embodiment, the bolus may include a housing.

Throughout the present specification, reference to the term "housing" should be understood as meaning a structure which can receive and hold a core containing the at least one inhibiting agent.

In preferred embodiments, the housing comprises a body which has a cavity in which a core is located.

However, it should also be understood that the housing may take other forms. For instance, the housing may include two or more cavities which can each receive and hold a separate core.

In one embodiment, the housing may include an open end.

The bolus may be used with an open end e.g. administered to an animal with the end open. As a result, in these embodiments the open end provides an opening to in use expose the contents of the core to fluids in the rumen.

In yet a further and preferred embodiment, the housing may completely cover and surround the core e.g. it has a sealed cavity in which the core is located.

For instance, the bolus may include a housing with a cavity in which at least a portion of the core can be located, and an open end to facilitate insertion of the core into the cavity. A cap can be used to cover the open end.

The cap may be formed separately of the housing and releasably or permanently secured thereto. Alternatively, the cap may be formed integrally to the housing.

In yet a further embodiment, the housing may be provided in at least two-parts, each of which has a cavity to receive a respective portion of the core. Together the at least two parts completely surround the core and define a closed and sealed cavity in which the core is located.

In yet further embodiments, the housing may be formed around the core e.g. by moulding. Alternatively, the housing and cap may together define a substantially closed and sealed cavity in which the core is located.

The inventors believe that the provision of a substantially or completely closed and sealed cavity is preferred because it can assist in achieving a desired controlled release of the inhibiting agent from the bolus of the present invention. For instance, in such an embodiment, the inhibiting agent can pass through the material forming the housing e.g. by mass diffusion.

In embodiments, the housing may be configured to have sufficient structural integrity to remain intact for a predetermined period of time.

In a preferred embodiment, the housing may be configured to degrade over a predetermined period of time.

Throughout the present specification, reference to the term "predetermined period of time" should be understood as meaning the period of time over which the inhibiting agent is to be released to the animal.

In a particularly preferred embodiment, the predetermined period of time may be at least two months, preferably six months, and more preferably 12 months.

The inventors have surprisingly found that housings of the present invention may assist with the controlled release of the inhibiting agent. For instance, the housing is able to withstand the conditions in the rumen for the predetermined period of time. During this time, the housing protects the core from fluid in the rumen, yet can facilitate or contribute to the controlled release of the inhibiting agent. However, the design of the housing may allow the housing to disintegrate or degrade over the predetermined period of time. This can contribute to mitigating adverse effects of device administration to an animal, and could also ensure that an animal can be treated with multiple bolus e.g. a second bolus is administered at or towards, or after, the end of the predetermined period of time.

In embodiments of the invention, the thickness of the housing may be selected to contribute to the rate of release of the inhibiting agent. For instance, the inventors have identified that thickness of the housing can affect the rate of release of the inhibiting agent from the bolus. In these embodiments, a relatively thicker housing will have a relatively slower release rate than a relatively thinner housing.

In a preferred embodiment, the housing may have a thickness of at least 1 mm.

In yet a further preferred embodiment, the housing may have a thickness of less than 3 mm.

In yet another preferred embodiment, the housing may have a thickness of between 1.5 to 2 mm, or between 0.5 to 2 mm.

In a particularly preferred embodiment, the housing has a thickness of 1 mm.

Adapting the thickness of the housing may be particularly useful for achieving a desired controlled release for the inhibiting agent in embodiments such as those where the core is entirely encapsulated by the housing. This should become clearer from the following discussion.

In an embodiment, the dimensions of the cavity may vary along the length of the housing.

In a preferred embodiment, the cavity includes at least two regions which have a different cross-sectional area to each other e.g. a first region having a first cross-sectional area and a second area having a second cross-sectional area.

In a particularly preferred embodiment, the first region has a relatively smaller cross-sectional area and the second region has a relatively larger cross-sectional area.

In yet a further preferred embodiment, the first region may be located closer to the open end than the second region.

Having a cavity with regions having different cross-sectional areas to each other may facilitate more controlled release of the inhibiting agent(s) to better meet an animal's requirements. For instance, a relatively smaller across-sectional area can be provided closer to the open end to deliver a relatively smaller dose of the inhibiting agent(s), whereas the relatively larger cross-sectional area may be provided closer to the distal end; this may be useful where the dose of the inhibiting agent advantageously increases over time e.g. to match animal growth.

It should also be understood that the reverse arrangement may be provided e.g. the relatively larger cross-sectional area is provided closer to the open end and the relatively smaller cross-sectional area may be provided closer to the distal end. This arrangement may be useful where an initially higher dose of the inhibiting agent(s) is desired, to be followed by a subsequently smaller dose at a subsequent time. For instance, this arrangement may be used where an animal has a high demand for the inhibiting agent e.g. at periods of relatively high feed intake and energy requirements such as during milking but to be followed by a period of relatively low feed intake e.g. during the dry-period.

Furthermore, it should be understood that the cross-sectional area of the cavity may increase gradually and continuously from the first region to the second region e.g. there is no defined "step" between the first region and the second region.

In other embodiments, the housing may include a third region having a third-cross sectional area. This may be further used to control the dose of the inhibiting agent(s) to the animal. Accordingly, the foregoing should not be seen as limiting on the scope of the present technology.

In an embodiment, the thickness of a wall of the housing may vary along the length of the housing. In such an embodiment, the wall thickness at or towards one end of the housing may be thicker than at the distal end. For example, the thickness of the wall at or towards the open end may be thinner in size than that of the distal end.

This arrangement may be particularly beneficial in assisting to control release of the inhibiting agent(s) over time. For instance, the relatively thinner wall(s) will degrade relatively quicker than the relatively thicker wall(s). This structure can be used to control the rate of degradation of the housing along its length. For instance, it may be used to ensure that the open end is the only site at which fluids in the rumen are able to come into contact with, and erode, the core.

In preferred embodiments, the housing made be made from a material through which the inhibiting agent can migrate in use e.g. by a mass diffusion process.

In a preferred embodiment, the housing may be made from at least one plastic material. For instance, the housing may be made from a degradable plastic or material that degrades over time in the rumen.

In a particularly preferred embodiment the housing may be made from a material selected from the list of one or more of poly lactic acid (PLA), poly glycolic acid (PGA), poly lactic glycolic acid (PLGA), polypropylene, Polycaprolactone (PCL), poly(d-lactic acid) (PDLA), Polybutylene succinate (PBS), Polybutylene adipate terephthalate (PBAT), SLA polymer, ABS, or a combination thereof. In a particularly preferred embodiment, the housing comprises PLA and PBS.

The material for the housing may comprise PLA, PBAT and/or PBS in different ratios as shown in examples 1 through 7 in the table below (% by weight):

|   | PLA (w %) | PBS (w %) | PBAT (w %) |
|---|---|---|---|
| 1 | 100 | | |
| 2 | 70 | 30 | |
| 3 | 40 | 60 | |
| 4 | 20 | 80 | |
| 5 | 70 | | 30 |
| 6 | 40 | | 60 |
| 7 | 20 | | 80 |

In a particularly preferred embodiment, the material for the housing comprises PLA and PBS in a weight ratio ranging from 100:0 to 40:60 PLA:PBS.

In a particularly preferred embodiment, the housing comprises PLA and PBS in a weight ratio ranging from 100:0 to 40:60 PLA:PBS, wherein the housing has a thickness of between 0.4 and 1.5 mm.

In another particularly preferred embodiment, the material for the housing comprises PLA and PBAT in a weight ratio ranging from 95:5 to 80:20 PLA:PBAT.

In a particularly preferred embodiment, the housing comprises PLA and PBAT in a weight ratio ranging from 95:5 to 80:20 PLA:PBAT, wherein the housing has a thickness of between 0.4 and 1.5 mm.

In another particularly preferred embodiment, the material for the housing comprises PLA and PBSA in a weight ratio ranging from 95:5 to 70:30 PLA:PBSA.

In a particularly preferred embodiment, the housing comprises PLA and PBSA in a weight ratio ranging from 95:5 to 70:30 PLA:PBSA, wherein the housing has a thickness of between 0.4 and 1.5 mm.

It has been observed that the housing materials used for the boli described herein provide advantageous release characteristics of the inhibiting agent from the described boli: When a bolus and particularly its housing are exposed to the rumen environment, thereby being heated to rumen temperature, i.e. above 35° C., and wetted by rumen fluids, the bolus housing becomes more permeable to the inhibiting agent, particularly to a haloform such as bromoform, which thus increases the release rate of the haloform from the bolus. In contrast, prior to administration when the bolus is situated outside of the rumen environment, i.e. in a dry state and at room temperature, the bolus housing more effectively retains the haloform, particularly bromoform, within the bolus and less haloform is released from the bolus. This was particularly observed for the methane inhibiting agent bromoform in a bolus comprising a housing material that comprises both PLA and PBAT. In a further embodiment the core of the bolus of the invention is covered by multiple housings which are arranged concentrically (e.g. akin to an onion). Such multiple housings (e.g. 2 or 3 or even more housings) have the advantage that the bolus will be degraded (e.g. by abrasion) in the rumen less quickly. As a consequence, the haloform in the core will last longer in the rumen and methane production is reduced for a longer time. In embodiments comprising multiple housings the material and thickness of the housing can be as described herein for other embodiments. In preferred embodiments a bolus of the invention comprises at least two housing layers, one outer housing and one inner housing, the material of each housing comprising a biodegradable polymer and preferably a biodegradable polymer selected from the group consisting of polylactic acid (PLA), polybutylene succinate (PBS), polybutylene adipate terephthalate (PBAT) and combinations thereof.

In addition, the housing may also be made from a non-biodegradable material, such as EVA, silicons, acrylates etc. As a result, the discussion herein should not be seen as limiting on the scope of the present invention.

In addition, the material from which the housing is made may include one or more other compounds e.g. plasticisers, hardeners, colourants etc.

However, in alternate embodiments, the housing may be made from one or more non-adsorbent materials i.e. a material into which, or through which, the inhibiting agent does not migrate. Using a non-absorbent material for the housing can assist with controlling the rate of release of the inhibiting agent(s) in certain embodiments such as an open-ended bolus. For instance, in these embodiments, the concentration of the inhibiting agent(s) in the core is not decreased by their absorption into the housing material.

In some embodiments, the bolus may include a barrier layer. In these embodiments, the barrier layer may be positioned between at least a portion of the core and the housing. For instance, the barrier layer can minimise, or completely prevent, contact between the portion of the core and the housing. This can be useful to prevent dissolution of the inhibiting agent (or other compounds) to better control the release of the inhibiting agent(s) and improve the stability of the device. This could be particularly useful where the inhibiting agent(s) has a high solubility in the material(s) from which the housing is made.

Alternatively, in an embodiment where the barrier layer is provided between only a portion of the core and the housing, it may reduce but not completely prevent, migration of the inhibiting agent into the housing. In effect, the barrier layer reduces the contact area between the core and the housing and so therefore may reduce the release rate of inhibiting agent than were the barrier layer not provided.

Alternatively, the bolus may not include a barrier layer. This configuration may be useful where the inhibiting agent(s) has a relatively low solubility in the material from which the housing is constructed. It may also be useful where the composition of the housing and/or carrier are selected to control the release rate e.g. the rate of diffusion of the inhibiting agent through the housing.

In another embodiment, the bolus may be adapted to have rates of dissolution of the core and the housing which provide substantially uniform dissolution of both components in the rumen over time.

In one embodiment, the cavity in the housing may provide a reservoir configured to receive an amount of the inhibiting agent(s). For instance, the reservoir may be a closed cavity in the housing which can receive and hold the amount of the inhibiting agent.

In one embodiment, the bolus may include a dispensing mechanism.

In one embodiment, the carrier may have a relatively higher affinity for the inhibiting agent compared to the affinity of the housing for the inhibiting agent. As discussed elsewhere in this document, this may be achieved by the relative polarity of the substances forming the carrier and the housing, and matching these materials appropriately to the inhibiting agent.

In another embodiment, the housing may be formed from a substance having a Shore D hardness of at least 40. In such an embodiment, it is believed that having a housing with a lower Shore D hardness of 40 to result in a bolus that is soft, which could hinder administration of the bolus to an animal or lead to it being otherwise damaged or prematurely degraded before the full amount of inhibiting agent is administered.

In a further embodiment, the housing may be formed from a substance having a Shore D hardness of less than 80.

In another embodiment, the housing may be configured to facilitate the controlled release the inhibiting agent from the core. Without being limited to a specific mechanism, the inventors postulate that the inhibiting agent may be released through the housing by the mechanism of mass diffusion.

In a further embodiment, the invention provides a bolus for administration to a ruminant animal, wherein said bolus comprises:
  a core, wherein the core comprises a haloform (preferably bromoform) mixed with a carrier; and
  a housing which covers at least a portion of the core or preferably the entire core; wherein, the bolus is configured to release the haloform.

In a further embodiment, the invention provides a bolus for administration to a ruminant animal, wherein said bolus comprises:
  a core, wherein the core comprises a haloform (preferably bromoform) mixed with a carrier; and
  a housing which covers at least a portion of the core or the entire core;

wherein, the bolus is configured to release the haloform; and wherein the carrier comprises wax, preferably castor wax, paraffin wax or a mixture thereof.

In a further embodiment, the invention provides a bolus for administration to a ruminant animal, wherein said bolus comprises:
a core, wherein the core comprises a haloform (preferably bromoform) mixed with a carrier; and
a housing which covers at least a portion of the core or preferably the entire core; wherein, the bolus is configured to release the haloform; and wherein the carrier comprises wax, preferably castor wax, paraffin wax or a mixture thereof; and wherein the housing comprises a biodegradable polymer and preferably a biodegradable polymer selected from the group consisting of polylactic acid (PLA), polybutylene succinate (PBS), polybutylene adipate terephthalate (PBAT) and combinations thereof.

In a further embodiment, the invention provides a bolus for administration to a ruminant animal, wherein said bolus comprises:
a core, wherein the core comprises a haloform (preferably bromoform) mixed with a carrier; and
a housing which covers at least a portion of the core or preferably the entire core; wherein, the bolus is configured to release the haloform; and wherein the carrier comprises wax, preferably castor wax, paraffin wax or a mixture thereof; and wherein the housing has a layer thickness of between 0.4 and 1.5 mm.

In a further embodiment, the invention provides a bolus for administration to a ruminant animal, wherein said bolus comprises:
a core, wherein the core comprises a haloform (preferably bromoform) mixed with a carrier; and
a housing which covers at least a portion of the core or preferably the entire core; wherein, the bolus is configured to release the haloform; and wherein the carrier comprises wax, preferably castor wax, paraffin wax or a mixture thereof; and wherein the housing comprises a biodegradable polymer and preferably a biodegradable polymer selected from the group consisting of polylactic acid (PLA), polybutylene succinate (PBS), polybutylene adipate terephthalate (PBAT) and combinations thereof; and wherein the housing has a layer thickness of between 0.4 and 1.5 mm.

In a further embodiment, the invention provides a bolus for administration to a ruminant animal, wherein said bolus comprises:
a core, wherein the core comprises a haloform (preferably bromoform) mixed with a carrier; and
a housing which covers at least a portion of the core or preferably the entire core; wherein, the bolus is configured to release the haloform; and wherein the carrier comprises wax, preferably castor wax, paraffin wax or a mixture thereof; and wherein the housing comprises a biodegradable polymer and preferably a biodegradable polymer selected from the group consisting of polylactic acid (PLA), polybutylene succinate (PBS), polybutylene adipate terephthalate (PBAT) and combinations thereof; and wherein the housing has a layer thickness of less than 2 mm.

In a further embodiment, the invention provides a bolus for administration to a ruminant animal, wherein said bolus comprises:
a core, wherein the core comprises a haloform (preferably bromoform) mixed with a carrier; and
a housing which covers at least a portion of the core or the entire core;
wherein, the bolus is configured to release the haloform; and wherein the core further comprises at least one metal piece (such as metal pellets and/or a metal rod), preferably the metal being steel or zinc. The advantage of this embodiment is that the bolus density is increased, and the bolus is less likely of being regurgitated by the animal. Preferably the bolus of the invention further comprises a densifier, and preferably said densifier comprises at least one piece of metal, preferably the densifier is provided in the core.

In a further embodiment, the invention provides a bolus for administration to a ruminant animal, wherein said bolus comprises:
a core, wherein the core comprises a haloform (preferably bromoform) mixed with a carrier; and
a housing which covers at least a portion of the core or preferably the entire core; wherein, the bolus is configured to release the haloform; and wherein the carrier comprises wax, preferably castor wax, paraffin wax or a mixture thereof; and wherein the housing comprises polylactic acid (PLA); and wherein the housing preferably has a layer thickness of less than 2 mm.

In a further aspect, the invention provides a delayed release dosage form for administration to a ruminant animal, wherein said delayed release dosage form comprises: a core, wherein the core comprises a haloform (preferably bromoform); and a coating which covers at least a portion of the core or preferably the entire core; wherein the delayed release dosage form is configured to release the haloform.

In a further embodiment, the invention provides a delayed release dosage form for administration to a ruminant animal, wherein said delayed release dosage form comprises: a core, wherein the core comprises a haloform (preferably bromoform); and a coating which covers art least a portion of the core or preferably the entire core; wherein the delayed release dosage form is configured to release the haloform; and wherein the core further comprises wax, preferably castor wax, paraffin wax or a mixture thereof.

In a further embodiment, the invention provides a delayed release dosage form for administration to a ruminant animal, wherein said delayed release dosage form comprises: a core, wherein the core comprises a haloform (preferably bromoform) mixed with a carrier; and a coating which covers at least a portion of the core or preferably the entire core; wherein the delayed release dosage form is configured to release the haloform; and wherein the carrier comprises wax, preferably castor wax, paraffin wax or a mixture thereof; and wherein the coating comprises a biodegradable polymer and preferably a biodegradable polymer selected from the group consisting of polylactic acid (PLA), polybutylene succinate (PBS), polybutylene adipate terephthalate (PBAT) and combinations thereof.

In a further embodiment, the invention provides a delayed release dosage form for administration to a ruminant animal, wherein said delayed release dosage form comprises: a core, wherein the core comprises a haloform (preferably bromoform) mixed with a carrier; and a coating which covers at least a portion of the core or preferably the entire core; wherein the delayed release dosage form is configured to release the haloform; and wherein the carrier comprises wax, preferably castor wax, paraffin wax or a mixture thereof; and wherein the coating has a layer thickness of between 0.4 and 1.5 mm.

In a further embodiment, the invention provides a delayed release dosage form for administration to a ruminant animal, wherein said delayed release dosage form comprises: a core, wherein the core comprises a haloform (preferably bromoform) mixed with a carrier; and a coating which covers at least a portion of the core or preferably the entire core; wherein the delayed release dosage form is configured to release the haloform; and wherein the carrier comprises wax, preferably castor wax, paraffin wax or a mixture thereof; and wherein the coating comprises a biodegradable polymer and preferably a biodegradable polymer selected from the group consisting of polylactic acid (PLA), polybutylene succinate (PBS), polybutylene adipate terephthalate (PBAT) and combinations thereof; and wherein the coating has a layer thickness of between 0.4 and 1.5 mm.

In a further embodiment, the invention provides a delayed release dosage form for administration to a ruminant animal, wherein said delayed release dosage form comprises: a core, wherein the core comprises a haloform (preferably bromoform) mixed with a carrier; and a coating which covers at least a portion of the core or preferably the entire core; wherein the delayed release dosage form is configured to release the haloform; and wherein the carrier comprises wax, preferably castor wax, paraffin wax or a mixture thereof; and wherein the coating comprises a biodegradable polymer and preferably a biodegradable polymer selected from the group consisting of polylactic acid (PLA), polybutylene succinate (PBS), polybutylene adipate terephthalate (PBAT) and combinations thereof; and wherein the coating has a layer thickness of less than 2 mm.

In a further embodiment, the invention provides a delayed release dosage form for administration to a ruminant animal, wherein said delayed release dosage form comprises: a core, wherein the core comprises a haloform (preferably bromoform) mixed with a carrier; and a coating which covers the core; wherein the delayed release dosage form is configured to release the haloform; and wherein the core further comprises at least one metal piece (such as metal pellets and/or a metal rod), preferably the metal being steel or zinc. An advantage of this embodiment is that the delayed release dosage form density is increased, and the delayed release dosage form is less likely of being regurgitated by the animal.

In a further embodiment, the invention provides a delayed release dosage form for administration to a ruminant animal, wherein said delayed release dosage form comprises: a core, wherein the core comprises a haloform (preferably bromoform) mixed with a carrier; and a coating which covers a portion of the core or the entire core; wherein the delayed release dosage form is configured to release the haloform; and wherein the carrier comprises wax, preferably castor wax, paraffin wax or a mixture thereof; and wherein the coating comprises polylactic acid (PLA); and wherein the coating preferably has a layer thickness of less than 2 mm. Experiments have shown that coating layer thickness less than 2 mm are preferably because this thickness lets the haloform permeate from the core material outwardly in an optimal rate.

In a delayed release dosage form or a bolus of the invention preferably less than 50% of the haloform comprised in the core is released over a time of three months. In a preferred embodiment of the delayed release dosage form or a bolus of the invention the core comprises at least 100 grams of haloform. The core of the bolus or of the delayed release dosage form of the invention preferably comprises between 30 wt % and 70 wt % of haloform (preferably bromoform).

At present, it is understood that controlled release of the inhibiting agent through the housing may be influenced by a number of factors. For example, the affinity of the inhibiting agent for the carrier may play a role in the diffusion of the inhibiting agent through the housing. It is understood that more polar carriers or carriers containing a high degree of polar functional groups will have a higher affinity with the inhibiting agent than less polar carriers or carriers with a lower degree of functional groups.

The relative affinity of the materials forming the housing and the core for the inhibiting agent may also affect controlled release of the inhibiting agent from the core. For example, having a housing with a relatively lower affinity for the inhibiting agent compared to the affinity of the carrier for the inhibiting agent, could be a factor in controlling the rate of release of the inhibiting agent from the core. These aspects of the invention should become clearer from the description herein.

Throughout the present specification, reference to the term "release mechanism" should be understood as meaning an arrangement to release a predetermined amount of the inhibiting agent(s) over time. For instance, the release mechanism may comprise a valve arrangement which can release an amount of the inhibiting agent(s) via an outlet. Alternatively, the release mechanism may be a syringe-type mechanism having a plunger and actuator; over time, the actuator moves the plunger in the reservoir to drive the inhibiting agent(s) out of the reservoir.

Also, the following items are according to the invention:

Item 1 provides a bolus for administration to a ruminant animal, wherein said bolus is configured to release an effective amount of at least one inhibiting agent.

Item 2 provides the bolus of any one of item 1, wherein the at least one inhibiting agent is a methane inhibitor.

Item 3 provides the bolus of items 1 or 2, wherein the at least one inhibiting agent is a haloform selected from chloroform, bromoform, iodoform, or combinations thereof.

Item 4 relates to the bolus of any one of items 1-3, wherein the at least one inhibiting agent is bromoform.

Item 5 relates to the bolus of any one of items 1-4, wherein the bolus includes a core which comprises an amount of the inhibiting agent.

Item 6 provides the bolus of item 5, wherein the core includes a carrier mixed with the inhibiting agent.

Item 7 relates to the bolus of item 6, wherein the carrier is a waxy substance, selected from the bee's wax, paraffin wax, PEG4000, Carnauba, Candellila, Jojoba, or Lanolin or a combination thereof.

Item 8 relates to the bolus of any one of items 5-7, wherein the core has a melting point greater than 37° C.

Item 9 relates to the bolus of any one of items 5-8, wherein the bolus includes a housing to receive and hold the core.

Item 10 relates to the bolus of item 9, wherein the housing includes a cavity which can receive and hold the core.

Item 11 relates to the bolus of item 9 or 10, wherein the housing includes an opening to facilitate, in use, exposure of the core to fluid in the rumen of the ruminant.

Item 12 relates to the bolus of item 10 or 11, wherein the cavity includes a first region which has a first cross-sectional area and a second region which has a second cross-sectional area, and wherein the first cross-sectional area and the second cross-sectional area are different to each other to facilitate controlled release of the inhibiting agent from the core.

Item 13 relates to the bolus of any one of items 9-12, wherein the housing is configured to degrade over a predetermined period of time.

Item 14 relates to the bolus of any one of items 9-13, wherein housing is made from one or more non-adsorbent materials selected from the following: poly lactic acid (PLA), poly glycolic acid (PGA), poly lactic glycolic acid (PLGA), polypropylene, SLA polymer, PBS, or a combination thereof.

Item 15 relates to the bolus of any one of items 9-14, further comprising a barrier layer between at least a portion of the housing and the core to isolate the portion of the housing and the core from contact with each other.

Item 16 relates to the bolus of any one of items 1 to 15, wherein the bolus is adapted to release a dose of approximately 0.1 g to 0.5 g of the inhibiting agent per day into the ruminant animal's rumen.

Item 17 relates to the bolus of any one of items 1 to 16, wherein the bolus is adapted to release the inhibiting agent over a period of at least six months.

Item 18 relates to the bolus of any one of items 1 to 17, wherein the bolus is adapted to release the inhibiting agent within two years.

Item 19 provides a method for reducing emission of gas from a ruminant animal, the method comprising the step of administering to said ruminant animal the bolus of any one of items 1-18.

Item 20 provides a method for reducing methane production in a ruminant animal, the method comprising the step of administering to said ruminant animal the bolus as item in any one of items 1-18.

Item 21 provides the use of a methane inhibitor and a carrier in a bolus for reducing methane production in a ruminant animal.

Item 22 provides the use of a methane inhibitor and a carrier in a bolus for reducing methane emission from a ruminant animal.

Item 23 provides the use of a haloform in the manufacture of a bolus for reducing the emission of one or more greenhouse gases ("GHGs") from a ruminant animal.

Item 24 provides a method of manufacture of a bolus of any one of items 1 to 18, comprising:
a. forming a housing which has a cavity;
b. forming a core which includes the inhibiting agent;
c. transferring the core to the cavity.

Item 25 relates to the method of item 24, wherein the step of forming the core involves mixing a carrier material with the inhibiting agent.

Item 26 provides the method of item 25, wherein the step of forming the core involves heating the carrier material to melt the carrier material prior to mixing the carrier material with the inhibiting agent to create a mixture.

Item 27 relates to the method of any one of items 24 to 26, wherein the step of transferring the core to the cavity involves pouring the mixture into the cavity.

Further aspects of the invention, which should be considered in all its novel aspects, will become apparent to those skilled in the art upon reading of the following description which provides at least one example of a practical application of the invention.

BRIEF DESCRIPTION OF THE DRAWINGS

Particularly preferred embodiments of the invention will be described below by way of example only, and without intending to be limiting, with reference to the following drawings, in which.

The term "bromet" as used in the above figures refers to a bromoform containing bolus.

Figure 19:
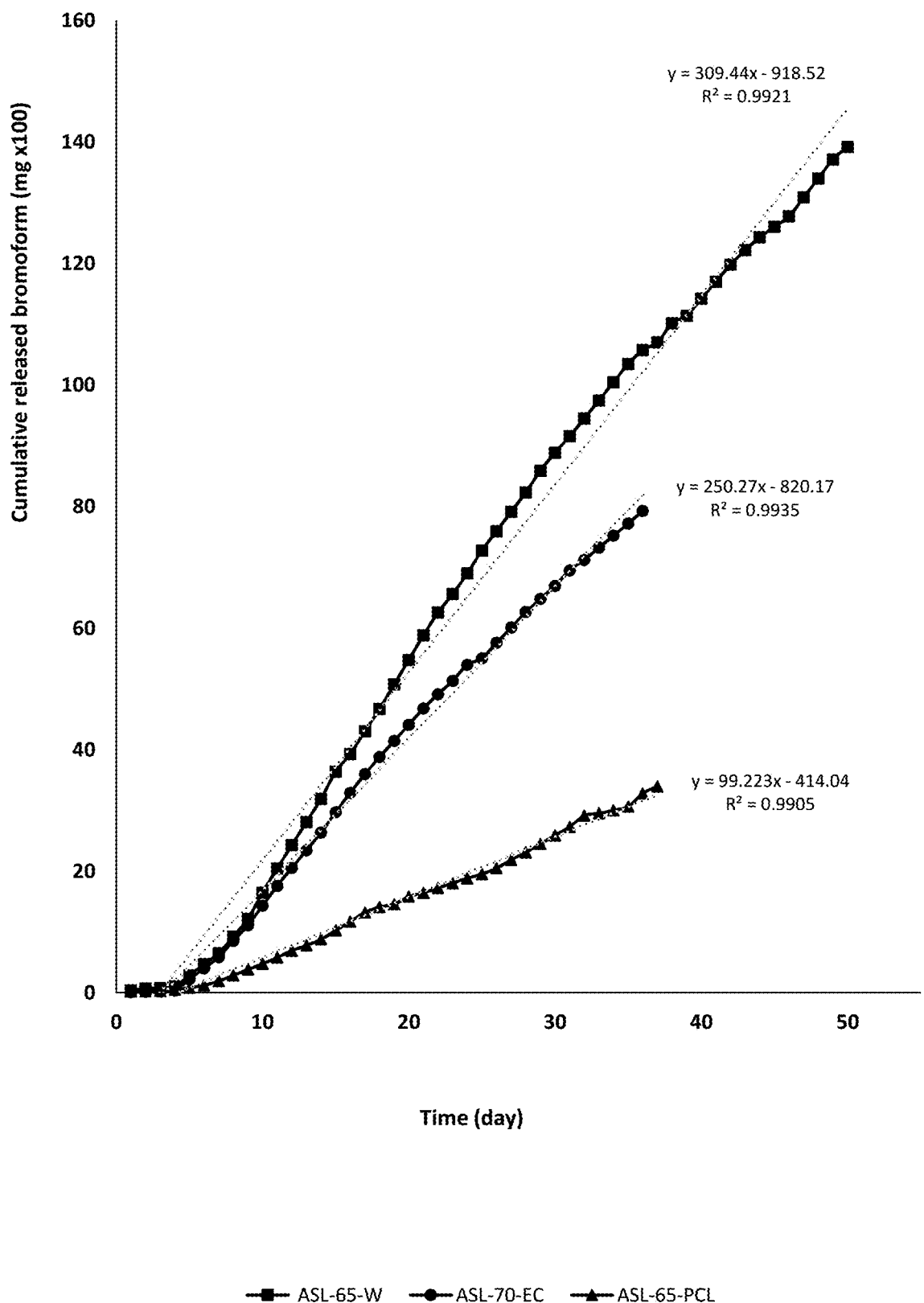

FIG. 19 shows the cumulative release of tribromomethane from ASL-65-W, ASL-70-EC, and ASL-65-PCL carriers.

Figure 20:
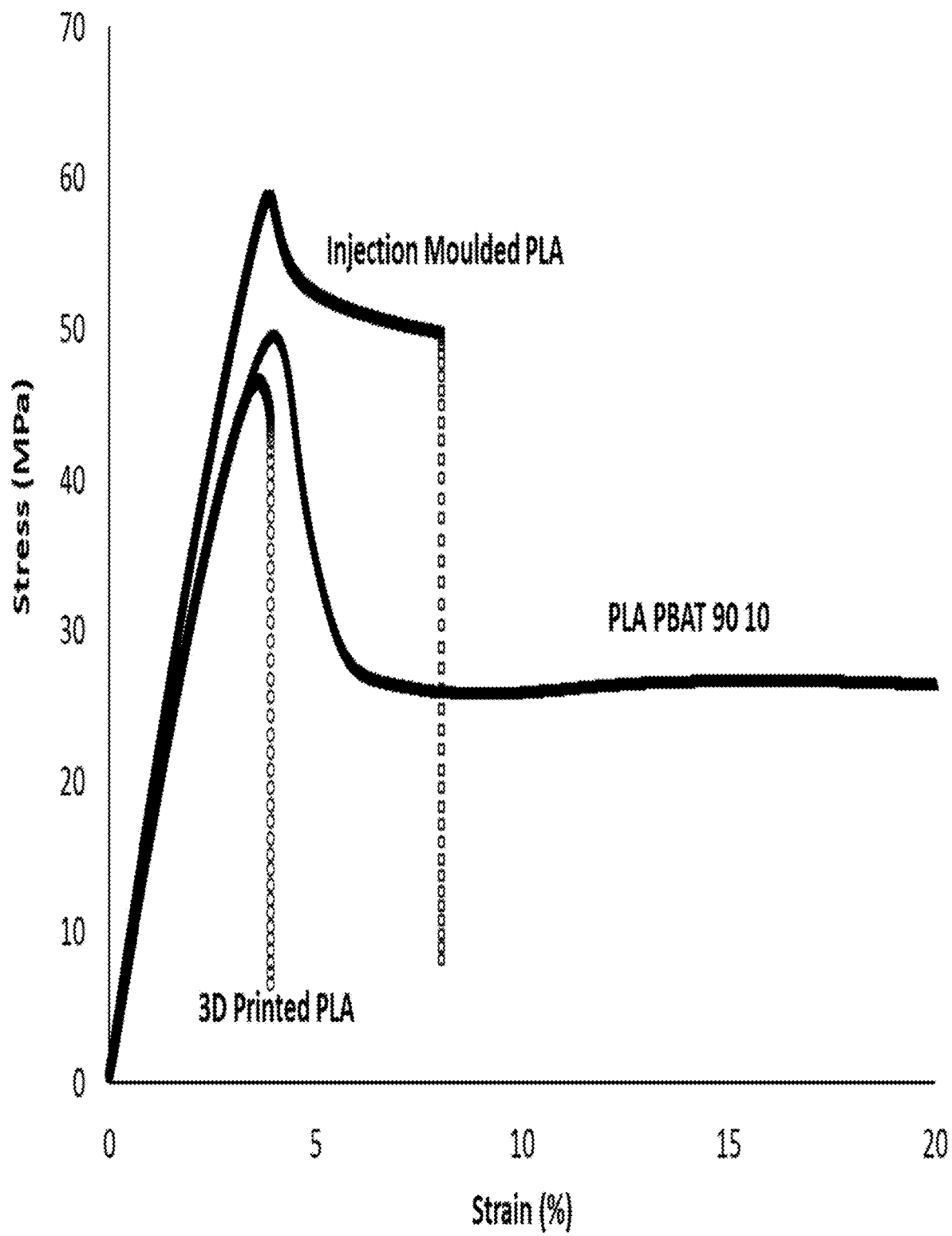

FIG. 20 shows tensile properties of injection moulded PLA, PLA blend and 3 D printed PLA dog bones, when measured by standardized ASBTM D638 method. Sharp fall in strain stress curve is observed for both injection moulded and 3 D printed PLA indicates the breaking of the tested material. Blending with PBAT has a noticeable effect on the ductile properties of the blends as indicated by higher value of elongation at break when compared to pure PLA.

Figure 21:
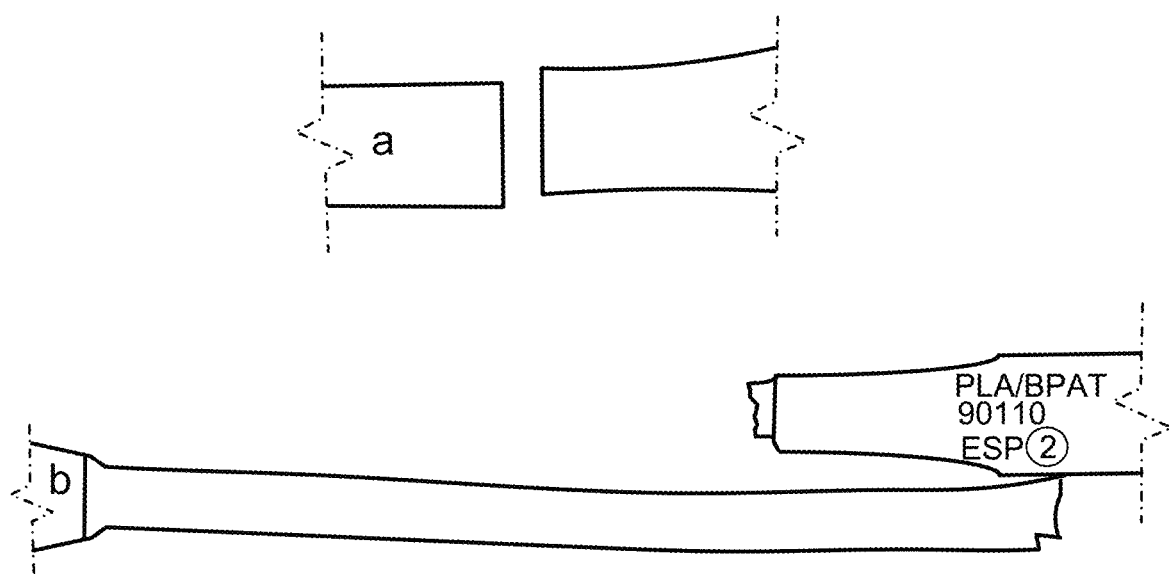

FIG. 21 shows the fractured area of a) an injection moulded PLA, b) PLA/PBAT 90:10 dog bones after tensile test. For pure PLA dog bones, poor mechanical property is evident with a brittle fracture, while ductile fracture is evident in PLA/PBAT dog bones indicating an improvement in mechanical property over pure PLA.

FIGS. 22A-22B show an SEM micrograph of fractured injection moulded PLA dog bone (PLA IM). FIG. 22A) middle and FIG. 22B) a side section of the fracture surface, where there is no visible sign of shear patterns as the surface is smooth due to brittle fracture. Although the inventive bolus embodiments can be housed in pure PLA it is preferred that the housing comprises both PLA and a polybutylene polymer, such as PBAT, PBS or PBSA.

Figure 23:
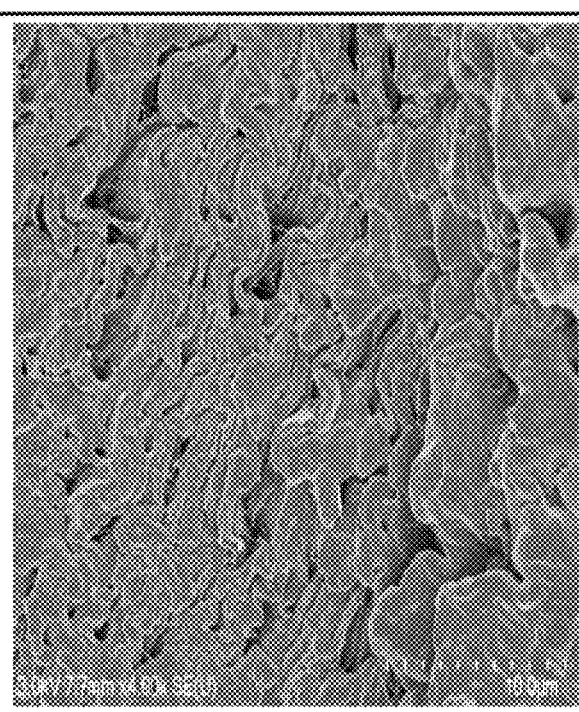
Figure 23:
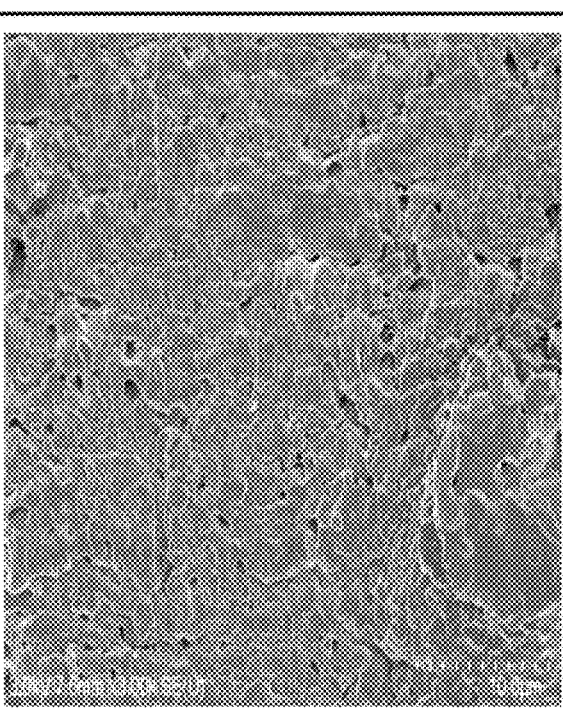
Figure 23:
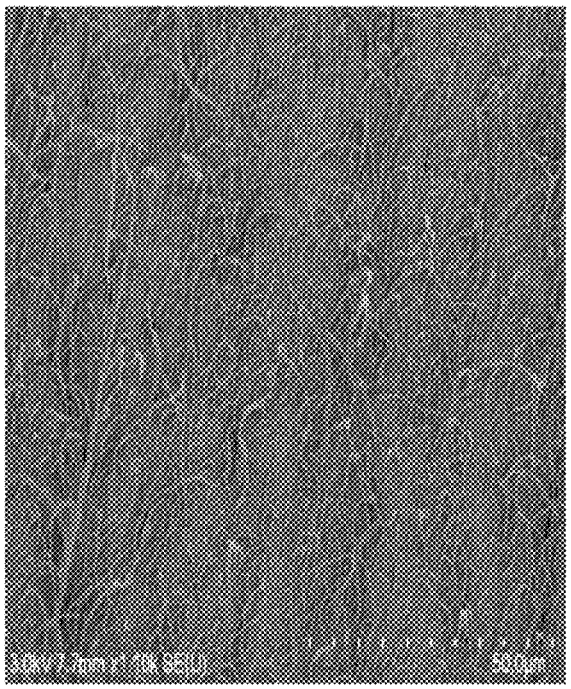
Figure 23:

FIG. 23 shows a SEM micrograph of fractured PLA-PBAT 90:10 dog bone, panel a) middle and panel b) side section of the fracture surface, panel c) fibril structures appeared on the fracture surfaces, panel d) shear patterns on the side of the surface fracture. There is a visible sign of shear patterns as the surface is non-homogenous due to ductile fracture, which is typically characterized by a plastic deformation or necking that occurs before the material finally cracks or breaks apart.

Figure 24:
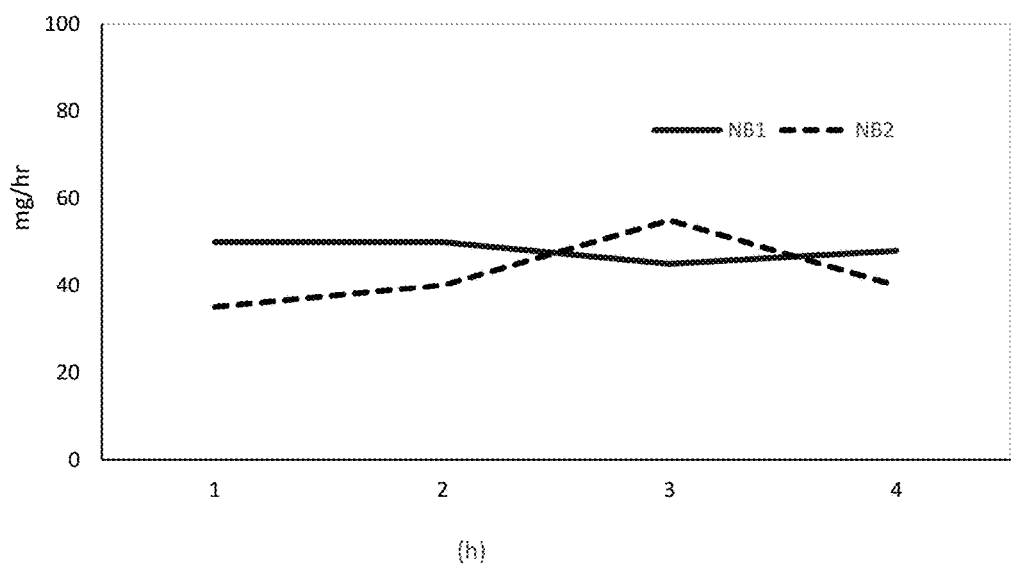

FIG. 24 shows the release rate of bromoform from naked bolus.

Figure 25:
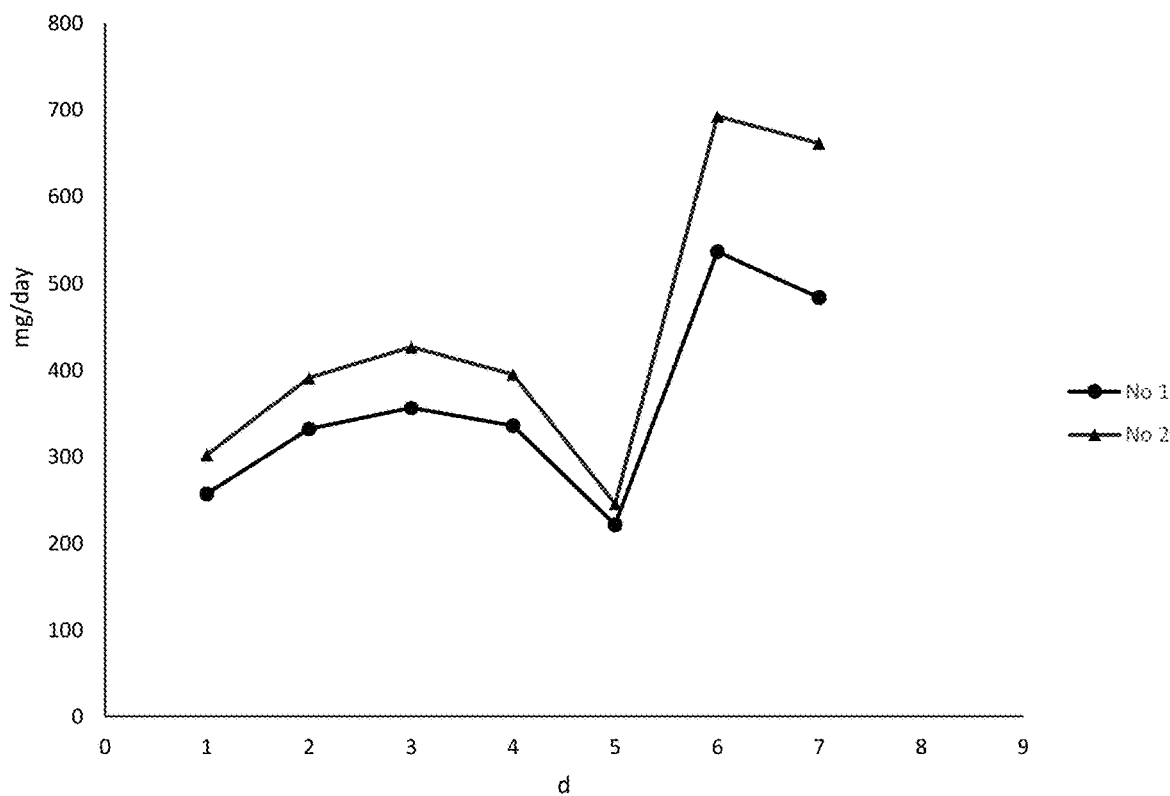

FIG. 25 shows the release rate of bromoform without the caps.

Figure 26:
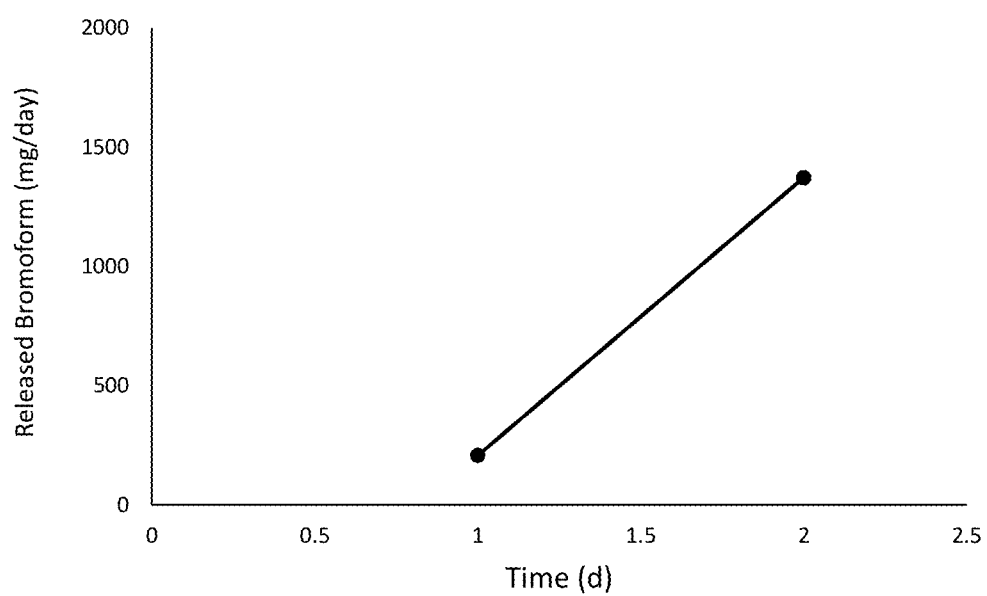

FIG. 26 shows the release rate of bromoform from a bolus filled with ASL-80-L.

Figure 27:
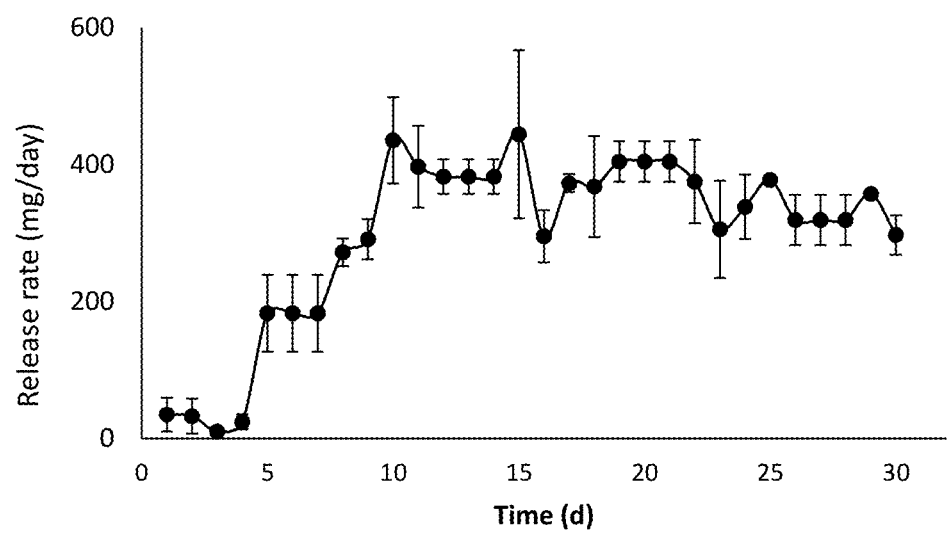
Figure 27:
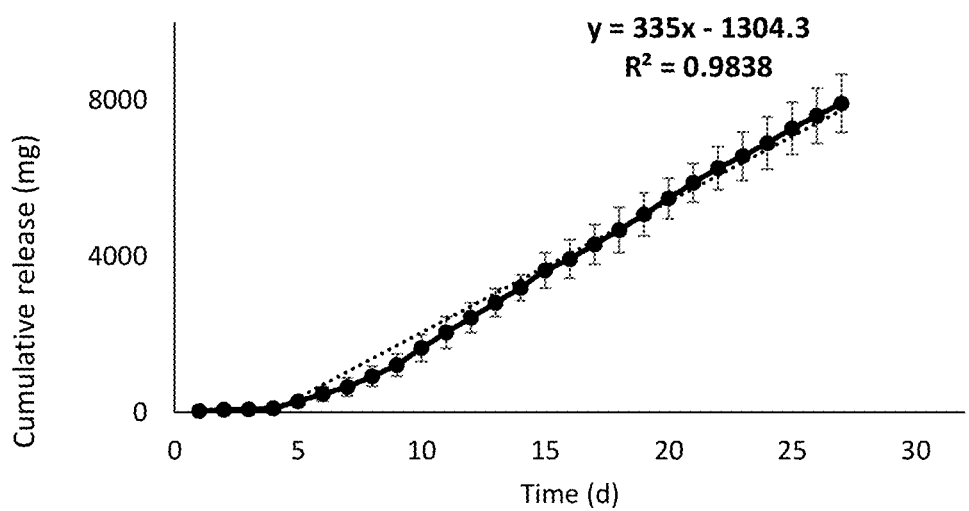

FIG. 27 shows the release rate (mg/d) and cumulative release (mg) of bromoform from ASL-65-W.

Figure 28:
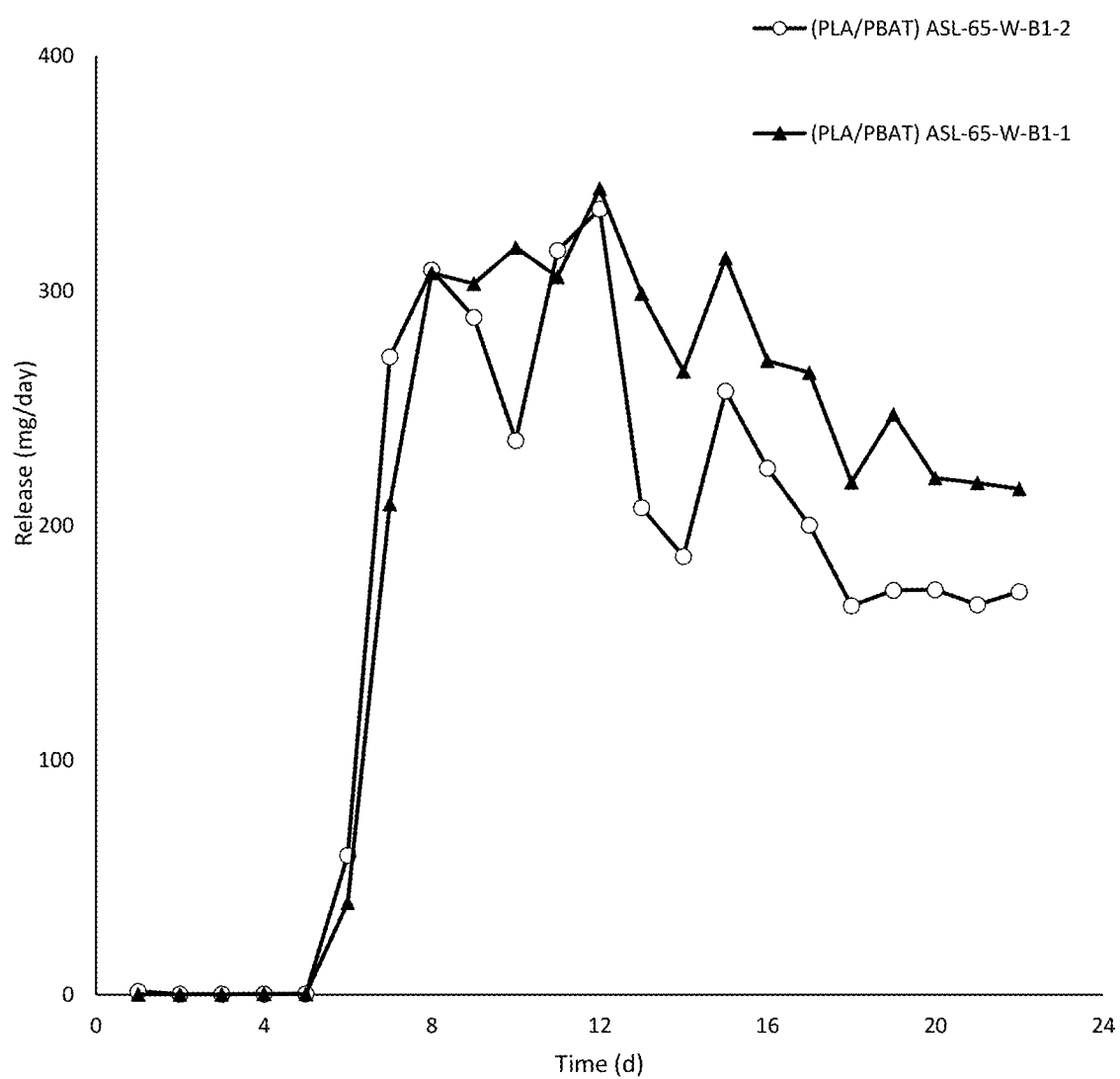

FIG. 28 shows the release rate (mg/d) of ASL-65-W filled in injection molded PLA/PBAT casings.

Figure 29A:
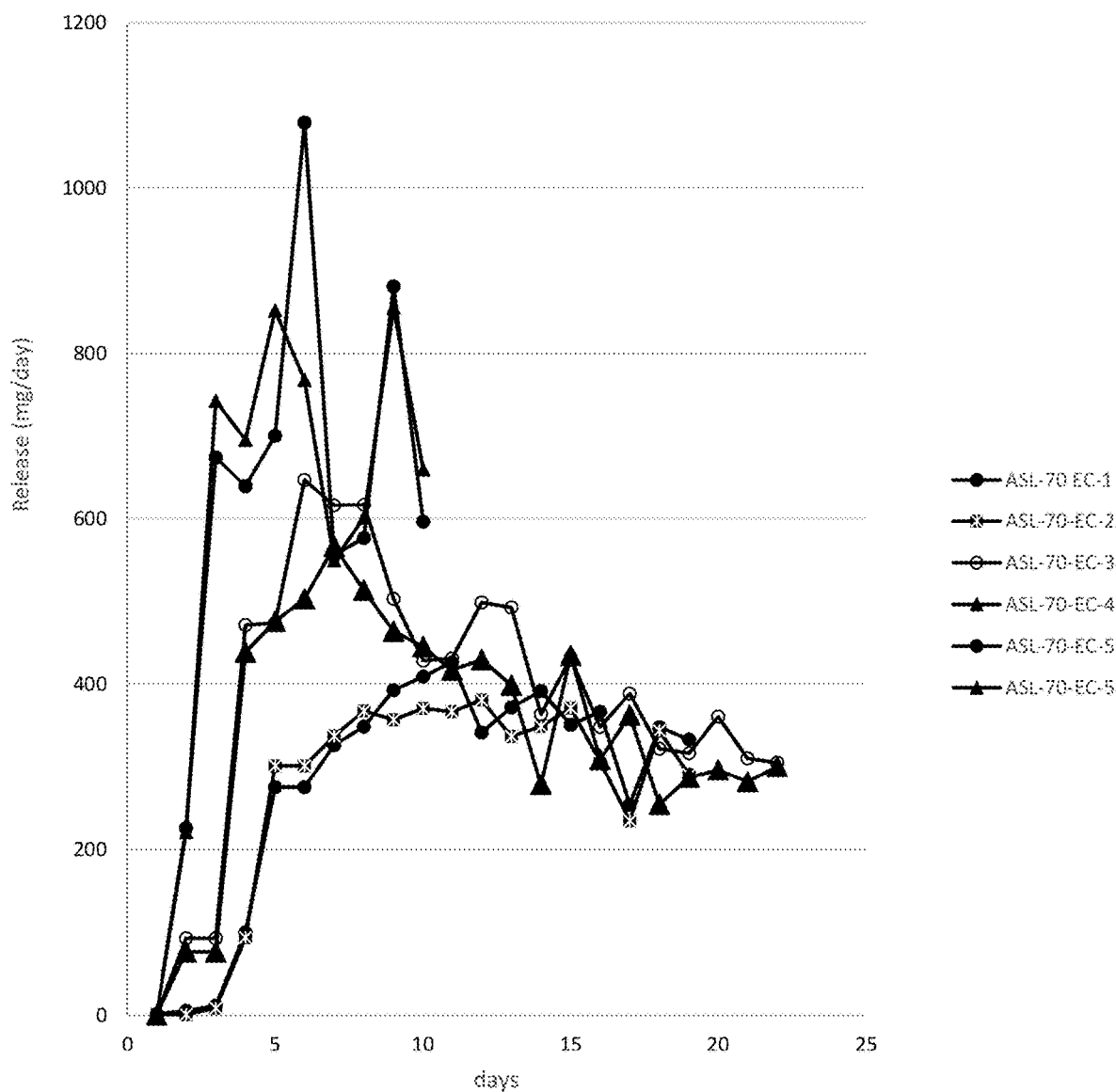
Figure 29B:
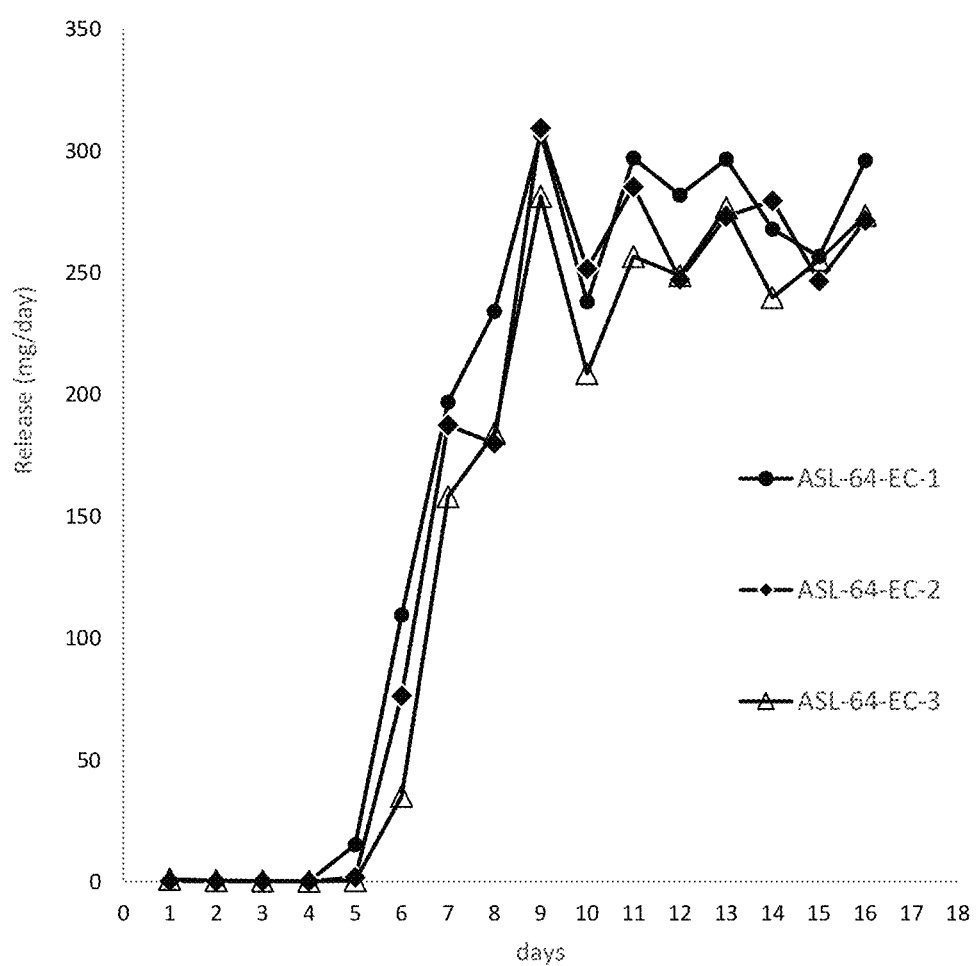

FIGS. 29A-29B show release rates from the ethyl cellulose system FIG. 29A 70% Bromoform and FIG. 29B 64% Bromoform formulation filled in PLA/PBAT casing.

Figure 30A:
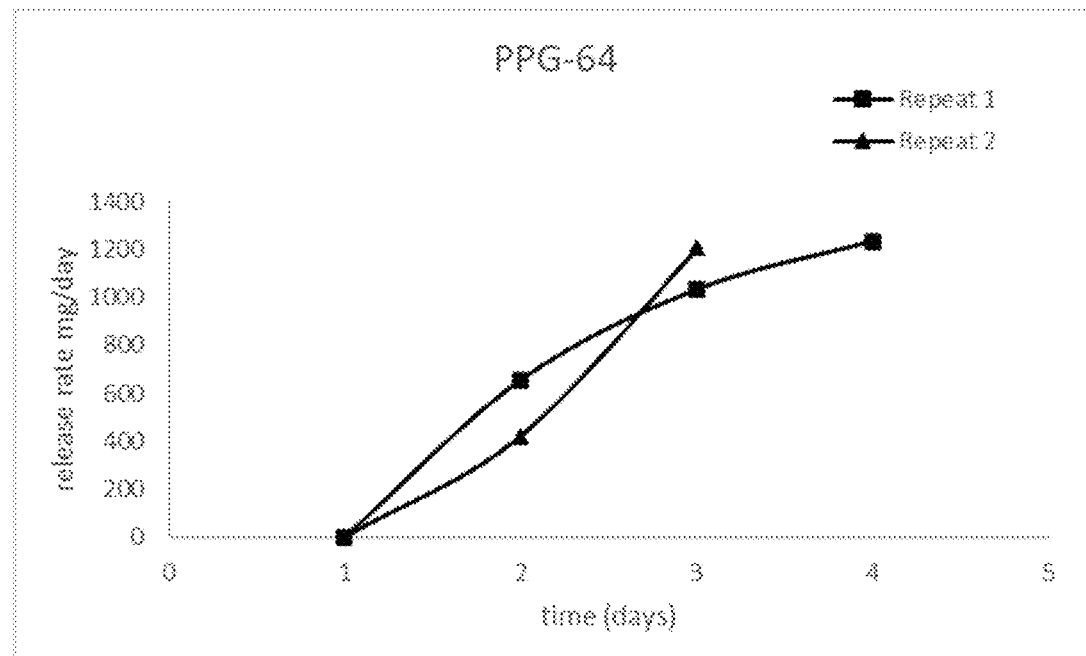
Figure 30B:
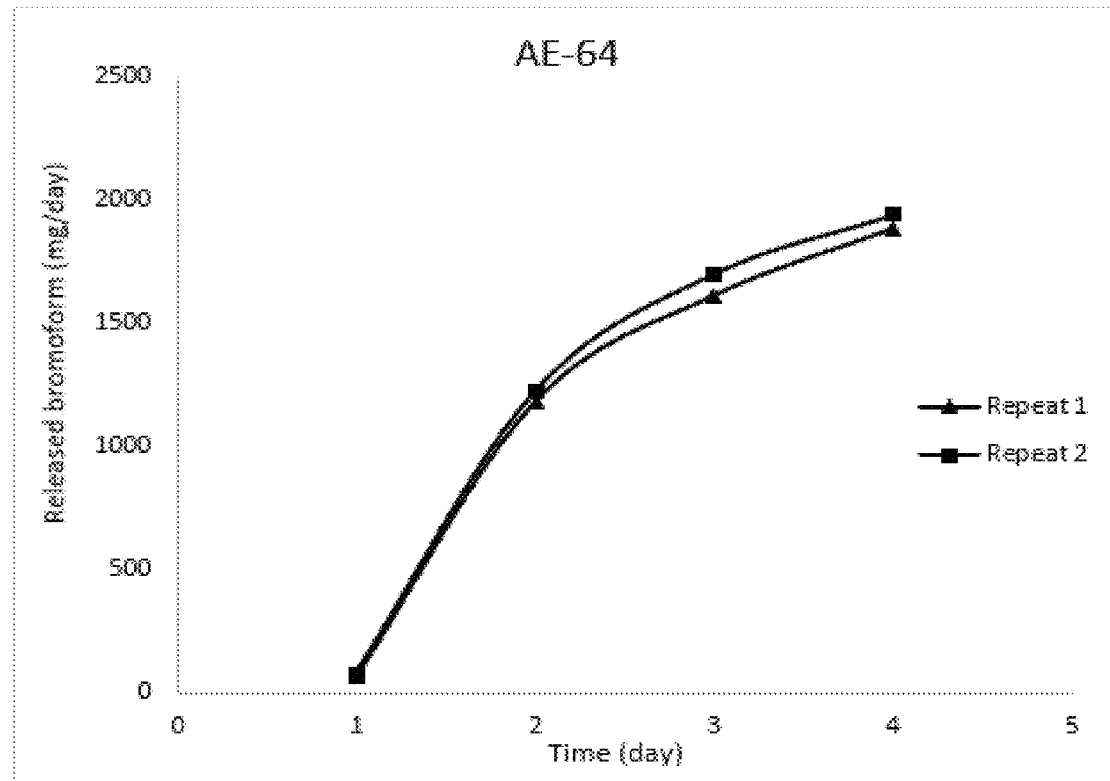

FIGS. 30A-30B show bromoform release rates from boli with the carrier systems FIG. 30A) PPG-64 (propylene glycol) and FIG. 30B) AE-64 (fumed silica). Both carrier systems lead to an immediate release at a high release rate.

Figure 31A:
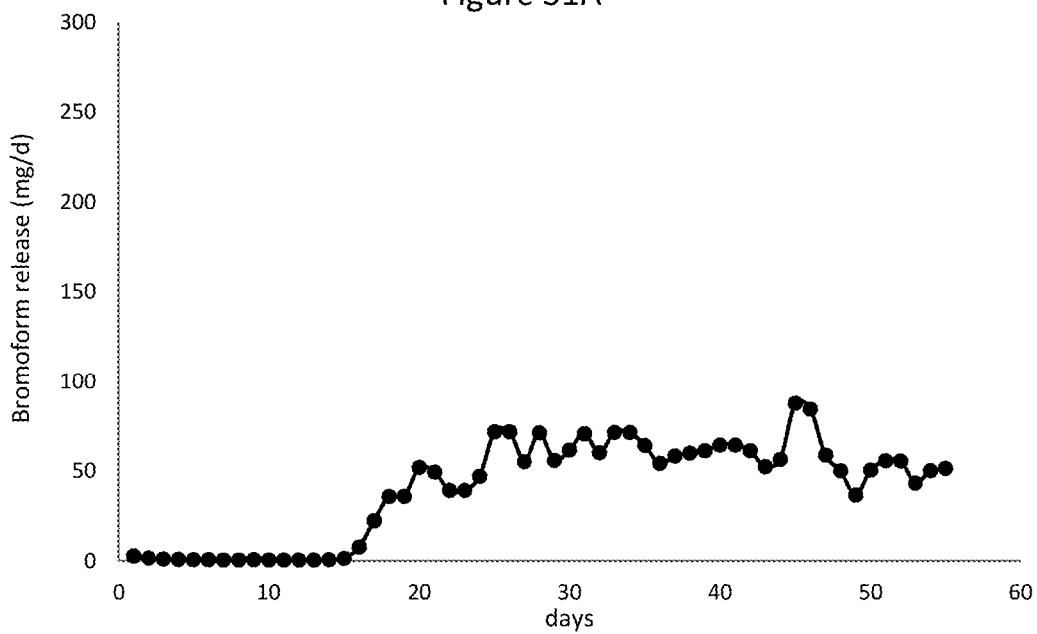
Figure 31B:
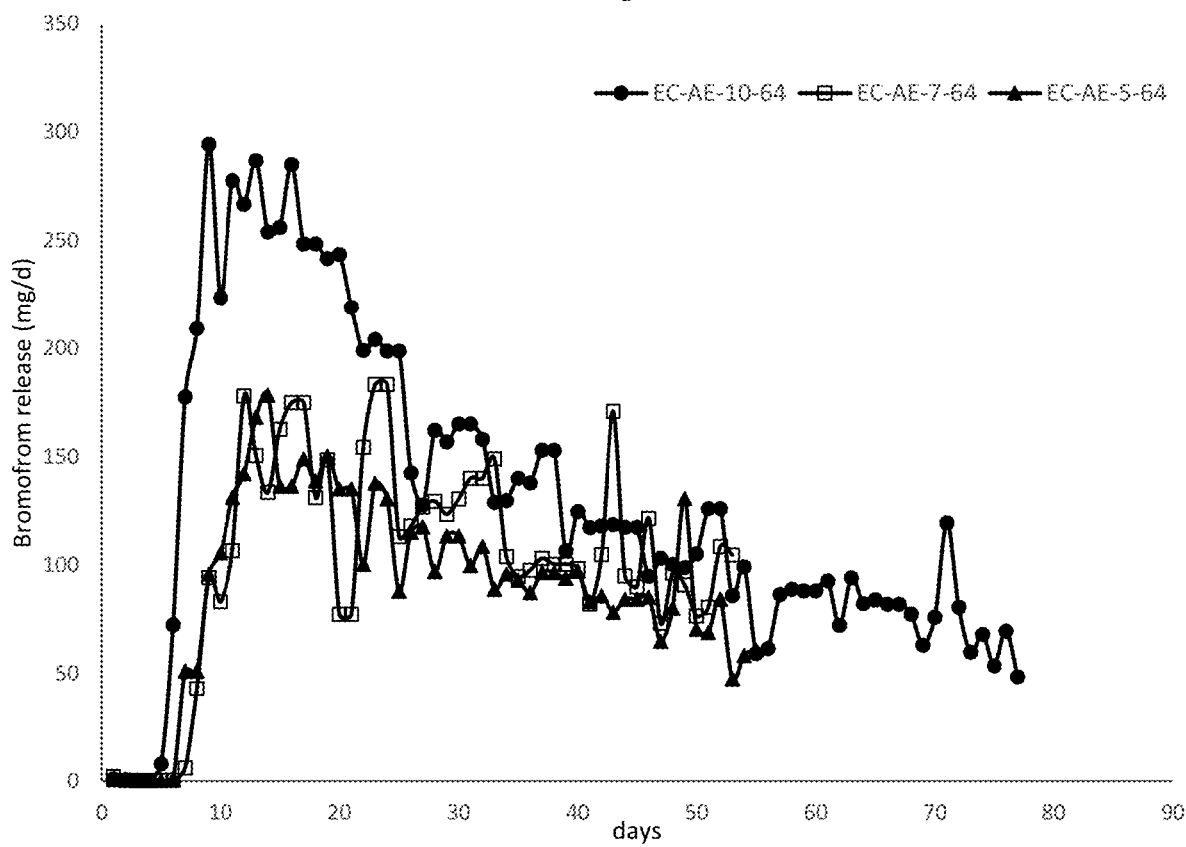

FIGS. 31A-31B show the release rates of bromoform from the carrier systems FIG. 31A ethyl cellulose (EC-64) and FIG. 31B ethyl cellulose mixed with 10 w/w % (EC-AE-10-64), 7 w/w % (EC-AE-7-64) or 5 w/w % (EC-AE-5-64) colloidal silicon dioxide, each with 64 w/w % bromoform and each filled in PLA/PBAT casing. Data in FIG. 31B are presented as mean of n=2.

Figure 32A:
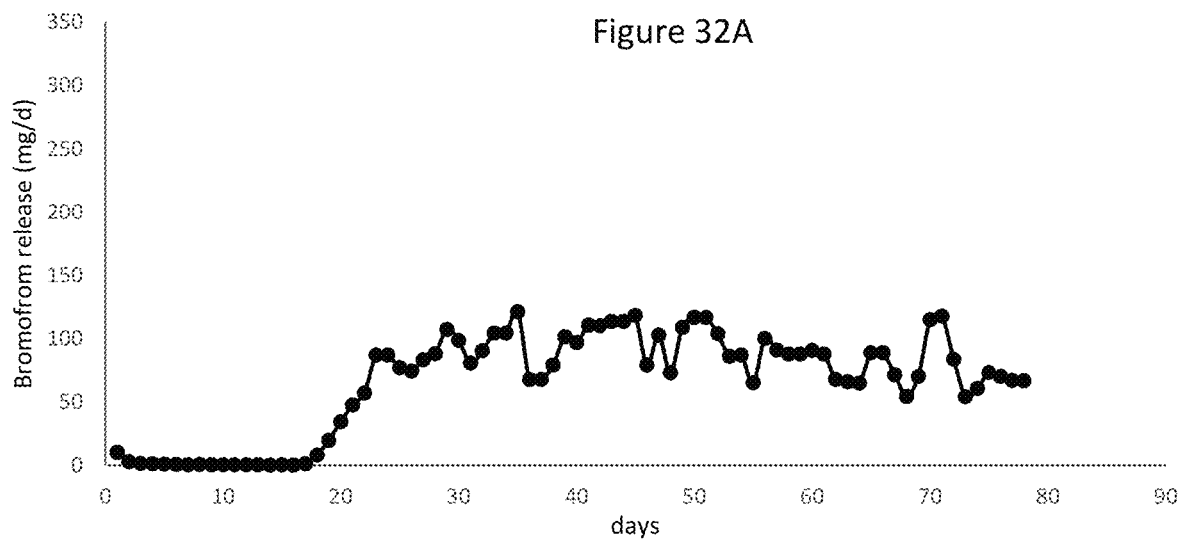
Figure 32B:
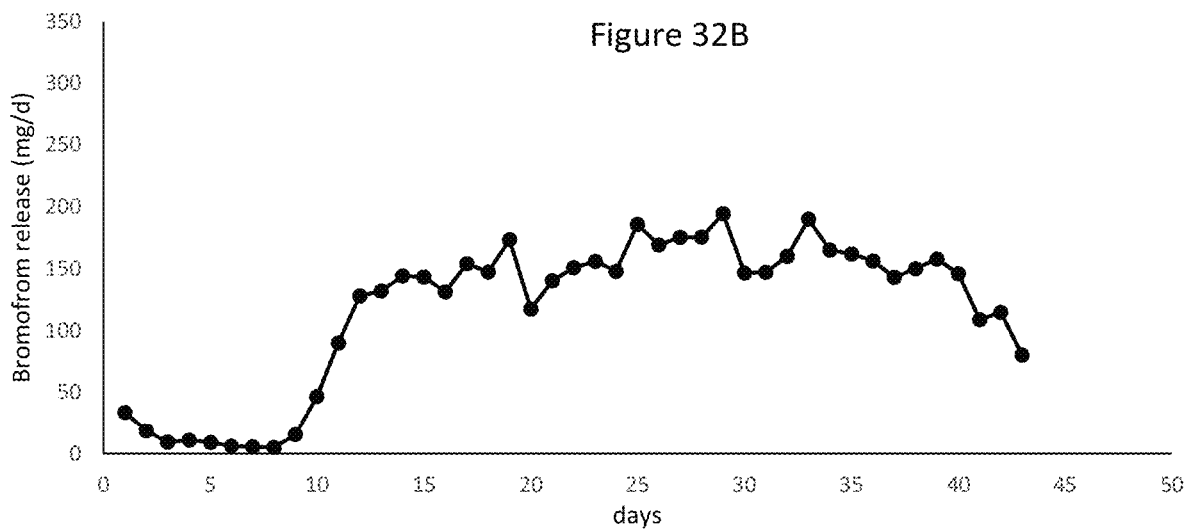
Figure 32C:
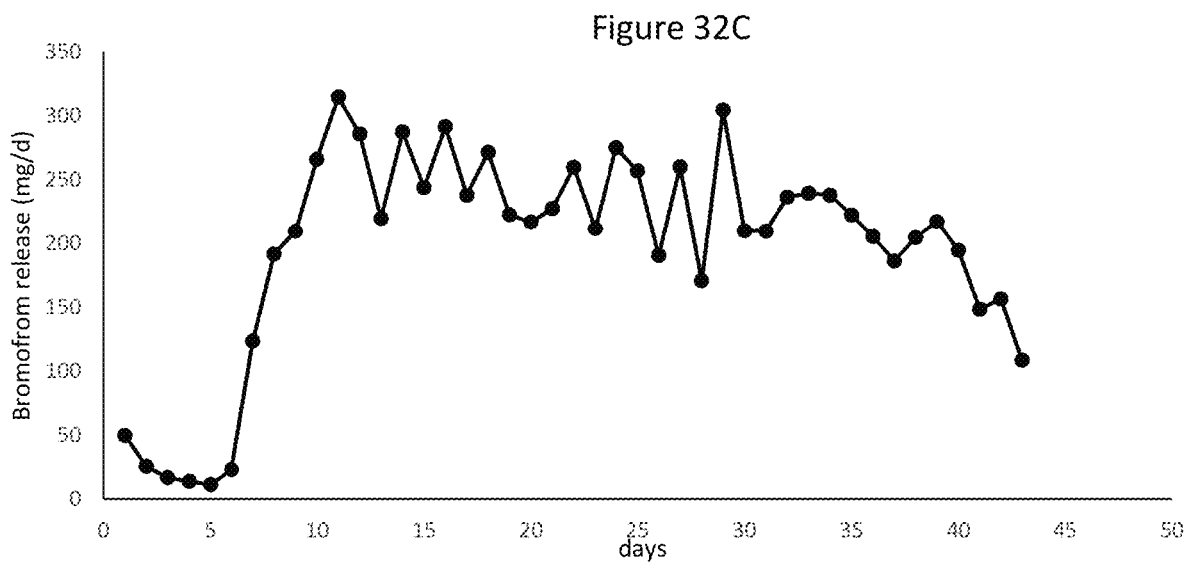

FIGS. 32A-32C show the release rate of bromoform from boli with carrier systems (see also Table 13) of FIG. 32A) ethyl cellulose mixed with 14.3 w/w % hydroxypropyl methyl cellulose with 58.3 w/w % bromoform (EC-HPMC-58) FIG. 32B) ethyl cellulose mixed with 20 w/w % hydroxypropyl methyl cellulose with 60 w/w % bromoform (EC-HPMC 60) and FIG. 32C) ethyl cellulose mixed with 24 w/w % hydroxypropyl methyl cellulose with 61 w/w % bromoform (EC-HPMC 61), each filled into PLA/PBAT casings. Data are presented as mean of n=2.

Figure 33:
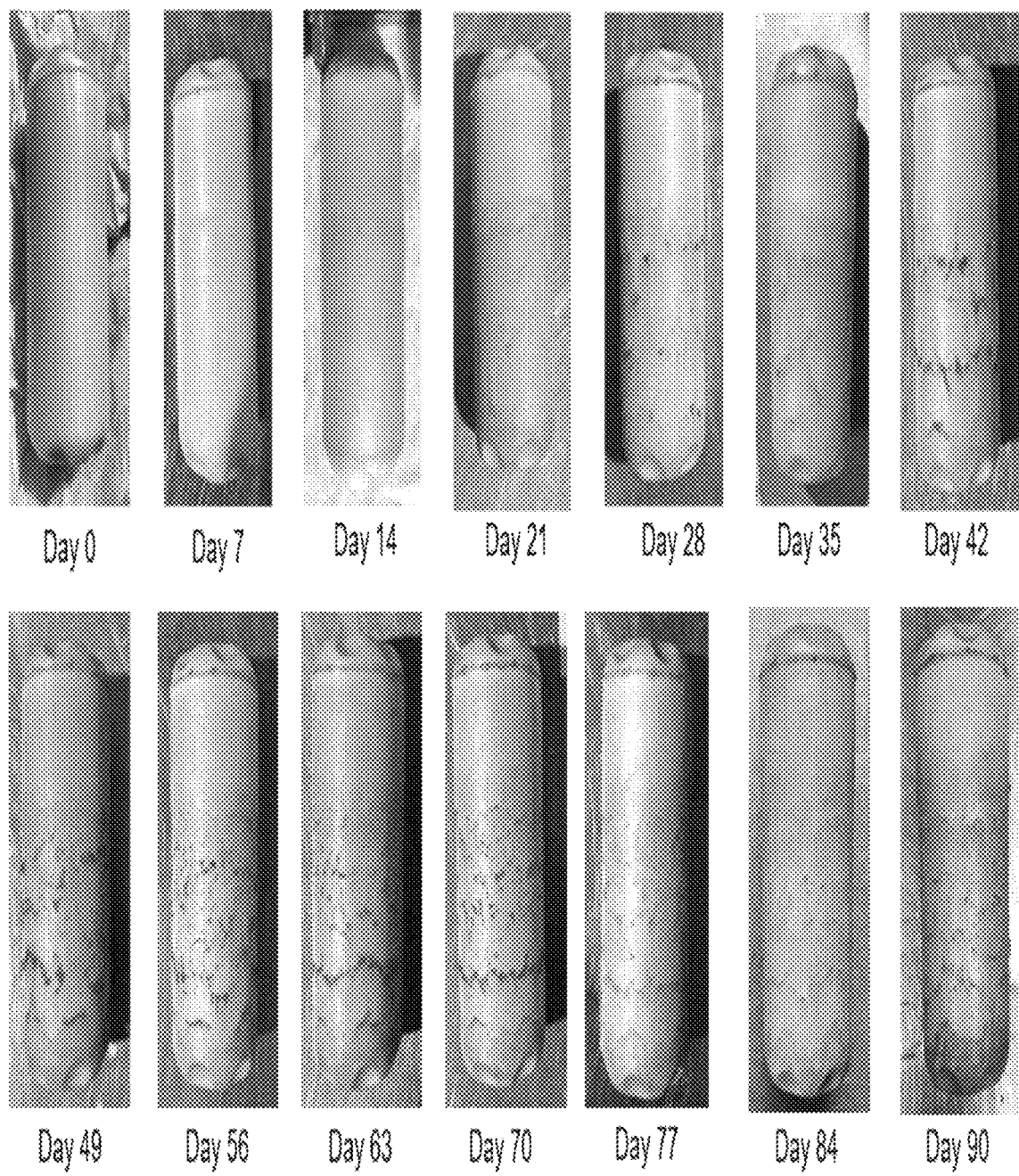
Figure 33B:
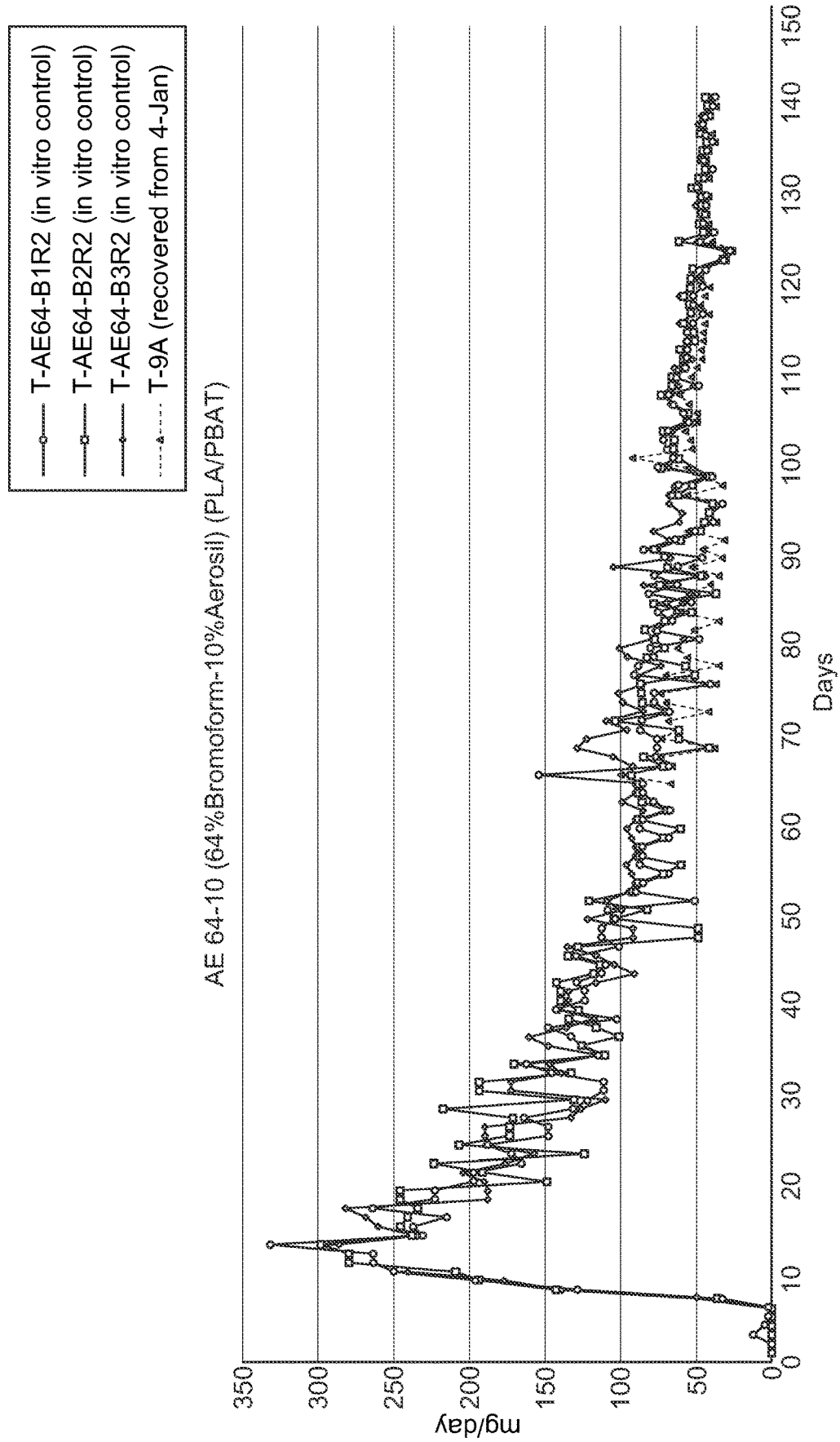

FIG. 33A shows wear of boli with a housing made of PLA/PBAT in a ratio of 90:10 polymer blend in fistulated animals over a period of 3 months. Depicted is a time series of bolus integrity in the rumen environment from day 0 to day 90. At day 21 there is a slight discolouration difference and swelling of the lower portion of the bolus as compared to the upper portion of the bolus containing the densifier. From days 28 onwards, there is increasing micro-peeling and discolouration of the bolus surface proportion that contains the carrier. However, the bolus remains intact and stable throughout the testing period. FIG. 33B shows release rates from boli of this type in the fistulated animals, demonstrating that the bolus housing remains stable. The trial could be extended to 5 months with only minor surface peeling of the bolus.

Figure 34:
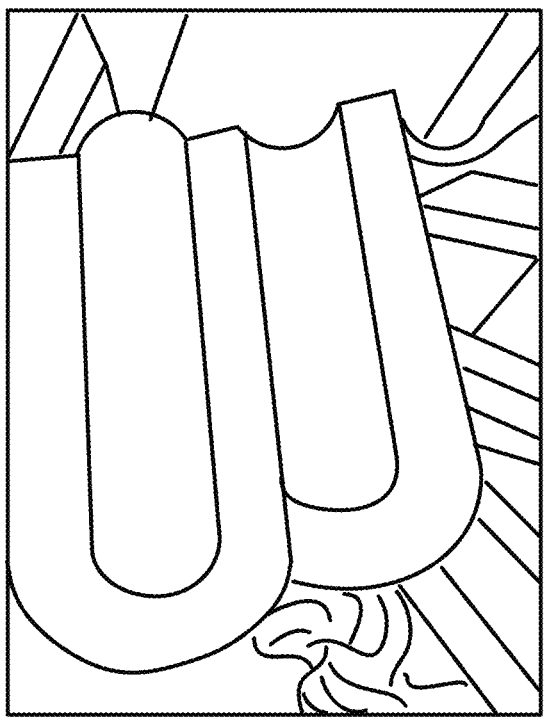
Figure 34:
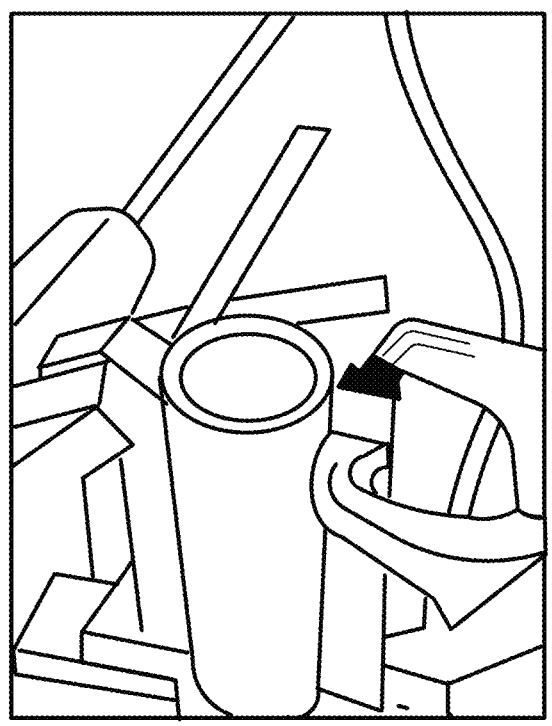

FIG. 34 shows the process of production of a wax based bolus without housing. The left panel shows two halves of a mould for forming the bolus with the hardened carrier matrix moulded. The right panel shows the two halves of the mould clamped together to enable filling by the carrier, wherein the carrier matrix is depicted as being filled into the clamped mould.

Figure 35:
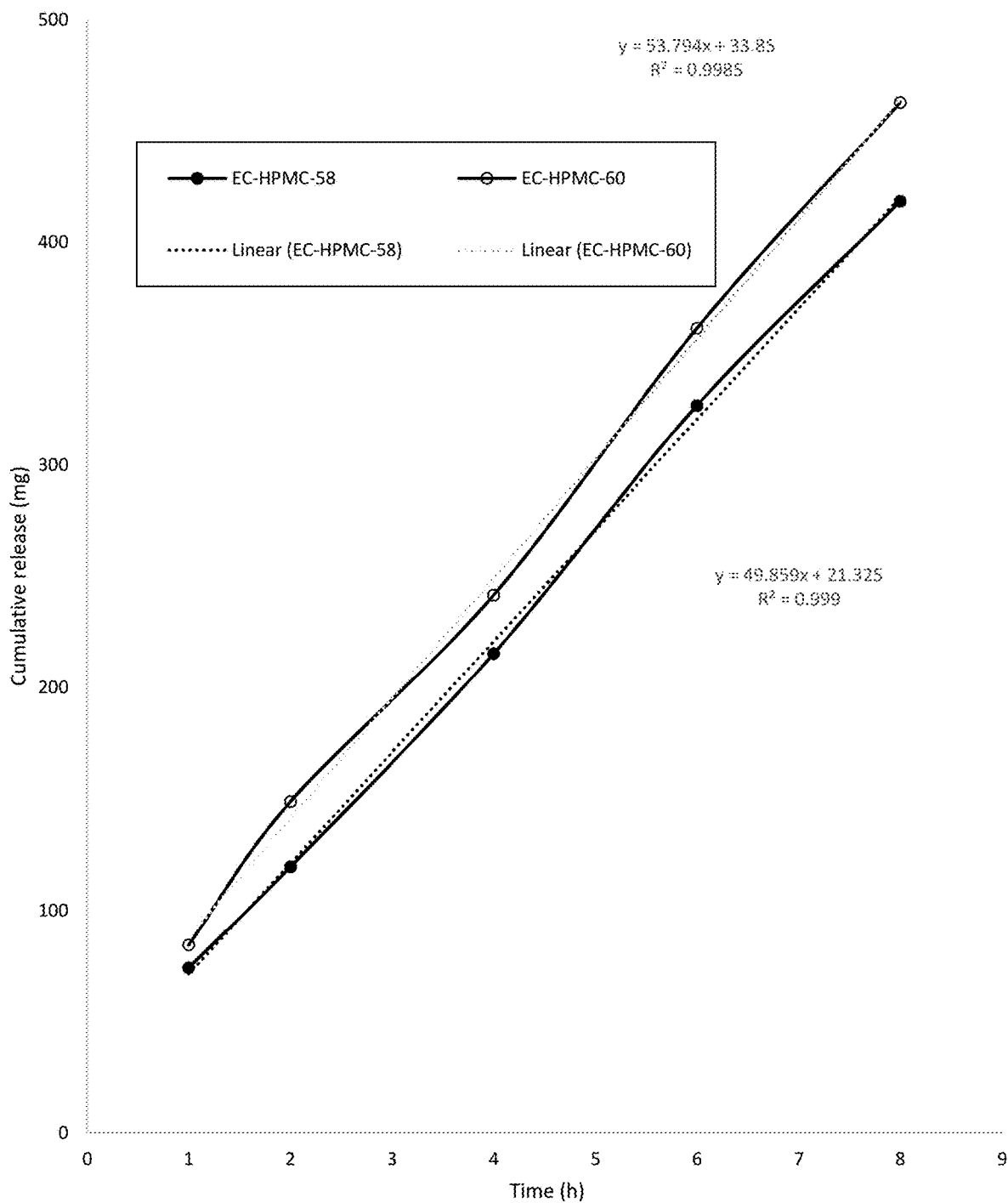

FIG. 35 shows the in vitro bromoform release rates from boli with polymeric based carrier system, wherein the boli do not comprise a housing. Release rates are high and no lag phase is observed.

Figure 36:
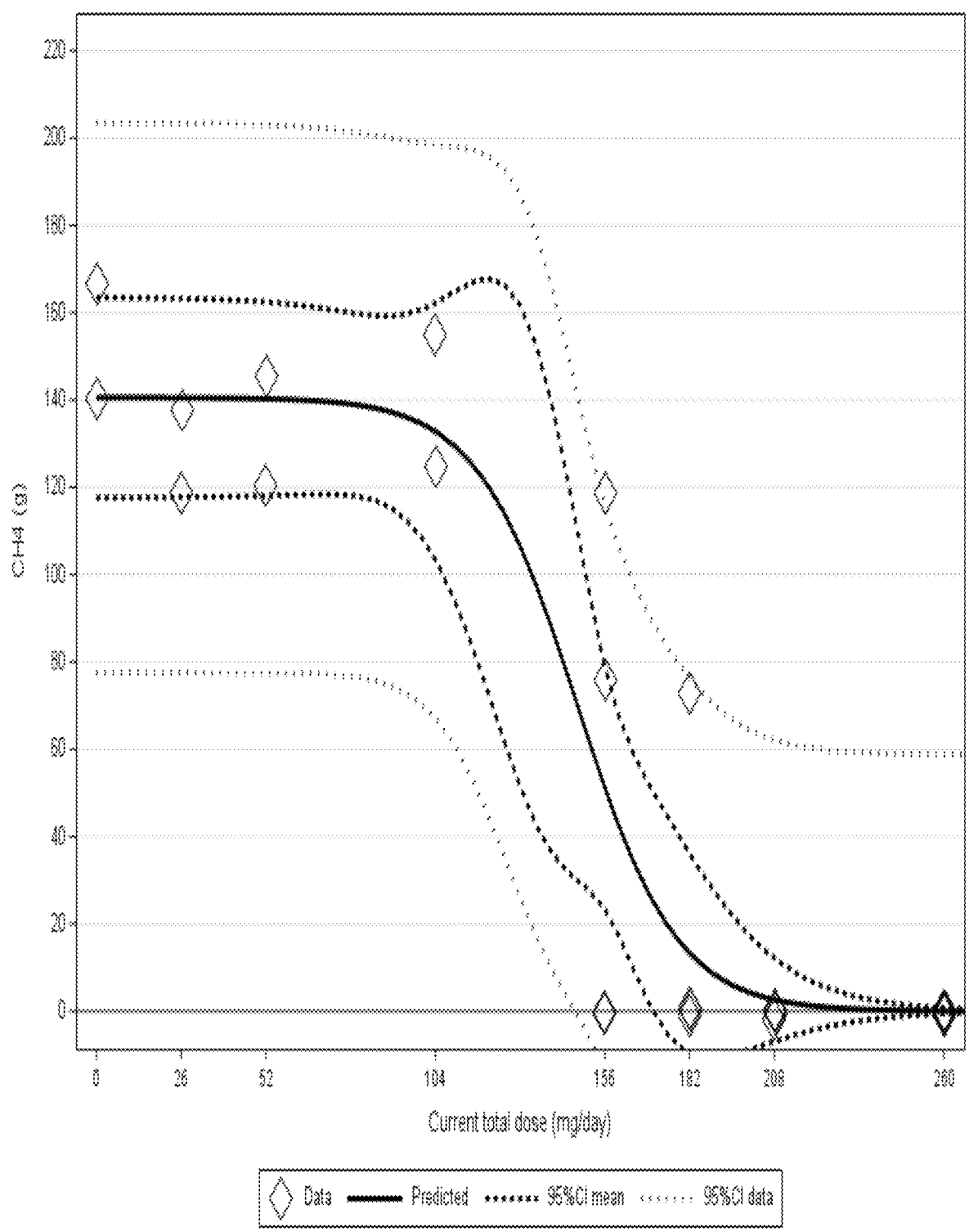

FIG. 36 shows $CH_4$ emission from animals versus nominal tribromomethane dose rates administered to the animals—display by means of a non-linear 3-parameter logistic model. The bold line represents the predicted dose response curve. Bold dashed lines delimit the 95% confidence interval (95% CI) for the mean response. Thin dashed lines delimit the 95% confidence interval for all datapoints.

Figure 37:
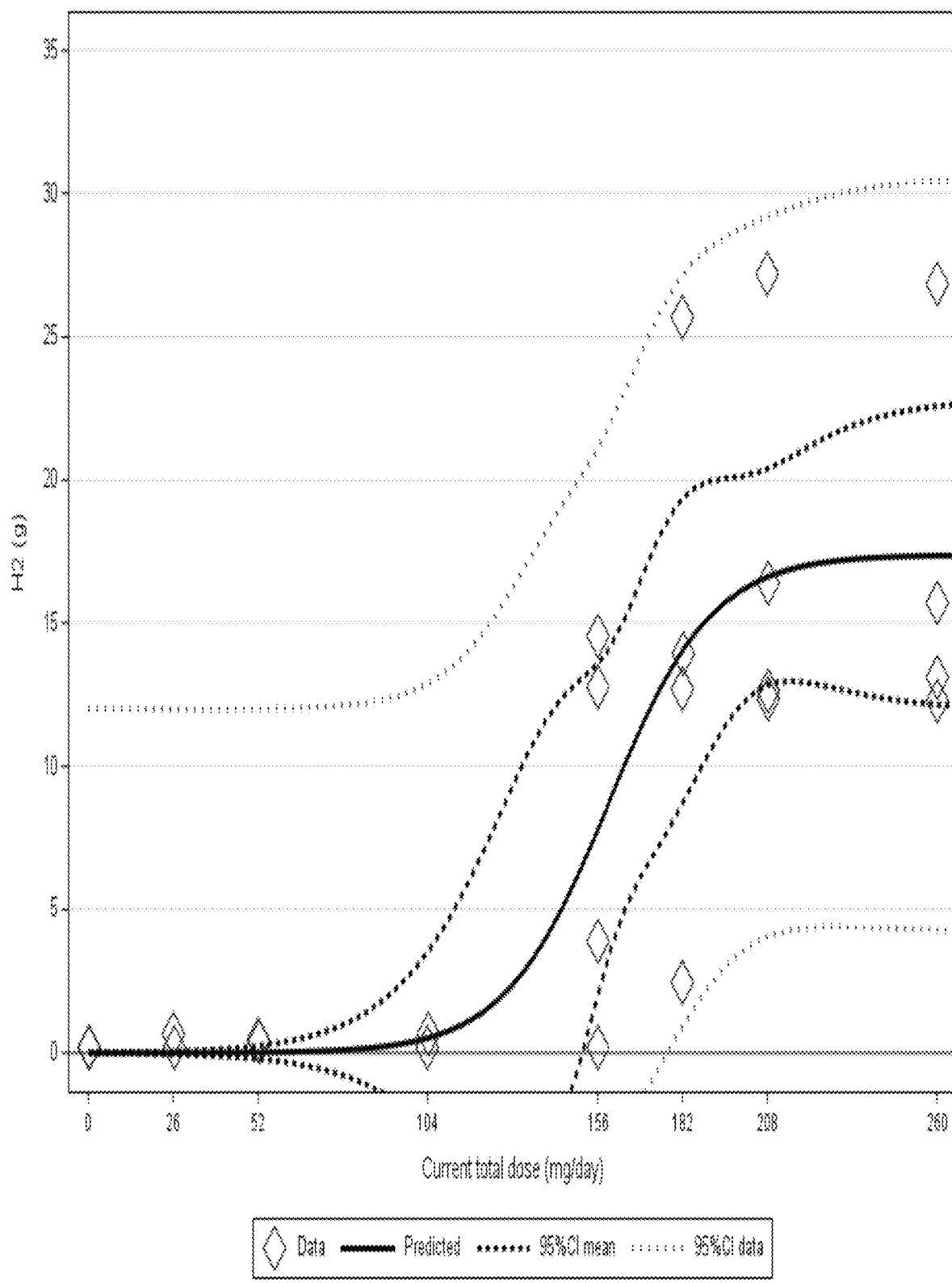

FIG. 37 shows $H_2$ emission from animals versus nominal tribromomethane dose rates administered to the animals-display by means of a non-linear 3-parameter logistic model. The bold line represents the predicted dose response curve. Bold dashed lines delimit the 95% confidence interval for the mean response. Thin dashed lines delimit the 95% confidence interval for all datapoints.

Figure 38:
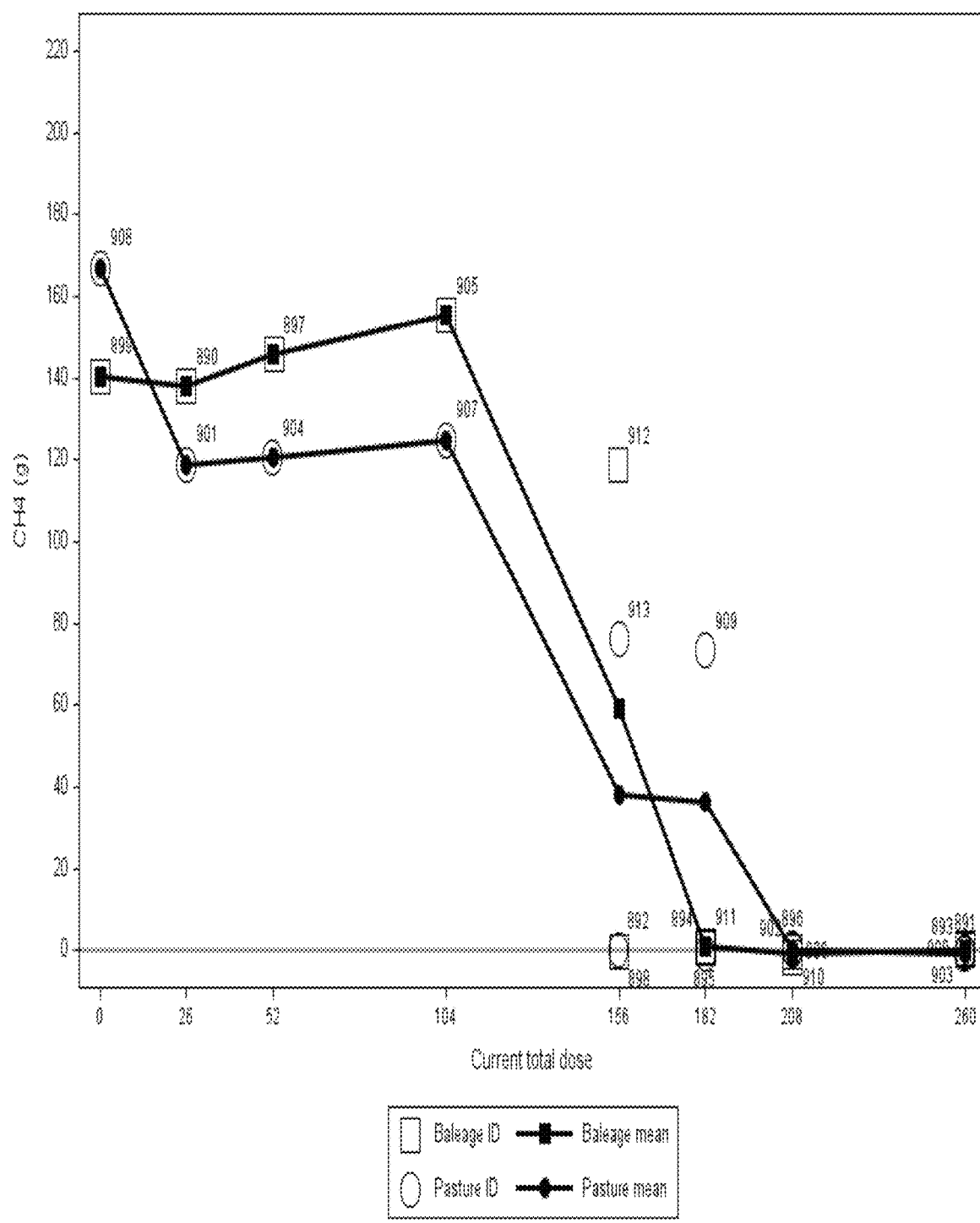

FIG. 38 shows methane production/emission from animals per day versus tribromomethane dose (nominal) administered to the animals for individual animals fed with baleage (squares) and pasture (circles). Filled out symbols connected by lines represent mean values.

Figure 39A:
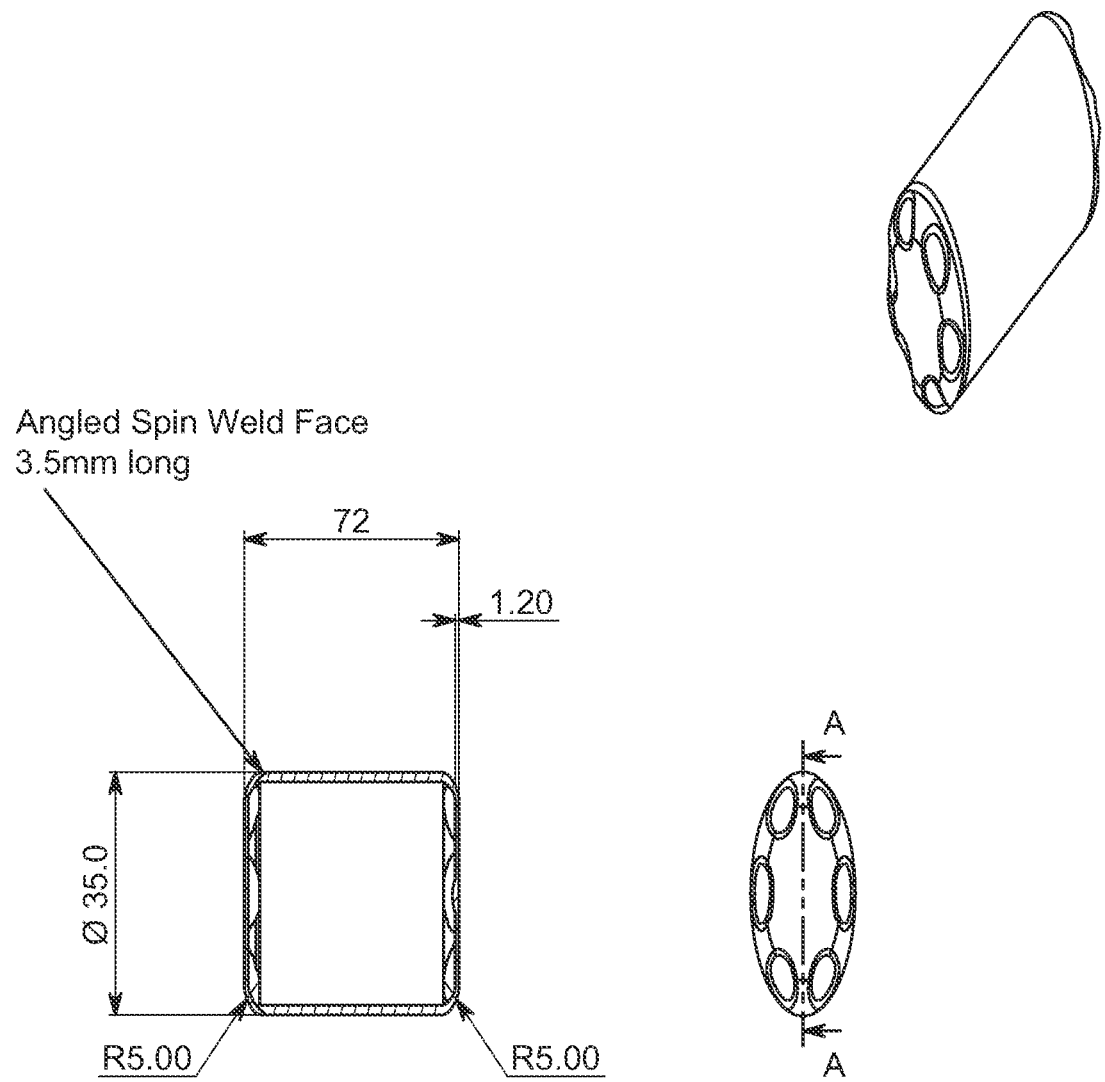
Figure 39B:
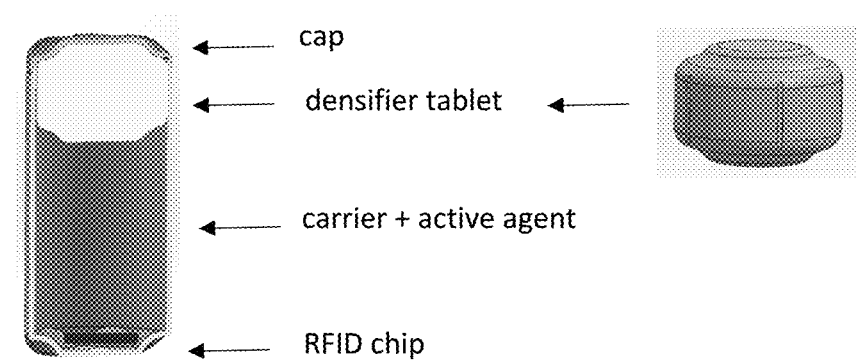

FIGS. 39A-39B show an exemplary, particularly suitable and improved bolus design. FIG. 39A shows an injection moulded bolus housing with top and bottom indents for gripping/holding the cap and housing body to allow closing via spin welding performed with a spin welding device. Depicted is a cross section of the bolus with cap. The image on the top right shows an oblique view of the bolus from the cap end. The bottom right image shows a front on view of the cap of the bolus showing the grip design to facilitate the spin welding and sealing of the bolus. FIG. 39B is a schematic figure of an advantageous bolus construction. Depicted is a cutaway of the bolus, with the densifier tablet located in the top section of the bolus, carrier in the middle to lower portion with a RFID chip at the bottom of the bolus. A densifier tablet is designed to allow air to escape from the bolus by means of vertical channels/groves, when the tablet is placed and optionally pressed down on top of the excipient dough (carrier and active agent) filled into the bolus housing. The RFID chip is an optional component. Said separate densifier tablet shown to the right of the bolus image comprises for instance stainless steel microparticles and paraffin wax. Its convex shape mirrors the shape of the cap that it fits into and has small channels down its sides to facilitate the removal of air as it is pressed down on the carrier contents.

Figure 40:
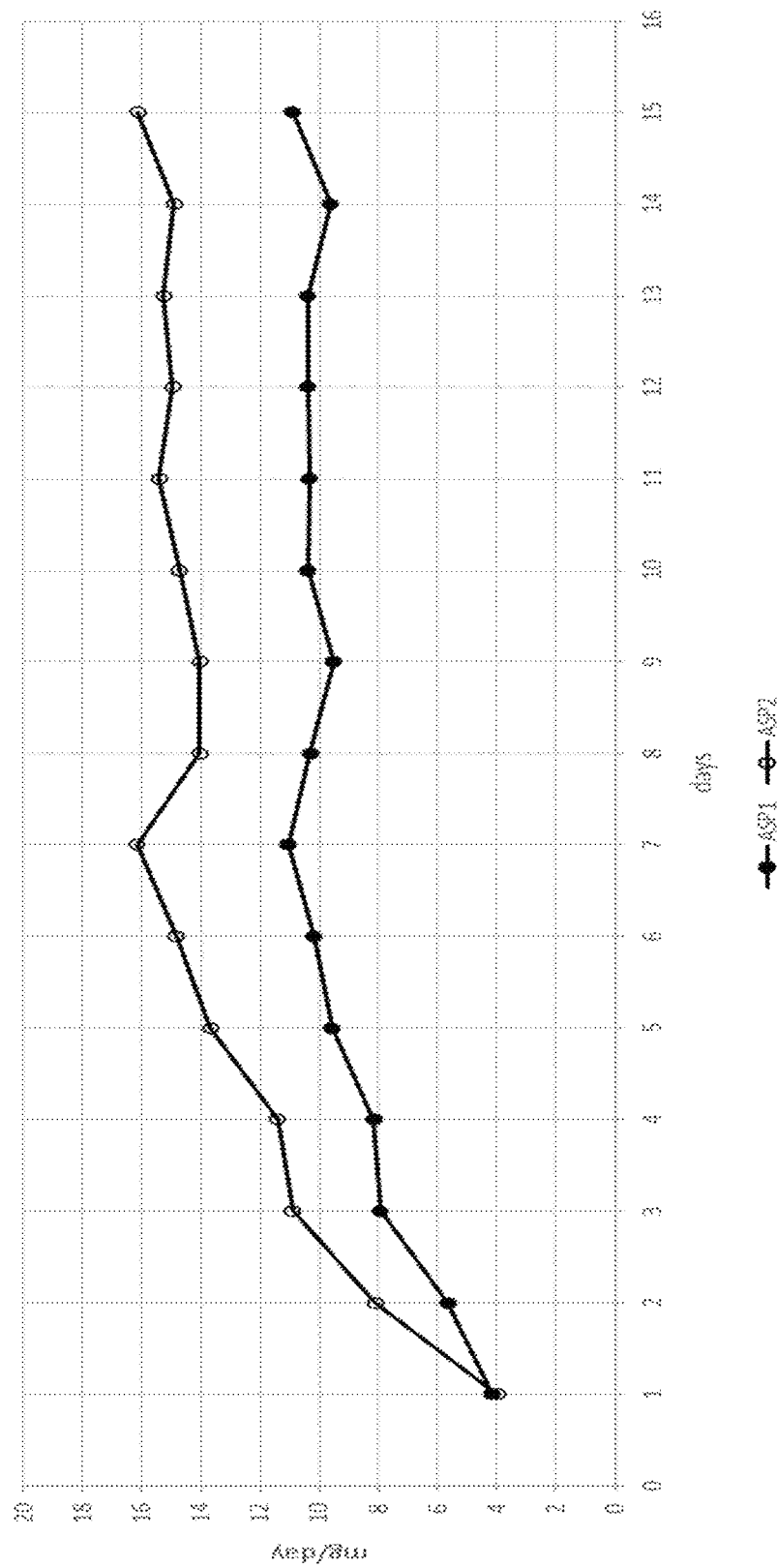

FIG. 40 shows in-vitro tested bromoform release from boluses filled with *Asparagopsis taxiformis* extract as an active agent.

Figure 41A:
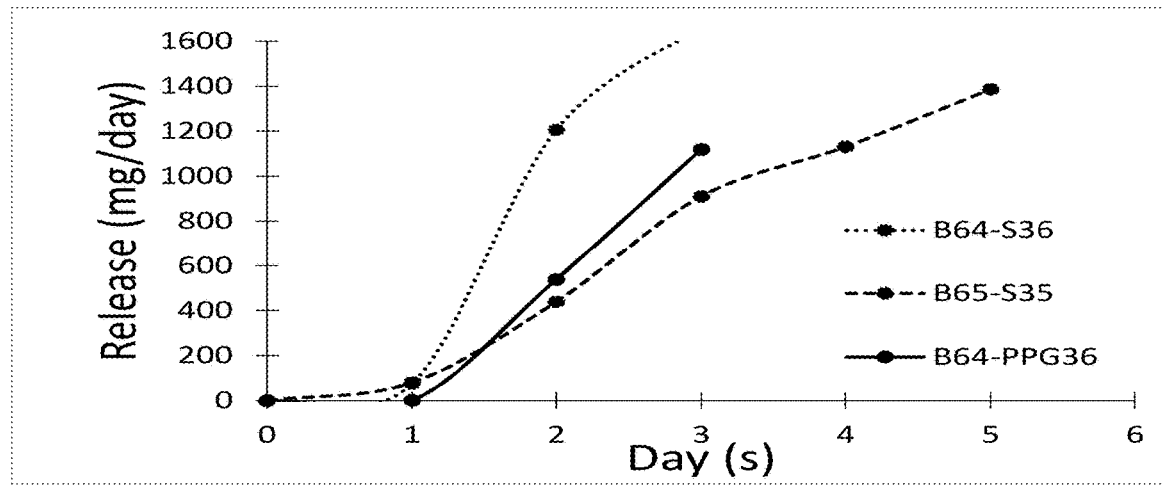
Figure 41B:
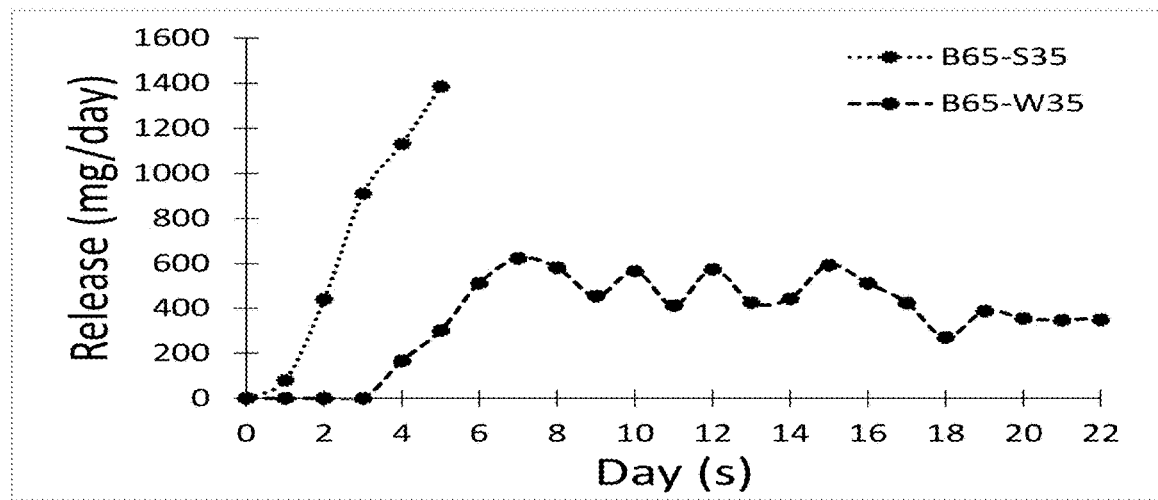
Figure 41C:
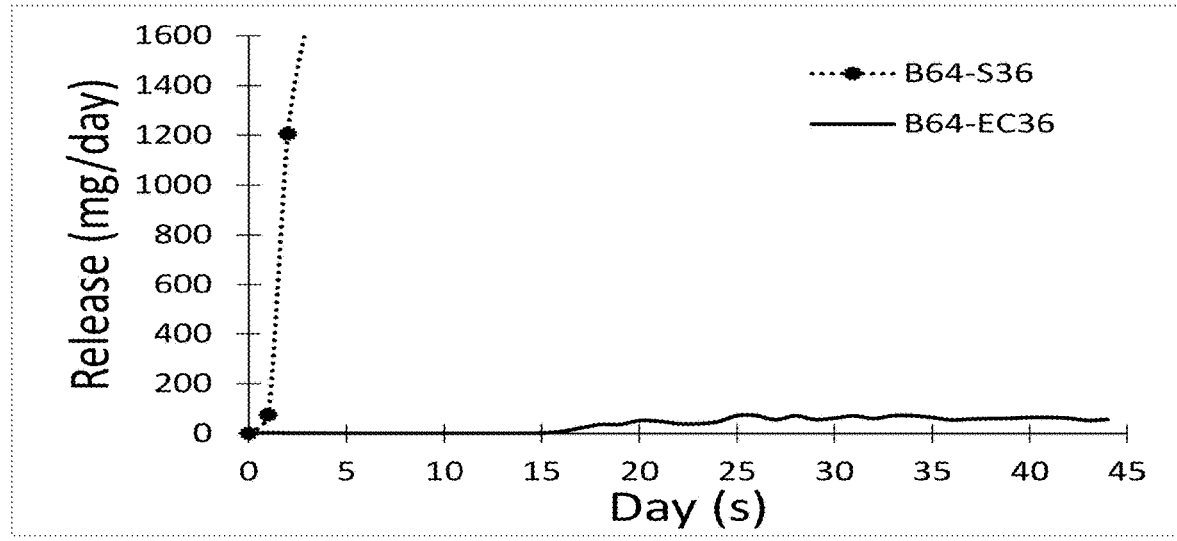

FIGS. 41A-41C show in-vitro release profiles of bromoform from boluses comprising different core formulations. In this figure "B" stands for bromoform, "W" stands for castor wax, "EC" stands for ethyl cellulose, and "S" stands for silica and "PPG" stands for propylene glycol. The number after the abbreviation indicates the amount of the respective substance in % w/w. The bolus housing was in each case a housing comprising PLA/PBAT in a ratio of 90:10. FIG. 41A shows the in-vitro release profile of bromoform from boluses with silica and propylene glycol based formulations containing 64% w/w (boluses B64-S36 and B64-PGG36) and 65% w/w (bolus B65-S35) of bromoform. FIG. 41B shows the in-vitro release profile of bromoform from boluses with silica based (B65-S35) and castor wax based (B65-W35) formulations, each comprising 65% w/w bromoform. FIG. 41C shows the in-vitro release profile of bromoform from boluses with silica based (B64-S36) and ethyl cellulose based formulation (B64-EC36) containing 64% w/w bromoform.

Figure 42A:
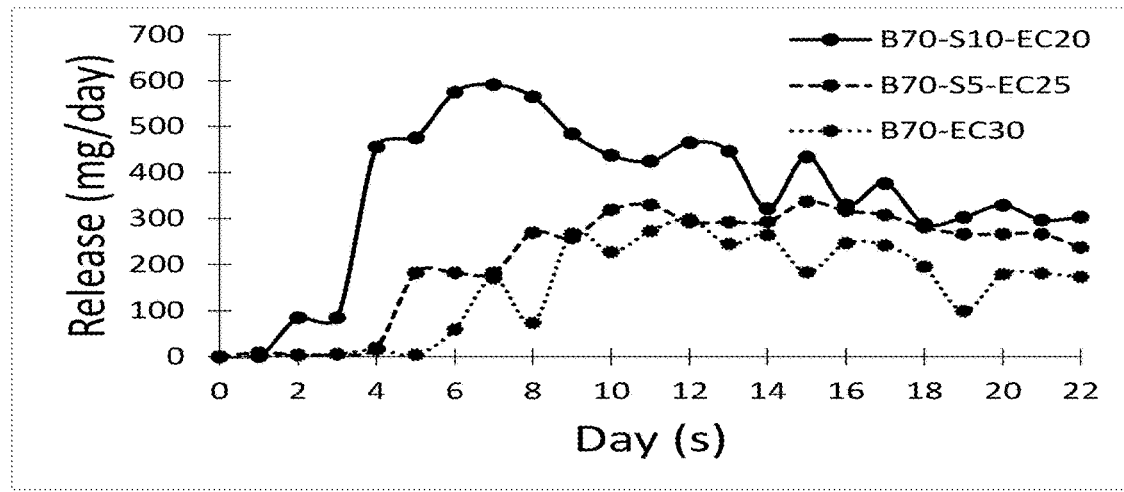
Figure 42B:
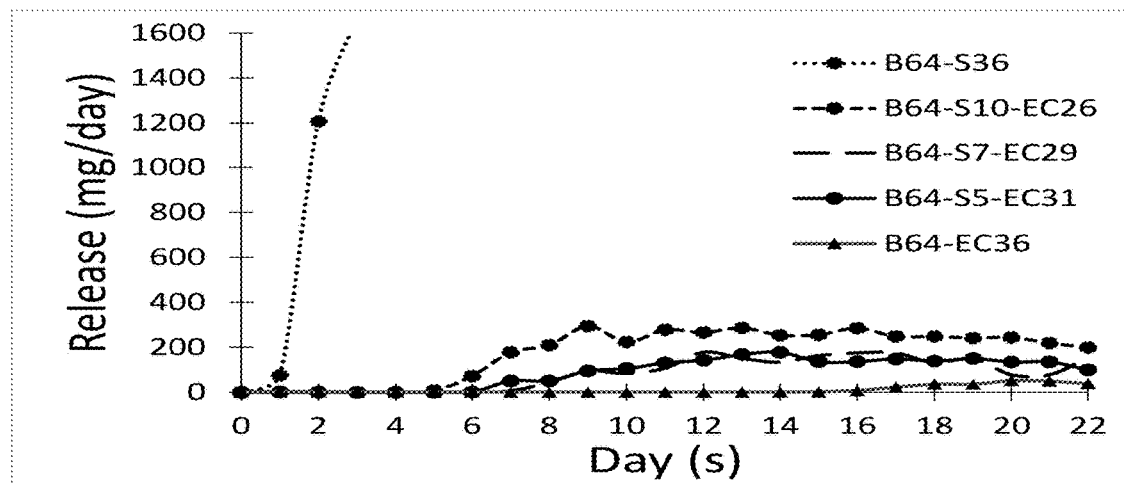
Figure 42C:
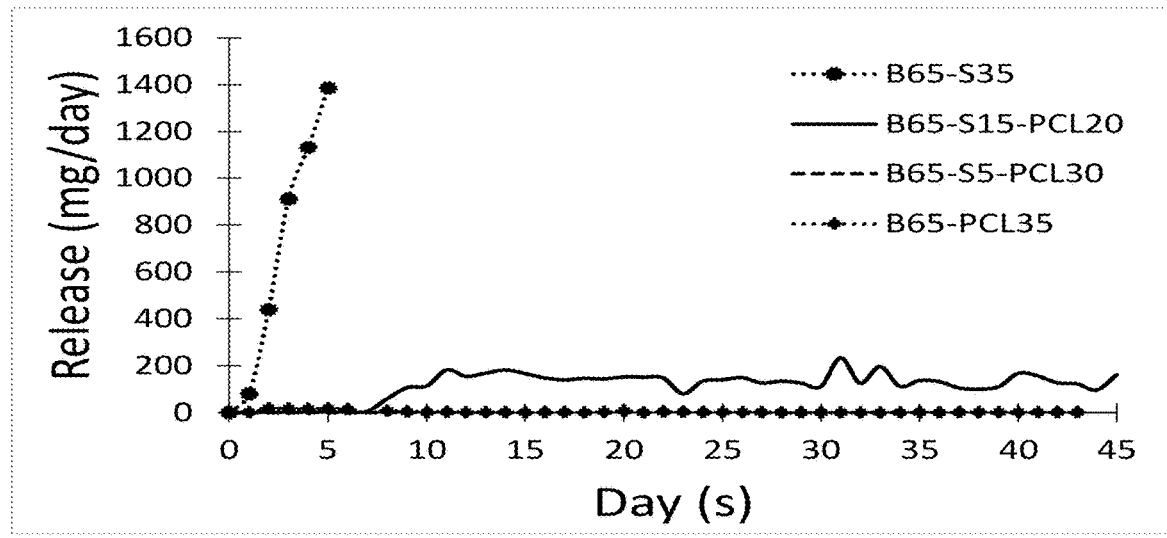

FIGS. 42A-42C show in-vitro release profiles of bromoform from boluses comprising different core formulations. In this figure "B" stands for bromoform, "EC" stands for ethyl cellulose, and "S" stands for silica and "PCL" stands for polycaprolactone. The number after the abbreviation indicates the amount of the respective substance in % w/w. The bolus housing was in each case a housing comprising PLA/PBAT in a ratio of 90:10. FIG. 42A shows the in-vitro release profile of bromoform from boluses with 0% (B70-EC30), 5% (B70-S5-EC25) or 10% (B70-S10-EC20) w/w silica, each loaded with 70% w/w bromoform. FIG. 42B shows the in-vitro release profile of bromoform from boluses with 0% (B64-EC36), 5% (B64-S5-EC31), 7% (B64-S7-EC29), or 10% (B70-S10-EC20) w/w silica each loaded with 64% w/w bromoform. FIG. 42C shows the in-vitro release profile of bromoform from boluses with 0% (B65-PCL35), 5% (B65-S5-PCL30), or 15% (B65-S15-PCL20) w/w silica each loaded with 64% w/w bromoform.

Figure 43:
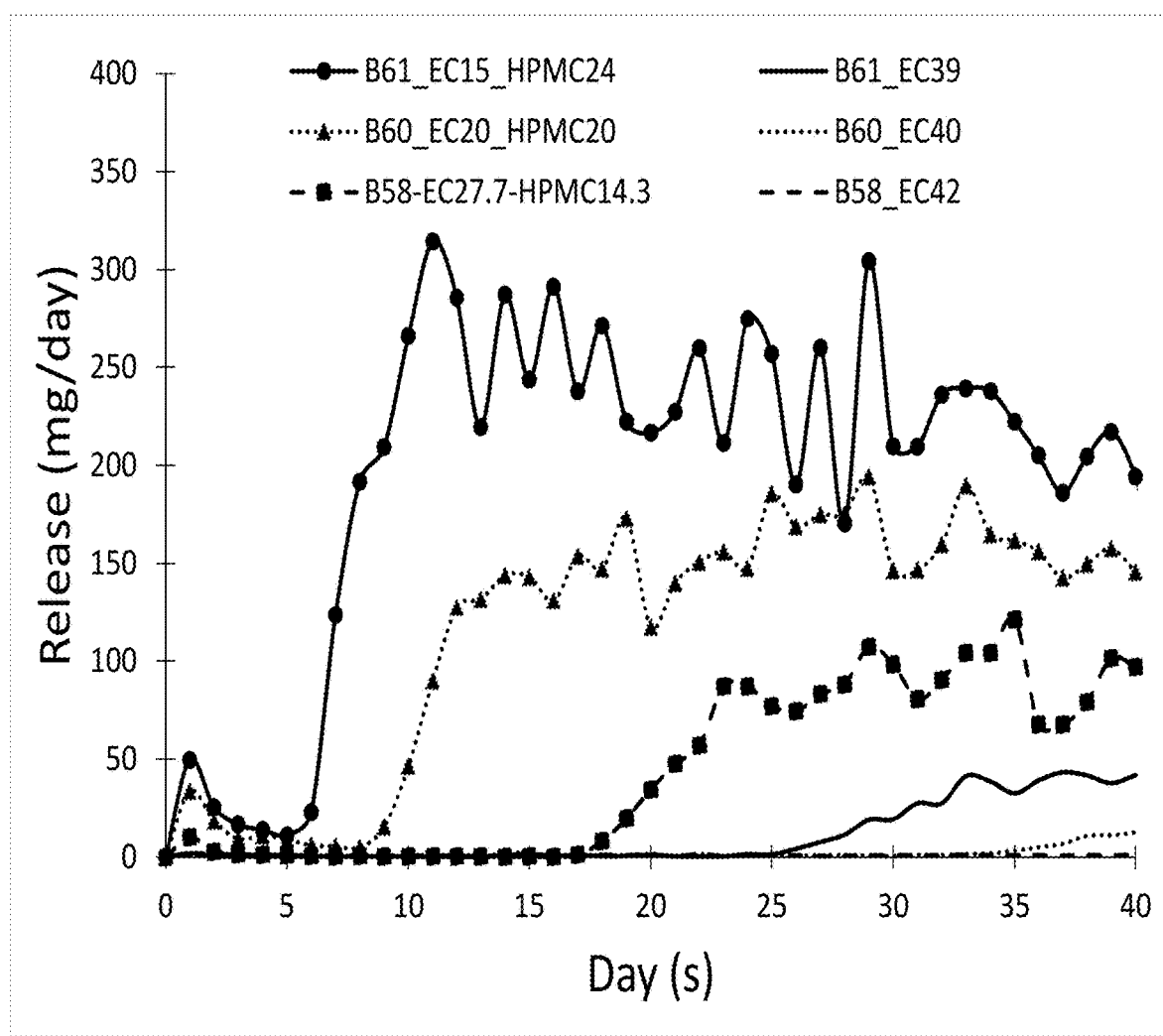

FIG. 43 shows the in-vitro release profiles of different formulations based on ethyl cellulose (EC) and/or hydroxypropyl methyl cellulose (HPMC) in different ratios. In this figure "B" stands for bromoform, "EC" stands for ethyl cellulose and "HPMC" stands for hydroxypropyl methylcellulose. The number after the abbreviation indicates the amount of the respective substance in % w/w. The bolus housing was in each case a housing comprising PLA/PBAT in a ratio of 90:10. Tested formulations are: B61-EC15-HPMC24 (Bromoform/EC/HPMC with w/w % content of 61%/15%/24%), B61-EC39 (Bromoform/EC with w/w % content of 61%/39%), B60-EC20-HPMC20 (Bromoform/EC/HPMC with w/w % content of 60%/20%/20%), B60-EC40 (Bromoform/EC with w/w % content of 60%/40%), B58-EC27.7-HPMC14.3 (Bromoform/EC/HPMC with w/w % content of 58%/27.7%/14.3%) and B58-EC42 (Bromoform/EC with w/w % content of 58%/42%).

Figure 44A:
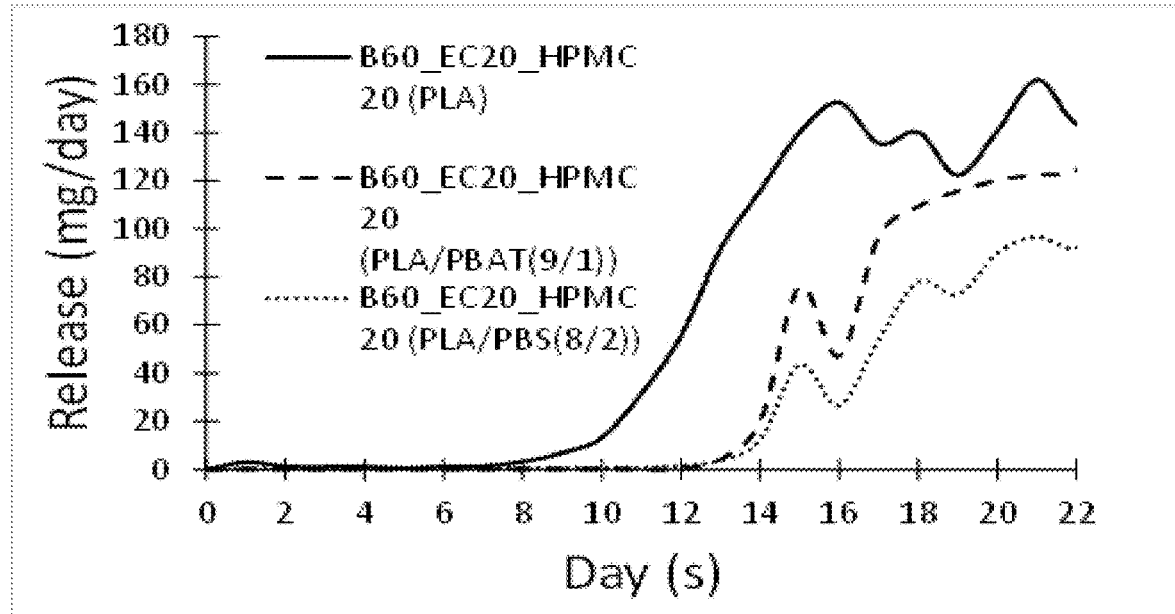
Figure 44B:
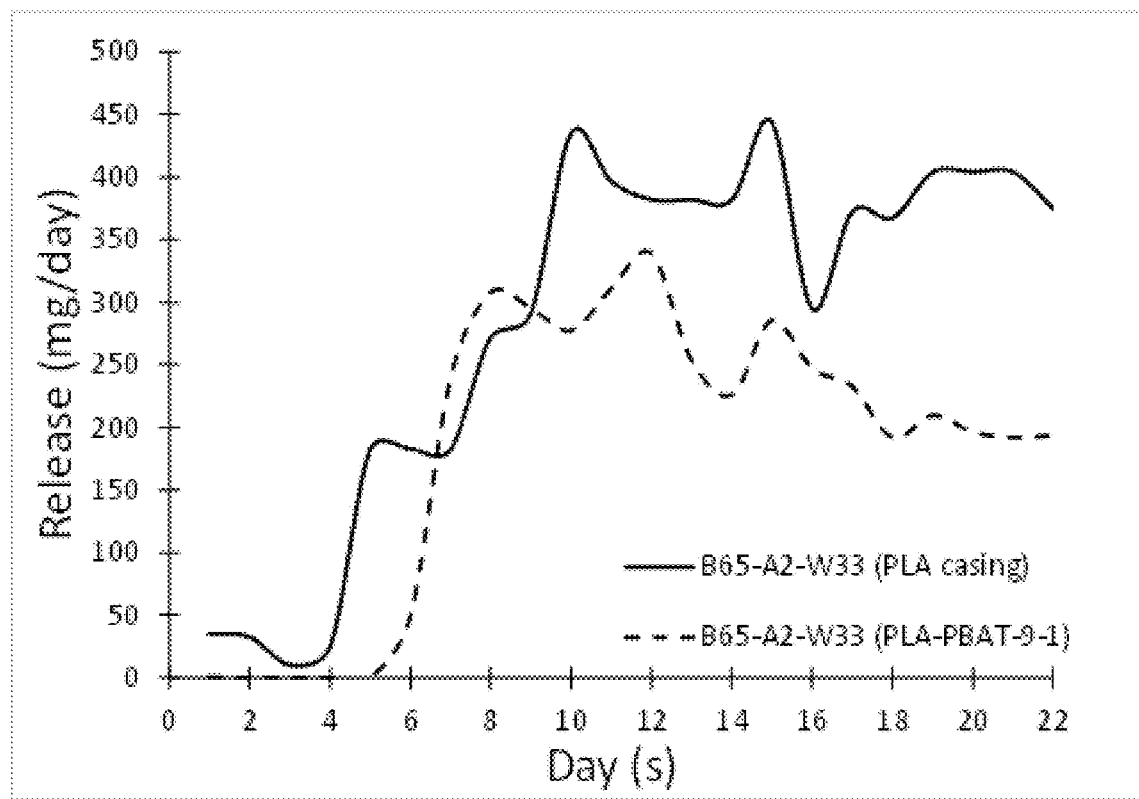
Figure 45:
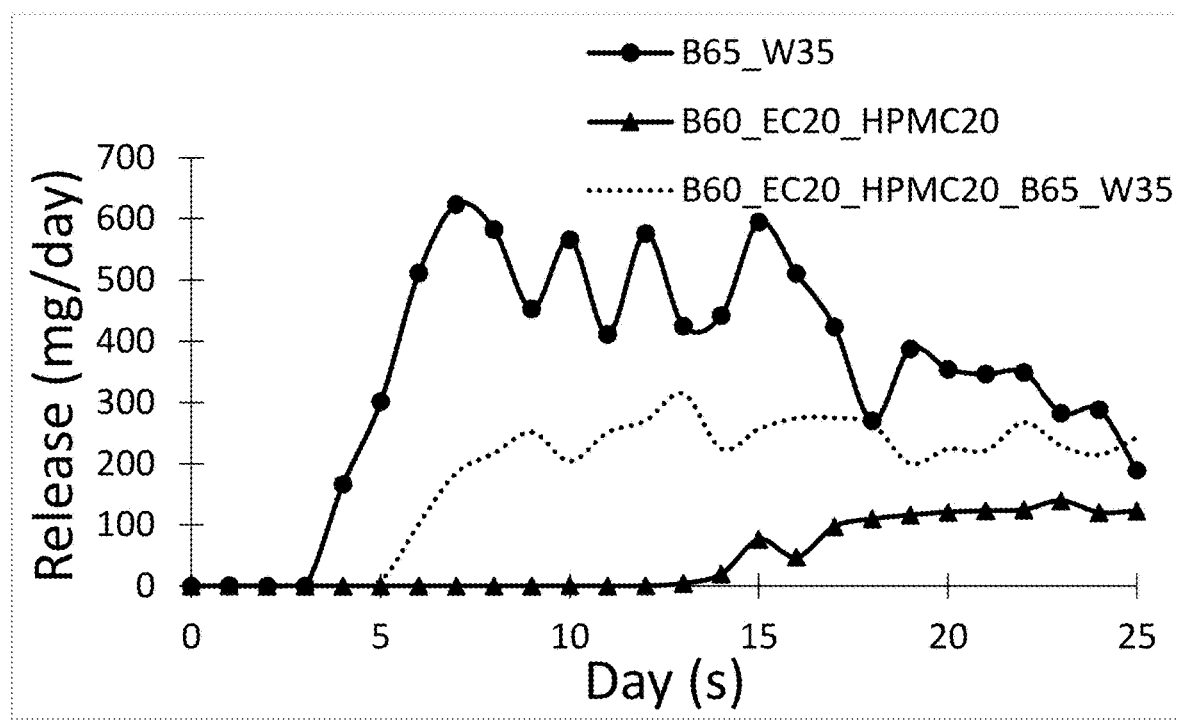

FIGS. 44A-44B show the in-vitro release profiles of bromoform release from boluses with different housing material compositions. In this figure "B" stands for bromoform, "EC" stands for ethyl cellulose, "W" stands for castor wax, "A" is analogous to "S" used in other figures and stands for silica (e.g. Aerosil) and "HPMC" stands for hydroxypropyl methylcellulose. The number after the abbreviation indicates the amount of the respective substance in % w/w. Shown in FIG. 44A is the in-vitro release profile of bromoform from a bolus formulation comprising bromoform 60%, EC 20% and HPMC 20% w/w in a 3D printed PLA casing, in an injection molded PLA/PBAT (90:10) casing, and in an injection molded PLA/PBS (80:20) casing, respectively. FIG. 44B shows the in-vitro release profile of bromoform from a bolus formulation comprising 65%, silica 2% and castor wax 33% w/w in a 3D printed PLA casing or in an injection molded PLA/PBAT (ratio 90:10) casing FIG. 45 shows in-vitro release profiles of two single core boluses B65-W35 (bromoform 65%/castor wax 35% w/w) and B60-EC20-HPMC20 (Bromoform 60%/EC 20%/HPMC 20% w/w) compared to the in-vitro release profile of a dual core bolus B60-EC20-HPMC20_B65-W35, i.e. with one half being a bolus segment comprising bromoform 60%/EC 20%/HPMC 20% w/w and the other half being a bolus segment comprising bromoform 65%/castor wax 35% w/w. In this figure "B" stands for bromoform, "W" stands for castor wax, "EC" stands for ethyl cellulose, and "HPMC" stands for hydroxypropyl methylcellulose. The number after the abbreviation indicates the amount of the respective substance in % w/w. The bolus housing was in each case a housing comprising PLA/PBAT in a ratio of 90:10.

DETAILED DESCRIPTION

The present invention relates to devices and methods to deliver substances to animals, particularly hydrophobic substances to animals. In preferred forms, the substance is an inhibiting agent such as a methane inhibitor. The present invention is exemplified with reference to a preferred embodiment. However, this should not be seen as limiting on the scope of the invention. One skilled in the art would understand how to apply the teachings herein to devices for delivery of other substances to animals.

Figure 1A:
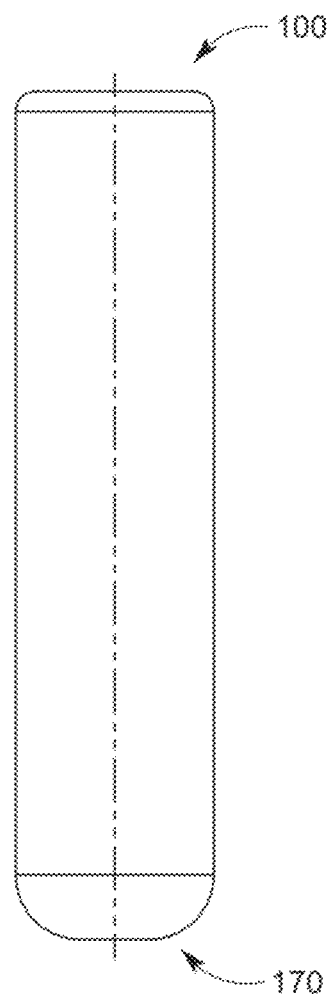
FIG. 1A is a front view of an exemplary bolus according to some embodiments of the invention.
Figure 1B:
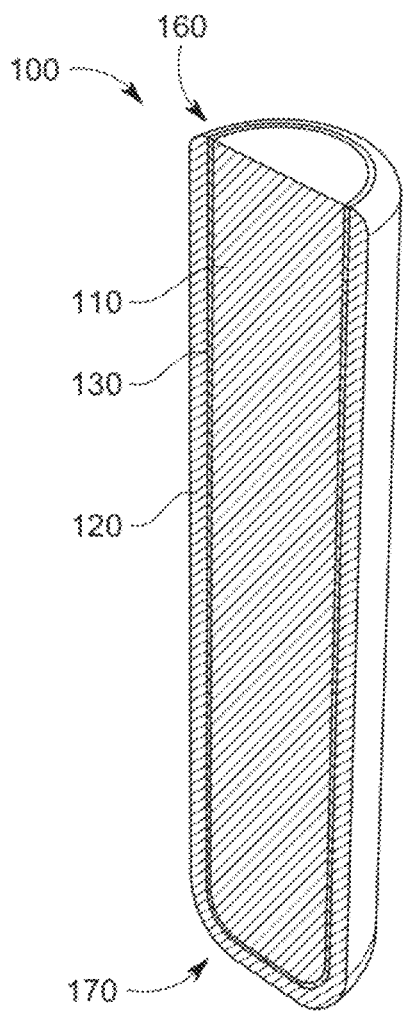
FIG. 1B is a perspective cross sectional view of the bolus of FIG. 1A.

Referring first to FIGS. 1A and 1B, there is provided a bolus (100). The bolus (100) is configured to reduce or eliminate release of one or more greenhouse gases ("GHGs") from a ruminant animal. For instance, the bolus (100) may reduce or eliminate production of GHGs by the ruminant animal, and therefore reduce the gases which are released by the animal.

In addition, or in the alternative, the bolus (100) may improve animal production by preventing the conversion of feed into one or more GHGs from a ruminant animal. The bolus (100) includes a core (110) and a housing (120).

In some embodiments, the bolus (100) also includes a barrier layer (130). The barrier layer (130) is configured to separate the core (110) from the housing (120).

The housing (120) is generally cylindrical and has an open end indicated generally as (60), and a rounded, closed end (170). The open end (160) can allow fluids in the ruminant animal's rumen to contact the core (110).

Further aspects of the bolus (100) should become clearer from the following discussion.

Core

The core (110) includes at least one inhibiting agent, which can be optionally mixed with a suitable carrier(s). Particularly preferred carriers include PEG4000, PEG400, natural and synthetic waxes, fatty acids, fatty alcohols, fatty amines, phospholipids-lecithin, and adsorbents, and combinations thereof.

Suitable waxes include beeswax, paraffin, castor wax, Carnauba wax, Candellila wax, Jojoba wax, and Lanolin.

In addition, minerals such as zeolite, bentonite, kaolin, activated carbon or a combination thereof may also be suitably mixed with the inhibiting agent. It is also possible to include other compounds such a zinc (i.e. in powdered form) or zinc oxide.

Alternatively, the core (110) may include a concentrated (substantially pure) form of the inhibiting agent.

In a preferred embodiment, the inhibiting agent is a methane inhibiting agent. Particularly preferred forms include haloforms e.g. halomethanes such as bromoform ($CHBr_3$)— as is discussed in more detail below.

It should be appreciated by a person skilled in the art that other carriers may be selected or used depending on the application. It is envisioned that certain carriers can be selected in order to provide a desired release profile for the inhibiting agent, or alternatively provide the desired physical properties of the core material-density or volume etc.

In preferred embodiments the carrier used in the present invention is a natural waxy substance, with a preferred melting point between 50-90° C., or more preferably 60-80° C.

It was found by the inventors that having a carrier with this melting point range allowed for melting of the carrier and mixing with the inhibiting agent(s) to form a homogenous core (110), and to subsequently solidify at room temperature.

A particularly preferred carrier is a mixture containing castor wax with one or more of paraffin wax, beeswax, and carnauba wax. Further preferred, the carrier is a mixture containing castor wax and paraffin wax.

It should be appreciated that the ratio of carrier to inhibiting agent may be chosen to optimise the function of the bolus (100) e.g. to suit the desired release profile for the inhibiting agent(s).

When formed, the core (comprising both the carrier and inhibiting agent(s)) preferably has a melting point of at least 45° C. Having this minimum melting point will assist with ensuring that the core (110) does not melt when the bolus (100) has been administered to the ruminant animal. In addition, it will assist to ensure that the bolus (100) is unlikely to melt on inadvertent exposure to elevated temperatures e.g. those temperatures that could reasonably be experienced during transport and/or storage.

It should be appreciated that the range of melting points for the core (110) may be adapted by varying the ratio of inhibiting agent(s) to carrier forming the core (110).

A preferred ratio of inhibiting agent to carrier may include substantially 80:20 w/w % to substantially 50:50 w/w %, or preferably substantially 70:30 w/w % to substantially 60:40 w/w %, or more preferably substantially 66:33 w/w %.

Additional preferred embodiments of the core are also disclosed in the claims of this patent application and outlined further above and below.

Inhibiting Agent(s)

In a preferred embodiment, the inhibiting agent is one or more methane inhibiting compounds such as a haloform. The most preferred methane inhibiting agent is bromoform.

Suitable methane inhibitors include haloforms such as bromoform, chloroform, iodoform and combinations thereof. It is envisioned that any methane inhibitor that is suitable for internal administration to a ruminant animal may be used with the present invention.

The inventors have surprisingly found that bromoform is a particularly well suited for use in a bolus (100) according to the present invention. Accordingly, reference herein will be made to the inhibiting agent(s) as bromoform. However, this should not be seen as limiting on the scope of the present invention as alternatives are also envisaged as being within the scope of the present invention.

Bromoform is reactive and has a short half-life in animals (0.8 hrs in rats, 1.2 hours in mice, US Dept of Health, 2003). It is a liquid at room temperature and is denser than water. Previous trials demonstrated no residues in meat and tissue from slaughtered steers, after 48 hour with holding period (Kinley et al. Mitigating the carbon footprint and improving productivity of ruminant livestock agriculture using a red seaweed, *Journal of Cleaner Production* 259 (2020) 120836), and no significant increase in the level in milk (Roque et al. Inclusion of *Asparagopsis armata* in lactating dairy cows' diet reduces enteric methane emission by over 50 percent; *Journal of Cleaner Production* 234 (2019) 132-138).

Bromoform has a relatively high efficacy e.g. effect per administered dose. This enables sufficient quantities to be provided in a core (110) to manufacture a bolus (100) which can deliver controlled release of the inhibiting agent over an extended term.

Additionally, bromoform also has a relatively high density. This can assist with achieving a higher retention of the bolus (100) in the rumen, as the density of the bolus can be optimised to promote the bolus (100) sinking to the ventral part of the rumen, rather than floating.

The above points notwithstanding, there is a prevailing concern about using bromoform in animals. The compound is thought to have adverse effects such as being carcinogenic at certain exposure levels.

In addition, there are technical challenges which exist when bromoform is administered to animals. These include the volatility of the substance, and its ability to dissolve substances which could be used for its delivery. Furthermore, achieving a precise (and relatively low) dose rate over a period of time is a challenge.

Housing

The housing (120) includes a cavity (not numbered in the Figures) which is sized and dimensioned to receive the core (110). The housing (120) forms the external structure of the bolus (100).

The housing (120) is configured to provide structural integrity for the bolus (100) but yet is also adapted to degrade over time. Degradation of the housing (120) can facilitate release of the inhibiting agent over the predetermined period of time.

The housing (120) is preferably non-toxic and resists erosion in the rumen of the ruminant for a sufficient period of time to facilitate release of inhibiting agent from the core (110) at the desired rate. It should be appreciated by the person skilled in the art that the dissolution rate of the housing (120) and the core (110) can be configured to allow the controlled release of the inhibiting agent in the ruminant animal's rumen.

Preferably, the housing (120) is composed of a biodegradable, non-absorbent material, or a material which is otherwise compatible with waste disposal in slaughter facilities. It should be appreciated that any material that is suitable for internal administration to a ruminant animal with the desired dissolution rates can be used with the present invention.

In a preferred embodiment, the housing (120) is preferably selected from a biodegradable material, particularly preferred biodegradable materials include polymers such as polylactic acid (PLA), polyglycolic acid (PGA), polylactic glycolic acid (PLGA), polypropylene, SLA polymer, PBS and combinations thereof. In a particularly preferred embodiment, the housing (120) is made of a material comprising PLA and PBAT.

In a preferred embodiment the housing (120) is composed of PLA. PLA is available in three forms, D-, L- and a racemic mixture of both D and L. All three types of PLA may be used in the housing (120) of the present invention.

In a preferred form, PLA is preferred as it degrades into lactic acid and is commonly used as medical implants. Depending on the type of PLA used, PLA breaks down inside the body within six months to two years.

It should be appreciated by the person skilled in the art that other suitable biodegradable materials can be used as the housing (120).

In an optional embodiment, further fillers, binders, surfactants, active agents and/or absorbents may be included in the bolus of the present invention.

As can be seen in FIGS. 1A and 1B, the bolus (100) has a substantially cylindrical form. The housing (120) includes a smooth external surface to assist with ingestion of the bolus (100) by the ruminant animal.

It should be appreciated by the person skilled in the art that the size, thickness and/or dimensions of the bolus (100), including the core (110), barrier layer (130) if provided, and the housing (120) can be adjusted depending on the dose of inhibiting agent to be delivered to the ruminant, without departing from the spirit and scope of the invention. For example, a smaller size bolus (100) can be adapted for use in smaller ruminant animals such as sheep or goats, while a larger sized bolus (100) can be used in larger ruminant animals such as cattle. A bolus for a large animal, such as cattle, may have the dimensions of 13 cm length, 3.4 cm diameter and 257 gm in weight (Throughout the application "gm" refers to gram). A bolus for a relatively small animal, such as a sheep, may have the dimensions of 8.5 cm length, 2 cm diameter and 60 gms in weight. Alternatively, a smaller bolus may be administered to a relatively larger ruminant animal, such as cattle; such a relatively smaller bolus may have the dimensions of 3.4-3.8 cm length and 2.6-3.0 cm diameter.

In it also envisaged that multiple smaller boluses may be used in combination. In preferred embodiments, the bolus and the delayed dosage form of the invention has a length of at least 5 cm and most preferably a length of at least 10 cm, preferably 10.3 cm. In preferred embodiments, the bolus and the delayed dosage form of the invention has a diameter of at least 2 cm, preferably 3.4 cm and a length of at least 10 cm, preferably 10.3 cm. Preferably, the bolus and the delayed dosage form of the invention has a weight of at between 100 and 300 grams.

Additionally, the housing (120) may also be configured to control the release rates of the core (110) and/or degradation of the bolus (100). For example, the internal cross-sectional area of the cavity may be adapted to control the amount of the core (110) present in the bolus (100). In such an embodiment, the internal volume of the cavity may be adapted to increase in size from the open end (160) to the closed end (170). This may be useful for increasing the amount of inhibiting agent(s) over time. This may account for animal growth where feed intake of the animal increases.

Additionally, or alternatively, the cross-sectional thickness of the wall(s) forming the housing (120) may increase along the length of the housing (120). For instance, the wall(s) may be a thicker at one end of the housing (120) than the other. In such an embodiment, the thickness of the wall at the open end (160) may be thinner in size than towards closed end (170). This can assist with providing controlled dissolution of the core formulation from the bolus.

Additional preferred embodiments of the housing are also disclosed in the claims of this patent application and outlined further above and below.

Barrier Layer

The barrier layer (130) is an optional component of the bolus (100) of the present invention and may be included to provide additional stability to the bolus (100). The barrier layer (130) can be configured to partially or completely prevent contact between the core (110) and the housing (120). The barrier layer (130) is preferably selected from a waxy material, epoxy or a silicon material.

It should be appreciated by the person skilled in the art, the barrier (130) layer may be selected dependent on the desired application and/or release profile. For example, where further control of the release rate of the inhibiting agent is desired, choosing a barrier layer (130) material, shape and configuration can facilitate obtaining the desired release profile.

Exemplified Composition

As an exemplified embodiment, the bolus may comprise a core enclosed by a housing. The bolus may be about 13 cm in length and about 3.4 cm in diameter with an approximate weight of 257 gm.

The housing may be made of PLA (3052D, 3001D, 3251D, L130, etc), e.g. by injection moulding, and have a thickness of 1 mm.

The matrix of the core may be made of a blend of castor wax and paraffin wax in a ratio of 50:50 (by weight). This matrix may contain bromoform as an inhibiting agent in a concentration of about 50% (by weight).

Further exemplified embodiments of the housing material are described in the examples provided herein.

Method of Treatment

The bolus (100) is delivered orally into the rumen of the ruminant animal to be treated, entering the rumen via the oesophagus. In the rumen, stomach fluids (and other matter such as plant fibre mat) act to eventually erode or dissolve the core (110) to release the inhibiting agent over time. However, for the duration of the treatment period, the housing is substantially intact.

The open end (160) allows stomach fluids and fibrous matter to come into contact with the core (110). In addition, it assists to control release of the core (110) therefrom to the rumen.

The core (110) and the housing (120) are designed to facilitate release of the inhibiting agent over a period of time for which an animal is to be treated according to a method disclosed herein.

The bolus (100) is adapted to release the inhibiting agent over a period of at least six months, preferably 12 months, and potentially up to two years.

Preferably, the release rates of the inhibiting agent may be calculated based on the weight of the ruminant animal to be treated and the type of inhibiting agent used. As such, it will be appreciated that the desired release rates may vary from animal to animal. Typically, the desired release rates may be calculated on an amount of inhibiting agent/weight of animal. Alternatively, the desired release rates may also be calculated based on the amount of feed consumed by the animal. Particularly preferred release rates for bromoform include from approximately 0.1-approximately 0.5 g/day, and more preferably approximately 0.2 g/day.

Additionally, it should be appreciated by a person skilled in the art that a ruminant animal can be treated by multiple boluses (100) according to the present invention in order to achieve a preferred dosage of the inhibiting agent. This can allow a bolus (100) to be manufactured which has a concentration and total load of the inhibiting agent. Multiple of those bolus (100) can be administered to an animal concurrently or sequentially. This will allow the desired dosage to be provided to the animal. This can be particularly beneficial to allow the bolus (100) to be used with animals requiring different doses of inhibiting agent e.g. larger or smaller animals, or to compensate for natural growth over time.

The bolus (100) is adapted to deliver a dose of inhibiting agent directly into the rumen of the animal. For instance, bromoform may be released at a rate at which it can effectively reduce or eliminate methane production during digestion. That will reduce the emission of greenhouse gases by the animal and therefore reduce the environmental impacts of agriculture.

In addition, the bolus (100) may improve the ruminant's conversion of feed for animal production. For example, by reducing methane production during digestion, it is believed that this may lead to more efficient utilization of ingested feed, and result in improved growth and weight gain, or other production such as milk production. In addition, the compositions for the core and synergistic effects arising from the combination of carrier and inhibiting agent(s) may enable the provision of a slow-release, long term delivery device to improve animal productivity and/or reduce emission of greenhouse gases.

First Alternate Housing Embodiment

Figure 2A:
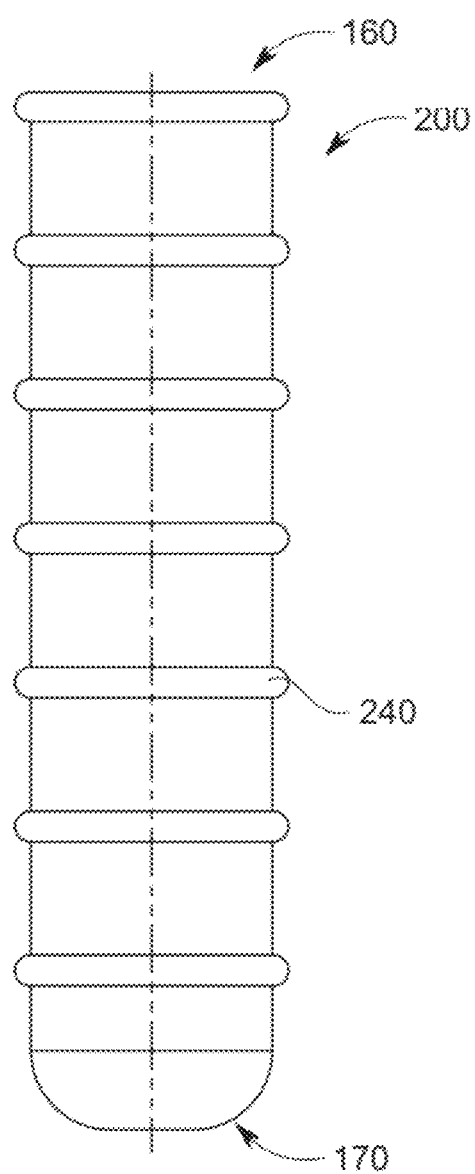
FIG. 2A is a front view of an alternative embodiment of a bolus according to some embodiments of the invention.
Figure 2B:
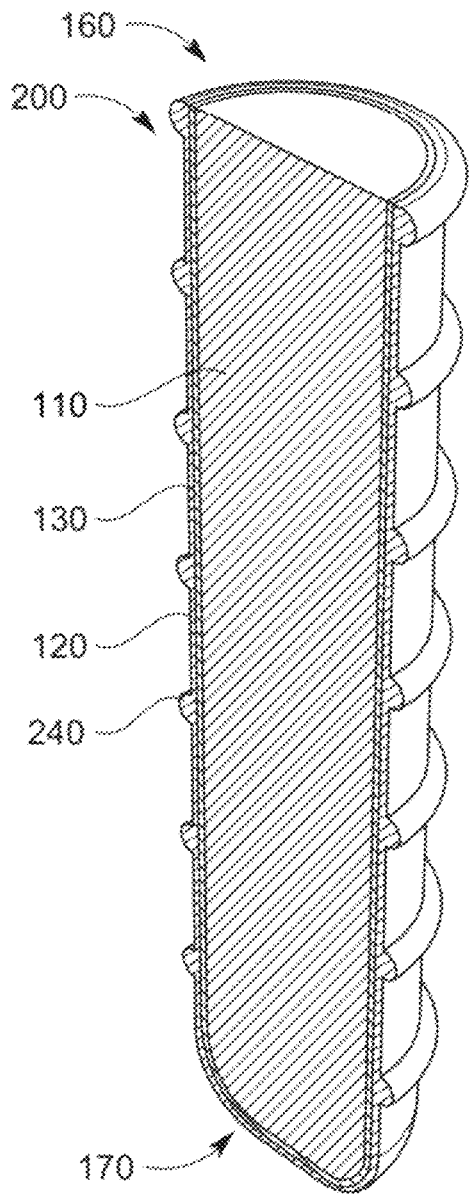
FIG. 2B is a perspective cross sectional view of the bolus of FIG. 2A.

Referring now to FIG. 2A-2B which shows an alternative embodiment of a bolus (200) according to an embodiment of the invention.

Aspects of the bolus (200) are similar to those of the bolus (100), and therefore like references refer to like components.

A series of ribs (240) are provided along an external surface of the housing (120). The ribs (240) may provide additional structural strength to the bolus (200), and can assist to prevent it rupturing if the core (110) were to swell. Additionally, or alternatively, the (240) ribs may also assist the administration of the bolus (200) to the ruminant animal.

As illustrated, the ribs (240) are provided as a series of concentric "hoops". However, the ribs (240) could be a series of parallel or non-parallel ribs (not illustrated) which extend along the length of the bolus (200)

Second Alternate Housing Embodiment

Figure 3A:
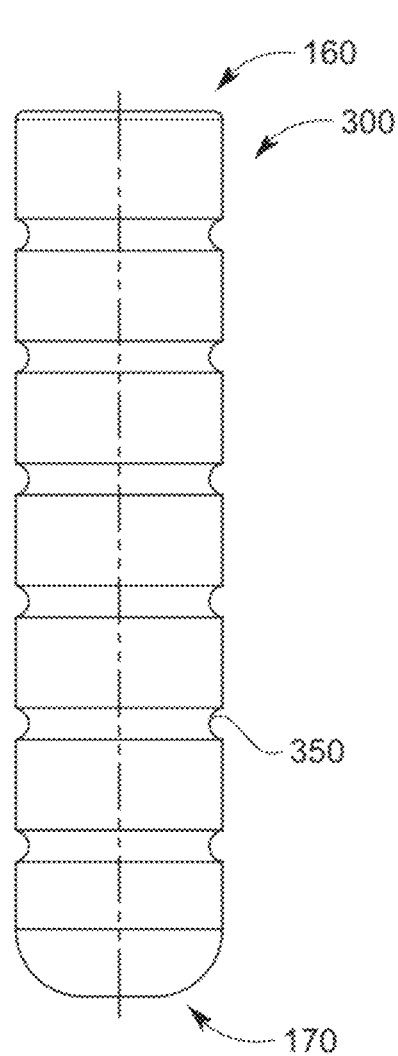
FIG. 3A is a front view of an alternative embodiment of a bolus according to some embodiments of the invention.
Figure 3B:
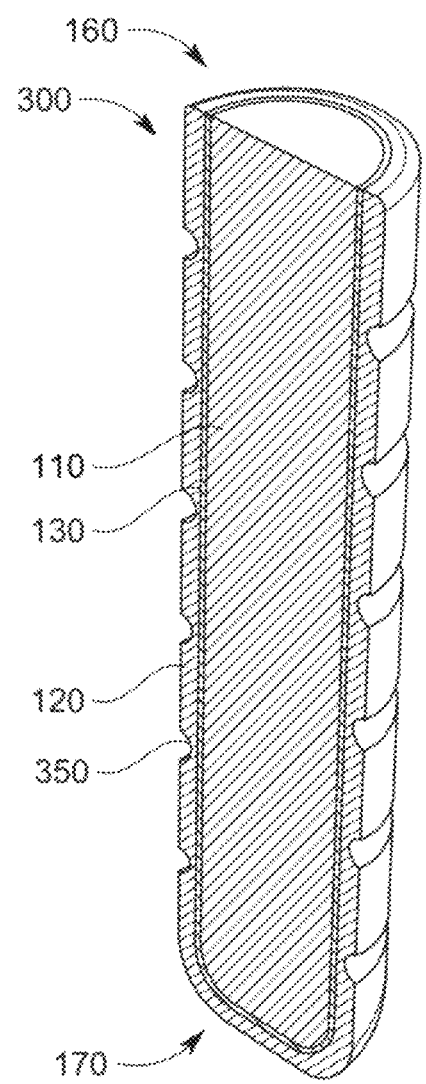
FIG. 3B is a perspective cross sectional view of the bolus of FIG. 3A.

Referring now to FIGS. 3A-3B which show an alternative embodiment of a bolus (300) according to an embodiment of the invention.

Aspects of the bolus (300) are similar to those of the bolus (100) described above, and therefore like references refer to like components.

The bolus (300) includes additional features on the external surface of the housing (120), including depressions or grooves (350).

The grooves (350) may promote portions of the housing (120) breaking away as it degrades. This can be used to further control the release profile for the inhibiting agent.

Third Alternate Housing Embodiment

Figure 4A:
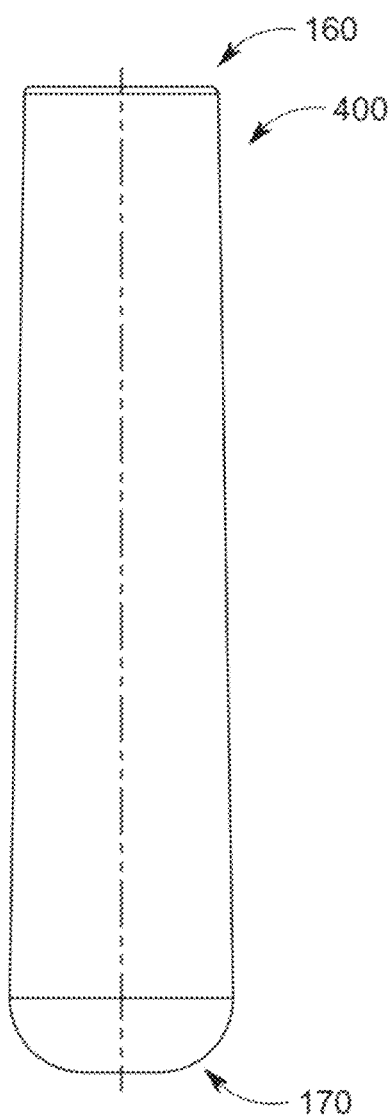
FIG. 4A is a front view of an alternative embodiment of a bolus according to some embodiments of the invention.
Figure 4B:
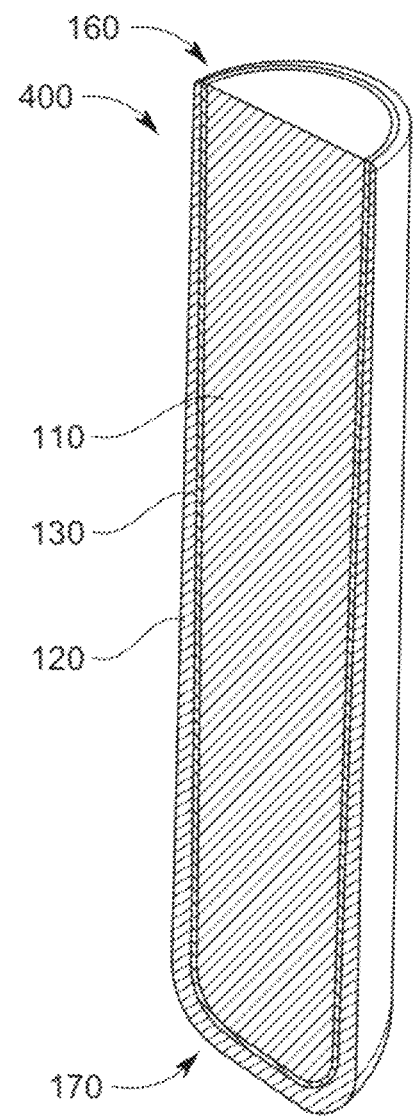
FIG. 4B is a perspective cross sectional view of the bolus of FIG. 4A.

Referring now to FIGS. 4A-4B which show an alternative embodiment of a bolus (400) according to an embodiment of the invention.

Aspects of the bolus (400) are similar to those of the bolus (100) described above, and therefore like references refer to like components.

The bolus (400) includes a housing (120) which has a cavity (not illustrated in the Figures) that is configured to receive and hold the core (110).

The housing (120) tapers along its length. For instance, the distance between the external surfaces of distal sides of the housing (120) increases along the length of the bolus (400). For instance, as is indicated in FIG. 4A, the width (X) is less than the width (Y).

Alternatively, the bolus (400) may have side walls of substantially constant thickness, but which are structured and orientated to define a taper for the bolus (400).

This configuration may allow for better controlled degradation of the core (110) and thereby provide additional control for release of the inhibiting agent.

Fourth Alternate Housing Embodiment

Figure 5:
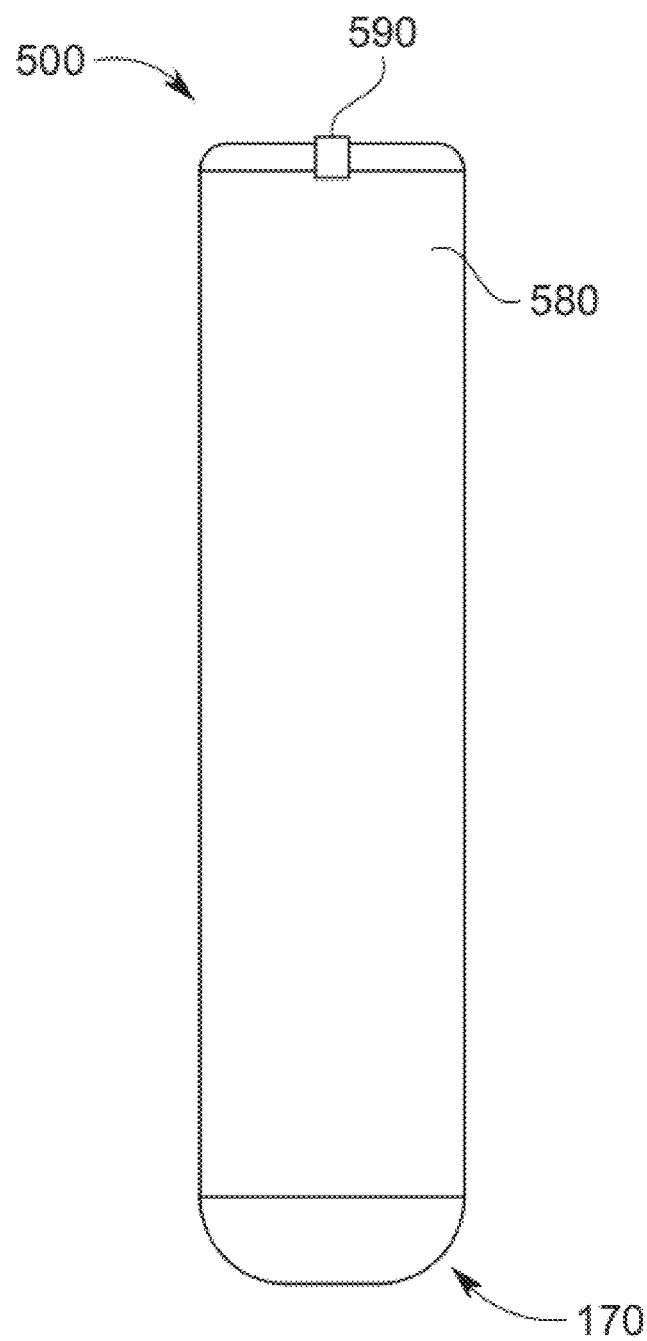
FIG. 5 is a front view of an alternative embodiment of a bolus according to some embodiments of the invention.

Referring now to FIG. 5A which shows an alternative embodiment of a bolus (500) according to an embodiment of the invention.

Aspects of the bolus (500) are similar to those described above, and therefore like references refer to like components.

The bolus (500) includes a reservoir (580) adapted to hold a relatively concentrated form of the inhibiting agent e.g. bromoform in a substantially pure, liquid form.

The bolus (500) includes a dispensing mechanism which is configured to dispense predetermined dose(s) of the inhibiting agent from the reservoir (580).

In the illustrated embodiment, the dispensing mechanism is a pump (590) in communication with a valve. At predetermined times, the pump (590) dispenses a dose of the inhibiting agent via the valve (590), to release the inhibiting agent to the rumen to which the bolus (500) has been administered.

The dispensing mechanism may be configured to release a consistent e.g. the same, amount of the inhibiting agent at defined intervals.

Alternatively, the dispensing mechanism may be configured to vary the amount of inhibiting agent released at different times. This may be useful to enable the bolus (500) to provide an effective amount of inhibiting agent which accounts for growth of the animal. In addition, or alternatively, it may compensate for other factors changes e.g. seasonal variations in methane production, in which case a higher dose of inhibiting agent may be useful.

In a further embodiment, the bolus (500) may include sensors (not shown). For example, temperature sensors may be included within the bolus (500). Additionally, or alternatively, other sensors may also be included in the bolus, such as locomotion and pH. The addition of such sensors can provide valuable information on the feed intake of the animal and assess whether the amount of inhibiting agent is sufficient for the animal.

Fifth Alternate Housing Embodiment

Figure 6A:
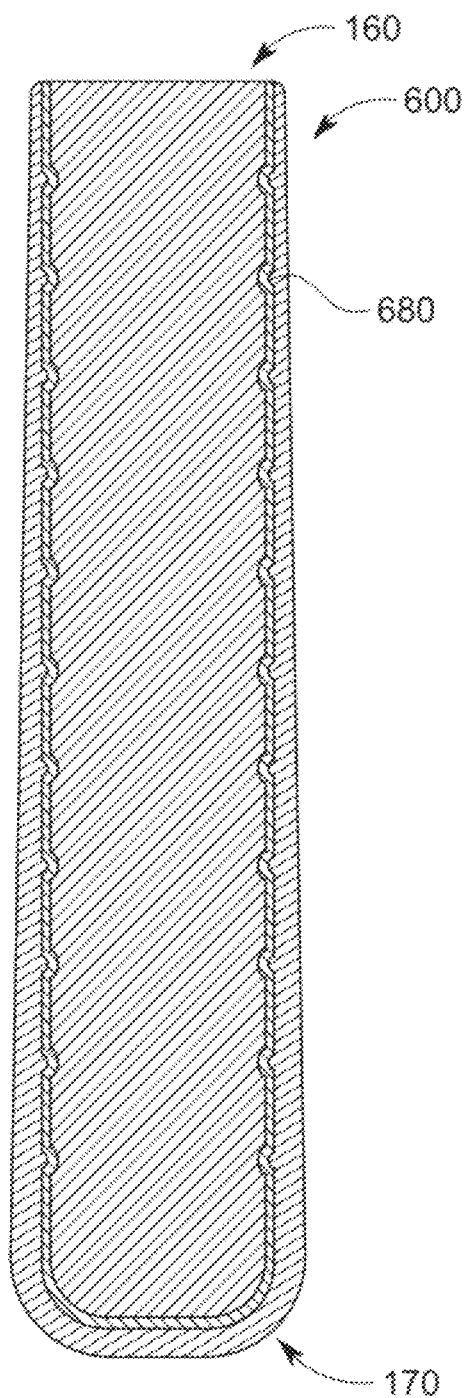
FIG. 6A is a front cross sectional-view of an alternative embodiment of a bolus according to some embodiments of the invention.
Figure 6B:
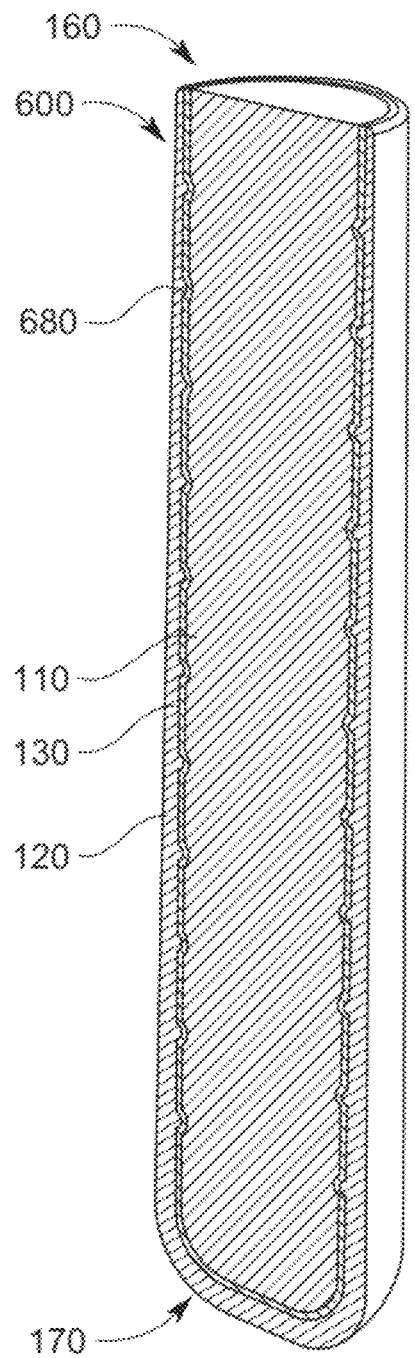
FIG. 6B is a perspective cross-sectional view of the bolus of FIG. 6A.

Referring now to FIGS. 6A and 6B which show an alternative embodiment of a bolus (600) according to an embodiment of the invention.

The bolus (600) can be adapted to include additional features within the cavity of the housing, such as grooves or ribs (680) formed on an inner wall of the housing (120) that defines the cavity.

Aspects of the bolus (600) are similar to those of the bolus (100), and therefore like references refer to like components.

A series of ribs (680) are provided along an internal surface of the housing (120). The ribs (680) may provide additional structural strength to the bolus (600), and/or provide additional means to retain the contents of the core formulation within the cavity of the housing. Additionally, or alternatively, the (680) ribs may also assist with the retention of the core within the housing. Further, the ribs may also provide controlled dissolution of the core formation from the bolus (600) to the ruminant animal.

In one embodiment, the external surface of the housing will remain smooth or uniform.

Sixth Alternate Housing Embodiment

Referring now to FIGS. 15A to 15D which show a further embodiment of a bolus (700) according to an aspect of the present invention. Dimensions of the bolus in the Figure are provided in mm. Preferably, the bolus has a length of 13 cm, a diameter of 3.4 cm and preferably a weight of about 250 gm.

The bolus (700) can be adapted to include additional features with the internal reinforcing structure on the housing.

Aspects of the bolus (700) are similar to those of the bolus (100), and therefore like references refer to like components.

The bolus (700) includes at least one reinforcing rib (710) located inside a cavity (unnumbered) defined by the housing structure. A cap (720) may also be provided e.g. releasably attached to the bolus (700) to close the open end of the bolus (700). Attachment may be provided by a friction fit arrangement, or a screw thread arrangement in which corresponding screw threads on the housing and cap engage each other. Alternatively, the cap may be attached to the housing by an adhesive or other mechanical fastener.

The reinforcing rib(s) (720) may improve the structural integrity of the bolus (700) and assist it to hold its shape.

Method of Manufacture

Figure 7:
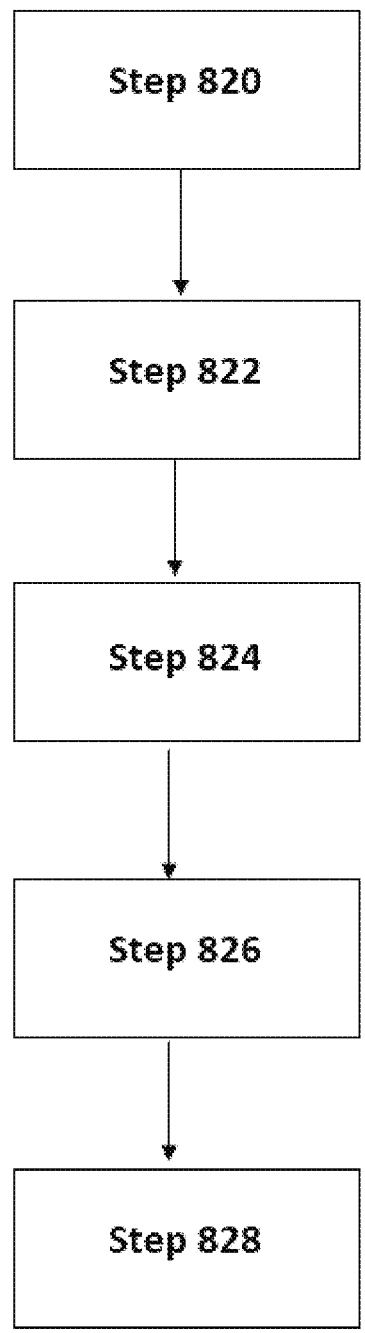
FIG. 7 is a flow diagram showing representative steps in a method of manufacturing a bolus.

Referring now to FIG. 7, which is a flow chart showing representative steps in a method of manufacturing (800) a bolus e.g. (100), (200), (300), (400), according to the present invention.

In general terms, the method includes the step (810) of forming the housing (120) and the step (820) forming a core (110).

Housing

Forming the housing (120) may occur using any technique as should be known to one skilled in the art. For instance, a suitable material may be extruded into a desired shape defining a cavity. Alternatively, an additive layering manufacturing process could also be used to build the housing shape defining a cavity. It is also envisaged that a moulding process could be used e.g. a sacrificial moulding or injection moulding process, 3D printing or hot melt extrusion processes may be used.

Core

In step 820, the core (110) is manufactured.

Step 820 may include one or more of the following steps:

Step 822 which involves melting a carrier material to provide a melted carrier material;

Step 824 which involves adding the inhibiting agent(s) to the melted carrier material;

Step 826—which involves mixing the inhibiting agent and the melted carrier material to create a substantially homogenous mixture.

Step 828 which involves forming the substantially homogeneous mixture into a desired shape.

It should be understood that the substantially homogenous mixture contains the inhibiting agent(s) at a concentration sufficient to achieve the desired release profile for the inhibiting agent on administration of the device to a ruminant animal. The concentration can be varied according to the type of ruminant animal to be treated, the shape and dimensions of the device, or the desired release profile to be achieved.

It should be understood that the step of forming the substantially homogeneous mixture into a desired shape may involve providing the mixture to a mould. In a particularly preferred form, the substantially homogenous mixture is added (poured) into a cavity in a housing (120) manufactured at step 810.

Alternatively, the mould may be a separate component which receives the substantially homogenous mixture. In these embodiments, once the desired shape has been formed, the core can subsequently be provided to a cavity in a housing (120).

The method also includes the step of allowing the substantially homogenous mixture to cool. As it cools, the carrier material hardens and assumes a shape according to the shape of the mould or housing into which it has been provided.

Example Formulations

The following cores were formulated for use in the bolus of the disclosure.

| | | | | | | Amount (w/w %) | | | | | | | | | |
|---|---|---|---|---|---|---|---|---|---|---|---|---|---|---|---|
| Example | 1 | 2 | 3 | 4 | 5 | 6 | 7 | 8 | 9 | 10 | 11 | 12 | 13 | 14 | 15 |
| Bromoform | 20 | 20 | 20 | 25 | 12.5 | 8.3 | 25 | 12.5 | 8.3 | 25 | 12.5 | 8.3 | 20 | 33 | 33 |
| Paraffin | 80 | 30 | 30 | 50 | 50 | 50 | — | — | — | — | — | — | — | 66 | — |
| Beeswax | — | 50 | — | — | — | — | 50 | 50 | 50 | — | — | — | — | — | 66 |
| PEG 4000 | — | — | 50 | — | — | — | — | — | — | 50 | 50 | 50 | 50 | — | — |
| PEG 400 | — | — | — | — | — | — | — | — | — | — | — | — | 30 | — | — |

-continued

| Example | \multicolumn{15}{c}{Amount (w/w %)} |
|---|---|---|---|---|---|---|---|---|---|---|---|---|---|---|---|
|  | 1 | 2 | 3 | 4 | 5 | 6 | 7 | 8 | 9 | 10 | 11 | 12 | 13 | 14 | 15 |
| AC | — | — | 25 | — | — | 25 | — | — | 25 | — | — | — | — | — | — |
| Kaolin | — | — | — | 37.5 | — | — | 37.5 | — | — | 37.5 | — | — | — | — | — |
| Zeolite | — | — | — | — | 41.7 | — | — | 41.7 | — | — | 41.7 | — | — | — | — |

The following additional high bromoform content cores were also formulated for use in the bolus of the disclosure.

| Example | \multicolumn{12}{c}{Amount (w/w %)} |
|---|---|---|---|---|---|---|---|---|---|---|---|---|
|  | 16 | 17 | 18 | 19 | 20 | 21 | 22 | 23 | 24 | 25 | 26 | 27 |
| Bromoform | 33 | 50 | 67 | 75 | 33 | 50 | 67 | 75 | 33 | 50 | 67 | 75 |
| Beeswax | 67 | 50 | 33 | 25 | — | — | — | — | — | — | — | — |
| Paraffin wax | — | — | — | — | 67 | 50 | 33 | 25 | — | — | — | — |
| Carnauba wax | — | — | — | — | — | — | — | — | 67 | 50 | 33 | 25 |
| Castor Wax | — | — | — | — | — | — | — | — | — | — | — | — |
| Activated Carbon | — | — | — | — | — | — | — | — | — | — | — | — |
| Bentonite | — | — | — | — | — | — | — | — | — | — | — | — |
| Zinc Oxide | — | — | — | — | — | — | — | — | — | — | — | — |

| Example | \multicolumn{9}{c}{Amount (w/w %)} |
|---|---|---|---|---|---|---|---|---|---|
|  | 28 | 29 | 30 | 31 | 32 | 33 | 34 | 35 | 36 |
| Bromoform | 33 | 50 | 67 | 75 | 50 | 50 | 50 | 50 | 50 |
| Beeswax | — | — | — | — | — | — | — | 25 | 25 |
| Paraffin wax | — | — | — | — | — | — | — | — | — |
| Carnauba wax | — | — | — | — | — | — | — | — | 25 |
| Castor Wax | 67 | 50 | 33 | 25 | — | — | — | 25 | — |
| Activated Carbon | — | — | — | — | 50 | — | — | — | — |
| Bentonite | — | — | — | — | — | 50 | — | — | — |
| Zinc Oxide | — | — | — | — | — | — | 50 | — | — |

NUMBERED ASPECTS

The present disclosure also includes the following non-limiting numbered aspects.

1. A bolus for administration to a ruminant animal, wherein said bolus is configured to release a methane inhibiting agent in the animal, wherein said bolus comprises:
   a core, wherein the core comprises the inhibiting agent and a carrier; and
   a housing which covers at least a portion of the core;
   wherein said carrier comprises hydrophobic fumed silica and/or comprises a combination of ethyl cellulose and HPMC.
2. A bolus for administration to a ruminant animal, wherein said bolus is configured to release a methane inhibiting agent in the animal, wherein said bolus comprises:
   a core, wherein the core comprises the inhibiting agent and preferably a carrier; and
   a housing which covers at least a portion of the core;
   wherein the material of the housing comprises poly lactic acid (PLA) and polybutylene adipate terephthalate (PBAT); or
   wherein the material of the housing comprises poly lactic acid (PLA) and polybutylene adipate terephthalate (PBAT) in a PLA:PBAT weight ratio of between 95:5 to 80:20; or
   wherein the material of the housing comprises poly lactic acid (PLA) and polybutylene succinate (PBS) in a PLA:PBS weight ratio of between 95:5 to 70:30; or
   wherein the material of the housing comprises poly lactic acid (PLA) and polybutylene succinate adipate (PBSA) in a PLA:PBSA weight ratio of between 95:5 to 70:30.
3. The bolus of aspect 1, wherein the material of the housing comprises poly lactic acid (PLA) and polybutylene adipate terephthalate (PBAT) in a PLA:PBAT weight ratio of between 95:5 to 70:30.
4. The bolus according to any of the preceding aspects wherein the methane inhibiting agent is a haloform, preferably selected from the list of bromoform, chloroform, iodoform, and combinations thereof.
5. The bolus according to aspect 4, wherein the methane inhibiting agent is bromoform.
6. The bolus according to any one of aspects 1 to 3, wherein the methane inhibiting agent is *Asparagopsis* or a derivative thereof, preferably a bromoform containing algae extract.
7. The bolus according to any one of aspects 1 to 6, wherein the hydrophobic fumed silica is amorphous or consists of or comprises hydrophobic fumed silica nanoparticles (HFSNPs).
8. The bolus according to any preceding aspect, wherein the carrier comprises at most 20 wt %, at most 10 wt % or at most 4 wt % of said hydrophobic fumed silica.
9. The bolus according to any one of aspects 1 to 7, wherein the carrier comprises from 1 wt % to 25 wt % of hydrophobic fumed silica in relation to the total weight of the carrier and the methane inhibiting agent, preferably from 3 wt % to 15 wt % of said hydrophobic fumed silica, more preferably from 3 wt % to 10 wt %, even more preferably from 3 wt % to 7 wt % and most preferably from 5 wt % to 7 wt % of said hydrophobic fumed silica.
10. The bolus according to any one of aspects 1 to 9, wherein the average particle diameter of said hydrophobic fumed silica is between 5 nm and 15 nm.
11. The bolus as in any one of aspects 1 to 10, wherein the hydrophobic fumed silica consists of or comprises treated fumed silica which is fumed silica that has been contacted with a hydrophobic silane and preferably contacted with a compound or compounds chosen from the group of DDS, methyl acrylic silane, octyl silane, octamethylcyclotetrasiloxane, hexadecyl silane, octylsilane, methylacrylsilane, polydimethylsiloxane, hexamethyldisilazane (HMDS), silicone oil, silicone oil plus aminosilane, HMDS plus aminosilane, and organic phosphates and most preferably contacted with dimethyldichlorosilane (DDS) and/or HMDS (hexamethyldisilazane).
12. The bolus as in any one of aspects 1 to 11, wherein said core further comprises a wax and/or a polyol and/or a polyester;

wherein the wax is preferably a compound selected from the group consisting of myristic acid, stearic acid, steryl alcohol, cetyl alcohol, cetosteryl alcohol, castor wax, bee's wax, paraffin wax, PEG 4000, Carnauba, Candellila, Jojoba, Lanolin, and a combination thereof, preferably castor wax; and wherein the polyol is preferably a compound selected from the group consisting of polyols, preferably cellulose derivates, more preferably ethyl cellulose and/or hydroxypropyl methylcellulose (HPMC); and wherein the polyester is preferably Poly(ε-caprolactone) (PCL).

13. The bolus as in any one of aspects 1 to 12,
wherein the core comprises ethyl cellulose and/or HPMC,
more preferably wherein the core comprises ethyl cellulose and HPMC, preferably wherein HPMC is HPMC K-100,
preferably wherein the weight ratio of ethyl cellulose: HPMC is from 35:65 to 70:30.

14. The bolus as in any one of aspects 1 to 12, wherein the core comprises ethyl cellulose and fumed silica, preferably in a weight ratio of ethyl cellulose:fumed silica of from 70:30 to 90:10.

15. The bolus as in any one of aspects 1 to 14, wherein the core comprises ethyl cellulose in an amount of from 10 to 40 wt %, preferably of from 15 to 30 wt %.

16. The bolus as in any one of aspects 1 to 15, wherein the core comprises HPMC in an amount of from 10 to 30 wt %, preferably of from 12 to 25 wt %.

17. The bolus according to any one of aspects 1 to 16, wherein at least 50% of the core comprises said methane inhibiting agent.

18. The bolus according to aspects 1 to 5 or 7 to 16, wherein the haloform, preferably bromoform, is comprised in the core in an amount of between 30 wt % to 80 wt % and preferably in an amount of between 30 wt % and 70 wt %, preferably in an amount of at most 55 wt %.

19. The bolus according to any one of aspects 13 to 18, wherein the haloform, preferably bromoform, is comprised in the core in an amount of at least 50 wt %, of at least 58 wt %, of at least 60 wt %, of at least 61 wt %, or of at least 64 wt %, wherein the wt % is the wt % in relation to the total weight of the core.

20. The bolus according to aspects 2 to 19, wherein the PLA:PBAT weight ratio is 90:10; wherein the PLA:PBS weight ratio is 90:10; or wherein the PLA:PBSA weight ratio is 90:10.

21. The bolus according to any one of aspects 2 to 19, wherein the PLA:PBS weight ratio is about 80:20.

22. The bolus according to any one of aspects 2 to 20, wherein the material of the housing comprises PLA:PBAT in a weight ratio of about 90:10 and preferably wherein the housing remains stable in the environment of an animal's rumen for at least 5 months.

23. The bolus according to any of the preceding aspects, wherein the methane inhibiting agent can perfuse through the housing material.

24. The bolus according to any of the preceding aspects, wherein the housing material comprises one or more excipients.

25. The bolus as in aspect 24, wherein the one or more excipients includes plasticisers, hardeners and/or colourants.

26 The bolus according to any one of the preceding aspects, wherein the housing has a wall thickness of below 2 mm and preferably a wall thickness in the range of 0.3-1.5 mm, more preferably a wall thickness of about 1.2 mm.

27 The bolus as in any of the preceding aspects, wherein the housing is configured to degrade over a predetermined period of time.

28. The bolus according to any of the preceding aspects, wherein the housing includes a cavity in which at least a portion of the core is located.

29. The bolus according to any of the preceding aspects, wherein the housing includes an opening.

30. The bolus according to any of the preceding aspects, wherein the housing includes a cap configured to close the opening.

31. The bolus as in any preceding aspect, wherein the housing comprises no openings and completely surrounds the core.

32. The bolus according to any of the preceding aspects, wherein the housing completely covers and surrounds the core.

33. The bolus according to any of the preceding aspects, wherein the housing is formed from a substance having a Shore D hardness of at least 20.

34. The bolus according to any of the preceding aspects, wherein the housing is formed from a substance having a Shore D hardness of less than 70.

35 The bolus according to any of aspects 1 to 33, wherein the housing is formed from a substance having a Shore D hardness of less than 90.

36. The bolus according to any of the preceding aspects, wherein the core of the bolus comprises one or more metal particles (preferably steel particles), wherein the particles are preferably rounded and wherein the total of all particles per bolus has a mass of at least 100 g.

37. The bolus according to any of the preceding aspects, wherein the core of the bolus comprises a portion, which comprises metal particles and a filling agent, preferably wherein the weight ratio of metal particles: filling agent is from 90:10 to 95:5, preferably wherein the filling agent is a wax, preferably wherein the wax is paraffin wax, and/or preferably wherein the metal particles are stainless steel particles, and/or preferably wherein the metal particles are evenly distributed throughout the filling agent.

38. The bolus according to any of the preceding aspects, wherein the core has a melting point greater than 37° C., preferably greater than 42° C., more preferably greater than 45° C.

39. The bolus according to any of the preceding aspects, further comprising a barrier layer between at least a portion of the housing and the core to isolate the portion of the housing and the core from contact with each other.

40. The bolus according to any of the preceding aspects, wherein the bolus is adapted to reach a maximum release rate of approximately 0.05 g to 2 g of bromoform per day into the rumen.

41. The bolus according to any of the preceding aspects, wherein the bolus is adapted to release the substance over a period of at least two months, preferably over a period of at least three months, more preferably over a period of at least six months.

42. A bolus for administration of a first and a second active agent in the rumen of a ruminant animal, wherein said bolus comprises a first segment and a second segment, wherein said first segment comprises a first core comprising said first active agent, and
wherein said second segment comprises a second core comprising said second active agent,
wherein said first and said second active agent may be the same or different.

43. The bolus of aspect 42, wherein the first and second segment are respectively defined by a first and second housing, wherein the first and the second segment are detachable from each other.

44. A bolus for administration to a ruminant animal comprising at least a first and a second segment, wherein said first and said second segment are each configured to release an active agent in the rumen of the ruminant animal,
wherein said first segment comprises
  (a) a first core comprising a first active agent, and
  (b) a first housing which covers at least a portion of said first core, and
wherein said second segment comprises
  (c) a second core comprising a second active agent, and
  (d) a second housing which covers at least a portion of said second core,
wherein said first and said second active agent may be the same or different.

45. The bolus according to aspect 44, wherein said first and said second segment are detachable from each other.

46. The bolus according to any one of aspects 42 to 45, wherein the first and the second active agent are the same active agent, preferably wherein the first and the second active agent is each a methane inhibiting agent, more preferably wherein the active agent is bromoform.

47. The bolus according to any one of aspects 42 to 46, wherein the active agent is a haloform, preferably bromoform, and each of the first and the second core comprises the respective active agent in an amount of between 30 wt % to 80 wt % related to the total weight of the respective core, preferably in an amount of between 30 wt % and 70 wt %, preferably in an amount of between 50 wt % and 70 wt %, preferably wherein each of the first and the second core comprises the haloform in a different amount.

48. The bolus according to any one of aspects 42 to 47, wherein the first core and/or second core comprises one or more compounds as defined in aspects 1, 7, 11 to 16, or wherein said first core comprises at least one compound selected from the group consisting of PCL, ethyl cellulose and HPMC, and wherein said second core comprises at least one compound selected from the group consisting of hydrophobic fumed silica and waxes as defined in aspect 11, and preferably castor wax.

49. The bolus according to any one of aspects 42 to 48, wherein said first housing comprises at least one compound selected from the group consisting of PLA, PCL, talc and PDLA, and wherein said second housing comprises at least one compound as defined in any one of aspects 2, 3, or 19, or at least one compound selected from the group consisting of PBAT, PBSA, PBS and PVA.

50. The bolus according to any one of aspects 42 to 49, wherein each of the first and the second segments has a length of between 50 and 100 mm, preferably a length of about 72 mm.

51. The bolus according to any one of aspects 42 to 50, wherein each of the first and the second segments has a cylindrical shape.

52. The bolus according to any one of aspects 42 to 51, wherein each of the first and the second segments is encapsulated by its own housing.

53. The bolus according to any one of aspects 42 to 52, wherein the housing of each of the first and the second segment has a wall thickness of below 2 mm and preferably a wall thickness in the range of 0.3-1.5 mm, more preferably a wall thickness of about 1.2 mm.

54. The bolus according to any one of aspects 42 to 53, wherein said first and said second segment are attached to each other, preferably via an attachment, more preferably via an attachment selected from the group consisting of an adhesive, a string, a tape and a pluggable connector, preferably wherein said attachment is dissolvable in the animal's rumen and/or comprises a compound that is dissolvable in water.

55. The bolus according to any one of aspects 42 to 54, wherein said first and/or said second segment comprise one or more metal particles, preferably steel particles.

56. A bolus for administration to a ruminant animal, wherein said bolus is configured to release an active agent in the rumen of the animal, wherein said bolus comprises a first and a second core, wherein the first core is located within the second core.

57. The bolus of aspect 56, wherein the first core comprises a first active agent and the second core comprises a second active agent.

58. The bolus of any one of aspects 56 or 57, wherein the bolus comprises a third core which is located in the second core and wherein the third core comprises a third active agent.

59. The bolus according to any one of aspects 56 to 58, wherein said first, said second and said third active agent are the same active agent, preferably wherein said active agent is a haloform, more preferably bromoform.

60. The bolus according to aspect 59, wherein the active agent is comprised within said first and second core in different concentrations.

61. The bolus according to any one of aspects 56 to 60, wherein each core comprises a carrier compound selected from the group consisting of compounds as defined in aspects 1, 7 and 11 to 16 or a mixture comprising one or more of these compounds, and preferably wherein the first core comprises PCL and/or wherein the second core comprises ethyl cellulose.

62. The bolus according to any of the preceding aspects, wherein the bolus is coated with a material that is impervious to a haloform and preferably to bromoform, and wherein said coating has a thickness that allows the coating to become permeable for said haloform when exposed to the abrasive forces within the rumen or dissolved in ruminal fluid of a living animal.

63. The bolus according to aspect 62, wherein said coating comprises at least one compound selected from the group consisting of hydrophobic polymers, methyl cellulose, PLA, silicates, metal coatings, wax, gelatin, starch, collagen, chitosan, polyvinylpyrrolidone, vinylpyrrolidone-vinyl copolymer, polyvinyl acetate, hydroxypropyl methylcellulose, methacrylate copolymer or mixtures thereof, glucose, dextrose, fructose, lactose, maltose, xylose, sucrose, corn syrup, sorbitol, hexitol, maltitol, xylitol and mannitol, glycerol, polyethylene glycol and propylene glycol.

64. The bolus according to any one of aspects 62 or 63, wherein said coating has a thickness of from 50 to 250 μm.
65. The bolus according to any one of aspects 62 to 64, wherein said coating is partially or completely removable in the rumen within a time period of less than 12 hours after administration to the animal, preferably of less than 6 hours, more preferably of less than 1 hour after administration to the animal.
66. A method for administering a methane inhibitor to an animal, the method comprising the step of administering to said animal the bolus as defined in any one of aspects 1 to 65.
67. A method for reducing methane production in the rumen of a ruminant animal, the method comprising the step of administering to said ruminant animal the bolus as defined in any one of aspects 1 to 65.
68. A bolus as defined in any one of aspects 1 to 65 for use in the treatment of an animal and preferably of a ruminant animal and most preferably of cattle or sheep.
69. A bolus as defined in any one of aspects 1 to 65 for use in reducing methane emission in a ruminant animal and most preferably in cattle or sheep.
70. A method of manufacturing a bolus, comprising the steps:
    (1) providing a housing made of a polymer material, preferably a biodegradable polymer and most preferably a housing as defined in any of aspects 1 to 65; and
    (2) filling a core preferably as further defined in any of aspects 1 to 65 into said housing;
    wherein the bolus comprises:
    a core, wherein the core comprises a methane inhibiting agent that inhibits the production of methane in the rumen of a ruminant animal and a carrier; and
    a housing which houses the core.
71. The method of aspect 70, wherein the method further comprises the step
    (3) closing the housing that contains the core with a cap, wherein the housing is closed with the cap by friction-welding the cap to the housing.
72. The method of any one of aspects 69 or 70, wherein the housing is provided in step (1) by injection molding.
73. The method of any one of aspects 71 or 72, wherein the method further comprises a step (4) which is carried out prior to step (3), wherein in step (4) said housing and/or said core is exposed to a reduced pressure in order to reduce the amount of gas remaining inside of the bolus after closing the housing in step (3).
74. The method of any one of aspects 70 to 73, wherein the closed bolus comprises less than about 1 cm$^3$ of gases at 20° C. at atmospheric pressure.
75. Bolus obtainable or obtained by carrying out a method as defined in aspects 70 to 74.
76. A methane inhibitor for use in the reduction of methane production in a ruminant animal, wherein the methane inhibitor is administered to the animal in an amount of from 30 to 300 mg per day, preferably in an amount of from 104 to 260 mg per day, more preferably in an amount of from 150 to 220 mg per day, most preferably in an amount of about 208 mg per day.
77. A methane inhibitor for use in the reduction of methane production in a ruminant animal, wherein the methane inhibitor is administered to the animal in an amount of at least 0.20 mg per kg animal weight per day, preferably in an amount of at least 0.30 mg per kg animal weight per day, preferably in an amount of between 0.30 and 0.70 mg per kg animal weight per day and even more preferably in an amount of at least 0.55 mg per kg animal weight per day.
78. A methane inhibitor for use according to any one of aspects 76 or 77, wherein the rumen of said ruminant animal is exposed to said methane inhibitor over a time period of at least 10 days, preferably of at least 15 days, more preferably of at least 20 days, even more preferably of at least 1 month, and even more preferably over a time period of at least 3 months.
79. A methane inhibitor for use according to any one of aspects 76 to 78, wherein the methane inhibitor is a haloform, preferably wherein the haloform is bromoform.
80. A methane inhibitor for use according to any one of aspects 76 to 79, wherein the animal is cattle.
81. Method of treating an animal comprising administering to said animal a bolus as defined in any one of aspects 1 to 75 to said animal, wherein said animal is preferably a ruminant animal such as cattle.
82. A bolus for administration to a ruminant animal, wherein said bolus comprises an active agent and preferably an active agent as defined in any one of the preceding aspects and more preferably a methane inhibiting agent as defined in any one of the preceding aspects; and a housing in which interieur said active agent is comprised; and
    wherein the bolus further comprises a densifier tablet; wherein said densifier tablet has the same cross-section as said housing but includes at least one channel through which air can escape when inserting the densifier tablet into the housing and preferably wherein said channel extends in a vertical direction across at least one side of the densifier tablet; and wherein the densifier tablet comprises one or more metal particles.
83. The bolus of aspect 82, wherein the bolus further comprises an RFID chip and wherein the distance between the RFID chip and the densifier component is preferably at least 3 cm.
84. The bolus of aspect 82 or 83, wherein the housing is cylindrical and comprises at its top and/or bottom indentations and wherein the housing is preferably manufactured by closing the housing with a lid that comprises said indentations by spin-welding said lid onto the housing.

EXAMPLES

Example 1: Release/Diffusion Study

Trials with 2 mm thick 3D printed large capped boluses (LCB2) filled with 66.7% (by weight) bromoform and 33.3% (by weight) beeswax in the RME (Rumen Emulator) (RME trial 2) were conducted to determine the diffusion rate of bromoform from the bolus.
Bolus Design
A reinforced bolus as shown in FIGS. 15A-15D was used for this study. It includes an internal reinforcing structure as well as ribs spread apart to support the wall, an upper part was adapted for the attaching a cap. The bolus with reinforcing was found to be more robust and held its shape better than without reinforcing when the molten bromoform/beeswax mixture was poured in and cooled, as well as a more physically robust bolus for the trial.

Method

Materials

Bromoform (reagent grade, Sigma Aldrich, 96% bromoform, 4% ethanol), beeswax (food grade, NZ Beeswax, MP 65° C.) and zinc oxide from Native Ingredients NZ.

Bolus Manufacture

The boluses were drawn in Solidworks, converted to .stl files, opened in FlashPrint to create the print jobs. The boluses were printed in three parts (case, internal structure and cap) on FlashForge Creator Pro 3D printers using E-Sun PLA+ at 100% fill, standard resolution, first layer height 0.27 mm, layer height 0.18 mm, 2 perimeter shells, 3 top solid layers, 3 bottom solid layers, fill pattern hexagon, print speed 60 mm/s, extruder temperature 200° C. and plate temperature 50° C.

Eight LRB boluses were prepared at 67% (by weight) bromoform, eight LRB boluses were prepared at 75% (by weight) bromoform, and six LCB2 boluses with no bromoform (controls). Ingredients are listed below (Table 1). All ingredients were weighed in beakers on a calibrated 4 dp electronic balance. Bromoform solutions were covered with parafilm to prevent evaporation. Ingredients were prepared by melting pre-weighed beeswax and zinc oxide in beakers at 100° C. (Thermoprism Oven), letting the mixture cool to 80° C., adding the bromoform and the mixture kept well mixed to prevent the zinc oxide from settling out, before pouring into the boluses. Caps were press fitted and soldered to seal the bolus.

TABLE 1

Preferred compositions for the shortened reinforced boluses

| | | Per bolus | | | Total | | |
|---|---|---|---|---|---|---|---|
| Type | Quantity | Zinc Oxide (g) | Beeswax (g) | Bromoform (g) | Zinc Oxide (g) | Beeswax (g) | Bromoform (g) |
| LCB2 | 6 | 28.0 | 80.4 | 0.0 | 168.0 | 482.7 | 0.0 |
| LRB1 | 8 | 28.0 | 47.3 | 96.1 | 224.0 | 378.8 | 769.0 |
| LRB1 | 8 | 28.0 | 39.7 | 119.0 | 224.0 | 317.3 | 952.0 |
| Total | | | | | 616.0 | 1178.7 | 1721.0 |

The boluses were placed in 500 ml polypropylene bottles with approximately 380 ml 0.02M phosphate buffer (Merck) in distilled water, prepared in 2 L or greater batches, adjusted to pH 6.5 using 1M HCl (Merck) and a pre-calibrated pH meter (using pH 4, 7, and 10 pH buffers). The bottles were sealed and placed in the incubator at 40° C. 10 ml samples were collected and the entire solution changed every 24 hours.

10 ml samples was collected using a 10 ml autopipette in 15 ml Falcon tubes. 1 g of sodium chloride was added to each Falcon tube. For GC-MS analysis, 1 ml of ethyl acetate (analytical grade, Merck) was added to each Falcon tube. When GC-FID was used 2 ml of ethyl acetate was added to each Falcon tube. The Falcon tubes were capped, well mixed using a Vortex, and centrifuged at 4000 rpm for 15 minutes.

For GC-MS analysis, all the ethyl acetate was recovered using a graduated glass syringe and the volumes noted.

For GC-FID analysis, 0.5 ml of ethyl acetate was recovered. For GC-FID analysis, 200 ul of sample was injected using an autosampler, and analysed using a ZBSHT 30 m capillary column using a temperature ramp of 30-300° C. over 20 minutes, at 5 ml/min nitrogen gas flow, in splitless mode. Bromoform had a retention time of 7.5 minutes. Peak areas were compared to calibration standards made up in ethylene acetate to determine the mass of bromoform (mg). This was divided by the volume injected to obtain the concentration of bromoform in the ethyl acetate (mg/L). The concentration in ethyl acetate was multiplied by the total volume of ethyl acetate added to the sample and divided by the recovery to obtain mass of bromoform in the sample. This was then divided by the volume of sample collected to obtain a concentration in the solution, which was then multiplied by the volume of solution in the Shott bottle to obtain mass transferred from the bolus to the solution. Bromoform recovery from solution was checked using standard solutions made up to different concentrations of bromoform and was typically 43%. GC-FID performance was checked for each run of ten samples using a calibration sample as a reference.

Results

Figure 8:
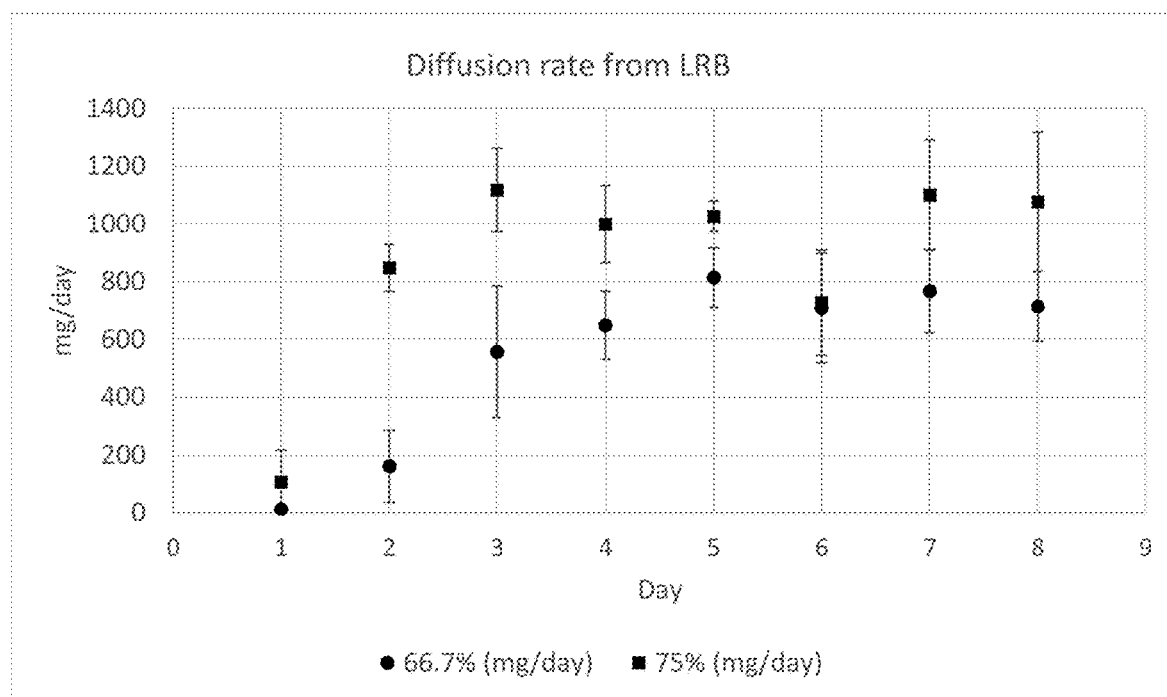
FIG. 8 is a graph showing the daily diffusion/release rate of bromoform from bolus in the media.

A lower diffusion rate followed by a rapid increase in diffusion rate was observed for both boluses (FIG. 8). The 67% bolus had a lag time of 4-5 days before reaching its maximum diffusion rate, whereas the 75% reached maximum diffusion rate with 3 days.

The rate of diffusion was higher for the 75% bolus at 1010 mg/day when compared to 66.7% which was 730 mg/day. This was a surprising, but also good result (as it means that a single bolus could be used to dose 700 kg bulls and achieve methane reduction), as the predicted diffusion rates for an LCB1 bolus for 67% bromoform was 300 mg/day and 462 mg/day for an LCB1 bolus with 75% bromoform. The expectation for the LRB boluses was a lower diffusion rate because it had a reduced surface area at 1 mm thick (about 71% that of a LCB1 bolus) (Table 2). In theory the LRB bolus may be delivering 220 mg/day for 67% bromoform and 344 mg/day for 75%.

TABLE 2

Expected diffusion rate for an LRB bolus from the different parts of the bolus.

| Bits of the bolus | Quantity | Length (cm) | Width (cm) | Diameter (cm) | Area (cm2) | Thickness (mm) | Expected rates (mg/cm2/day) 0.67 | Expected rates (mg/cm2/day) 0.75 | Exposed wax (mg/cm2/day) 0.67 | Exposed wax (mg/cm2/day) 0.75 | Total (mg/day) 0.67 | Total (mg/day) 0.75 | Contribution (%) 0.67 | Contribution (%) 0.75 |
|---|---|---|---|---|---|---|---|---|---|---|---|---|---|---|
| Cap | 1 | 1.7 | | 3.4 | 27.2 | 2 | 0.357 | 0.49 | 85.0 | 116.2 | 9.7 | 13.3 | 4.4 | 3.9 |
| Ribs | 4 | 0.3 | | 3.4 | 12.8 | 3 | 0.082 | 0.086 | 85.0 | 116.2 | 1.1 | 1.1 | 0.5 | 0.3 |
| Active diffusion area | 3 | 3 | | 3.4 | 96.1 | 1 | 1.939 | 3.042 | 85.0 | 116.2 | 186.4 | 292.4 | 84.3 | 84.9 |
| Eye | 1 | 3.0 | 1.2 | | 3.6 | 3 | 0.082 | 0.086 | 85.0 | 116.2 | 0.3 | 0.3 | 0.1 | 0.1 |
| Curved bit | | | | | 12.2 | 1 | 1.939 | 3.04 | 85.0 | 116.2 | 23.7 | 37.3 | 10.7 | 10.8 |
| | | | | | | | Total (mg/day) | | | | 221.2 | 344.4 | Total Grand total | |
| | | | | | | | Actual (mg/day) | | | | 731 | 1064 | | |
| | | | | | | | Factor out | | | | 3.30 | 3.09 | | |

TABLE 3

Calculation of the porous area to achieve the same diffusion rate as what was measured from the LRB boluses using previously determined diffusion rates.

| | 67% bromoform | | | 75% bromoform | |
|---|---|---|---|---|---|
| Proportion area open | mg/day through open area | mg/day through closed area | Proportion area open | mg/day through open area | mg/day through closed area |
| 0.01 | 23.2 | 9.6 | 0.01 | 31.6 | 13.2 |
| 0 | 0.0 | 1.1 | 0 | 0.0 | 1.1 |
| 0.06 | 449.4 | 176.1 | 0.06 | 614.1 | 276.4 |
| 0 | 0.0 | 0.3 | 0 | 0.0 | 0.3 |
| 0.06 | 57.3 | 22.4 | 0.06 | 78.2 | 35.2 |
| Total (mg/day) | 529.8 | 209.6 | | 724.0 | 326.2 |
| Grand total (mg/day) | 739.4 | | | 1050.2 | |

Figure 9:
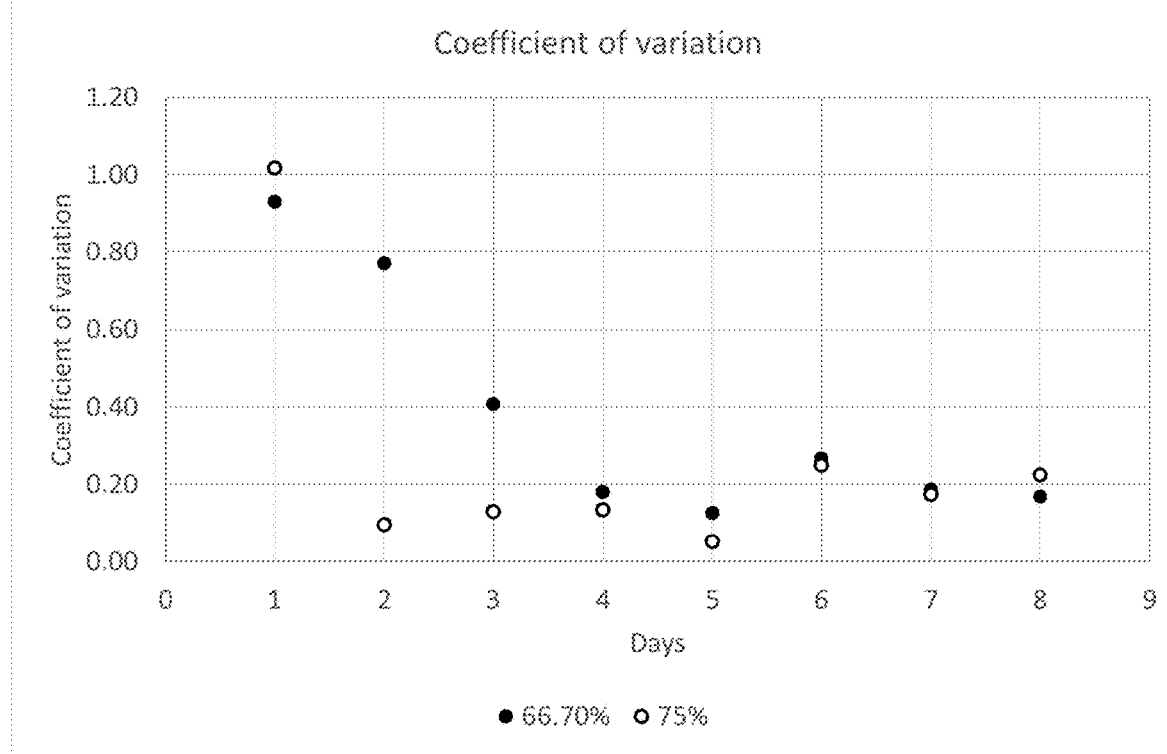
FIG. 9 is a graph showing variability in the diffusion results.
Figure 10:
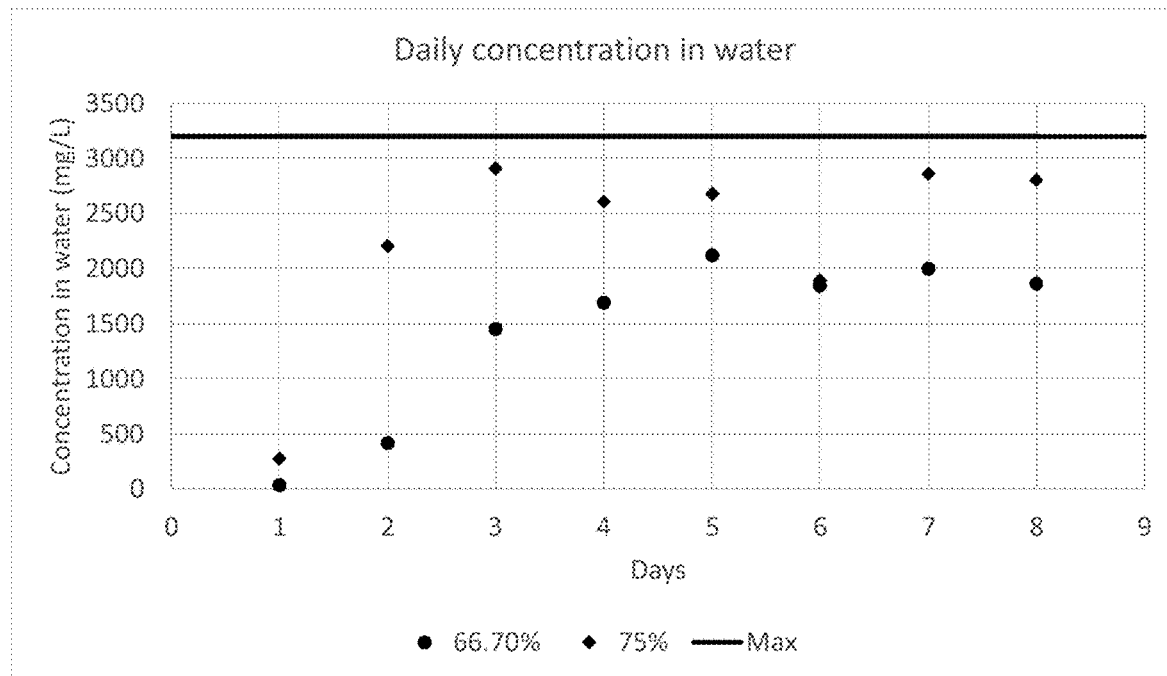
FIG. 10 is a graph showing the concentration of Bromoform in a diffusion media over time.

Variability in diffusion data was high initially with a coefficient of variation of around 1, and this decreased to between 0.05-0.22, as the boluses reached their maximum diffusion rates (FIG. 9). The 75% bolus settled within 2 days, while the 67% bolus settled within 4 days.

Figure 11:
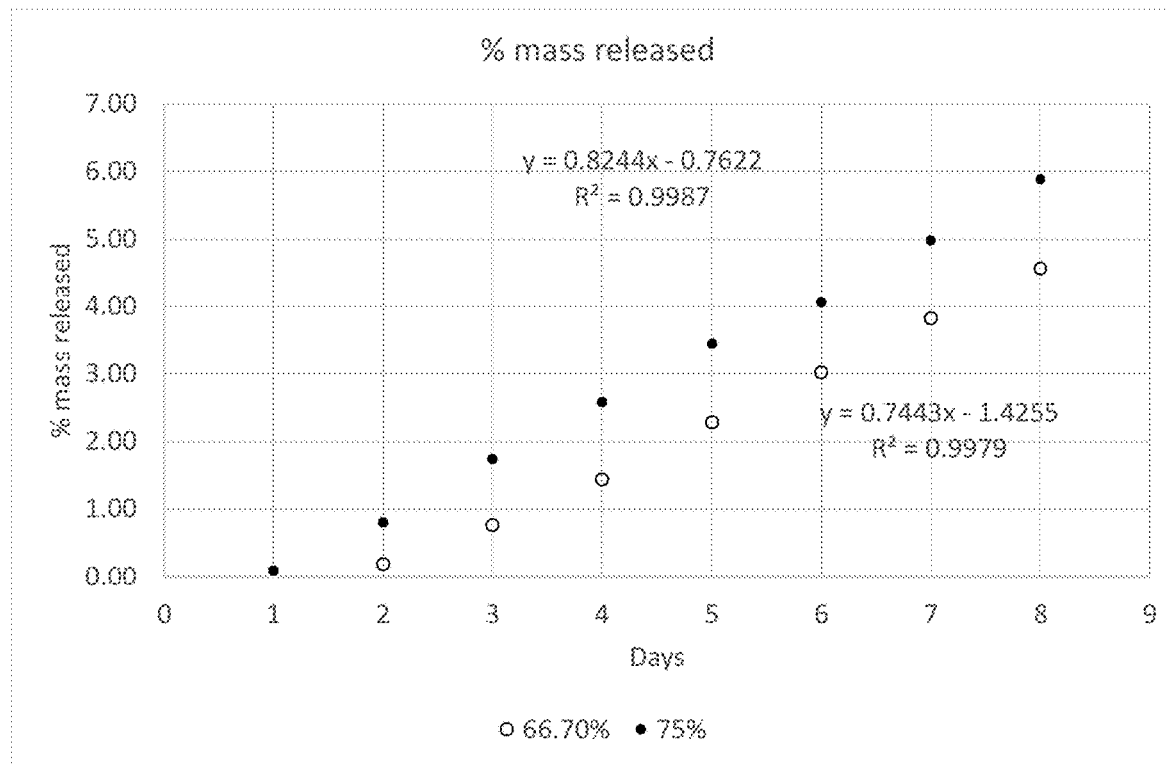
FIG. 11 is a graph showing the mass of Bromoform released (%) over time.
Figure 12:
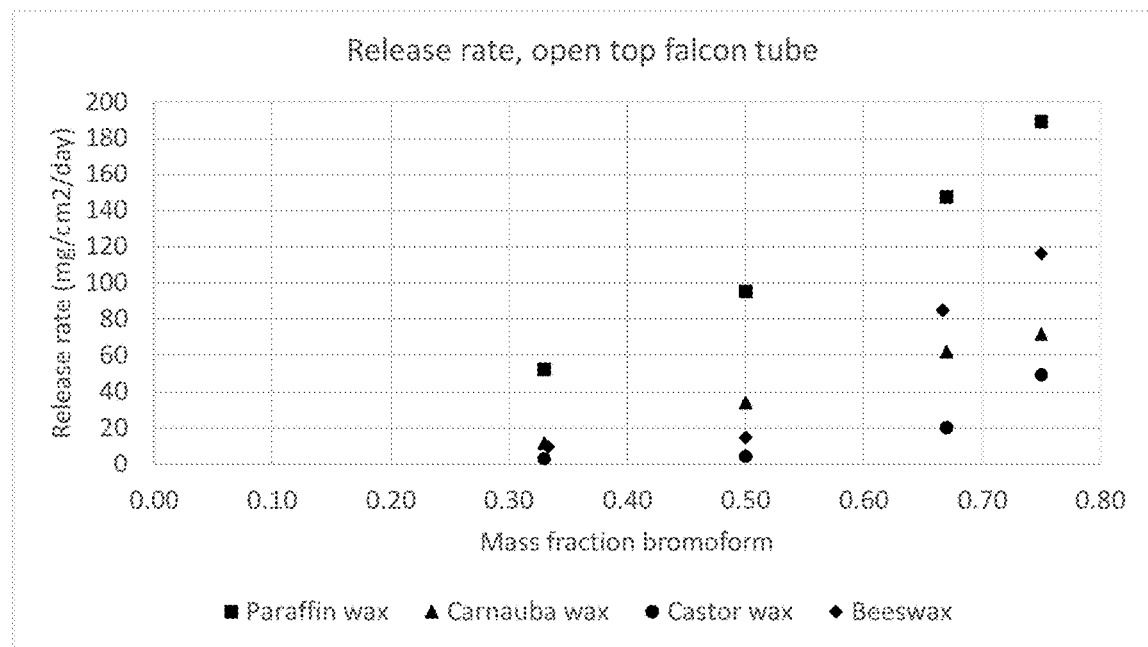
FIG. 12 is a graph showing the release rates of bromoform from different carriers in open top falcon tubes.

A zero-order release was observed for both boluses indicating the rate of release was independent of concentration of bromoform in the bolus (FIG. 11).

Conclusion

The rate of diffusion for LRB boluses was 1010 mg/day for the 75% bolus, and 730 mg/day for the 66.7% bolus which was higher than predicted from the previous diffusion studies.

The concentration of bromoform in the media for the 75% bolus, is close to the solubility limit of bromoform in water (3.2 g/L), therefore diffusion rates may be higher than measured in this study.

Example 2: Release Testing of Carriers

Release testing of various carriers was undertaken for this study.

Method

Materials

Bromoform (reagent grade, Sigma Aldrich, 96% bromoform, 4% ethanol), ruminal fluid (Dairy NZ Trial), paraffin waxes (MPs 46-48, 55 and 65° C., Sigma Aldrich), castor wax (Lotus Oils), carnauba wax (PureNature NZ), zinc oxide (PureNature NZ).

pH and Buffer Capacity of Ruminal Fluid

The rumen fluid collected from Dairy NZ was thawed and centrifuged before analysing for pH and buffer capacity. A volume of 10 ml of Rumen fluid received from each cow was taken and titrated against 0.05 N NaOH with continuous pH monitoring. Volume of NaOH to change the pH by a unit was recorded.

Release and Testing of Various Carriers

Small capped boluses were prepared as described in example 1 above.

Paraffin waxes, beeswax, carnauba wax and castor wax were mixed with bromoform to 33%, 50%, 67% and 75% by weight bromoform. The mixes were placed in the following:
 a. Paraffin waxes: 2 mm thick small capped boluses and 15 ml falcon tube;
 b. Castor, carnauba and beeswaxes: 1, 2, and 3 mm small capped boluses and 15 ml falcon tubes.

These were placed in 500 ml polypropylene bottles with 400 ml 0.02M phosphate buffer (Merck) in distilled water, prepared in 21, or greater batches, adjusted to pH 6.5 using 1M HCl (Merck) and a pre-calibrated pH meter (using pH 4, 7, and 10 pH buffers). The bottles were sealed and placed in the incubator at 40° C. 10 ml samples were collected and the entire solution changed every 2 days (Monday, Wednesday, Friday), except for the weekend hours.

Samples were analysed by GC-MS and GC-FID as described in example 1 above.

Results pH and Buffer Capacity

The mean pH and the buffer capacity were 6.9±0.2 (n=4) and 7.47±1.4 mMol/L/delta pH (n=4) respectively. While there has been published literatures for pH values for ruminal fluid, no data for buffer capacity is available. The buffer capacities obtained for ruminal fluid indicates that the rumen environment is resilient as it is 5-6-fold higher than that of phosphate buffer saline. We found the pH of phosphate buffer in diffusion experiment remained stable even around 3 mg/ml of bromoform concentration. Given the volume of rumen fluid 91 L, the maximum concentration of bromoform at extreme condition of complete bolus rupture would reach around 1.09 mg/ml, which is lower than observed earlier in PBS. Therefore, with this concentration and given the strong buffer capacity of Rumen fluid, there is a less possibility of pH drop in the event of abrupt bolus rupture.

Release Testing of Carriers

Paraffin wax had the highest release rate at 190 mg/cm2/day, followed by beeswax, carnauba and castor wax (FIG.

12). Carnauba and castor wax seem better options for the carrier as the release rate is 50 to 40% less compared to beeswax.

Figure 13A:
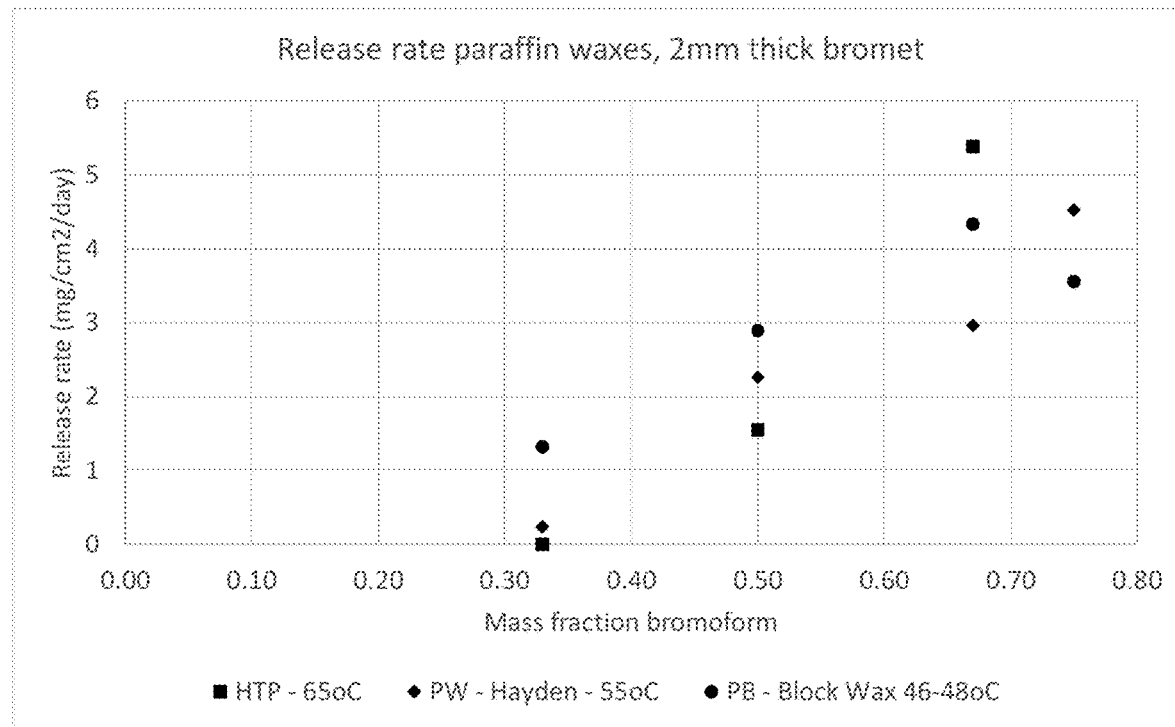
FIG. 13A is a graph showing the release rate of bromoform from paraffin wax as a carrier.
Figure 13B:
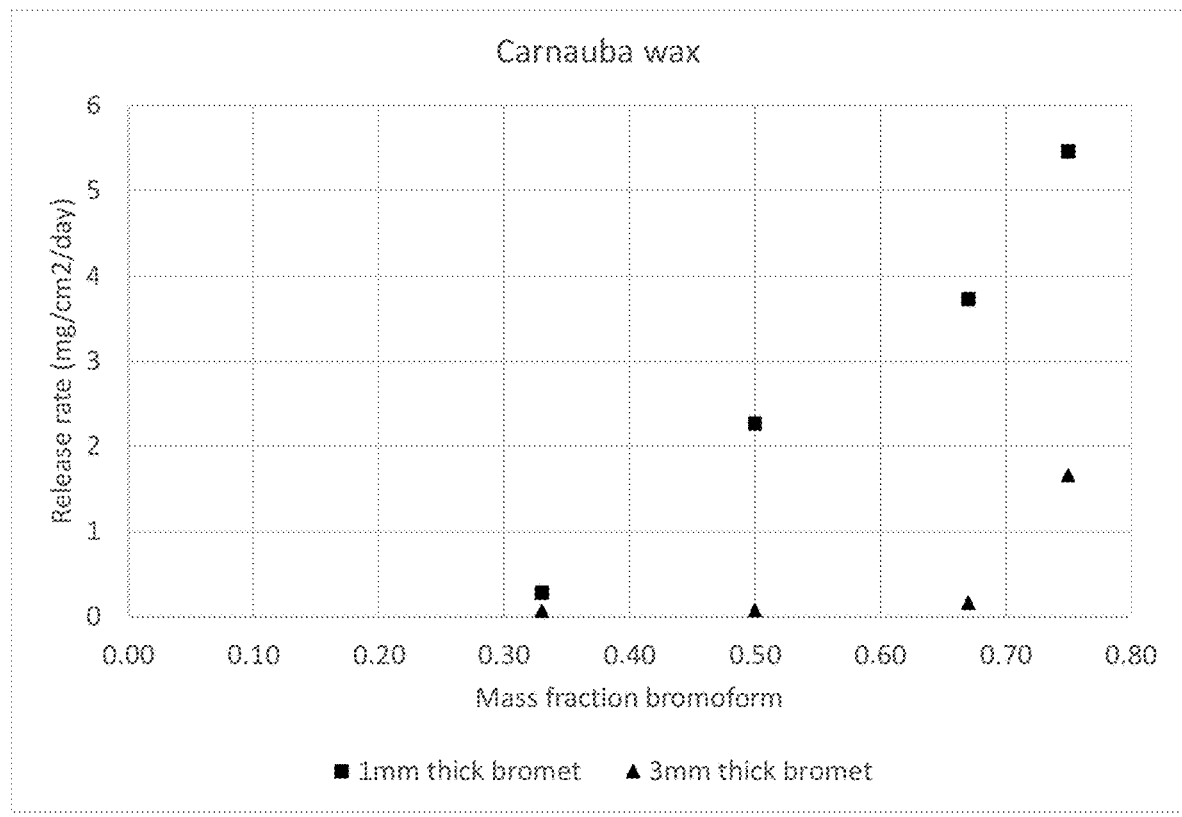
FIG. 13B is a graph showing the release rate of bromoform from carnauba wax as a carrier.
Figure 13C:
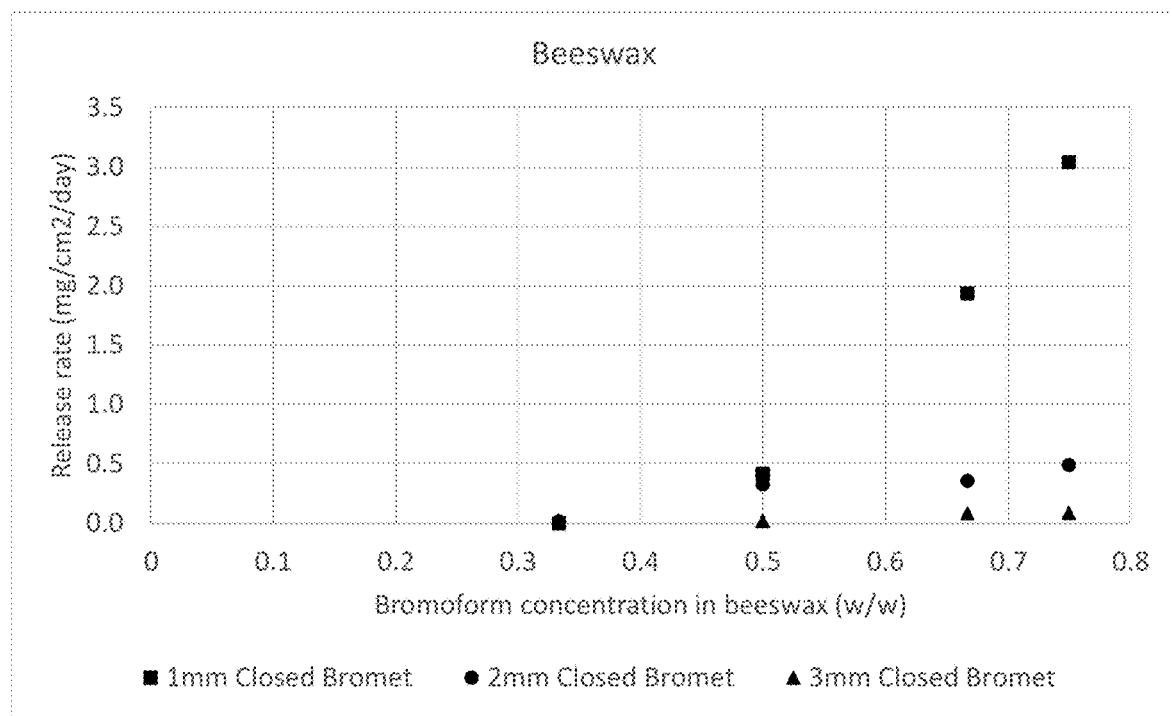
FIG. 13C is a graph showing the release rate of bromoform from Beeswax as a carrier.

Bromoform had the greatest release rate in boluses made with paraffin waxes at 3.5 to 5.4 mg/cm2/day in the 2 mm thick small capped boluses (FIGS. 13A-13C).

Boluses made with carnauba wax had release rates up to 5.5 mg/cm2/day in the 1 mm thick bolus and 1.66 mg/cm2/day in the 3 mm thick bolus.

In comparison, boluses made with beeswax had a release rate of 3 mg/cm2/day at 75% (by weight) bromoform (FIG. 13C).

The bromoform had dissolved the castor wax and it had diffused through the bolus and pooled on the bottom of the container, dissolving the container, and no release rates were able to be determined as bromoform was not detected in the water for the samples that had been collected. The trials with castor wax can be repeated in glass bottles.

Release Rates from Reinforced Bolus

Figure 14:
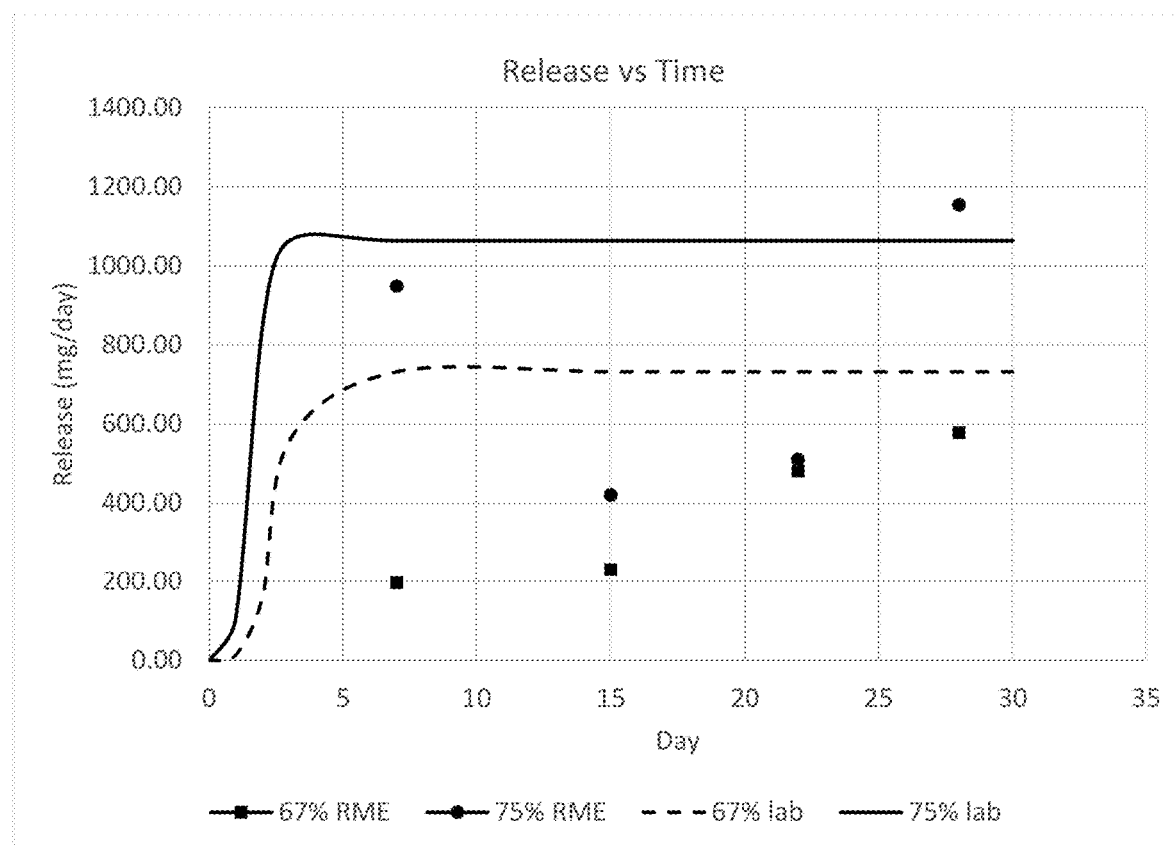
FIG. 14 is a graph showing the average release rate of bromoform for a reinforced bolus.
Figures 15A, 15B:
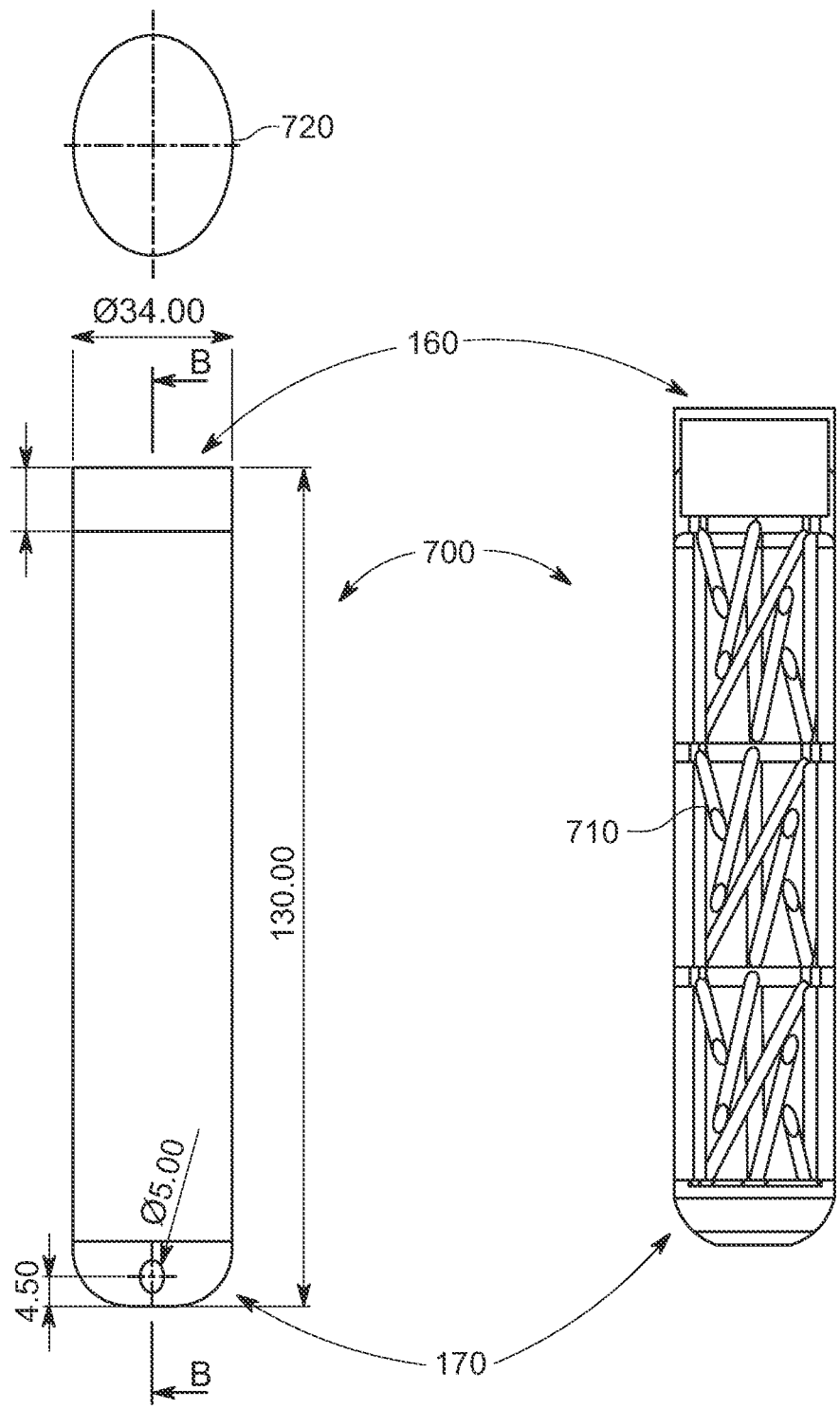
FIG. 15A is a side view showing a reinforced bolus design in accordance with some embodiments of the invention.
FIG. 15B is a side cross section view of a reinforced bolus design in accordance with some embodiments of the invention.
Figures 15C, 15D:
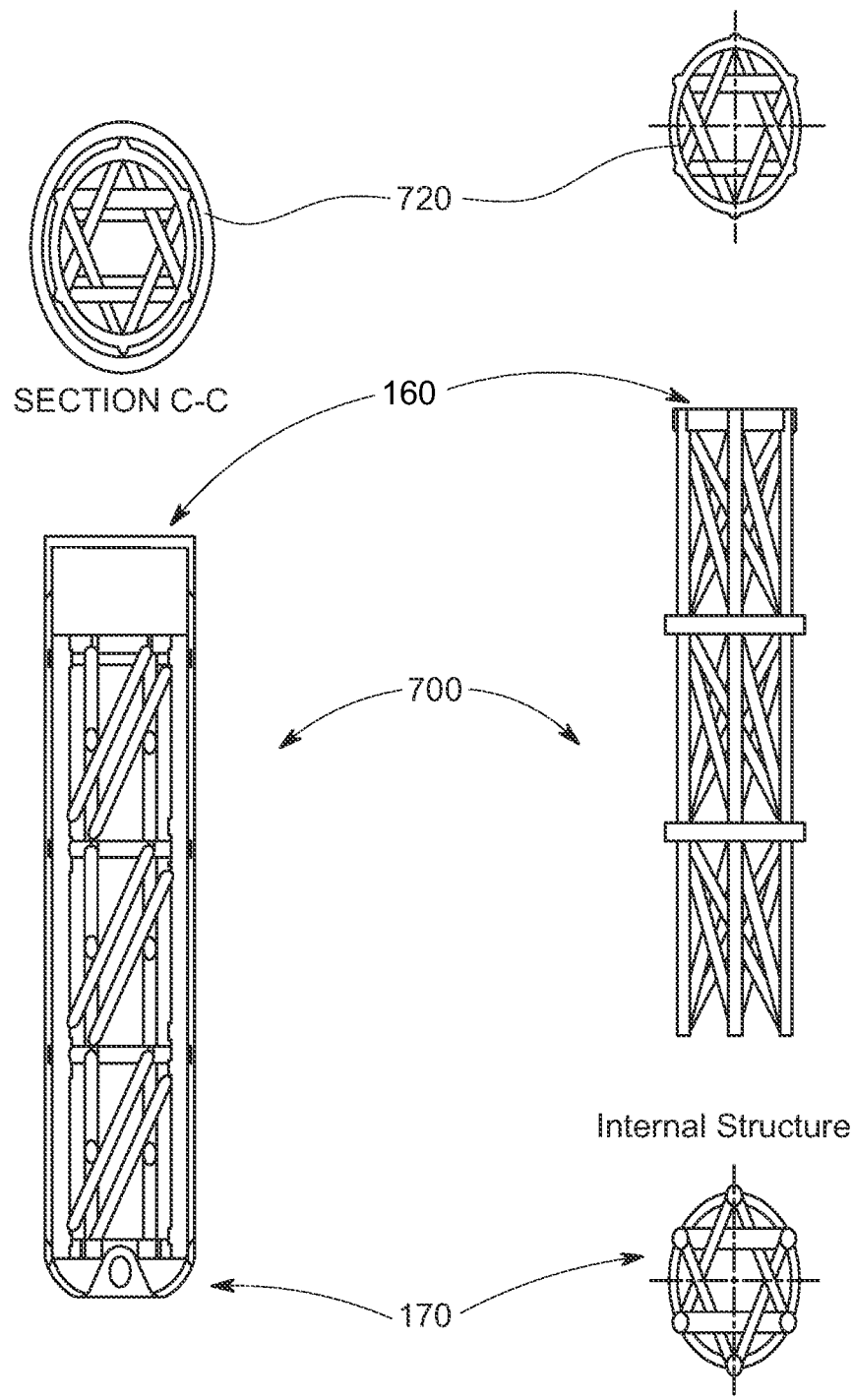
FIG. 15C is a side cross section view of a reinforced bolus design in accordance with some embodiments of the invention.
FIG. 15D is a cross section view of the internal structure of a reinforced bolus design in accordance with some embodiments of the invention.

Average release rates for large reinforced boluses with 67% (by weight) and 75% (by weight) bromoform, prepared as described previously in example 1 above, from another trial are shown in FIG. 14 and compared to release rates from the same boluses measured in the lab. Half of the boluses were in 20 L buckets with 1 kg of sand filled with buffer at pH 6.5, and the other half were in 20 L buckets with 400 g of wood shavings and 1 kg of sand. Release rates are comparable at day 28 to those observed in the lab. Little difference in bromoform concentration was observed between buckets containing wood shavings and buckets without wood shavings. Boluses have largely remained intact, with some compression due to sand, and some have had their lids opened.

Example 3: Animal Study

An animal study was conducted to determine methane emissions from an animal implanted with a bolus of the disclosure. The experiment was designed as an unbalanced, completely randomized design with three treatments and three repeated measurements over time in three periods 8 to 12 weeks apart.

Nineteen dairy beef heifers (312±14 kg live weight), including three spare animals, were selected from a mob of 50 based on behaviour traits and liveweight from a research farm in the Manawatu, New Zealand. They were assigned to one of three treatments: a bolus containing no bromoform (CONTROL; n=4); a bolus releasing bromoform at a rate of about 300-400 mg/day (LOW, n=6); or a bolus releasing about 450-580 mg/day (HIGH, n=6). SmaXtec boluses were administered at the same time to monitor rumen temperature as an animal health monitor and to complement the weekly blood samples.

The heifers were transported from research farm to a testing centre for diet adaptation and gas measurements using respiration chambers. The heifers were adapted to the environment of the cattle yards and the fresh cut pasture for 7 days before receiving their allocated treatment bolus. Gas measurements started 13 days after the boluses were administrated. Each heifer was in the respiration chambers for 48 hours during the period of gas measurements, which took two weeks for four measurement groups. At the end of the measurements in respiration chambers, the animals were transported back to research farm.

Bolus Preparation

The boluses were manufactured in accordance with the procedure described in example 1 above. The following formulations used in this trial are shown table 4 below.

TABLE 4

| Formulation for the shortened reinforced boluses for the Research Trial | | | | | | | | |
|---|---|---|---|---|---|---|---|---|
| | Bromoform | | Per bolus | | | Total | | |
| Type | mass fraction in wax | Quantity | Zinc Oxide (g) | Beeswax (g) | Bromoform (g) | Zinc Oxide (g) | Beeswax (g) | Bromoform (g) |
| LCB2 | 0 | 6 | 28.0 | 80.4 | 0.0 | 168.0 | 482.7 | 0.0 |
| LRB1 | 0.67 | 8 | 12.1 | 21.3 | 43.2 | 93.4 | 164.0 | 332.9 |
| LRB1 | 0.75 | 8 | 12.1 | 17.8 | 53.5 | 93.4 | 137.4 | 412.1 |

Bolus Administration

The three versions of boluses were made within the first 10 days of the experiment. The first version was a short bolus which was regurgitated by all animals within the 5 days after the boluses were administered. Because the control boluses were longer than the treatment boluses and these had not been regurgitated during the first 3 days, it was assumed that the bolus size was the major factor for regurgitation. All first-version treatment boluses were replaced with second-version boluses on day 5 after administration. However, the longer boluses of the second version were also regurgitated. Therefore, these boluses were then replaced with a third version treatment bolus, which was a significantly heavier bolus of the same size as the second version bolus. The third-version boluses have not been regurgitated to-date. Currently almost all heifers have been dosed with third-version boluses, except for three of the LOW treatment heifers. Details of boluses regurgitation and re-administration are in Table 5.

Two control boluses were regurgitated, but only one was identified because the bolus ID was illegible. None of control boluses were re-administered because it was not possible to identify the heifer-bolus match.

TABLE 5

Bolus administration events of the different bolus versions during the first three weeks after initial administration.

| Animal ID | Treatment | V1 * bolus ID | V2 bolus ID | V2 bolus administration | V3 bolus ID | V3 bolus administration |
|---|---|---|---|---|---|---|
| 780 | CONTROL | 1 | | | | |
| 782 | CONTROL | 2 | | | | |
| 789 | CONTROL | 3 | | | | |
| 796 | CONTROL | 5 | | | | |
| 797 | CONTROL | 4 | | | | |
| 783 | LOW | 1 | 1 | 30 Jul. 2021 | 1 | 13 Aug. 2021 |
| 787 | LOW | 3 | 3 | 30 Jul. 2021 | | Not regurgitated |
| 788 | LOW | 2 | 2 | 31 Jul. 2021 | | Not regurgitated |
| 790 | LOW | 5 | 5 | 30 Jul. 2021 | 5 | 7 Aug. 2021 |
| 791 | LOW | 5 | 4 | 30 Jul. 2021 | | Not regurgitated |
| 793 | LOW | 6 | 6 | 30 Jul. 2021 | 6 | 13 Aug. 2021 |
| 794 | LOW | 7 | 7 | 30 Jul. 2021 | 7 | 10 Aug. 2021 |
| 784 | HIGH | 9 | 9 | 1 Aug. 2021 | 9 | 10 Aug. 2021 |
| 785 | HIGH | 10 | 10 | 30 Jul. 2021 | 10 | 10 Aug. 2021 |
| 786 | HIGH | 11 | 14 | 30 Jul. 2021 | 8 | 7 Aug. 2021 |
| 792 | HIGH | 12 | 12 | 31 Jul. 2021 | 12 | 13 Aug. 2021 |
| 795 | HIGH | 13 | 13 | 30 Jul. 2021 | 13 | 12 Aug. 2021 |
| 798 | HIGH | 14 | 11 | 1 Aug. 2021 | 11 | 9 Aug. 2021 |
| 781 | HIGH | 15 | 8 | 30 Jul. 2021 | 14 | 13 Aug. 2021 |

* V1: all boluses administration on 27 Jul. 2021

Feed Intake and Liveweight

The heifers were fed cut ryegrass-based pasture offered ad libitum. The forage was harvested daily at approximately 10:00 at research farm and transported to the testing centre. The harvested forage was divided into two allocations, the first allocation was fed in the afternoon at 15:30 and the second allocation was stored at 4° C. until the next morning feeding at 08:30. Samples were collected from each pasture delivery for dry matter determination and feed analysis. Dry matter (DM) was determined from triplicate subsamples by oven drying at 105° C. for 24 h. A separate subsample was oven dried at 65° C. for 48 h for chemical nutrient analyses. Both drying ovens used were forced-air ovens (Avantgarde FED 720, Binder GmbH, Germany).

Two days prior to entering respiration chambers for methane measurements, the cows were put into metabolic crates to adapt them to confined spaces and being tied. When the animals were in metabolic crates or respiration chambers, feed refusals were collected twice daily, and refusal DM was determined as described above. Daily dry matter intake of the heifers was then determined from the difference of the dry matter offered and refused.

Liveweight was recorded pre-trial when animals were grazing at the research farm on two occasions (21 Jul. 2013 and 16 Jul. 2021). The animals were weighed again on 19 Jul. 2021 on arrival at testing farm and every 7-10 days while on site. Initial liveweight was measured on 23 Jul. 2021 before bolus administration and final liveweight was once animals left the respiration chambers. Final liveweight dates are different for some animals because measurements were undertaken over two weeks.

Gas Measurements

Fermentation gases methane ($CH_4$), carbon dioxide ($CO_2$) and hydrogen ($H_2$) were quantified in four open-circuit respiration chambers at the New Zealand Ruminant Methane Measurement Centre (AgResearch, Palmerston North, New Zealand). Each chamber is 15.4 $m^3$ (3.5 m long×2 m wide×2.2 m high) with an air flow rate of around 1.0 $m^3$/min, which was continuously monitored by measuring differential pressure using a Venturi flowmeter. Temperature inside respiration chambers was approximately 20° C. and the relative humidity was on average approximately 79%. All gases were measured at ~2.8-min intervals using a 4900C Continuous Emission analyser (Servomex Group Ltd, East Sussex, UK) and daily production of each gas was calculated from the difference between concentration flowing in- and out of the chamber (Pinares-Patiño et al., 2012). Respiration chambers were opened twice daily (~20 min each time) for cleaning, feeding, faecal sampling and feed refusal collection. No measurements were performed during the period when chambers were opened, and missing data were interpolated by taking the average of the last 12 values (~45 min) before the doors were opened.

Statistical Analyses

Data from the first period of gas measurements was analysed using the 'predictmeans' and 'lme4' packages in the statistical software R 4.0.3 (R Core Team, 2020). Data for dry matter intake and gas emissions for each heifer were averaged across the two measurement days. Heifer served as the experimental unit. The mixed model included treatment as fixed effect and respiration chamber nested in measurement group as random effect.

Liveweight analyses included treatment as a fixed effect and time as a repeated measurement, with heifer as a subject for the repeated measurements. Only initial and final liveweight were included in this analysis.

Results

Dry Matter Intake and Gas Emissions

Dosing heifers with bromoform at about 300-400 mg/day (LOW) or about 450-580 mg/day (HIGH) did not affect the dry matter intake measured over the two days the animals were in respiration chambers compared with the control group (p=0.42). Both: $CH_4$ production (g/day) and $CH_4$ yield (g/kg unit of dry matter intake) decreased by more than 99% in LOW and HIGH compared with CONTROL (p<0.01). The decrease in $CH_4$ emissions at LOW and HIGH treatments was accompanied by an increase in $H_2$ emissions per day (Table 7). As both treatments decreased methane emissions completely, a lower dose can be used to achieve levels of methane reduction between 30 and 90%. A reduction in the daily dose would ensure that not more bromoform than necessary is used to increase the lifetime of the bolus and would decrease the risk of negative effects on the animal and potential contamination of animal products. Given that methane emissions are fully inhibited, it is noteworthy that dry matter intake was not negatively affected as has been observed when bromoform containing Asparagopsis is fed (Roque et al. 2019).

TABLE 7

Dry matter intake (DMI) methane (CH4) and hydrogen (H2) emissions measured in respiration chambers over two days in heifers dosed boluses releasing no bromoform (CONTROL), 300 mg/d (LOW) or 450 mg/d (HIGH) of bromoform

|  | CONTROL | LOW | HIGH | SED | p-value |
|---|---|---|---|---|---|
| DMI [kg/d] | 5.20 | 4.98 | 4.50 | 0.79 | 0.420 |
| $CH_4$ (g/d) | $120.25^a$ | $0.34^b$ | $0.77^b$ | 2.74 | <0.01 |
| $CH_4$ [g/kg DMI] | $23.32^a$ | $0.14^b$ | $0.11^b$ | 0.33 | <0.01 |
| $H_2$ (g/d) | $0.15^b$ | $20.60^a$ | $20.08^a$ | 3.48 | <0.01 |

Conclusion

As observed, the results above indicate treatment using a bolus with the present invention may be highly effective a few weeks after the boluses were administered, as demonstrated by the ~99% reduction in methane.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

The entire disclosures of all applications, patents and publications cited above and below, if any, are herein incorporated by reference.

Reference to any prior art in this specification is not, and should not be taken as an acknowledgement or any form of suggestion that that prior art forms part of the common general knowledge in the field of endeavour in any country in the world.

The invention may also be said broadly to consist in the parts, elements and features referred to or indicated in the specification of the application, individually or collectively, in any or all combinations of two or more of said parts, elements or features.

Where in the foregoing description reference has been made to integers or components having known equivalents thereof, those integers are herein incorporated as if individually set forth.

It should be noted that various changes and modifications to the presently preferred embodiments described herein will be apparent to those skilled in the art. Such changes and modifications may be made without departing from the spirit and scope of the invention and without diminishing its attendant advantages. It is therefore intended that such changes and modifications be included within the present invention.

Example 4

Methods

Materials

PLA (3052D), PBS (supplier Convex) and PBAT (supplier Convex) were freeze dried in aluminium foil trays using a Labcono freeze drier before use to reduce water content in the blends.

Manufacture of Boluses

Blends of PLA (3052D), PBS, PBAT were made by mixing the pellets in the following ratios:

TABLE 8

Formulations of blends made (% by weight)

|  | PLA | PBS | PBAT |
|---|---|---|---|
| 1 | 100 |  |  |
| 2 | 70 | 30 |  |
| 3 | 40 | 60 |  |
| 4 | 20 | 80 |  |
| 5 | 70 |  | 30 |
| 6 | 40 |  | 60 |
| 7 | 20 |  | 80 |

Blends were prepared by melt blending in a LabTech corotating twin screw extruder (L/D 44:1) with a screw speed of 200 rpm. Temperature profile increased over 11 barrel heating sections, from 70° C. at the feed throat to 220° C. along the main barrel, and increasing to 230° C. at the die. Blends were granulated using a triblade granulator with a 4 mm plate (Castin Machinery, NZ). The blends were stored in aluminium foil trays and bagged in zip lock bags before use. All blends oven dried overnight at 40° C. before injection moulding. Tensile bars (ASTM D368) and impact bars (ISO 179) were produced in a BOY 35A injection moulding machine, with a temperature profile of 70 to 220° C. from feed to nozzle. Mould temperature was kept constant at 50° C. Lanolin was used as a mould release agent and was sprayed into the mould prior to each tensile bar being produced.

Analysis of Boluses

Shrinkage from injection moulding was determined by measuring the width and thickness of the tensile specimens, subtracting this from the mould width and depth, and dividing by the mould width and depth and multiplying by 100 to obtain a percentage. Tensile bars were cut into ~2 cm lengths using a bandsaw and the edges sanded using 500 grit sandpaper until smooth. 120 cm diameter flat bottom glass petri dishes were filled with beeswax/bromoform mixtures at the following bromoform concentrations: 33, 50, 67, 75% by weight. Three samples of each PLA blend were labelled, weighed in a 4 dp electronic balance, and thickness, length and width measured using digital calipers. These were then placed flat and gently pressed into each bromoform/beeswax formulation to ensure good contact between the beeswax and PLA surfaces. Glass lids were then placed on the petri dishes and sealed using insulation tape, before being placed in the incubator at 40° C.

Samples were also tested for hardness using the Shore D hardness tester at a 7 kg weight, and structural properties using the XRD.

Every two or three days samples were removed from the petri dishes, cleaned using tissue paper, weighed using the 4 dp electronic balance, and measured using the digital calipers.

Bromoform absorption was determined by measuring the total change in mass of the sample and dividing by the starting mass of the sample. Rate of absorption was determined by dividing the change in mass of the sample between measurements by the area of sample in contact with the bromoform/beeswax mixture and dividing by the change in time between measurements.

Swelling was determined by measuring the change in volume of the sample and dividing by the original volume of the sample.

Results
Injection Moulding

Figure 16A:
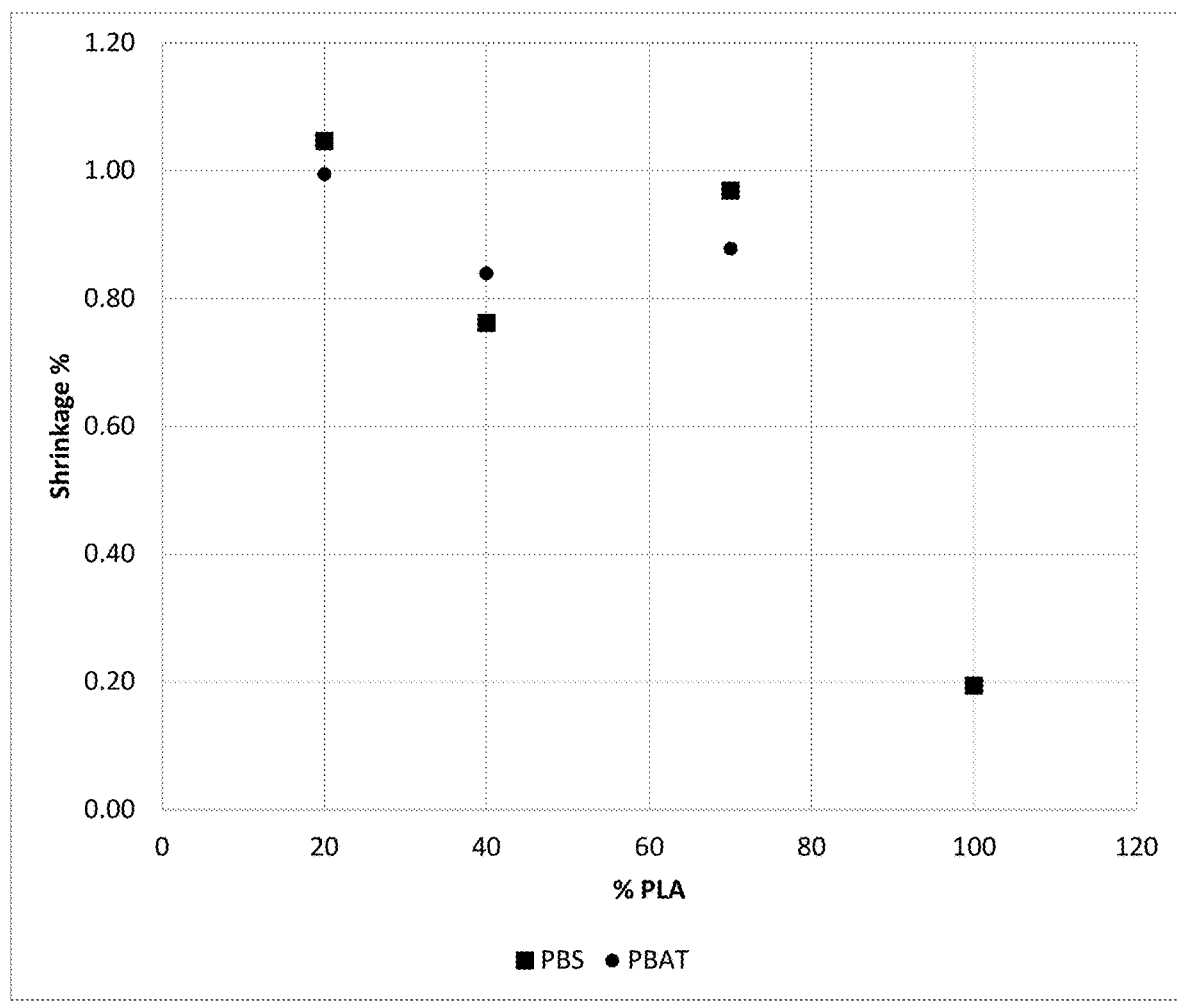
FIG. 16A shows tensile specimen shrinkage from injection moulding.

Shrinkage for PLA was around 0.2% and increase to around 1-1.2% for increasing PBS and PBAT blends (FIG. 16A). The average skilled person knows how to adjust for shrinkage to produce a bolus of a desired size and dimension. It should be appreciated that various sizes of the bolus are possible, and they are not critical for achieving a delayed release of the haloform in view of the teachings of the present patent application.

Figure 16B:
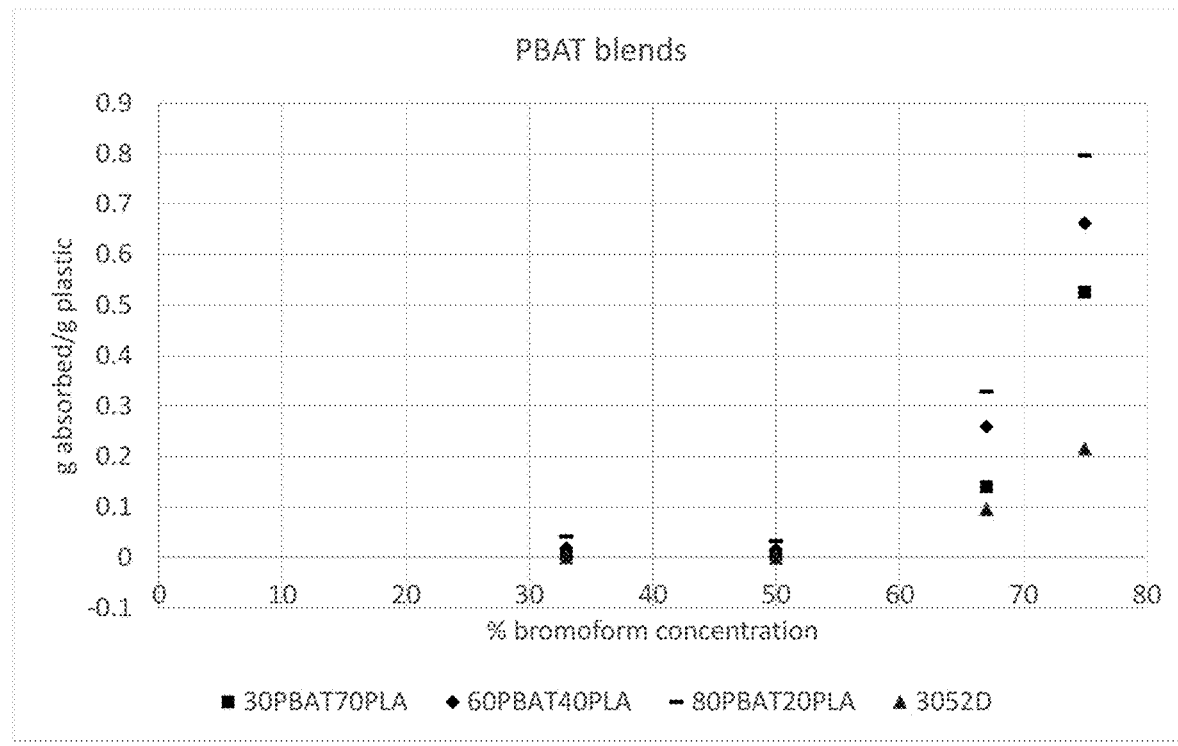
FIG. 16B shows bromoform absorbed vs bromoform composition in beeswax for different compositions of PLA blended with PBS and PBAT.
Figure 16B:
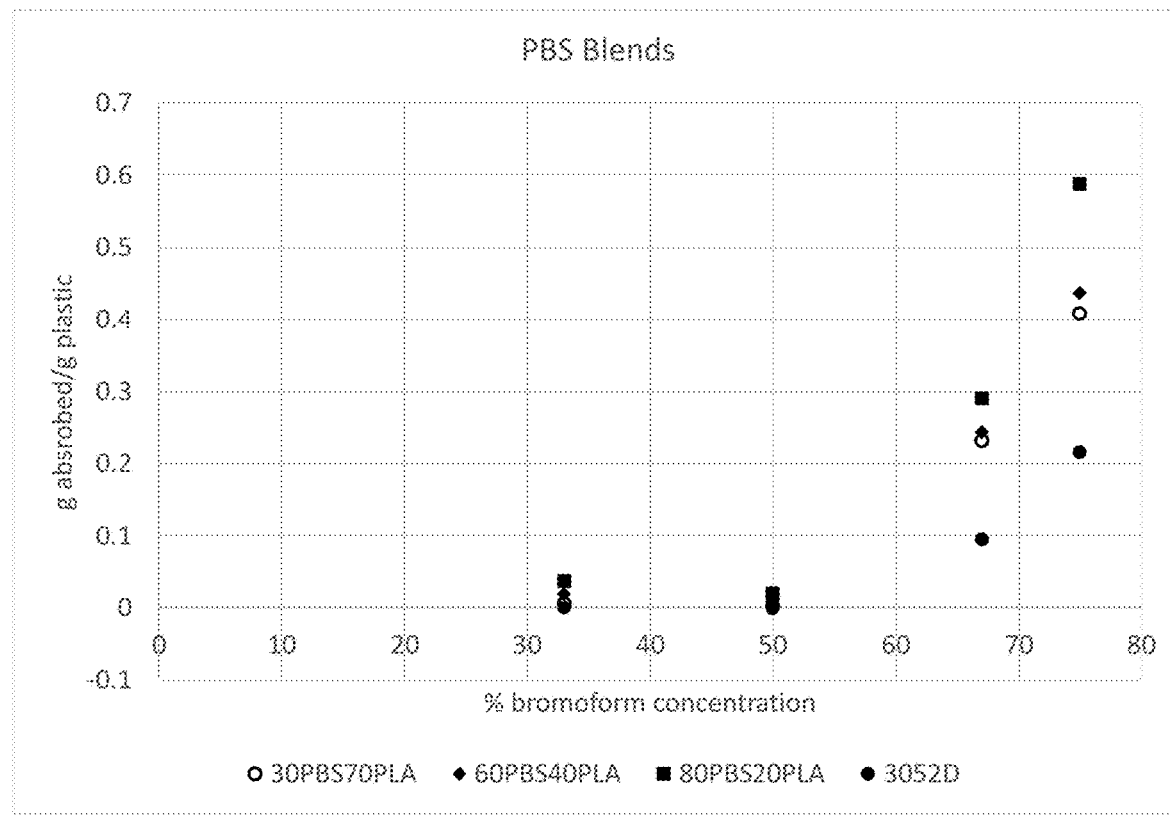
Figure 16C:
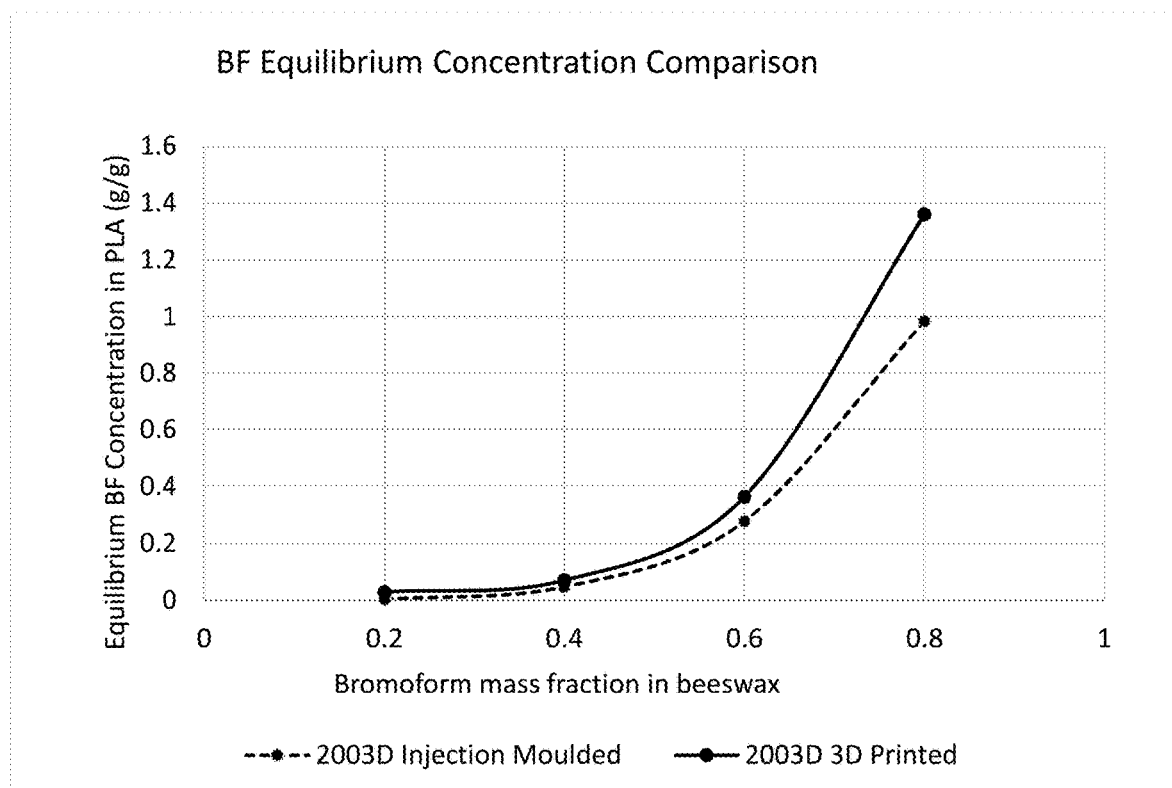
FIG. 16C shows bromoform absorbed vs bromoform composition in beeswax for 3D printed PLA and injection moulded 2003D PLA.
Figure 16D:
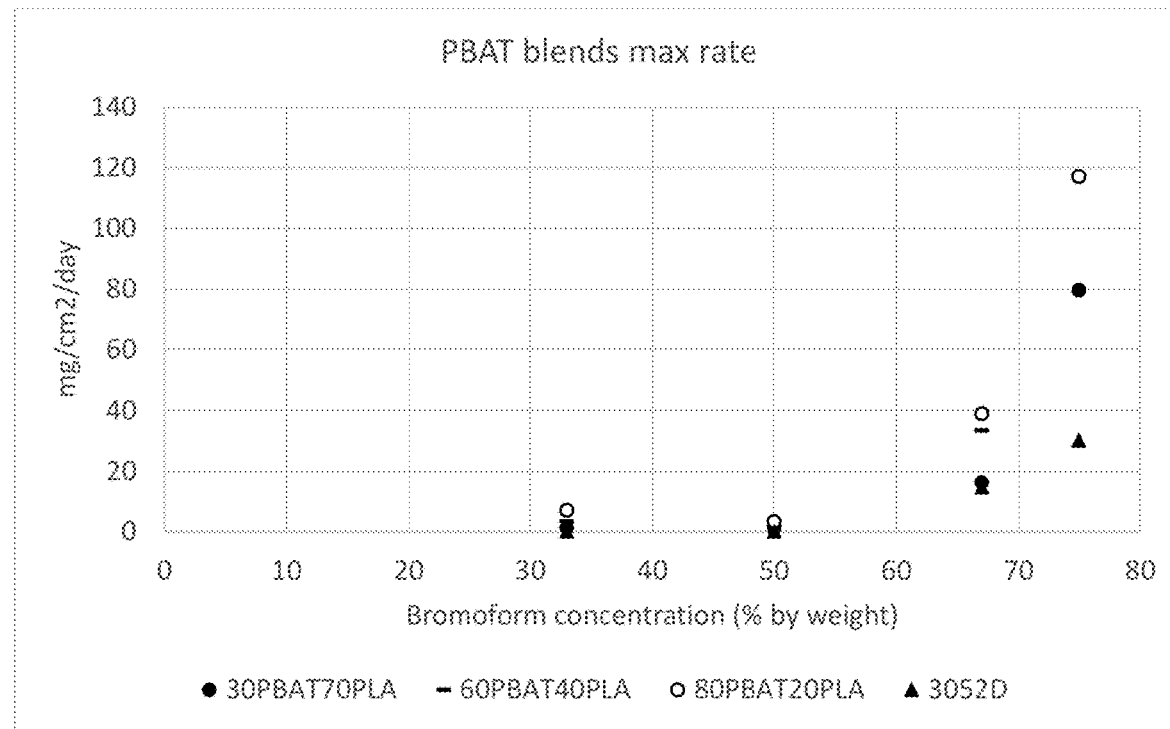
FIG. 16D shows bromoform absorption rate vs bromoform composition in beeswax for different compositions of PLA blended with PBS and PBAT.
Figure 16D:
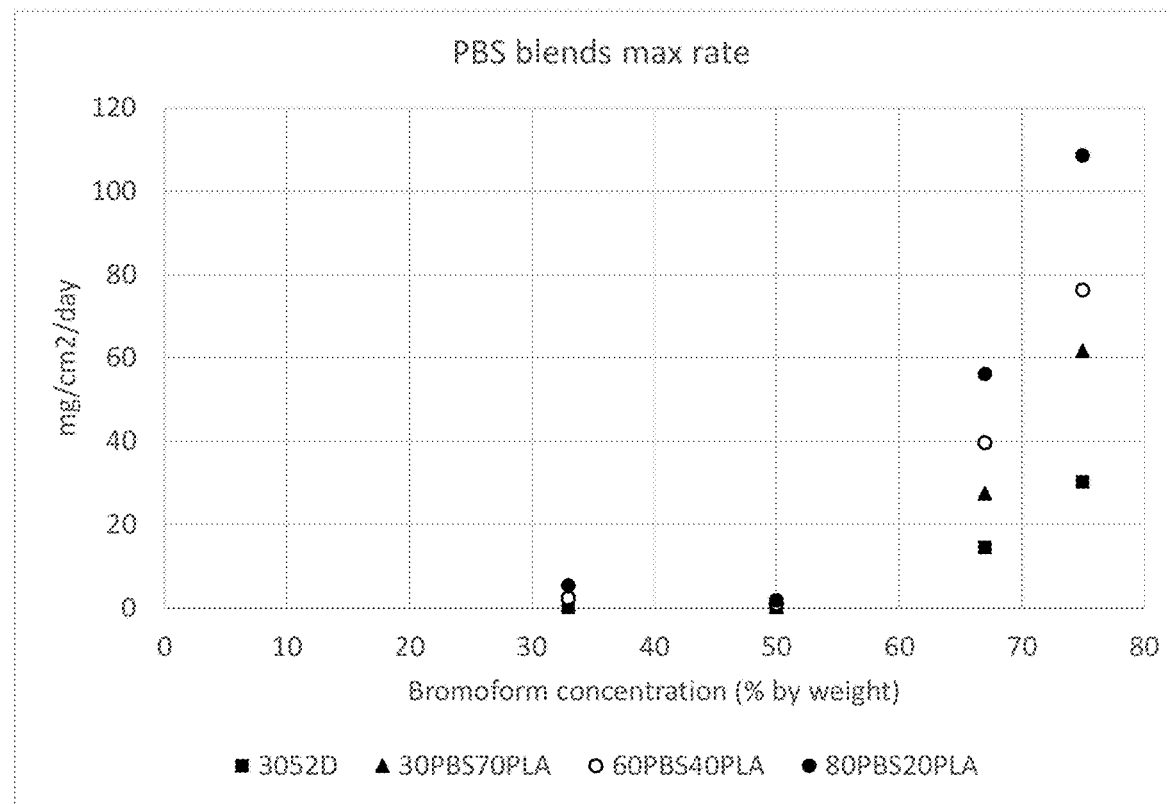
Figure 16E:
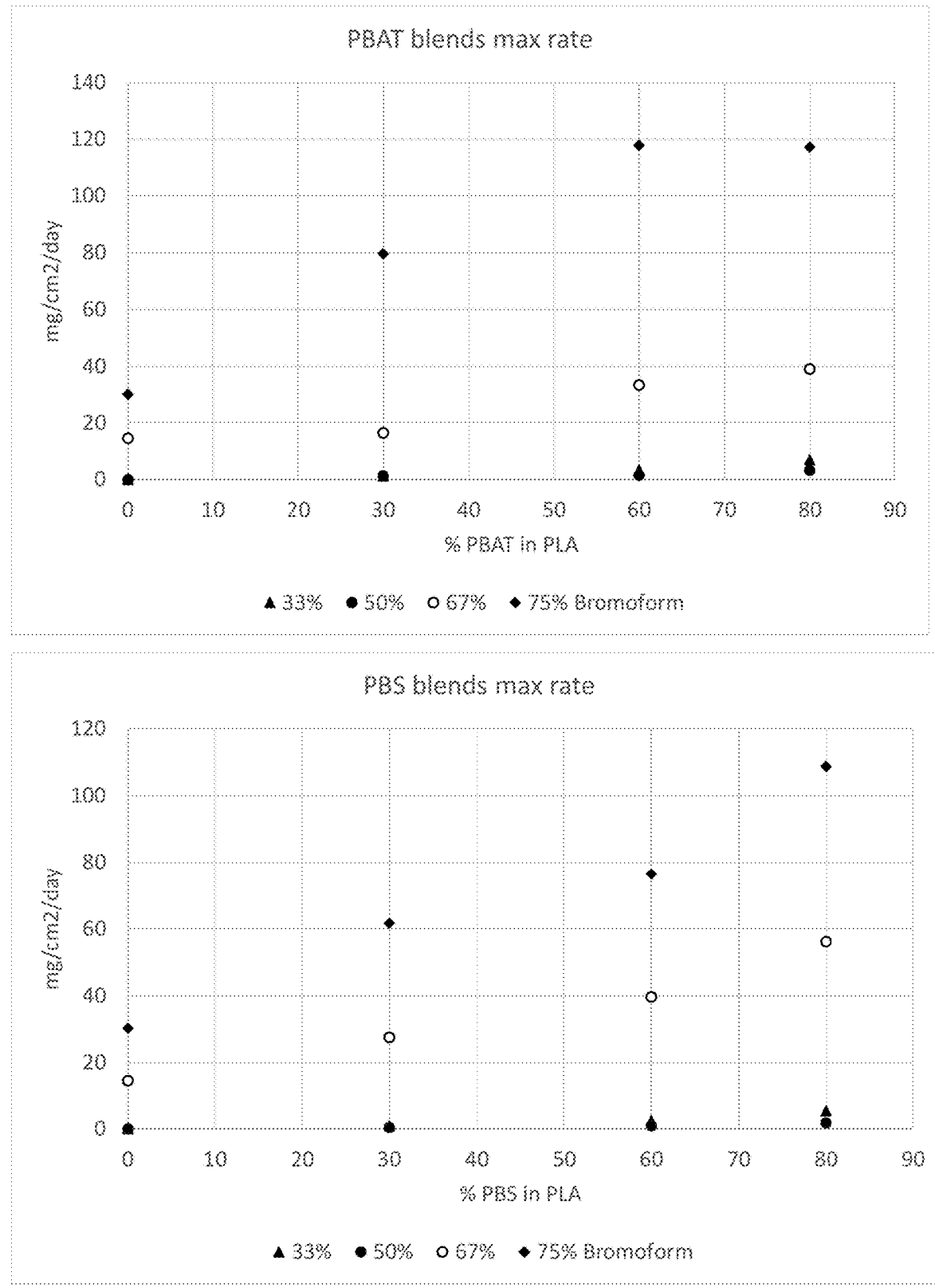
FIG. 16E shows bromoform absorption rate vs PLA composition in beeswax with different concentrations of bromoform.

Less bromoform was absorbed at bromoform concentrations in beeswax below 50% by weight, suggesting limited mobility of bromoform at low concentrations of bromoform in beeswax, and a strong holding capacity of beeswax for bromoform (FIG. 16B). As bromoform concentration increased in beeswax and the mass fraction of PBAT and PBS increased in PLA, the mass of bromoform absorbed increased, and the maximum rate of absorption also increased (FIGS. 16C and 16D). The masses absorbed for the PLA blends were lower than that for 2003D PLA and 3D printed PLA (FIG. 16E).

Example 5

Methods

Samples were prepared and analysed as described in Example 4, unless indicated otherwise.

Samples were also tested for hardness using the Shore D hardness tester at a 7 kg weight, and structural properties using the XRD before and after exposure to the bromoform/beeswax mixtures.

A PANalytica Empyrean XRD was used for XRD analysis with a flat sample stage holder with an adjustable beam to maintain an exposed area of 1 cm by 5 mm at all angles between 5 and 70 2 Theta, with the following configuration:

TABLE 9

Configuration for XRD analysis:

| | |
|---|---|
| Configuration | Flat Sample Stage, Owner-User-1, Creation date = 30 May 2013 9:05:47 AM |
| Goniometer | Theta/Theta; Minimum step size 2Theta: 0.0001; Minimum step size Omega: 0.0001 |
| Sample stage | Stage for flat samples/holders |
| Diffractometer system | EMPYREAN |
| Anode material | Cu |
| K-Alpha1 wavelength | 1.540598 |
| K-Alpha2 wavelength | 1.544426 |
| Ratio K-Alpha2/K-Alpha1 | 0.5 |
| Monochromator used | NO |
| Generator voltage | 45 |
| Tube current | 40 |
| Scan axis | Gonio |
| Scan range | 5-70 |
| Scan step size | 0.01313 |
| No. of points | 4417 |
| Scan type | CONTINUOUS |
| Time per step | 39.27 |

XRD data was exported to Excel, smoothed with a 10 point smooth, and baseline corrected between 5 and 60 2 theta.

Results

Figure 17:
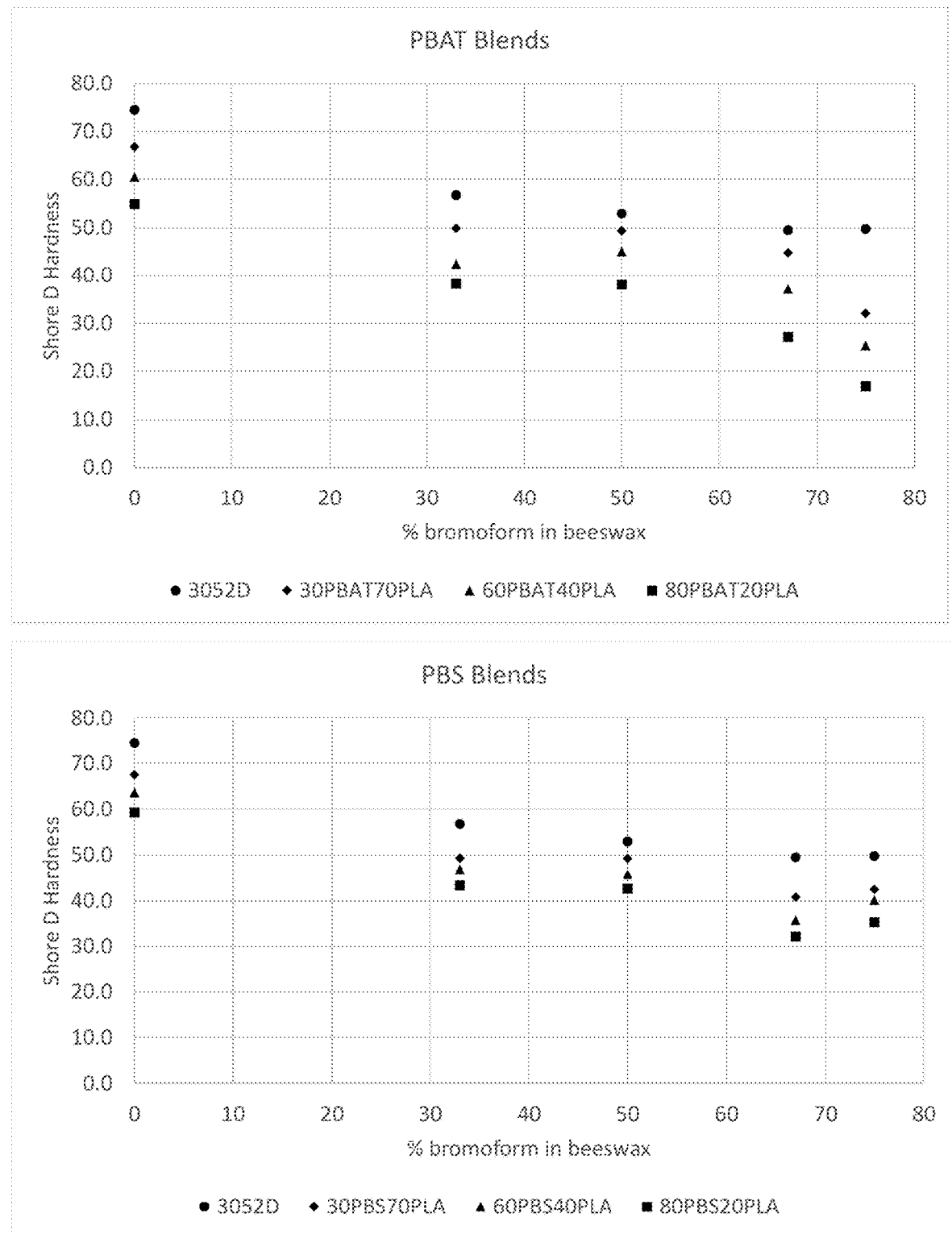
FIG. 17 shows hardness analysis of PLA blends before and after exposure to bromoform.

FIG. 17 shows hardness analysis of PLA blends before and after exposure to bromoform. Thus, by including PBS in the carrier, the mixture becomes less sensitive to bromoform exposure, which may facilitate shelf life.

Example 6

Release Testing of Large, Reinforced Bolus (Rissington Trial)

The boluses were drawn in Solidworks, converted to .stl files, opened in FlashPrint to create the print jobs. The boluses were printed in three parts (case, internal structure, and cap) on FlashForge Creator Pro 3D printers using E-Sun PLA+ at 100% fill, standard resolution, first layer height 0.27 mm, layer height 0.18 mm, 2 perimeter shells, 3 top solid layers, 3 bottom solid layers, fill pattern hexagon, print speed 60 mm/s, extruder temperature 200° C. and plate temperature 50° C.

Two Individual formulations comprising of 67% and 55% (by weight) bromoform in a castor wax:paraffin wax (in this example: the ratio was 50:50) as carrier mixture were prepared. Next, individual bromoform wax mixture was poured into the 1 mm thick casing after inserting a zinc rod as a densifier. The cap was mounted and sealed using the soldering gun. The release test was carried out as per the method described in Example 1 with a slight modification, where a 2 L media was used instead and replaced daily. A volume of 10 ml sample was taken and extracted with ethyl acetate suitably before injecting into the GC to quantify the bromoform release.

Figure 18A:
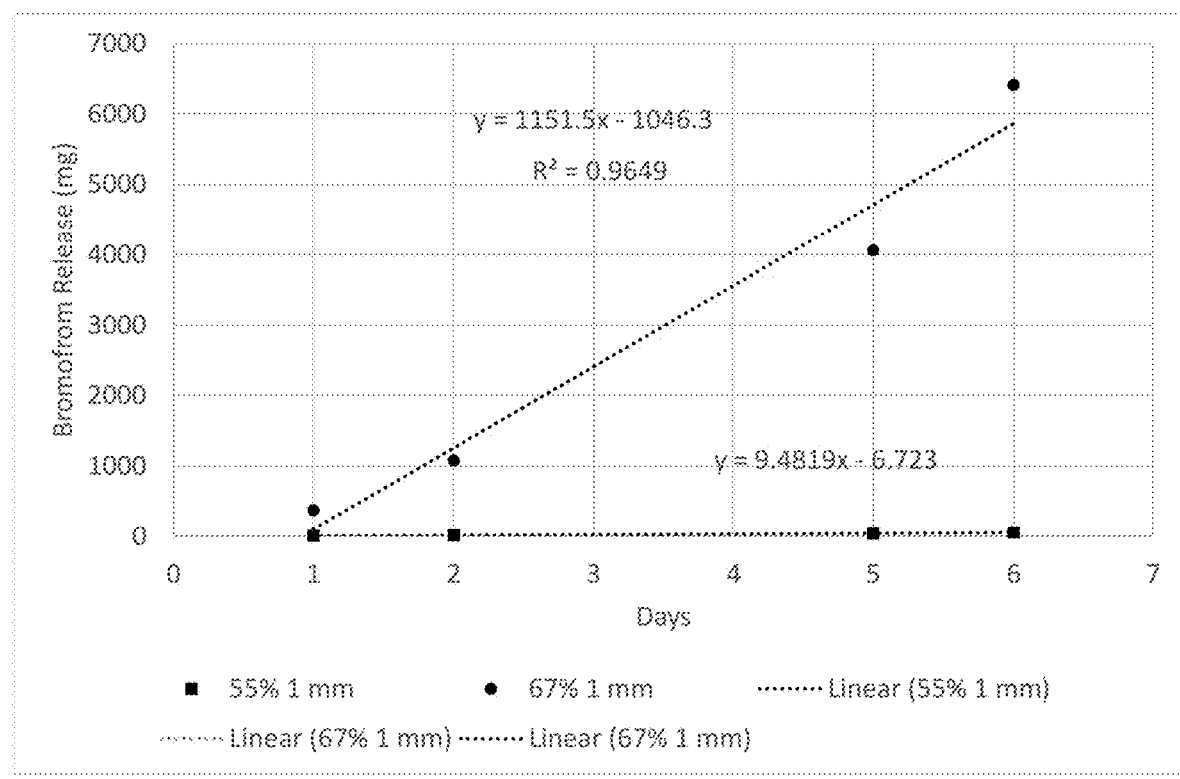
FIG. 18A shows the release of Bromoform from 67% (by weight) and 55% (by weight) Bromoform loaded 1 mm thick boluses.

The Bromoform released at a higher rate from the bolus with 67% (by weight) bromoform (1150 mg/day). Meanwhile, the release rate was slower from the bolus with 55% (by weight) bromoform loading with 9.5 mg/day (FIG. 18A).

Figure 18B:
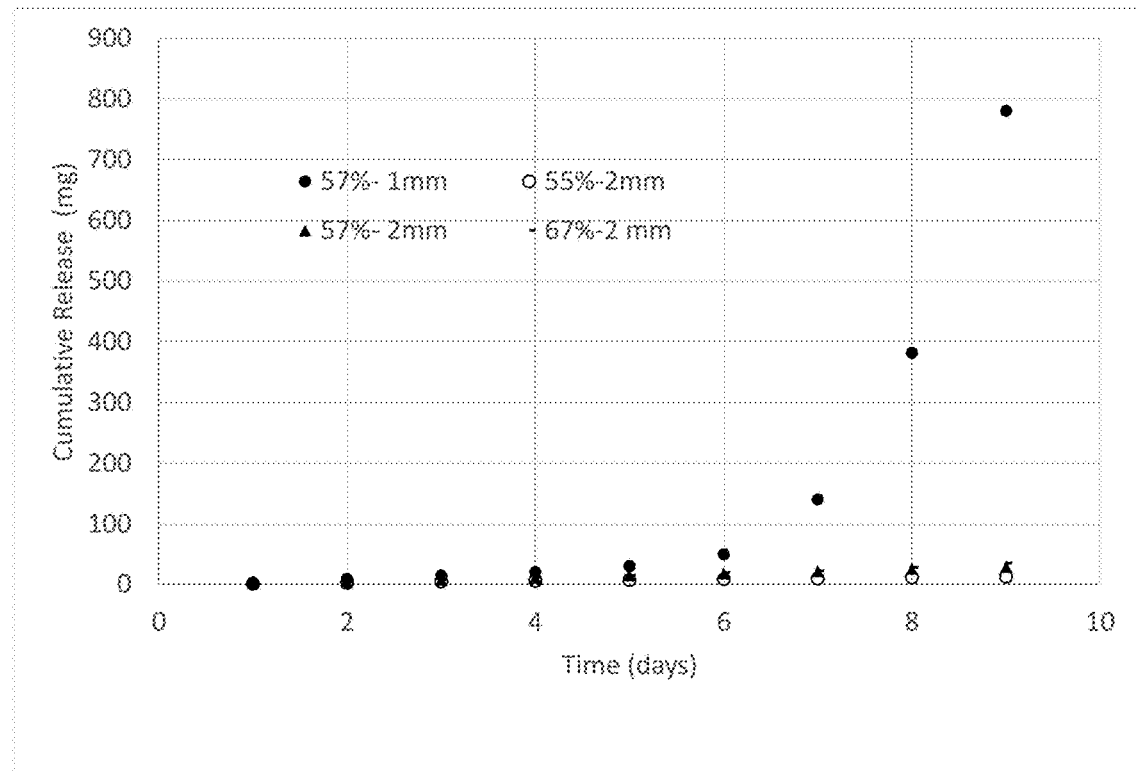
FIG. 18B shows cumulative release of Bromoform from boluses.
Figure 18C:
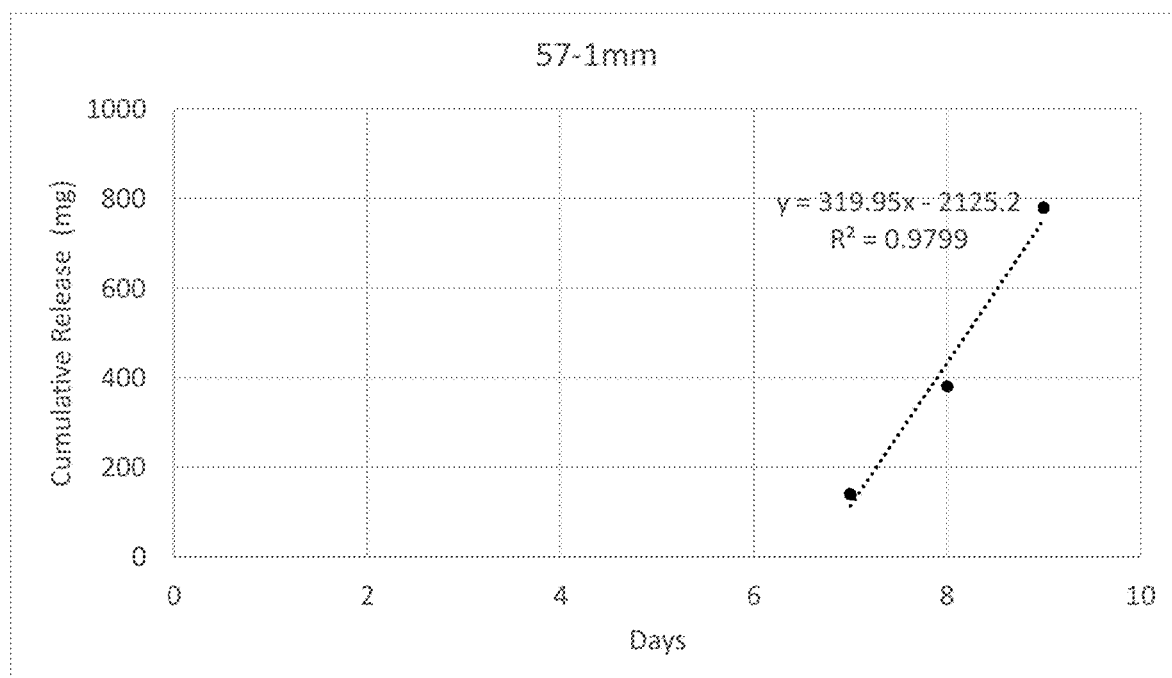
FIG. 18C shows cumulative plot of 7, 8 and 9 days for 57-1 mm bolus.
Figure 18D:
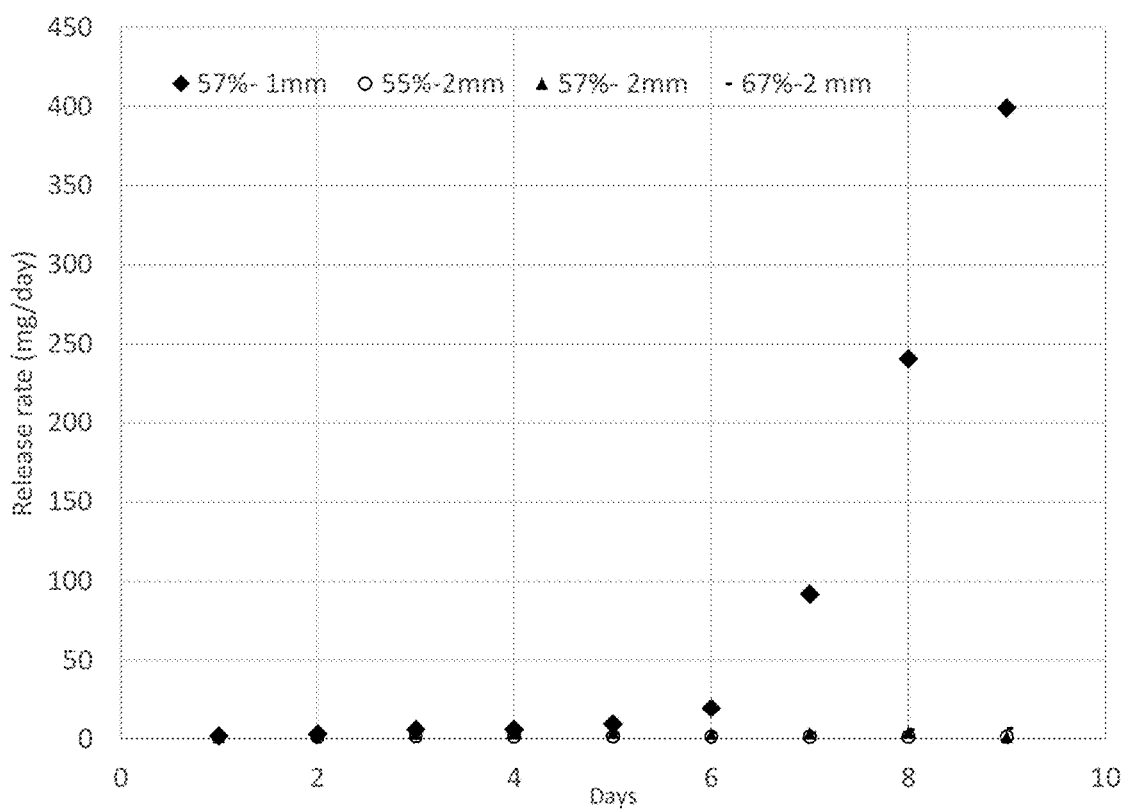
FIG. 18D shows release rate from different boluses.

Next, 4 different types of boluses (2 each) with 57% (by weight) Bromoform with 1 mm and 2 mm casing and 55% (by weight) and 67% (by weight) bromoform with 2 mm casing with similar carrier composition with zinc rod were prepared. The release testing was carried out as per the method described above. It was found that the release rate was slow with 2 mm casing and release rate was slow regardless of the bromoform content (FIGS. 18B-18D). Meanwhile, the 1 mm casing bolus with 57% (by weight) bromoform had a lag time for 7 days with reaching 240 mg at 8th day and 400 mg at 9th day (FIG. 18D). Cumulative plot for 7, 8 and 9 days showed best fit indicating release rate of 319 mg/day (FIG. 18C).

Each of the respective boluses were tested in RME as per the method described in the Examples above. The boluses were recovered after 6 days of study and examined visually. The boluses remained intact with no signs of any breakage or deformations.

Example 7

Design of a Bromoform Containing Bolus

In one preferred embodiment tested in this example the bolus comprises a housing and a core composed as defined below:

| | |
|---|---|
| Bolus dimensions | 13 cm length; 3.4 cm diameter; 257 gm weight |
| Housing design | Including a cap; wall thickness: 1 mm; |
| Core matrix | Blend of two or more waxes, e.g. Castor wax/Paraffin wax blend |
| Bromoform concentration in the core | 33%-75% (by weight) |

Example 8

Improved Mechanical Properties and Higher Load of Tribromomethane

To load even higher content of an active agent, such as tribromomethane, an alternative carrier that could allow to load a higher amount of tribromomethane was developed, providing a sustained release bolus for release over a prolonged period.

Furthermore, PLA is somewhat brittle, thus may in some cases be associated with premature bolus failure in the rumen. Therefore, to further improve the mechanical properties, such as for instance durability, of the casing material, blends of PLA were tested.

Example 8.1: Excipient Extensions

Materials and Methods

Colloidal silicon dioxide (hydrophobic) was purchased from EVONIK. Tribromomethane was purchased from Thermofisher. Ethyl cellulose (ethoxy content of 48.2%) was purchased from Sigma. Four ethoxyl grade types are defined for ethyl cellulose, which are G-type (44.5%-45.5%), K-type (45.5%-46.8%), N-type (47.5%-49.0%), and T-type (49.0% and higher). The N-type was used herein; however, other grades may be suitably used. Castor wax (Lotus), Polycaprolactone (PCL) (Mw 600). Stainless steel granule was purchased from Industrial Minerals NZ limited.

Preparation of Carriers and Densifier

Preparation of Densifier

Paraffin wax (10 g) was initially melted at 100° C. degree. Next, stainless-steel granules (90 g) added to prepare a slurry before pouring into a bolus at 85° C.

Also, in combination with bolus materials enduring higher temperatures, paraffin wax (8 g) can be initially melted at 100° C. Next, stainless-steel microparticles (92 g for a bolus of 72 mm×35 mm dimensions) are added to prepare a slurry before pouring into a bolus at 65° C. For scalable processing the paraffin wax and densifier are pre-formed into a tablet to be inserted into the housing containing the excipients, and optionally an RFID chip.

Carrier 1

The colloidal silicon dioxide-wax (ASL-65-W) carrier was prepared using materials and ratios summarized in Table 10.1. Silicon dioxide powder (ASL) (1.6 g) was manually mixed with tribromomethane (52 g) using a glass rod. Castor wax (26.4 g) was melted in a separate beaker at 100° C. using hot plate stirrer. The ASL-tribromomethane mixture was then added to the melted wax. The mixture was removed from the hot plate and homogenised for 7500 rpm for 1 min using a homogeniser (Daihan Scientific, China). The mixture was poured into a bolus (75×34 mm, 3-D printed PLA casing) when the temperature reaches down to 75-80° C. Stainless steel granule-wax mixture was poured in the bolus cap and on top of the carrier once the carrier surface solidified. The bolus was sealed using a soldering iron.

TABLE 10.1

Excipient composition of ASL-wax carrier

| ASL-65-W | Castor wax | Tribromomethane | Silicon dioxide | Total |
|---|---|---|---|---|
| Weight (g) | 26.4 | 52 | 1.6 | 80 |
| % (w/w) | 33 | 65 | 2 | 100 |

Carrier 2

Ethyl cellulose (EC) powder (20 g) was mixed with tribromomethane (56 g) using mortar and pestle (Table 10.2). Silicon dioxide (4 g) was gradually added to the EC-tribromomethane mixture. The obtained paste (ASL-70-EC) was loaded into the 75 mm bolus (3-D printed PLA casing). The mixture of paraffin wax and stainless-steel granules was prepared as described previously. The mixture was poured on top of the ASL-EC paste and partly inside the bolus's cap until filled completely. The bolus was sealed using a soldering iron.

TABLE 10.2

Excipient composition of ASL-Ethyl cellulose carrier

| ASL-70-EC | Ethyl cellulose | Tribromomethane | Silicon dioxide | Total |
|---|---|---|---|---|
| Weight (g) | 20 | 56 | 4 | 80 |
| % (w/w) | 25 | 70 | 5 | 100 |

Carrier 3

Tribromomethane (52 g) was mixed with Silicon dioxide (12 g) using a mortar and pestle. PCL (16 g) was melted on a hot magnetic stirrer at 100° C. The melted PCL was then added to the ASL-tribromomethane mixture (Table 10.3) and mixed thoroughly using a mortar and pestle until a homogenous dough, ASL-65-PCL carrier, was obtained. The obtained paste was loaded into a 75×34 mm bolus (3-D printed PLA casing). Stainless-steel granule mixture was loaded on top of the ASL_PCL paste and in the cap of the bolus. The bolus sealed using a soldering iron.

TABLE 10.3

Excipient composition of ASL-PCL carrier

| ASL-65-PCL | PCL | Tribromomethane | Silicon dioxide | Total |
|---|---|---|---|---|
| Weight (g) | 16 | 52 | 12 | 80 |
| % (w/w) | 20 | 65 | 15 | 100 |

Preparation of Casings and Dog Bones (Used in Experiments Outlined Below)

Bolus cases and dog bones can be manufactured by applying typical manufacturing methods and on the basis of the information disclosed herein.

Tribromomethane Content

To quantify the tribromomethane content in a prepared bolus, a specific amount of carrier was weighed right after preparation (TO) and incubated at 40° C. The weight of carrier was recorded every day until a constant weight was obtained (T1), i.e. until no further evaporation of bromoform was observed. The tribromomethane content was calculated using below equation.

$$\text{Tribromomethane content } (\%\ w/w) = \left(\frac{\text{Weight of carrier at } T0 - \text{Weight of carrier at } T1}{\text{Weight of carrier at } T0}\right) \times 100$$

In Vitro Release Test

Phosphate buffer (pH:6.5) at 40° C. was used as release medium. The pH of the working solution was measured every time (average pH: 6.5±0.2), although pH had little impact on the experiment. The release medium was replaced with fresh medium (1 L, 0.02M) daily. The released bioactive (tribromomethane) was extracted using organic solvent and analyze by GC-FID (gas chromatography in connection with flame ionization detector).

Results

Tribromomethane Content

The tribromomethane content after manufacturing was summarized in Table 11. The wax-based and ethyl cellulose formulations have shown a tribromomethane content of above 98% w/w after preparation. The minimum tribromomethane content of PCL based formulation was around 92% w/w. However, this increased to 96% w/w when PCL carrier was prepared without heating.

TABLE 11

Tribromomethane content of different formulations.

| Formulation | Theoretical tribromomethane content (% w/w) | measured tribromomethane content (% w/w) |
|---|---|---|
| ASL-65-W | 65 | 65.0 |
| ASL-70-EC | 70 | 69.4 |
| ASL-65-PCL | 65 | 60.0 |

Release Profile of Tribromomethane from Different Carriers

The tribromomethane loading capacity was successfully increased to 70% w/w in different formulations, while the integrity of the bolus remained intact during the entire duration of release study. The highest loading capacity for tribromomethane in the wax-based formulations was 65% w/w. At this rate, control over tribromomethane release rates in the wax-based system was well possible, while at tribromomethane loading levels higher than this, the release rate became less controllable. The slope of the cumulative plots indicated release rate of 300 mg/day (FIG. 9).

Ethyl cellulose (EC) is another excipient explored to increase the tribromomethane loading capacity. It can provide a matrix to bind colloidal silicon dioxide and tribromomethane for improving the texture properties of the binary mixture. It has the potential to contribute to the mechanical stability of the bolus as we found out that the stiffness of the paste increased over time when observed visually. With all the EC-based formulations under the release tests, it was understood that it is possible to adjust the daily release of tribromomethane to for example between 100-350 mg/day. The release profile of ASL-70-EC can be observed in FIG. 19. The slope of the cumulative plots indicated the average release rate of around 250 mg/day. PCL-based formulation showed an average release rate of around 100 mg/day (FIG. 19). PCL based formulation can be prepared with and without heating treatment. The PCL-based carriers have shown a slow release from 3-100 mg/day (i.e. an elongated lag time).

At a tribromomethane loading of about 55% w/w, use of the PCL based carrier still resulted in a quite low release rate of around 10 mg/d (data not shown). A bolus with a long release time based on a slow-release PCL formulation described herein or coupled with a shorter release formulation can be made, which overall achieves a prolonged release pattern and cumulatively a higher release rate. For instance, a co-extruded carrier, in which there are different inner and outer layers of the extruded carrier dough with different release characteristics, is one option of such coupled release systems. Furthermore, PCL based carriers could also be used for smaller size ruminants like sheep or immature cattle, wherein the effective release rate of bromoform released to the animal may be lower than for larger ruminants to mitigate methane production. Unexpectedly, a more sustained release compared to a wax-based carrier system was observed when using carrier blends comprising fumed silica (ASL-70-EC, and ASL-65-PCL). The inclusion of ethyl cellulose and fumed silica allows for a greater tribromomethane loading capacity than the wax-based system, a better control of release rates, and potentially a greater release duration, while avoiding premature breaking of the bolus.

The beneficial effect of including fumed silica on the release profile and loading capacity of a bolus of the invention was further confirmed for a range of carrier formulations as demonstrated in FIG. 42A-42C. The experiments leading to the results displayed in FIGS. 42A-42C were conducted analogously to the experiments regarding testing bromoform release rates from a bolus comprising other carrier formulations described herein. Using silica along with carrier components, which can contribute to a sustained release (such as for instance ethyl cellulose and PCL) lead to a quicker (i.e. after administration) release and/or increased release rate over the tested time period compared to release from boluses not comprising silica. This effect was confirmed for different contents of bromoform as well as for the alternative carrier component PCL, see FIG. 42C, wherein an increased release over a sustained period of time, albeit at a comparably lower release level than for other tested formulations, was obtained.

Furthermore, incorporating fumed silica can generally tune release profiles when admixed with a variety of different bolus carrier components, as demonstrated in FIGS. 41A-41C, which may not be the case when using fumed silica as a carrier for loading bromoform alone. The experiments leading to the results displayed in FIG. 41A-41C were conducted analogously to the experiments regarding testing bromoform release rates from a bolus comprising other carrier formulations described herein. Using fumed silica alone leads to a burst release profile for bromoform release and may therefore be rather suitable for immediate release forms of bromoform, which however may also be combined with other sustained release forms. Mixing fumed silica with further excipients like castor wax (W), ethyl cellulose (EC) or poly caprolactone (PCL) allows to delay bromoform release, tune the release rates (i.e. prevent a burst release) and/or contributes to a sustained release over a prolonged period of time.

Example 8.2: Housing Improvement

Mechanical Properties

The mechanical properties of polymeric dog bones were examined using a tensile testing machine (Instron 5982) with a 5 kN load cell following ASTM D638 method. Standard dog bone specimens of 13 mm wide and 3.2 mm thick for each dog bone of 3 D printed PLA, injection moulded PLA and PLA/PBAT blend were mounted onto a probe and pulled away at a rate of 5 mm/min to measure the tensile strength and elongation at break.

PLA itself can be brittle on its own and thus may have a chance of premature bolus fracture. The brittleness of PLA can be further enhanced in the presence of bromoform to the extent that pure PLA injection moulded boluses were observed to disintegrate in a matter of weeks. Thus, bromoform can have an effect on polymers used for the bolus. To introduce more ductility into the polymer housing many different polymers and polymer blends were investigated (Table 8.A). To improve the mechanical property of the PLA, blends of PLA were prepared, and mechanical property was measured against 3D printed and injection molded PLA. While screening the blends, those blends were preferred that had superior mechanical properties when compared to 3D printed PLA (FIG. 20), as bolus prepared with 3D printed PLA casings was already intact in for 6-8 weeks in vivo studies. The casing made from these compositions, i.e. blended compositions exhibiting extension in tensile strength testing, can have a better chance of staying intact inside the ruminal environment when compared to casings made from 3D printed PLA. This was confirmed in in vivo testing using fistulated animals (FIG. 33B).

TABLE 8.A

Polymers and polymer blends investigated (J* - epoxide based chain extender). Threshold was based on 3D printed PLA dog bones. Polymer blends indicated to have "less ideal" features are less ideal in their properties compared to those candidate blends found to have the most suitable properties in the respective category, i.e. indicated as "good".

| Blend | Blend Ratio's | Tensile | Injectability/ Homogeneity |
|---|---|---|---|
| 1. PLA/PBSA | 80/20 wt % | Improved ductility | Good |
| 2. PLA/PBSA/J* | 79.5/19.5/1 wt % | No obvious advantage of including J | Less ideal |
| 3. PLA/PBS | 80/20 wt % | Improved ductility | Average *[1] |
| 4. PLA/PBS/J* | 79.5/19.5/1 wt % | no obvious advantage of including J | Less ideal |
| 5. PLA/PHBV | 80/20 wt % | No obvious improvement in ductility | Less ideal |
| 6. PLA/PHBV/J* | 79.5/19.5/1 wt % | No obvious improvement in ductility | Less ideal |
| 7. PLA/PHBV | 20/80 wt % | No obvious improvement in ductility | Less ideal |
| 8. PLA/PVA/J* | 89.5/9.5/1 wt % | No obvious improvement in ductility | Less ideal |
| 9. PLA/PBAT | 80/20 wt % | Improvement in ductility, but less strength | Good |
| 10. PLA/PBAT/J* | 79.5/19.5/1 wt % | Improvement in ductility, but less strength and no obvious advantage of including J | Less ideal |
| 11. PLA/PBAT/wood flour | 75/15/10 wt % | Brittle fracture | Less ideal |
| 12. PLA/PBAT | 90/10 wt % | Improved ductility | Good |
| 13. PLA/PCL/Talc | 79.5/19.5/1 wt % | Less strength, though slight improvement in ductility | Less ideal |
| 14. PLA/PCL/Talc | 89.5/9.5/1 wt % | Less ideal ductility | good |
| 15. PLA/PCL/Talc/J* | 89/9/1/1 wt % | Less ideal ductility | |
| 16. PLA/PCL/PDLA | 77.5/17.5/5 wt % | Less ideal ductility | Less ideal |
| 17. PLA/PCL/PDLA | 87.5/7.5/5 wt % | Less ideal ductility | Less ideal |
| 18. PLA/PCL/PDLA/J* | 87/7/5/1 wt % | Less ideal ductility | Less ideal |
| 19. PLA Wood Flour | 90/10 wt % | Less ideal ductility | Less ideal |
| 20. PLA PCL | 60/40 wt % | Improved ductility but less strength | good |
| 21. PLA PCL | 80/20 wt % | Improved ductility, but PCL components tend to dissolve in bromoform | good |
| 22. PCL | | Dissolves rapidly in bromoform | N/A |
| 23. PLA PBAT | 60/40 wt % | Less strength, though improvement in ductility | Good |
| 24. PLA PBS | 70/30 wt % | Rather brittle | Less ideal *[1] |
| 25. PLA PBS | 90/10 wt % | Rather brittle and less ideal ductility | Less ideal *[1] |

*[1] Note:
At ratios of the minor polymer at 20% or greater the blend tensile strength decreases, which increases the likelihood of release rates being potentially high. Furthermore, in some cases the mechanical strength of the bolus may be decreased. With ratios of the minor component at less than 10% the blend properties are more like those of a bolus housing made of PLA alone, with a tendency of being brittle, and in these blends the ductile characteristic of the minor blend is reduced.

The blends were visually examined for homogeneity or less pronounced homogeneity. The following blends were selected based on their mixing homogeneity, compatibility and brittleness properties and tested by use of a texture analyzer:
1) PLA PBAT (90/10)
2) PLA PBS (80/20)
3) PLA PBSA (80/20)

The ductile property was greatly improved by the incorporation of either PBS, PBSA or PBAT when tested against neat PLA (see FIG. 20). While PLA/PBSA blend showed improved ductility, the housings prepared were less homogenous than the other two blends (resulting in distinct PLA or PBSA areas and less consistent quality moulds on injection), and further studies were carried out with PLA/PBAT and PLA/PBS blends.

Analysis of these materials resulted in the further selection of PLA/PBAT in a ratio of 90:10. The PLA/PBAT blend demonstrated high ductility with a good mechanical strength (FIG. 21 (panel b)). The bolus housing manufactured from PLA/PBAT 90:10 blend has a potential to absorb energy (forces exerted by the rumen) and remain intact to deliver the sustained release of bromoform over the desired time period, e.g. over at least 1, at least 3 or at least 6 months. Results of in vivo testing in fistulated animals are provided further below.

Morphology of Fracture Surface

The morphology of the fracture surface of the dog bones was observed using Scanning Electron Microscope (SEM). The sample was adhered to a carbon stud and coated with platinum until 5 nm coating thickness was obtained. The morphology of the impact section was observed under different magnifications.

The impact fracture surface of injection molded PLA (PLA IM) was flat and exhibited a brittle fracture (FIG. 21 (panel a)), with no heterogeneity, pores, or plastic deformation (FIGS. 22A-22B). It was further unexpectedly found that upon contact with bromoform, the intrinsic brittleness of PLA material and thus susceptibility to crack or break under shear forces was increased, at least when using pure PLA as the housing material.

In contrast, a ductile deformation was observed for PLA/PBAT 90:10 (FIG. 21 (panel b)). The impact fracture surface was non-homogenous with brittle fracture on the sides and ductile fracture in the middle. Macro and microvoids observed on the surface fractures which can be (without wishing to being bound by theory) due to the low intermolecular adhesion between PLA and PBAT (FIG. 23 panels a, b). FIG. 23 panel c demonstrates the protruding ductile polymeric fibers out of the matrix at the site of the fracture. A shear pattern observed for PLA/PBAT (FIG. 23 panel d) with long and thin filaments at the ductile deformation site indicates high ductility of PLA/PBAT.

In Vivo Trial: Mechanical Integrity of the Housing

For in vivo testing of resistance and sustainability of the bolus housing, PLA/PBAT 90:10 polymer blend housings were extruded and filled with a high concentration of bromoform that the presently used carrier excipient material would allow (bolus specifications:injection moulded PLA/PBAT at a ratio of 90:10, housing thickness of 1.2 mm, bolus dimensions of 35 mm×72 mm, 64 w/w % bromoform content, ethyl cellulose and fumed silica as carrier material, stainless steel microparticles (balls) embedded in paraffin wax as densifier).

The thickness of the bolus wall was found to have an influence as well. If the wall thickness exceeds 1.5 mm this results in a long release lag period and low release may be observed. The bolus wall should ideally have a suitable thickness to enable injection moulding and reasonable mechanical strength to withstand rumen forces, as well as enabling suitable release rates as described further herein.

To ensure taking into account the possibility of a strong plasticization effect of bromoform to the polymer, and greatest source of compromise, a high concentration of bromoform was used in in vivo trials, i.e. a concentration of 64 w/w %. The initial target period was a durability in the rumen for at least three months and up to even at least 6 months (see FIG. 33B). While some discoloration and deterioration of the bolus housing was observed (see FIG. 33A), the trial shows that a PLA/PBAT 90:10 polymer blend housing is surprisingly very sturdy and suitable in the rumen environment, even under the effects of bromoform on the polymer.

It can be concluded that, unexpectedly, an improvement for the blend PLA:PBAT in a ratio of 90:10 was observed in view of homogeneity, flexibility and ductility, particularly upon stress application and when combined with the polymer-aggressive active agent bromoform. The PLA:PBAT 90:10 housing blend allowed for higher bromoform loading and higher release rates without the stability of the bolus being compromised. Without wishing to be bound by theory, this may be due to the greater proportion of flexibility conferring functional groups in PBAT compared to pure PLA.

Interestingly it was found that the suitable selection of polymers and polymer blends has a window of particularly suitable ratios of major polymer to minor polymer. For example, if PLA was present in an amount of more than 90 wt %, the polymer blend was observed to retain most of PLA's characteristics and particularly its brittleness, which can be less desirable when aiming at a bolus that can flexibly yield to the forces of the rumen to some extent. On the other hand, if the minor polymer (such as PBS, PBSA or PBAT) is present in an amount of more than 20 wt %, the release rates from a respective bolus tend to be higher, which again can be less desirable when aiming for a sustained release bolus, even though advantageous more ductile characteristics of the minor polymer are retained by the bolus. For other polymer blends than PLA/PBAT and their respective ratios, slightly varying ratio ranges were observed, but effectively these polymer blends showed the same trend. Thus, it is preferred that a bolus of the invention comprises a housing wherein the housing material comprises PLA and one or more of the further compounds PBS, PBSA and PBAT wherein the ratio of PLA:PBAT is in the range of 95:5 to 80:20, in which range the housing properties were found to be suitable for an intraruminal bolus.

In Summary, a Good Performance and Duration of a Bolus in the Rumen can for Instance be Provided by a Bolus which is Tough (i.e. has a Suitable Hardness and Stability), but not Brittle, and has Some Flexibility to Adapt to the Forces Applied by the Rumen and its Mobility.

Conclusion to Example 8

Three further exemplary carrier components were investigated and developed to successfully generate a sustained release profile of tribromomethane from a bolus comprising bromoform mixed with one or more of these carrier components (FIG. 19). Fumed silica as a part of the carrier increased the tribromomethane loading capacity to more than 50% w/w. Ethyl cellulose in a carrier along with fumed silica demonstrated a potential to prevent a burst release of tribromomethane from the fumed silica-tribromomethane mixture, adjusting the tribromomethane release to a desired rate (FIG. 19, Table 11). All three tested formulations allow sustained release of tribromomethane in the rumen. Preferably, fumed silica and ethyl cellulose can be combined and used as a novel carrier for halomethanes. While allowing the sustained release of tribromomethane in vitro, the ability to load higher content of tribromomethane was an additional advantage.

The PLA/PBAT blend demonstrated a high ductility with a good mechanical strength. The bolus casing that can be manufactured from a mixture of PLA/PBAT at a w/w ratio of preferably 90:10 has a potential to absorb energy (forces exerted by the rumen) and remains intact to deliver the sustained release of tribromomethane over the desired time frame.

Example 9

Release Rate from the Boluses without the Casings

The formulation comprising 50% bromoform in 75/25 castor/paraffin wax were prepared by first melting the wax and then adding the bromoform before filling into a 3D printed PLA mould. The mould consisted of two units clamped together. After letting the wax bromoform mixture solidify the clamped was removed and the boluses made without the casings (naked boluses) were tested for their release performance (see FIG. 24). There was a rapid release of bromoform from the bolus without the casings averaging 50 mg/h (1.2 mg/d). This indicates that a bolus may advantageously have a casing to deliver bromoform at an optimal rate.

Release Rate for the Bolus without the Housing from a Polymeric Based Carrier System The carrier formulations EC-HPMC-58 and EC-HPMC-60 were prepared according to the method described for the use of these excipients further below (see Example 11) and filled manually into a mold to prepare a bolus without a housing. After filling, the mold was dismantled to recover the carrier formulation without housing. Despite the doughy consistency of the carrier excipient mixture, forming an uncased bolus using these carriers was possible.

Release performance of these boli was then evaluated in vitro according to the method described herein above with a slight modification: it was suspected that the release would be rapid and bromoform would quickly saturate the medium, and therefore samples were taken after short time intervals at 1, 2, 4, 6 and 8 h of incubation and bromoform was quantified by GC-FID (gas chromatography and flame ionization detector). It was found that bromoform release was rapid without housings. The cumulative plot in FIG. 35 indicates a release rate of around 59 mg/h and of around 49 mg/h for EC-HPMC-60 and EC-HPMC-58, respectively. In an extrapolation over a 24 h period this would mean an estimated 1416 mg/d or 1176 mg/d, i.e. a less desired release rate for a sustained release. Overall, this indicates that a housing is useful for a bolus to support a sustained and controllable bromoform release. A bolus without a housing, at least according to the design tested in this experiment, may be rather suitable for an immediate release form.

Release Rate of Boluses without Caps

The formulation comprising of 50% bromoform in 75/25 castor/paraffin wax were prepared by melting the wax first and then adding the bromoform before filling into a 3D printed PLA casings and the release testing were undertaking without cap sealing, i.e., with bolus housings with open ends (see FIG. 25). The release rates were 328 and 400 mg/day for two boluses investigated at a room temperature initially. Afterwards, the release rates increased to about 800 mg per day when measured at physiological temperature at 40° C. (increased from starting temperature of about 21° C., see day 5 to 6 in FIG. 25). This data indicates a bolus may advantageously have a proper cap to release bromoform at an optimal rate.

In conclusion, the absence of a housing or the housing's caps can lead to a burst release and an immediate release rate of bromoform. Thus, when a sustained and more uniform bromoform release is envisioned, a bolus without a housing or with an open housing may be less preferred. However, such a bolus design may be suitable for the administration of other active agents or for the administration of bromoform in combination with different carrier substances than bromoform tested herein.

Example 10

Formulation ASL-80-L

Formulation ASL-80-L was developed to investigate the use of a colloidal silicon-based formulation with bromoform alone. Formulation details for the colloidal silicon-based formulation are presented in Table 12.1. Initially, bromoform was blended with colloidal silicon dioxide to convert into a powder and then blended with lauric acid. After the formulation was prepared into a mortar and pestle, the formulation was filled into the casing and tested for it release performance. While 80% of the bromoform could be prepared, including an amount of 80% of bromoform showed a tendency of weakening the bolus housing resulting in a shorter lifetime of the bolus before breaking. PLA becomes more brittle with the addition of bromoform and loses some of its mechanical strength, which can lead to premature fracturing. Approximately 1500 mg was released within two days (see FIG. 26).

TABLE 12.1

Formulation containing Colloidal silicon dioxide

| Formulation code (ASL-80-L) | Weight (g) | Final concentration (% w/w) |
|---|---|---|
| Bromoform | 36 | 80 |
| Colloidal Silicon dioxide | 4.5 | |
| Lauric acid | 4.5 | |
| Total Weight | 45 | |

Formulation ASL-65-W

To improve the release profile and stability of the bolus, bromoform content was reduced and castor wax was included into the formulation along with colloidal silicon dioxide (Table 12.2). Briefly castor wax was melted before adding the bromoform and homogenized with colloidal silicon dioxide. The molten mixture was poured into a 3 D printed PLA casing and caps sealed with soldering iron before testing for their release performance.

TABLE 12.2

Formulation containing castor wax and colloidal silicon dioxide (ASL-65-W)

| ASL-65-W | Castor wax | bromoform | colloidal silicon dioxide | Total weight |
|---|---|---|---|---|
| Amount (g) | 33 | 65 | 2 | 100 |
| w/w % | 33 | 65 | 2 | |

The burst release of the bromoform was greatly reduced when castor wax was included into the formulation with colloidal silicon dioxide (FIG. 27). The cumulative plots indicated a release rate of 335 mg/d. This data was generated in a 3D printed PLA casing.

Formulation ASL-65-W-PLA/PBAT

The same formulation as described in Table 12.2, was prepared in a same method as described and filled in scalable injection moulded PLA/PBAT (90/10) and tested for their release performance. The release rates were higher when compared to the 3 D printed PLA counterparts. While the release rates were below the target limit, the release rates fluctuated over time. After a brief lag time for over a period of 8 d, it peaked releasing 340 mg/d and then decreased down to 170 mg/d at the 22 d (FIG. 28). Without wishing to be bound by theory, it is suspected that this may be due to PBAT having a higher capacity to absorb bromoform than for instance PLA, possibly due to higher amount of enabling functional groups, which results in a higher release rate than that observed for neat PLA.

The beneficial effects of certain housing material compositions for a bolus as of the invention is further confirmed in FIGS. 44A-44B, wherein FIGS. 44A and 44B confirm the effect for different carrier formulations. In this experiment the same core composition of ethyl cellulose and HPMC (ratio 1:1) with loaded with 60% w/w of bromoform and was tested for release in 3 different casings, namely neat PLA, PLA/PBAT (90:10 ratio) and PLA/PBS (80:20 ratio). The experiments leading to the results displayed in FIG. 42A-42C were conducted analogously to the experiments regarding testing bromoform release rates from other boluses (e.g. for testing different bolus core/carrier formulations) as described herein. The results confirm that the selection of the of casing can clearly modulate the release profile of a bolus, wherein PLA/PBAT and PLA/PBS can control the initial release profile as well as the overall release profile over the assessed time period, resulting in less extreme release peaks.

Formulation: ASL-70-EC and ASL-64-EC

To improve the release rates, carrier formulation was made with ethyl cellulose. The formulation details are presented in Table 12.3. Bromoform and ethyl cellulose were mixed, and colloidal silicon dioxide was added in a portion wise gradually and mixed until a homogenous paste was obtained. The carrier formulation was filled into an injection moulded PLA/PBAT casings, and the boluses were sealed using spin welding and/or soldering before testing them for their release performance.

TABLE 12.3

Formulation comprising ethyl cellulose and colloidal silicon dioxide (ASL-70 -EC and ASL-64-EC))

| Formulation | Ethyl cellulose | Tribromomethane | Silicon dioxide |
|---|---|---|---|
| ASL-70-EC | 20 | 70 | 10 |
| ASL-64-EC | 26 | 64 | 10 |

The release rates for ethyl cellulose formulations are displayed in FIGS. 29A-29B. There was a burst release for the bolus with 70% bromoform, reaching up to 1100 mg/d. Meanwhile, the release rate was steady with lower bromoform loading of 64%. After an initial lag time of seven days, the release rate plateaued after reaching 300 mg/d (c.f. FIG. 29A (70%) and 29B (64%), measured for 3 boluses).

Conclusion

Fumed silica alone is less suitable to provide a sustained release of bromoform. Lauric acid has a good binding efficacy, however the melting point of lauric acid is close to the animals' physiological temperature. Lauric acid may thereby exert a plasticization effect on PLA. Furthermore, the injection moulded PLA housing can be more susceptible to higher bromoform concentrations in terms of bromoform promoting brittleness and decreasing stability of PLA. Medium-chain saturated fatty acids may be used to adapt the melting point of a wax portion or mixture used as part of the carrier. The aforementioned formulation approaches can be suitable for formulation products for daily dosing. For instance a fumed silica and bromoform carrier mixture can be prepared for immediate release formulations such as tablets, powders, or capsules.

Furthermore, unexpectedly an improvement in view of preventing a burst release from the bolus was achieved by incorporating the carrier component ethyl cellulose, especially when used along with fumed silica, which could tune the bromoform release rate as desired. Unexpectedly, when fumed silica was used as part of the carrier an improvement in view of an increased loading capacity for bromoform of above 50 wt % and a more sustained/tuned bromoform release rate were achieved.

Surprisingly fumed silica on its own does not seem to control the release rate in the same manner (see FIG. 30B, described further below). Furthermore, it was unexpectedly shown that the bolus housing may have an influence on the bolus' release characteristics.

Use of a polymeric system (as further outlined in the following) enables a loading capacity of the bolus of up to 60% of bromoform content or more. Beyond this loading, a burst release of bromoform can occur. Without wishing to be bound by theory, this may be due to the carrier being unexpectedly saturated at a bromoform content of 70 wt % or higher, which can lead to burst release rates and can reduce the mechanical stability of the bolus to some extent.

Example 11

Polymeric Carrier Systems

Wax based carrier systems produced a sustained release over a prolonged period of time. To further increase bromoform loading capacity of boli and to provide an even more consistent bromoform release rate for an even steadier knock down of methane over a prolonged period of time, boluses with polymeric carrier systems were tested. Tested formulations are displayed in Table 13. Release rates from immediate release formulations also presented herein demonstrate the sustained and even release rate promoting effect of the polymeric systems of the invention, i.e. of carrier systems comprising cellulosic materials and fumed silica.

TABLE 13

Polymeric carrier system formulations prepared in PLA/PBAT housings (QS = quantum satis).

| | Composition (w/w %) | | | | |
|---|---|---|---|---|---|
| Formulations | Propylene Glycol (PG) | Ethyl cellulose (EC) | Fumed silica (AE) | HPMC (K-100) | Bromoform |
| PPG-64 | 36 | N/A | N/A | N/A | 64 |
| AE-64 | N/A | N/A | 36 | N/A | 64 |
| EC 64 | N/A | 36 | N/A | N/A | 64 |

TABLE 13-continued

Polymeric carrier system formulations prepared
in PLA/PBAT housings (QS = quantum satis).

Composition (w/w %)

| Formulations | Propylene Glycol (PG) | Ethyl cellulose (EC) | Fumed silica (AE) | HPMC (K-100) | Bromoform |
|---|---|---|---|---|---|
| EC-AE-10-64 | N/A | 26 | 10 | N/A | 64 |
| EC-AE-7-64 | N/A | 29 | 7 | N/A | 64 |
| EC-AE-5-64 | N/A | 31 | 5 | N/A | 64 |
| EC-HPMC-58 | N/A | 27.4 | N/A | 14.3 | 58.3 |
| EC-HPMC-60 | N/A | 20 | N/A | 20 | 60 |
| EC-HPMC-61 | N/A | 15 | N/A | 24 | 61 |

Propylene glycol (PG) was used as a vehicle to prepare an immediate release system (Formulation: PPG-64, prepared from liquid propylene glycol mixed with 64% bromoform and without housing). Propylene glycol alone provided a less sustained release of bromoform, as more than one gram of bromoform was released by the 4th day of release testing and the bolus housings collapsed (see FIG. 30A). When fumed silica was used as a sole excipient in the carrier (Formulation: AE-64, prepare analogously to PPG-64), a burst release of bromoform (1.2 g) was observed on the 2nd day of the study (FIG. 30B). These high release rates may be less suitable when a sustained continued release from a bolus is envisioned. Thus, it was unexpectedly found that while fumed silica improved the mixing properties of the carrier (see further below), fumed silica alone may rather serve as an immediate release carrier. Both propylene glycol and fumed silica seem less suitable to provide a sustained release on their own.

For polymeric system mixtures bromoform and ethyl cellulose were mixed initially, and fumed silica or HPMC were then added gradually and mixed until a homogenous paste was obtained. The carrier formulation was filled into an injection moulded PLA/PBAT housing, and the boluses were sealed using spin welding and/or soldering before testing for their release performance.

Ethyl cellulose was used as a carrier because of a suspected improved affinity to bromoform. Ethyl cellulose as the sole carrier for bromoform in a bolus (Formulation: EC-64) led to a lag time of about 15 days, and to an average release of about 60 mg/d (FIG. 31A). The incorporation of ethyl cellulose into the formulation along with fumed silica produced a sustained release of bromoform (FIG. 31B). Thus, by incorporating fumed silica improvements were achieved in terms of making a sustained release bolus.

Processing and particularly mixing was difficult in some cases due to cohesion, i.e. the carrier dough becomes sticky, which decreases the mixing efficacy. Surprisingly it was found that the incorporation of fumed silica reduced the cohesion of the paste and increased the mixing efficacy (including in formulations: EC-AE-10-64, EC-AE-7-64, EC-AE-5-64).

The release profile for such formulations is presented in FIG. 31B. Fumed silica altered the release rate of bromoform in that a higher content of fumed silica resulted in a faster release of bromoform as shown by the EC-AE-10-64 formulation in FIG. 31B (fumed silica at 10%, compared to 7% and 5% in the other two boli). Overall, a sustained release was observed, and the profile exhibited a first order release, wherein an initial higher release rate is followed by a lower but still sustained release rate.

In conclusion, there was, unexpectedly, an improvement in view of the ability to (further) tune the bromoform release rate from the bolus upon small increases of fumed silica content in a carrier mixture with ethyl cellulose, i.e. to obtain more sustained bromoform release with less fluctuation and a longer release time period.

For a sustained methane knockdown for a period of 3-6 months or even more, more consistent release rates were envisioned. To achieve this, hydroxypropyl methyl cellulose (HPMC), a swellable hydrophilic polymer, was included as part of a bolus carrier formulation. It was suspected that HPMC could stabilise release rates but also improve the mechanical integrity of the bolus due to its swelling properties. Once the bolus releases bromoform, the swellable HPMC will occupy the void space which will contribute to improve the mechanical stability of the bolus. After HPMC was included into the carrier formulation (Formulation: EC-HPMC-58), the release rates were stable (FIGS. 32A, 32B and 32C).

The discovery that the release rate was stabilised for the duration of the study (i.e., at least for 75 days) after the incorporation of HPMC, was made with a carrier formulation comprising 58% of bromoform (FIG. 32A). Starting from this, other formulations incorporating relatively higher amounts of bromoform (Formulations: EC-HPMC-60, EC-HPMC-61) were tested for their in vitro release performance (see FIGS. 32B and 32C). The three release profiles (FIGS. 32A, 32B and 32C) differ in that the higher the amount of active agent (bromoform, amount in % weight), the shorter the lag phase before a substantial release sets in and also before a peak release is reached. With the addition of HPMC a pseudo zero order release can be achieved, compared to tested compositions comprising ethyl cellulose alone, which lead to a pseudo first order release profile (FIG. 31B). Surprisingly, higher proportions of HPMC in the carrier also allowed for a higher loading capacity of the bolus for bromoform.

At the small batch sizes tested, fumed silica was not expected to further enhance the release characteristics. However, in larger production batch volumes incorporation of fumed silica is expected to be advantageous in small amounts (e.g. 0.1-2%) to reduce cohesion and improve mixing efficiency of the carrier mixture.

In conclusion, there was, unexpectedly, an improvement in view of a more sustained bromoform release rate, i.e. a more uniform release rate over an extended period of time, when HPMC and/or ethyl cellulose were included as carrier components. Furthermore, it was unexpectedly found that the incorporation of HPMC prevented an initial burst release of bromoform, reduced an initial burst peak and contributed to improving mechanical strength of the bolus as well as increased bromoform loading capacity.

The beneficial features of the use of ethyl cellulose and/or HPMC as carrier materials in a bolus of the invention are further confirmed by the experiments and data in FIG. 43. The experiments leading to the results displayed in FIGS. 42A-42C were conducted analogously to the experiments regarding testing bromoform release rates from a bolus comprising other carrier formulations described herein. Incorporating HPMC and increasing its ratio in a bolus carrier formulation can contribute to a substantially increased release of bromoform from a bolus while at the same time leading to a sustained release over a prolonged time. Furthermore, a higher amount of bromoform may be loaded into a bolus comprising HPMC.

Summary Regarding Examples 8 to 11

As a further development and in some cases as an improvement to a wax-based carrier system, three different carriers were tested to obtain a sustained release profile of bromoform (FIG. 19). Fumed silica as part of the carrier increased the bromoform loading capacity to above 50% w/w. A higher bromoform content (such as above 70% w/w) likely saturated the carrier, led to burst release rates and may have decreased the mechanical stability of the bolus. A carrier including ethyl cellulose along with fumed silica demonstrated a potential to prevent a burst release, tuning the bromoform release to a desired rate (FIG. 19 and FIG. 31B). Fumed silica also helped to improve mixing efficiency of the carrier excipient formulation and small increases in fumed silica content increased the release rate from the ethyl cellulose comprising formulation. Fumed silica on its own as an immediate release carrier led to high burst release rates, as did propylene glycol as a sole carrier. This indicates the applicability of fumed silica as a sole carrier rather as immediate release formulation. However, to develop a sustained release system, mixing in additional carriers such as EC and HPMC are useful. So far, fumed silica, HPMC and ethyl cellulose have not been used as a carrier for halomethanes, particularly not in an intraruminal bolus or other ruminal release form.

While all three formulations tested showed the potential to provide a sustained release of bromoform in the rumen, particularly the incorporation of HPMC was even further useful, as it reduced an initial burst release of bromoform and contributed to improving mechanical stability of the bolus. The absence of a housing or a housing cap led to burst release rates and may in some cases be unsuitable for a sustained and moderate long time release, at least in the context of the carrier excipients used in the present examples.

Example 12

Improved Bolus Shape Design

Different bolus shapes and designs were investigated to improve ease of production and assembly efficacy of the boluses. One particularly useful bolus design is displayed in FIGS. 39A and 39B. With this bolus design, an improvement was achieved in reducing overall buoyancy by reducing dead space volume (1) through a flatter cap design and (2) use of a densifier and binding wax tablet, which upon insertion (onto the carrier dough) removes trapped air from within the bolus (FIG. 39B). In addition, less wax was also sufficient to produce the densifier in the form of a wax tablet compared to alternative bolus designs not employing a wax tablet because merely a moldable rather than a flowable consistency is also suitable for forming the wax tablet (so adding a smaller amount of wax to steel particles was possible). Furthermore, the displayed bolus design in FIGS. 39A and 39B is useful for an increased manufacturing efficiency and bolus stability—i.e. a strong weld of the cap onto the housing by spin welding and the possibility to separately manufacture the wax densifier tablet in advance. The bolus comprises an improved grip design, i.e. comprises grip improving indentations for attachment of the spin welding device (FIG. 39A).

Example 13

Exemplary Bolus Assembly

Based on the above in vitro and in vivo results from various experiments regarding material selection as well as prototype products, the following is a particularly suitable bolus assembly. The bolus polymers were—as outlined above—selected from a large number of polymer blends based on Thermal Gravimetric Analysis (TGA), Differential Scanning calorimetry (DSC), tensile testing, and injection moulding characteristics (c.f. Table 8.A). Bolus dimensions, such as housing thickness, length and diameter are based on loading potential of the active agent and on performance in vivo in fistulated animals. The dimensions (per single bolus) allow release rates of up to about 250 mg/d in a pseudo zero order release profile, and up to 250 mg/d in a pseudo first order release profile. The following feature selection and assembly steps may be employed for a particularly suitable bolus:

- PLA/PBAT casing including cap(s), ratios of 90:10 PLA:PBAT, weight of the housing being for instance about 13.35 g (PLA for instance about 12.01 g and PBAT for instance about 1.335 g), housing being injection moulded with dimensions of about 1.2 mm (wall thickness)×35 mm (diameter)×72 mm (length).
- Radio Frequency Identification (RFID) chip/device can be placed in the bottom of the casing. Such a chip/device could for instance also use ultra-high frequency (UHF) signaling instead.
- Grade 316 stainless steel microparticles (balls) (about 67.16 g) are mixed with paraffin wax (about 5.84 g) and formed into a densifier tablet (c.f. FIG. 39B).
- Excipients are added into a mortar and pestle in the order:bromoform (about 36.18 g, total excipient weight being about 60 g, i.e. about 60 wt %) being mixed with ethyl cellulose (type 45 premium, about 12.06 g) until a homogenous paste is obtained. Then hydroxypropyl methylcellulose (HPMC K-100M, about 11.76 g, i.e. the weight ratio of EC:HPMC being about 50:50) is added to the paste and the components are mixed for about 10 min until a homogenous doughy substance is obtained. HPMC and ethyl cellulose may be kept at room temperature prior to use.
- About 60 g of the excipient dough is filled and pressed into the prepared housing and the densifier tablet is added on top (c.f. FIG. 39B). Suitably, the densifier tablet encompasses vertical grooves to allow excess air to escape as the densifier is pressed down onto the carrier dough.
- The casing is capped with a PLA/PBAT moulded cap and the cap is fixed by means of spin welding the cap into position.
- The weight of the bolus and carrier is recorded before pouring the densifier formulation and after finishing the bolus assembly, the total weight of the final (half size) bolus being about 146.35 g.

Example 14

Preliminary Field Trial: Investigation of Dose, Methane Inhibition and Influence of Feed Type The following preliminary field trial is an example of the methane inhibiting capabilities of the bolus invention in a live animal trial using recognised methane analysis techniques. The bolus used in the trial is outlined in Table 14 and the trial time schedule is outlined in Table 16.

TABLE 14

Trial boluses used in methane inhibition chamber study (prototype 4).

| Housing | Excipients/ Carrier Matrix | Bromoform Content | Densifier | Dimensions |
|---|---|---|---|---|
| 1 mm 3D printed PLA | 75% castor and 25% paraffin wax | 50% | Zinc rod | Single bolus, 130 mm × 34 mm |

Five different total bromoform doses across two different diets were tested, giving a total of ten treatments (Table 15). Due to no methane mitigation in a first chamber measurement session (session 1), an additional bolus releasing 156 mg/d bromoform (prototype 4) was administered to 4 out of 6 animals in each treatment group, increasing the nominal dose range from 0-104 mg/day to 0-260 mg/day over eight different doses, i.e. increasing nominal dose rates by 156 mg/d. Within each dose group, half of the animals were fed baleage (baled cut and covered pasture), and the other half were adapted to a diet of fresh cut ryegrass (New Zealand fresh pasture). Boluses were washed prior to administration to remove any bromoform that may have accumulated on the outside of the bolus. The additional boluses were administered on day 69 per os. (oesophagus). The second measurement session began 10 days after said bolus administration, with animals entering the respiration chambers for a 48-hour period in groups of four.

TABLE 15

Number of animals per treatment group split by diet (only for 2$^{nd}$ chamber session).

| Bolus treatment group | Bromoform dose (mg/day) | Feed: baleage | Feed: ryegrass fresh pasture |
|---|---|---|---|
| CON | 0 | 1 | 1 |
| CON + 156 | 156 | 2 | 2 |
| LOW + 156 | 182 | 2 | 2 |
| MED + 156 | 208 | 2 | 2 |
| HIGH + 156 | 260 | 2 | 2 |

Data Collection

Liveweights of the animals were recorded prior to the first bolus administration and following each measurement period. Gas production of methane, hydrogen, and carbon dioxide was assessed every 3 min over a 48-hour period in respiration chambers using a 4900C Continuous Emission Analyser. Daily gas production was calculated from these data using a standard method correcting for temperature and air flow. Rumen fluid contents were sampled prior to bolus administration and following measurement periods in the respiration chambers. Rumen samples were assessed for pH and short-chain fatty acids (SCFAs) content, and were stored for bromoform residue analysis later on. Blood samples were collected 16 days prior to bolus administration, and on days 34 and 94 following the measurement periods. Blood samples were assessed biochemical constitution and for liver enzymes.

TABLE 16

Animal trial time schedule

| Trial day(s) | Date(s) | Event(s) |
|---|---|---|
| −21 | 25 Feb. 2022 | Start diet adaptation |
| −16 | 20 Feb. 2022 | Blood sampling |
| 0 | 4 Feb. 2022 | Bolus administration |
| 7 | 11 Feb. 2022 | Transport from Aorangi (grazing farm) to Grasslands research Centre (Indoor Facility) |
| 8-24 | 12 Feb. 2022- 28 Feb. 2022 | Adaptation to indoor facilities |
| 15-26 | 19 Feb. 2022- 2 Mar. 2022 | Adaptation to individual animal crates |
| 17-28 | 21 Feb. 2022- 4 Mar. 2022 | Measurement 1 (Respiration chambers); Rumen, faecal, liveweight sampling |
| 30-50 | 6 Mar. 2022- 26 Mar. 2022 | Trial redesign, ethics modification |
| 34 | 10 Mar. 2022 | Blood sampling |
| 62 | 7 Apr. 2022 | Start period 2 diet adaptation |
| 69 | 14 Apr. 2022 | Administration of additional boluses, liveweight sampling |
| 75 | 20 Apr. 2022 | Bolus scanning |
| 79-91 | 24 Apr. 2022- 6 May 2022 | Measurement 2 (respiration chambers); Rumen, faecal, liveweight sampling |
| 94 | 9 May 2022 | Blood sampling, record of final liveweight, bolus scanning |
| 111 | 26 May 2022 | Trial conclusion |
| 152 | 6 Jul. 2022 | Animals euthanised |

Feed Composition

Chemical composition of feed was assessed by Hill Laboratories using standard methods and results are reported in Table 17, as provided in the study report. Differences are identified particularly in protein, fat, and acid content as well as in neutral detergent fibre content.

TABLE 17

Mean ± standard deviation of chemical composition of ryegrass-based baleage and ryegrass pasture fed to heifers during adaptation in crates and gas emission measurements in respiration chambers. NDF is neutral detergent fibre; ADF is acid detergent fibre; SS is soluble sugars, OMD is organic matter digestibility; % DM is percentage of total dry matter consumed.

| Component | Feed: Baleage | Feed: Pasture |
|---|---|---|
| Dry matter, % DM | 42.3 ± 3.5 | 21.1 ± 3.3 |
| Ash, % DM | 8.8 ± 0.5 | 9.6 ± 2.3 |
| Crude protein, % DM | 10.9 ± 0.8 | 18.1 ± 1.3 |
| Crude fat, % DM | 3.0 ± 0.5 | 4.7 ± 0.2 |
| NDF, % DM | 58.3 ± 1.4 | 47.6 ± 1.1 |
| ADF, % DM | 35.9 ± 1.3 | 24.8 ± 0.7 |
| SS, % DM | 9.9 ± 1.9 | 7.6 ± 0.8 |
| OMD, % DM | 63.7 ± 1.8 | 68.8 ± 1.7 |

Dry Matter Intake (DMI)

Average dry matter intake (kg/d) versus bromoform dose is presented in Table 18. The data are combined for both feed types during measurement session 2.

TABLE 18

Average dry matter intake in kg/day for all treatment groups. P-values calculated by single-factor ANOVA.

| CON | LOW | MED | HIGH | CON + 156 | LOW + 182 | MED + 208 | HIGH + 260 | P-VALUE |
|---|---|---|---|---|---|---|---|---|
| 6.14 | 5.11 | 5.72 | 5.54 | 5.54 | 5.15 | 3.86 | 4.47 | 0.185 |

Dry matter intake was not significantly different across treatments, though in general, a higher bromoform dose was correlated with a slightly lower dry matter intake.

Gas Emission Measurements

Emissions of methane ($CH_4$), hydrogen ($H_2$) and carbon dioxide ($CO_2$) were assessed in respiration chambers over 48 hour measurements and converted to a per-day-total. When methane was effectively inhibited, methane levels were decreased, and hydrogen levels were seen to increase. Average gas emission in grams per day±standard error is presented in Table 19. The data are combined for both feeds during measurement session 2 (cf. schedule table 16). P-values were calculated by single-factor ANOVA and differences were deemed particularly significant for p-value <0.05.

TABLE 19

Emissions data for period two for all animals. Data presented as the average ± standard error. P-values determined by single-factor ANOVA. Treatment duration at period 2 measurement was 10-22 days.

| Treatment Group | n | Bromoform dose (mg/d) | $CH_4$ (g/d) | $H_2$ (g/d) | $CO_2$ (g/d) |
|---|---|---|---|---|---|
| CON | 2 | 0 | 153.7 ± 13.2 | 0.2 ± 0 | 6273 ± 545 |
| CON + 156 | 4 | 156 | 48.7 ± 29.5 | 7.9 ± 3.5 | 5666 ± 327 |
| LOW + 156 | 4 | 182 | 18.6 ± 18.2 | 13.7 ± 4.7 | 5589 ± 295 |
| MED + 156 | 4 | 208 | −0.3 ± 0.5 | 17.2 ± 3.5 | 5011 ± 377 |
| HIGH + 156 | 4 | 260 | −0.2 ± 0.3 | 17 ± 3.4 | 5159 ± 308 |
| P-value | | | 0.00002 | 0.011 | 0.342 |

Measurements demonstrate a clear response to bromoform treatment above 156 g/day. Methane emissions are decreased in animals where an additional 156 mg/d bolus was administered for measurement period 2 (CON/LOW/MED/HIGH+156 mg/d), i.e. for exemplarily tested doses of 156 mg/d, 182 mg/d, 208 mg/d and 260 mg/d. Methane and hydrogen emission data are visualised in FIGS. 36 and 37, with predicted release profiles extrapolated using a 3-parameter logistic model. Bold dashed lines delimit the 95% confidence interval for the mean response. Thin dashed lines delimit the 95% confidence interval.

The extrapolated dose response curve in FIG. 36 reflects the underlying predicted dose response relationship of bromoform administration and methane emission reduction. For the 156 mg/day dose group (CON+156), two animals demonstrated complete methane inhibition, with methane emissions of about 0.2 and 0 g/d, respectively. One animal demonstrated a partial methane knockdown, with methane emissions of 76 g/d observed, which is approximately 50% of the average emissions observed for the untreated control group. In the dose range of 0-104 mg/day applied in chamber session 1, no substantial methane inhibition was observed (data not shown). In the LOW+156 group (dose of 182 mg/d), full methane inhibition was observed for three of the four treated animals, while the fourth animal showed at least partial inhibition with 73 mg/d of methane (i.e. again approximately 50% compared to the emission in control animals). Hydrogen emissions are also indicative of inhibition of methanogenesis at a dose of 156 mg/d and more (FIG. 37) (significant differences with p-value of 0.01 or less), since animals with lower methane emissions also demonstrated increased hydrogen emissions and vice versa (hydrogen being consumed for methane production).

Emissions in the Context of Diet

A randomly selected 50% of the animals from each group were fed baleage, while the other 50% were adapted to pasture feed to assess the effect of diet on bromoform's efficacy for methane inhibition. Average data in the context of feed is presented in Table 20.

TABLE 20

Average emission values for methane ($CH_4$), hydrogen ($H_2$), and carbon dioxide ($CO_2$) in the context of different feeds (data shown for chamber session 2).

| Feed | Treatment | Bromoform dose (mg/d) | n | $CH_4$ (g/d) | $H_2$ (g/d) | $CO_2$ (g/d) |
|---|---|---|---|---|---|---|
| Baleage | CON | 0 | 1 | 140.5 | 0.2 | 5728 |
| | CON + 156 | 156 | 2 | 59.1 | 7.4 | 5251 |
| | LOW + 156 | 182 | 2 | 0.9 | 13.3 | 5202 |
| | MED + 156 | 208 | 2 | −1.0 | 19.9 | 4919 |
| | HIGH + 156 | 260 | 2 | 0.3 | 12.7 | 4645 |
| Pasture | CON | 0 | 1 | 167.0 | 0.2 | 6818 |
| | CON + 156 | 156 | 2 | 38.2 | 8.4 | 6081 |
| | LOW + 156 | 182 | 2 | 36.2 | 14.1 | 5977 |
| | MED + 156 | 208 | 2 | 0.3 | 14.4 | 5104 |
| | HIGH + 156 | 260 | 2 | −0.7 | 21.3 | 5673 |

Emission data is shown in FIG. 38. Baleage fed animal values are plotted as square data points and pasture fed animal values are plotted as circular data points, wherein individual values are plotted as empty symbols and mean values are plotted as filled symbols. On average, higher emissions were observed for animals eating a diet of baleage when no methane inhibitor was administered, however differences seem small and are to be considered as a general guidance. Upon administration of the methane inhibitor, effective methane inhibition with increasing bromoform dose was observed for both diets as measured by methane and hydrogen emissions. Bromoform's methane inhibiting efficacy does not appear to be impacted much by the fed diet composition, i.e. bromoform seems equally effective irrespectively of the applied diet.

Discussion of Preliminary Field Trial Findings

A minimum dose of between 104 and 156 mg/d of bromoform for an effective mitigation of methanogenesis was identified. In few cases, inhibition was partial, with 2 out of 4 animals demonstrating full inhibition at 156 mg/d. This suggests that there may be a steep dose response within this dose range leading to an effective mitigation of methanogenesis and that the mode of action of bromoform may determine a tipping point in the dose response relation for methane inhibition. Further studies with additional doses within this range and larger animal numbers can help to confirm the extrapolated dose response relationship.

It may be suitable to quantify dose rates in mg/kg weight of the animal per day as this allows for a more accurate determination of suitable doses. The accordingly calculated values for the average weights of animals used in the present study are displayed in Table 21.

TABLE 21

Dose rates calculated as mg/kg per day (mg/kg/d) for the different treatment groups in the present study.

| Treatment | Bromoform dose (mg/d) | Average animal liveweight (kg) | Bromoform dose (mg/kg/d) |
|---|---|---|---|
| CON | 0 | 383 | 0.00 |
| CON + 156 | 156 | 380 | 0.41 |
| LOW + 156 | 182 | 387 | 0.47 |
| MED + 156 | 208 | 376 | 0.55 |
| HIGH + 156 | 260 | 369 | 0.70 |

In summary, an effective minimal dose of bromoform to mitigate ruminant methane production (in cattle, at least partial but even full inhibition) is to be expected in the range of 104-156 mg per about 378 kg cow weight (average weight of animals in this study at time of measurement, which is representative for the majority of animals in dairy herds, for instance in New Zealand), i.e. a daily dose of around 0.28-0.4 mg/kg/d. Applying these calculated effective dose rate ranges (0.28-0.4 mg/kg/d) to the average weights and weight ranges of, for instance, the New Zealand dairy cattle population gives the expected dose ranges listed in Table 22. No breed specific differences are expected in view of the effect of the inhibitor, i.e. dosing will be mainly dependent on the cattle's body weight.

TABLE 22

Population statistics and predicted dose rates for major dairy breeds of the NZ dairy herd (representative for 90.3% of the dairy animal population).

| Breed | Percentage population | Average liveweight (population weighted) | Weight Range | Predicted average bromoform dose (mg/d) | Predicted bromoform dose range (mg/d) |
|---|---|---|---|---|---|
| Holstein-Friesian/Jersey crossbreed | 49.6% | 458 | 410-500 | 425 | 325-530 |
| Holstein-Friesian | 32.5% | 497 | 440-550 | 460 | 350-580 |
| Jersey | 8.2% | 409 | 350-440 | 380 | 275-450 |
| Average | | 468 | 350-550 | 435 | 275-580 |

Summary of Some Preliminary Field Trial Findings

The following are a number of non-exhaustive findings of the preliminary in vivo animal field trial:
Methane inhibition was observed at doses equal to and greater than 156 mg/d for 15 out of 16 animals: partial inhibition was observed for about 2 out of 4 animals tested, and full inhibition was observed for the remaining animals. The onset of methane inhibition is estimated already at slightly lower doses than 156 mg/d, such as doses of between 100 and 156 mg/d.
Partial inhibition was observed for 1 out of 4 animals treated with a dose of 182 mg/d. The remaining animals treated with this dose exhibited full methane inhibition.
All animals dosed with 208 mg/d or more exhibited full methane inhibition.
While diet has an effect on total methane production, there was preliminary no significant difference between the effective bromoform dose rates determined in subjects of different feed groups, i.e. the methane inhibitor was effective irrespective of feed.
Dry matter intake was not significantly altered with bromoform treatment at all tested doses.
Animal liveweight was about the same for treated and for untreated control animals.
No differences in blood data between treated and untreated control groups were identified.

Furthermore, from the above shown animal trial it was found that, unexpectedly, lower dose rates per animal per kg per day were already efficient in reducing methane emissions than would be expected from the available literature referring to administering active substances derived from *Asparagopsis*.

Example 15

*Asparagopsis* (Extract) as Methane Inhibiting Agent

Methods to concentrate the bromoform content in Asparagopsis spp. have focused on the dissolution of the algae's components in oils. Since bromoform is lipophilic in nature, naturally occurring bromoform in various forms, for instance in ocean algae, can be extracted into oils. The excipients presented in this document can be combined with such a bromoform containing oil emulsion in much the same way as using synthetically derived bromoform. While the ability to load as much of the active agent will be somewhat lower for algae-extracted bromoform in oil compared to synthetic bromoform, the references from Kinley et. al 2016, Magnusson et. al 2020, and Alvarez-Hess et. al 2023 show that extraction into an oil emulsion is a suitable method to concentrate or partially purify bromoform from algal sources (Kinley Robert D., de Nys Rocky, Vucko Matthew J., Machado Lorenna, Tomkins Nigel W. (2016) The red macroalgae Asparagopsis taxiformis is a potent natural antimethanogenic that reduces methane production during in vitro fermentation with rumen fluid, *Animal Production Science* 56, 282-289; Marie Magnusson, Matthew J. Vucko, Tze Loon Neoh, Rocky de Nys, Using oil immersion to deliver a naturally-derived, stable bromoform product from the red seaweed Asparagopsis taxiformis, Algal Research, Volume 51, 2020, 102065; P. S. Alvarez-Hess, J. L. Jacobs, R. D. Kinley, B. M. Roque, A. S. O. Neachtain, S. Chandra, S. R. O. Williams, Twice daily feeding of canola oil steeped with *Asparagopsis armata* reduced methane emissions of lactating dairy cows, Animal Feed Science and Technology, Volume 297, 2023, 115579). This process improves the algae extract's efficacy of methane inhibition in ruminants and the oil emulsions containing *Asparagopsis* spp. extracts can be directly applied to the bolus as defined herein.

Exemplarily, the use of an oil emulsion containing *Asparagopsis* extract applied to the bolus as defined herein was prepared and tested for its compositional and release properties. Asparagopsis oil extract was prepared based on the method by Slong et. al (Shelf-Life stability of Asparagopsis bromoform in oil and freeze-dried powder. Slong Tan, Jessica Harris, Breanna M. Roque, Shane Askew, and Robert D. Kinley. Journal of Applied Physiology (2023) 35:291-299). Ocean harvested biomass was collected and spun to remove excess seawater and placed into a drum after collection. Canola oil was added to the drum in an oil-to-seaweed weight ratio of 1:1 and mixed well. The content was then kept in a cool dark room to incubate. At day 60 the seaweed/oil mix was macerated and shredded in a blender. The extract was not entirely homogenous and some phase separation was observed. A predetermined amount of ethyl cellulose and HPMC were placed into a mortar and pestle, Asparagopsis taxiformis extract in oil was added and mixed until a homogenous paste was obtained. The paste of ethyl cellulose, HPMC and Asparagopsis oil extract was filled manually into a PLA PBAT casings (weight ratio of 90:10) and the casings were sealed by soldering. 52 g of the prepared carrier Asparagopsis oil mixture could be filled into a bolus casing, which is equivalent to about 30 g of extract in the bolus. With the oil extract comprising about 3 mg per 1 ml of oil, about 100 mg of bromoform in total could be loaded into one 34 mm×72 mm bolus. The bolus formulation is summarized in Table 23. Two representative boluses were tested for their in vitro release performance according to the method described further above.

TABLE 23

Formulation details for *Asparagopsis* containing bolus

| Ingredients | Weight (g) |
| --- | --- |
| Ethyl cellulose (EC) | 40.2 |
| HMPC | 39.94 |
| *Asparagopsis taxiformis* extract | 120.6 |

There was some variation in release rates, which, without wishing to be bound by theory, may be due to observed inhomogeneity of the Asparagopsis oil extract. Release rate data (FIG. 40) showed that less than 18 mg/day of bromoform was released per day from either bolus, which as a release rate may be less suitable to achieve effective methane mitigation in larger ruminants. However, for smaller ruminants, for instance for sheep or young animals such as young cattle, the Asparagopsis containing bolus may well be suitable, particularly when using a more homogenous Asparagopsis oil extract in the making of the bolus. Furthermore, young animals and smaller ruminants such as sheep have been found to be more susceptible to bromoform. Thus, for these animals lower bromoform administration rates may already be suitable compared to the rates, which would be calculated by means of the respective animal mass from the values obtained in the animal trial with the bromoform containing boluses presented herein above.

The use of alternative or additional active agents, other than pure bromoform, will be applicable with some adaptions of excipient chemistry in order to provide a sustained release of the active agent, such as 3-Nitrooxypropanol (3-NOP), from a bolus. In addition, it is envisioned that for the use of hydrophilic 3-NOP it will be advantageous to adjust the bolus with one or more perforations for 3-NOP to pass through the housing comprising the material blends presented herein and for 3-NOP to be available in the rumen. Such a bolus design is not restricted to the application of 3-NOP but may also be used for administering other active agents, such as other methane inhibitors. Furthermore, alternative or additional active agents, such as 3-NOP, which differ in their chemical properties from those of bromoform, can be used in combination with the carrier compounds described herein, but can also be used with further carrier components than those that were found to be particularly suitable for mixing with and administering bromoform in a bolus.

Example 16: Release Rate from an Exemplary Multi-Segmented Bolus

To combine more than one of the beneficial release profiles found for certain advantageous bolus formulations described herein, an exemplary multi segmented bolus 60_EC20_HPMC20_B65_W35 was prepared, which comprises two segments, each comprising a distinct core composition. The core compositions/formulations were as follows:

Segment 1 core (30 g):bromoform (60%)/EC(20%)/HPMC (20%)

Segment 2 core (30 g):bromoform (65%)/castor wax (35%).

Each segment was prepared analogously to the preparation of other boluses described herein, except for that each segment formed one half of an assembled full size bolus. For comparison as a control two full size boluses (i.e. not assembled from two segments) were prepared comprising the respective core formulations as described for the segments above. For all boluses and segments, a PLA/PBAT housing (ration 90:10) was used. Comparative release testing of bromoform released from the three bolus types was then performed analogously to the experiments regarding bromoform release for other bolus forms described herein. The results are shown in FIG. 45.

Using a bolus comprising two bolus segments with distinct core/carrier formulations and/or bromoform content can provide advantages for bromoform release over the use of non-segmented boluses comprising only a single core/carrier formulation. The segmented bolus increased the initial release rate of bromoform and lead to an earlier onset of the release of bromoform compared to a non-segmented bolus comprising EC and HPMC (bolus comprising bromoform (60%)/EC(20%)/HPMC (20%)), which was previously shown herein to provide a more consistent and even release over time, while providing a sustained release. On the other hand, an initial burst release, as seen for the bolus comprising castor wax as a sole bromoform carrier (bolus composition bromoform (65%)/castor wax (35%)), was avoided when using the segmented bolus. FIG. 45 demonstrates that from about day 7 of release testing on, an advantageous zero order release profile was observed for the segmented bolus. In summary the segmented bolus successfully provided a bromoform release profile which was intermediate between the release profiles of the individual boluses comprising only one of the segment formulations.

In view of these observations it was confirmed that a multi-segment bolus, wherein each segment due to its composition/formulation individually provides a distinct bromoform release profile, is useful for further adjusting desired release rates and can be used for fine tuning.

These findings also suggest that a multi-segmented bolus, wherein each segment due to its composition/formulation provides a distinct release profile that can be combined, may also be beneficial when administering different compounds to be released from the respective bolus segment, wherein release rates of the respective compound may advantageously be individually adapted.

Example 17

Summary on Exemplary Boli Tested Herein

The following Table 24 provides an overview of the various bolus designs and carrier/excipient formulation examples used in the context of the present invention. Release rates are as tested in vitro unless specified otherwise.

TABLE 24

Bolus configurations and associated tables and figures. V2 cap - internal weld face, displacement 5.9 cm$^2$, V3 cap - lower displacement 2.95 cm$^2$, external weld face.

| Bolus Name | Housing manufacture | Housing material | Dimensions | Cap | Bromoform Content | Excipients/ Carrier Matrix | Densifier | Release Profile | References |
|---|---|---|---|---|---|---|---|---|---|
| Prototype 4 | 3D printed | PLA | 130 mm × 34 mm | Printed | 50% | 75% castor and 25% paraffin wax | Zinc rod | Pseudo 1$^{st}$ order, 156 mg/d | Table 7 |
| ASL-65-W | 3D printed | PLA | 34 mm × 130 mm | Printed | 65% | Fumed silica | Stainless steel granules | Pseudo 1$^{st}$ order, 300 mg/d | Table 10.1, FIG. 19 and FIG. 27 |
| ASL-65_W-PLA/PBAT | Injection moulded | PLA/PBAT 90:10 | 34 mm × 72 mm | V2 | 65% | Fumed Silica and Castor wax | Stainless steel granules | Pseudo 1$^{st}$ order, 300 mg/d | FIG. 28 |
| ASL-70-EC | Injection moulded | PLA/PBAT 90:10 | 34 mm × 72 mm | V2 | 70% | Ethyl cellulose, fumed silica | Stainless steel granules | Pseudo 1$^{st}$ order, 700-300 mg/d | Table 10.3, FIG. 29 |
| ASL-65-PCL | Injection moulded | PLA/PBAT 90:10 | 34 mm × 72 mm | V2 | 65% | PCL, fumed silica | Stainless steel granules | Pseudo 1$^{st}$ order, 300-100 mg/d | FIG. 19 |
| ASL-64-EC | Injection moulded | PLA/PBAT 90:10 | 34 mm × 72 mm | V2 | 64% | Ethyl cellulose, fumed silica | Stainless steel granules | Pseudo zero order, 250 mg/d | Table 12.3, FIG. 29 |
| ASL-80-L | Injection moulded | PLA/PBAT 90:10 | 34 mm × 72 mm | V2 | 80% | Fumed silica, lauric acid | Stainless steel granules | N/A | Table 12.1, FIG. 30B |
| PPG-64 | N/A | N/A | N/A | N/A | 64% | Propylene Glycol | N/A | N/A | Table 13; FIG. 30A |
| AE-64 | Injection moulded | PLA/PBAT 90:10 | 34 mm × 72 mm | V2 | 64% | Fumed silica | Stainless steel granules | N/A | Table 13; FIG. 30B |
| EC-64, prototype 8A | Injection moulded | PLA/PBAT 90:10 | 34 mm × 72 mm | V2 | 64% | Ethyl cellulose | Stainless steel granules | Pseudo zero order, 50 mg/d | FIG. 31A, FIG. 7 |
| EC-AE-10-64 | Injection moulded | PLA/PBAT 90:10 | 34 mm × 72 mm | V2 | 64% | Ethyl cellulose, fumed silica 10 wt % | Stainless steel granules | Pseudo 1$^{st}$ order, 250-50 mg/d | FIG. 31B; Table 13 |
| EC-AE-7-64 | Injection moulded | PLA/PBAT 90:10 | 34 mm × 72 mm | V2 | 64% | Ethyl cellulose, fumed silica 7 wt % | Stainless steel granules | Pseudo 1$^{st}$ order, 175-100 mg/d | FIG. 31B; Table 13 |
| EC-AE-5-64 | Injection moulded | PLA/PBAT 90:10 | 34 mm × 72 mm | V3 | 64% | Ethyl cellulose, fumed silica 5 wt % | Stainless steel granules | Pseudo 1$^{st}$ order 175-50 mg/d | FIG. 31B; Table 13 |
| EC-HPMC-58 | Injection moulded | PLA/PBAT 90:10 | 34 mm × 72 mm | V3 | 58.3% | Ethyl cellulose, HPMC 14.3 wt % | Stainless steel granules | Pseudo zero order, 80 mg/d | FIG. 31A; Table 13 |
| EC-HPMC-60, prototype 9B | Injection moulded | PLA/PBAT 90:10 | 34 mm × 72 mm | V3 | 60% | Ethyl cellulose 20 wt %, HPMC 14.3 wt % | Stainless steel granules | Pseudo zero order, 160 mg/d | FIG. 32B; Table 13 |

TABLE 24-continued

Bolus configurations and associated tables and figures. V2 cap - internal weld face, displacement 5.9 cm$^2$, V3 cap - lower displacement 2.95 cm$^2$, external weld face.

| Bolus Name | Housing manufacture | Housing material | Dimensions | Cap | Bromoform Content | Excipients/ Carrier Matrix | Densifier | Release Profile | References |
|---|---|---|---|---|---|---|---|---|---|
| EC-HPMC-61 | Injection moulded | PLA/PBAT 90:10 | 34 mm × 72 mm | V3 | 61% | Ethyl cellulose 15 wt %, HPMC 24 wt % | Stainless steel granules | Pseudo zero order, 250 mg/d | FIG. 32C; Table 13 |

We claim:

1. A bolus, comprising:
a core comprising a methane inhibiting agent and a carrier; and
a housing which covers at least a portion of the core, wherein:
the bolus is configured to be administered to a ruminant animal; and
one of the following holds:
the material of the housing comprises poly lactic acid (PLA) and polybutylene adipate terephthalate (PBAT) in a PLA:PBAT weight ratio of between 95:5 to 80:20;
the material of the housing comprises PLA and polybutylene succinate (PBS) in a PLA:PBS weight ratio of between 95:5 to 70:30; or
the material of the housing comprises PLA and polybutylene succinate adipate (PBSA) in a PLA:PBSA weight ratio of between 95:5 to 70:30.

2. The bolus of claim 1, wherein the methane inhibiting agent comprises a haloform.

3. The bolus of claim 1, wherein the methane inhibiting agent comprises bromoform.

4. The bolus of claim 1, wherein the core further comprises a wax and/or a polyol and/or a polyester.

5. The bolus of claim 1, wherein the core comprises ethyl cellulose and/or hydroxypropyl methylcellulose.

6. The bolus of claim 1, wherein the core comprises ethyl cellulose and fumed silica.

7. The bolus of claim 1, wherein the core comprises ethyl cellulose in an amount of from 10 to 40 wt %.

8. The bolus of claim 1, wherein the core comprises hydroxypropyl methylcellulose in an amount of from 10 to 30 wt %.

9. The bolus of claim 1, wherein at least 50% of the core comprises the methane inhibiting agent.

10. The bolus of claim 1, wherein the methane inhibiting agent is in the core in an amount of between 30 wt % to 80 wt % in relation to the total weight of the core.

11. The bolus of claim 1, wherein the methane inhibiting agent is in the core in an amount of at least 50 wt % in relation to the total weight of the core.

12. The bolus of claim 1, wherein the housing comprises PLA:PBS in a weight ratio that is about 80:20.

13. The bolus of claim 1, wherein the material of the housing comprises PLA:PBAT in a weight ratio of about 90:10.

14. The bolus of claim 1, wherein the methane inhibiting agent is configured to perfuse through the housing material.

15. The bolus of claim 1, wherein the housing material comprises one or more plasticisers, hardeners and/or colourants.

16. The bolus of claim 1, wherein the housing has a wall thickness of below 2 mm.

17. The bolus of claim 1, wherein the housing includes an opening and wherein the housing includes a cap configured to close the opening.

18. The bolus of claim 1, wherein the housing comprises no openings and completely surrounds the core.

19. The bolus of claim 1, wherein the core of the bolus comprises metal particles and wherein the total mass of the metal particles in the bolus is at least 100 g.

20. A method, comprising:
administering to a ruminant animal the bolus of claim 1 to reduce methane production in the rumen of the ruminant animal.

21. A method of manufacturing a bolus, the method comprising:
(1) providing a housing comprising a polymer material; and
(2) filling a core into the housing,
wherein the bolus comprises:
a core comprising:
a methane inhibiting agent configured to inhibit methane production in the rumen of a ruminant animal; and
a carrier; and
a housing which houses the core, and
wherein one of the following holds:
the material of the housing comprises poly lactic acid (PLA) and polybutylene adipate terephthalate (PBAT) in a PLA:PBAT weight ratio of between 95:5 to 80:20;
the material of the housing comprises PLA and polybutylene succinate (PBS) in a PLA:PBS weight ratio of between 95:5 to 70:30; or
the material of the housing comprises PLA and polybutylene succinate adipate (PBSA) in a PLA:PBSA weight ratio of between 95:5 to 70:30.

22. The method of claim 21, wherein the core comprises ethyl cellulose and/or HPMC.

23. The method of claim 21, further comprising, after (2), friction welding a cap to the housing to close the housing.

24. The method of claim 21, wherein (1) comprises injection molding the polymer material.

25. The method of claim 23, further comprising, prior to (3), exposing the housing and/or the core to a reduced pressure in order to reduce an amount of gas remaining inside of the bolus after closing the housing.

26. The method of claim 1, wherein the methane inhibiting agent comprises at least one member selected from the group consisting of bromoform, chloroform and iodoform.

27. The method of claim 1, wherein the core comprises Asparagopsis, the Asparagopsis comprises the methane inhibiting agent, and the methane inhibiting agent comprises bromoform.

28. The method of claim 1, wherein the housing completely covers and surrounds the core so that the housing defines a sealed cavity in which the core is located.

29. The method of claim 1, wherein the dosage form or bolus further comprises a cap, and together the housing and the cap together define a closed and sealed cavity in which the core is located.

30. The method of claim 1, wherein the methane inhibiting agent comprises bromoform, and the housing comprises PLA:PBAT in a weight ratio of about 90:10.

* * * * *

UNITED STATES PATENT AND TRADEMARK OFFICE
CERTIFICATE OF CORRECTION

| | |
|---|---|
| PATENT NO. | : 12,115,248 B2 |
| APPLICATION NO. | : 18/498661 |
| DATED | : October 15, 2024 |
| INVENTOR(S) | : Mark Christopher Lay et al. |

It is certified that error appears in the above-identified patent and that said Letters Patent is hereby corrected as shown below:

On the Title Page

Page 2, Column 2 item (56) (Other Publications), Line 46, delete "Reponse" and insert -- Response --.

Page 2, Column 2 item (56) (Other Publications), Line 63, delete "Properties,"Materials," and insert -- Properties," Materials, --.

In the Drawings

Sheet 25 of 51, Figure 21, Line 2, delete "PLA/BPAT" and insert -- PLA/PBAT --.

In the Specification

Column 1, Line 9, delete "22/205,176.5," and insert -- 22205176.5, --.

Column 5, Line 11, delete "inhomogencous." and insert -- inhomogeneous. --.

Column 6, Line 40, delete "octyl silane".

Column 6, Line 51, delete "steryl" and insert -- stearyl --.

Column 6, Line 51, delete "cetosteryl" and insert -- cetostearyl --.

Column 6, Line 52, delete "Candellila," and insert -- Candelilla, --.

Column 7, Line 54, delete "8A)." and insert -- 8.A). --.

Column 9, Line 60, delete "between-20%" and insert -- between -20% --.

Signed and Sealed this
Twentieth Day of May, 2025

Coke Morgan Stewart
*Acting Director of the United States Patent and Trademark Office*

CERTIFICATE OF CORRECTION (continued)
U.S. Pat. No. 12,115,248 B2

Column 9, Line 66, delete "between-10%" and insert -- between -10% --.

Column 10, Line 29, delete "nicolosamide," and insert -- niclosamide, --.

Column 10, Line 33, delete "emethine," and insert -- emetine, --.

Column 10, Line 37, delete "Bitin-S(Trade" and insert -- Bitin-S (Trade --.

Column 10, Line 38, delete "bromofenophos, menichlopolan," and insert -- bromofenofos, menichlopholan, --.

Column 10, Line 41, delete "dithiazanide" and insert -- dithiazanine --.

Column 10, Line 42, delete "trichlabendazole, chlorsulan" and insert -- triclabendazole, clorsulon --.

Column 11, Line 48, delete "steryl" and insert -- stearyl --.

Column 11, Line 49, delete "cetosteryl" and insert -- cetostearyl --.

Column 11, Line 50, delete "Candellila," and insert -- Candelilla, --.

Column 11, Line 56, delete "(&-caprolactone)" and insert -- (ε-caprolactone) --.

Column 12, Line 1, delete "steryl" and insert -- stearyl --.

Column 12, Line 1, delete "cetosteryl" and insert -- cetostearyl --.

Column 12, Lines 2-3, delete "Candellila," and insert -- Candelilla, --.

Column 13, Line 4, delete "on" and insert -- one --.

Column 13, Line 11, delete "steryl" and insert -- stearyl --.

Column 13, Line 12, delete "cetosteryl" and insert -- cetostearyl --.

Column 13, Line 13, delete "Candellila," and insert -- Candelilla, --.

Column 13, Line 31, delete "steryl" and insert -- stearyl --.

Column 13, Line 31, delete "cetosteryl" and insert -- cetostearyl --.

Column 13, Lines 32-33, delete "Candellila," and insert -- Candelilla, --.

Column 14, Line 26, after "may" delete "for".

CERTIFICATE OF CORRECTION (continued)
U.S. Pat. No. 12,115,248 B2

Column 14, Line 26, after "by" delete "as".

Column 14, Line 56, delete "lose" and insert -- loose --.

Column 18, Line 53, delete "steryl" and insert -- stearyl --.

Column 18, Line 54, delete "cetosteryl" and insert -- cetostearyl --.

Column 18, Line 58, delete "Candellila," and insert -- Candelilla, --.

Column 22, Line 28, delete "made be" and insert -- may be --.

Column 23, Line 47, delete "silicons," and insert -- silicones, --.

Column 25, Line 49, after "release" insert -- of --.

Column 26, Line 36, delete "art" and insert -- at --.

Column 27, Line 53, after "thickness" insert -- of --.

Column 28, Line 46, delete "Candellila," and insert -- Candelilla, --.

Column 30, Line 20, delete "cross sectional-view" and insert -- cross-sectional view --.

Column 31, Line 33, after "22A" delete ")".

Column 31, Line 34, after "22B" delete ")".

Column 31, Line 63, after "30A" delete ")".

Column 31, Line 64, after "30B" delete ")".

Column 32, Line 7, after "32A" delete ")".

Column 32, Line 10, after "32B" delete ")".

Column 32, Line 12, after "32C" delete ")".

Column 34, Line 26, after "casing" insert -- . --.

Column 34, Lines 63-64, delete "The bolus (100) includes a core (110) and a housing (120)." and insert the same on Column 34, Line 64, as a new paragraph.

Column 35, Line 16, delete "Candellila" and insert -- Candelilla --.

CERTIFICATE OF CORRECTION (continued)
U.S. Pat. No. 12,115,248 B2

Column 35, Line 20, delete "a" and insert -- as --.

Column 39, Line 61, after "(200)" insert -- . --.

Column 42, Line 25, delete "826—" and insert -- 826 --.

Column 44, Line 57, delete "octyl silane".

Column 45, Line 3, delete "steryl" and insert -- stearyl --.

Column 45, Line 3, delete "cetosteryl" and insert -- cetostearyl --.

Column 45, Line 5, delete "Candellila," and insert -- Candelilla, --.

Column 45, Line 66, after "26" insert -- . --.

Column 46, Line 5, after "27" insert -- . --.

Column 46, Line 28, after "35" insert -- . --.

Column 48, Line 62, after "vinylpyrrolidone-vinyl" insert -- acetate --.

Column 52, Line 5, delete "ZBSHT" and insert -- ZB5HT --.

Column 54, Line 39, delete "21," and insert -- 2L --.

Column 59, Line 14, delete "(g/d]" and insert -- [g/d] --.

Column 59, Line 16, delete "(g/d]" and insert -- [g/d] --.

Column 59, Line 34, delete "that that" and insert -- that --.

Column 59, Line 63, delete "Labcono" and insert -- Labconco --.

Column 61, Line 33, delete "PANalytica" and insert -- PANalytical --.

Column 61, Line 36, delete "2 Theta," and insert -- 2Theta, --.

Column 61, Line 41, delete "Owner-" and insert -- Owner= --.

Column 61, Line 48, delete "K-Alphal" and insert -- K-Alpha1 --.

Column 63, Line 25, delete "(47.5%49.0%)," and insert -- (47.5%-49.0%), --.

Column 64, Line 31, delete "ASL_PCL" and insert -- ASL-PCL --.

CERTIFICATE OF CORRECTION (continued)
U.S. Pat. No. 12,115,248 B2

Column 64, Line 50, delete "(TO)" and insert -- (T0) --.

Column 66, Line 41, delete "poly caprolactone" and insert -- polycaprolactone --.

Column 73, Line 35, before "casing" delete "of".

Column 73, Line 54, delete "(ASL-70 -EC" and insert -- (ASL-70-EC --.

Column 73, Line 54, delete "EC))" and insert -- EC) --.

Column 73, Line 66, delete "FIG." and insert -- FIGS. --.

Column 78, Line 3, delete "calorimetry" and insert -- Calorimetry --.

Column 85, Line 21, delete "PLA PBAT" and insert -- PLA/PBAT --.

Columns 87-88, Lines 12-13 (Table 24), delete "ASL-65_W-" and insert -- ASL-65-W- --.

In the Claims

Column 90, Line 61, in Claim 26, delete "1" and insert -- 21 --.

Column 90, Line 64, in Claim 27, delete "1" and insert -- 21 --.

Column 91, Line 1, in Claim 28, delete "1" and insert -- 21 --.

Column 91, Line 4, in Claim 29, delete "1" and insert -- 21 --.

Column 91, Line 8, in Claim 30, delete "1" and insert -- 21 --.